US011479530B2

(12) United States Patent
Edinger et al.

(10) Patent No.: US 11,479,530 B2
(45) Date of Patent: *Oct. 25, 2022

(54) SYNTHETIC SPHINGOLIPID-LIKE MOLECULES, DRUGS, METHODS OF THEIR SYNTHESIS AND METHODS OF TREATMENT

(71) Applicants: The Regents of the University of California, Oakland, CA (US); The Université de Montréal, Montreal (CA)

(72) Inventors: Aimee L. Edinger, Irvine, CA (US); Stephen Hanessian, Irvine, CA (US)

(73) Assignees: The Regents of the University of California, Oakland, CA (US); The Université de Montréal, Montreal (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/195,556

(22) Filed: Mar. 8, 2021

(65) Prior Publication Data
US 2021/0261504 A1 Aug. 26, 2021

Related U.S. Application Data

(63) Continuation of application No. 15/760,199, filed as application No. PCT/US2016/053815 on Sep. 26, 2016, now Pat. No. 10,995,068.

(60) Provisional application No. 62/232,377, filed on Sep. 24, 2015.

(51) Int. Cl.
C07D 207/08 (2006.01)
C07D 207/06 (2006.01)
A61K 31/40 (2006.01)
A61P 35/00 (2006.01)
A61K 45/06 (2006.01)

(52) U.S. Cl.
CPC ............ *C07D 207/08* (2013.01); *A61K 31/40* (2013.01); *A61K 45/06* (2013.01); *A61P 35/00* (2018.01); *C07D 207/06* (2013.01)

(58) Field of Classification Search
CPC .................................................. C07D 207/08
See application file for complete search history.

(56) References Cited

U.S. PATENT DOCUMENTS

| | | |
|---|---|---|
| 3,687,808 A | 8/1972 | Clercq et al. |
| 3,931,155 A | 1/1976 | Grisar et al. |
| 4,845,205 A | 7/1989 | Huynh Dinh et al. |
| 5,034,506 A | 7/1991 | Summerton et al. |
| 5,130,302 A | 7/1992 | Spielvogel et al. |
| 5,134,066 A | 7/1992 | Rogers et al. |
| 5,166,315 A | 11/1992 | Summerton et al. |
| 5,175,273 A | 12/1992 | Bischofberger et al. |
| 5,185,444 A | 2/1993 | Summerton et al. |
| 5,367,066 A | 11/1994 | Urdea et al. |
| 5,432,272 A | 7/1995 | Benner et al. |
| 5,434,257 A | 7/1995 | Matteucci et al. |
| 5,457,187 A | 10/1995 | Gmeiner et al. |
| 5,457,191 A | 10/1995 | Andrews et al. |
| 5,459,255 A | 10/1995 | Manoharan et al. |
| 5,484,908 A | 1/1996 | Froehler et al. |
| 5,502,177 A | 3/1996 | Matteucci et al. |
| 5,525,711 A | 6/1996 | Hawkins et al. |
| 5,552,540 A | 9/1996 | Haralambidis |
| 5,587,469 A | 12/1996 | Manoharan et al. |
| 5,587,470 A | 12/1996 | Cook et al. |
| 5,594,121 A | 1/1997 | Frohhler et al. |
| 5,596,091 A | 1/1997 | Switzer |
| 5,614,617 A | 3/1997 | Sanghvi et al. |
| 5,645,985 A | 7/1997 | Froehler et al. |
| 5,681,941 A | 10/1997 | Cook et al. |
| 5,698,685 A | 12/1997 | Summerton et al. |
| 5,750,692 A | 5/1998 | Cook et al. |
| 5,763,588 A | 6/1998 | Matteucci et al. |
| 5,808,027 A | 9/1998 | Manoharan et al. |
| 5,811,534 A | 9/1998 | Cook et al. |
| 5,830,653 A | 11/1998 | Froehler et al. |
| 5,859,221 A | 1/1999 | Kawasaki et al. |
| 5,948,903 A | 9/1999 | Cook et al. |
| 6,005,087 A | 12/1999 | Cook et al. |
| 6,005,096 A | 12/1999 | Matteucci et al. |
| 6,166,199 A | 12/2000 | Manoharan et al. |

(Continued)

FOREIGN PATENT DOCUMENTS

| | | |
|---|---|---|
| CA | 2627502 A1 | 5/2007 |
| CN | 108366990 A | 8/2018 |

(Continued)

OTHER PUBLICATIONS

Extended European Search Report for European Application No. 14825876.7, Search completed Feb. 22, 2017, dated Mar. 2, 2017, 9 Pgs.
Extended European Search Report for European Application No. 16849886.3, Search completed Jan. 11, 2019, dated Feb. 12, 2019, 8 Pgs.
International Preliminary Report on Patentability for International Application PCT/US2014/046711, Report dated Jan. 19, 2016, dated Jan. 28, 2016, 7 Pgs.
International Preliminary Report on Patentability for International Application PCT/US2016/053815, Report dated Mar. 27, 2018, dated Apr. 5, 2018, 7 Pgs.
International Search Report and Written Opinion for International Application No. PCT/US2016/053815, Search completed Nov. 11, 2016, dated Dec. 27, 2016, 8 Pgs.

(Continued)

*Primary Examiner* — Shawquia Jackson
(74) *Attorney, Agent, or Firm* — KPPB LLP

(57) ABSTRACT

Small molecules comprised of azacyclic constrained sphingolipid-like compounds and methods of their synthesis are provided. Formulations and medicaments are also provided that are directed to the treatment of disease, such as, for example, neoplasms, cancers, and other diseases. Therapeutics are also provided containing a therapeutically effective dose of one or more small molecule compounds, present either as pharmaceutically effective salt or in pure form, including, but not limited to, formulations for oral, intravenous, or intramuscular administration.

19 Claims, 80 Drawing Sheets

(56) References Cited

U.S. PATENT DOCUMENTS

| | | |
|---|---|---|
| 6,268,490 B1 | 7/2001 | Imanishi et al. |
| 6,525,191 B1 | 2/2003 | Ramasamy et al. |
| 6,531,584 B1 | 3/2003 | Cook et al. |
| 6,670,461 B1 | 12/2003 | Wengel et al. |
| 6,770,748 B2 | 8/2004 | Imanishi et al. |
| 6,794,499 B2 | 9/2004 | Wengel et al. |
| 7,034,133 B2 | 4/2006 | Wengel et al. |
| 7,053,207 B2 | 5/2006 | Wengel |
| 7,399,845 B2 | 7/2008 | Swayze et al. |
| 7,427,672 B2 | 9/2008 | Imanishi et al. |
| 7,547,684 B2 | 6/2009 | Seth et al. |
| 7,569,686 B1 | 8/2009 | Bhat et al. |
| 7,572,582 B2 | 8/2009 | Wengel et al. |
| 7,638,637 B2 | 12/2009 | Lynch et al. |
| 7,666,854 B2 | 2/2010 | Seth et al. |
| 7,696,345 B2 | 4/2010 | Allerson et al. |
| 7,741,457 B2 | 6/2010 | Swayze et al. |
| 7,750,131 B2 | 7/2010 | Seth et al. |
| 7,772,406 B2 | 8/2010 | Morimoto et al. |
| 7,875,733 B2 | 1/2011 | Bhat et al. |
| 7,939,677 B2 | 5/2011 | Bhat et al. |
| 7,968,733 B2 | 6/2011 | Suzuki et al. |
| 8,022,193 B2 | 9/2011 | Swayze et al. |
| 8,030,467 B2 | 10/2011 | Seth et al. |
| 8,034,909 B2 | 10/2011 | Wengel et al. |
| 8,080,644 B2 | 12/2011 | Wengel et al. |
| 8,088,746 B2 | 1/2012 | Seth et al. |
| 8,088,904 B2 | 1/2012 | Prakash et al. |
| 8,124,745 B2 | 2/2012 | Allerson et al. |
| 8,153,365 B2 | 4/2012 | Wengel et al. |
| 8,268,980 B2 | 9/2012 | Seth et al. |
| 8,278,283 B2 | 10/2012 | Seth et al. |
| 8,278,425 B2 | 10/2012 | Prakash et al. |
| 8,278,426 B2 | 10/2012 | Seth et al. |
| 8,309,768 B2 | 11/2012 | Chen et al. |
| 8,440,803 B2 | 5/2013 | Prakash et al. |
| 8,501,805 B2 | 8/2013 | Seth et al. |
| 8,530,640 B2 | 9/2013 | Seth et al. |
| 8,546,556 B2 | 10/2013 | Seth et al. |
| RE44,779 E | 2/2014 | Obika et al. |
| 8,796,437 B2 | 8/2014 | Prakash et al. |
| 9,005,906 B2 | 4/2015 | Prakash et al. |
| 9,012,421 B2 | 4/2015 | Migawa et al. |
| 9,115,054 B2 | 8/2015 | Dhar et al. |
| 10,077,236 B2 | 9/2018 | Edinger et al. |
| 2003/0158403 A1 | 8/2003 | Manoharan et al. |
| 2003/0175906 A1 | 9/2003 | Manoharan et al. |
| 2005/0256056 A1 | 11/2005 | North et al. |
| 2006/0019900 A1 | 1/2006 | Lam et al. |
| 2007/0258970 A1 | 11/2007 | Blumenthal et al. |
| 2008/0039618 A1 | 2/2008 | Allerson et al. |
| 2010/0022655 A1 | 1/2010 | Byrd et al. |
| 2010/0120858 A1 | 5/2010 | Caprathe et al. |
| 2013/0123366 A1 | 5/2013 | Byrd et al. |
| 2013/0203836 A1 | 8/2013 | Rajeev et al. |
| 2015/0191727 A1 | 7/2015 | Migawa et al. |
| 2016/0159739 A1 | 6/2016 | Edinger |
| 2020/0016161 A1 | 1/2020 | Perrine et al. |

FOREIGN PATENT DOCUMENTS

| | | |
|---|---|---|
| EP | 2058301 A1 | 5/2009 |
| EP | 3022176 A2 | 5/2016 |
| EP | 3352753 A1 | 8/2018 |
| EP | 3022176 B1 | 9/2019 |
| FR | 2968556 A1 | 6/2012 |
| HK | 1259078 A | 11/2019 |
| HK | 1259078 B | 4/2022 |
| IN | 201817010816 A | 7/2018 |
| IN | 382882 | 11/2021 |
| JP | 2008509931 A | 4/2008 |
| JP | 2010513532 A | 4/2010 |
| JP | 2016529236 A | 9/2016 |
| JP | 2018534256 A | 11/2018 |
| JP | 6617702 B2 | 11/2019 |
| WO | 1999014226 | 3/1999 |
| WO | 2004106356 A1 | 12/2004 |
| WO | 2006020951 A1 | 2/2006 |
| WO | 2007134181 A2 | 11/2007 |
| WO | 2008016674 A1 | 2/2008 |
| WO | 2008079382 A1 | 7/2008 |
| WO | 2008097819 A2 | 8/2008 |
| WO | 2008101157 A1 | 8/2008 |
| WO | 2008097819 A3 | 11/2008 |
| WO | 2009053481 A1 | 4/2009 |
| WO | 2009106599 A2 | 9/2009 |
| WO | 2009153191 A1 | 12/2009 |
| WO | 2010009762 A1 | 1/2010 |
| WO | 2011133876 A2 | 10/2011 |
| WO | 2012080641 A1 | 6/2012 |
| WO | 2014179620 A1 | 11/2014 |
| WO | 2015009731 A2 | 1/2015 |
| WO | 2015009731 A3 | 3/2015 |
| WO | 2015106128 A2 | 7/2015 |
| WO | 2016160102 A1 | 10/2016 |
| WO | 2016210134 A1 | 12/2016 |
| WO | 2017053990 A1 | 3/2017 |
| WO | 2019241739 A1 | 12/2019 |
| WO | 2021062168 A1 | 4/2021 |
| WO | 2021236389 A2 | 11/2021 |
| WO | 2022094615 A1 | 5/2022 |

OTHER PUBLICATIONS

International Search Report and Written Opinion for International Application No. PCT/US2019/037362, Search completed Jul. 30, 2019, dated Sep. 23, 2019, 16 Pgs.

International Search Report and Written Opinion for International Application PCT/US2014/046711, report completed Nov. 26, 2014, dated Dec. 30, 2014, 10 Pages.

"2-[(4-Hexylphenyl)methyl]pyrrolidine", PubChem, https://pubchem.ncbi.nlm.nih.gov/compound/82341685, Oct. 20, 2014, pp. 1-5.

"Antisense Drug Technology", edited by Crooke, Chapters 6 and 15, Antisense Drug Technology, CRC Press, 2008, pp. 163-166 and 442-443.

"Medline Plus", A service of the u.s. National Library of Medicine and the National Institutes of Health, Jul. 6, 2007, pp. 10.

"The Concise Encyclopedia of Polymer Science and Engineering", edited by Kroschwitz, John Wiley & Sons, 1990, 858-859.

Albaek et al., "Analogues of a Locked Nucleic Acid with Three-Carbon 2',4'-Linkages: Synthesis by Ring-Closing Metathesis and Influence on Nucleic Acid Duplex Stability and Structure", Journal of Organic Chemistry, 2006, vol. 71, No. 20, pp. 7731-7740, DOI: 10.1021/jo061225g, Online Publication Date Sep. 8, 2006.

Azuma et al., "Induction of Apoptosis in Human Bladder Cancer Cells in Vitro and in Vivo Caused by FTY720 Treatment", The Journal of Urology, vol. 169, Jun. 2003, pp. 2372-2377.

Azuma et al., "Marked Prevention of Tumor Growth and Metastasis by a Novel Immunosuppressive Agent, FTY720, in Mouse Breast Cancer Models", Cancer Research, Mar. 1, 2002, vol. 62, pp. 1410-1419.

Barraclough et al., "Synthesis of kainoid analogues", Tetrahedron, vol. 51, Issue 14, Apr. 3, 1995, pp. 4195-4212, https://doi.org/10.1016/0040-4020(95)00135-U.

Bauer et al., "Cytokine stimulation of aerobic glycolysis in hematopoietic cells exceeds proliferative demand", FASEB Journal, vol. 18, No. 11, Aug. 2004, pp. 1303-1305, published online Jun. 4, 2004, https://doi.org/10.1096/fj.03-1001fje.

Bird et al., "Metabolic Mapping of MCF10A Human Breast Cells via Multiphoton Fluorescence Lifetime Imaging of the Coenzyme NADH", Cancer Research, Oct. 2005, vol. 65, Issue 19, pp. 8766-8773, DOI: 10.1158/0008-5472.CAN-04-3922.

Birsoy et al., "Metabolic determinants of cancer cell sensitivity to glucose limitation and biguanides", Nature, vol. 508, Apr. 3, 2014, pp. 108-112, doi:10.1038/nature13110, first published Mar. 16, 2014.

Braasch et al., "Novel Antisense and Peptide Nucleic Acid Strategies for Controlling Gene Expression†", Biochemistry, 2002, vol. 41, No. 14, pp. 4503-4510, DOI: 10.1021/bi0122112, Online Publication Date Mar. 9, 2002.

(56) References Cited

OTHER PUBLICATIONS

Brinkmann, "FTY720 (fingolimod) in Multiple Sclerosis: therapeutic effects in the immune and the central nervous system", British Journal of Pharmacology, 2009, vol. 158, pp. 1173-1182.
Camm et al., "Cardiac and vascular effects of fingolimod: Mechanistic basis and clinical implications", American Heart Journal, Jul. 11, 2014, vol. 168, No. 5, pp. 632-644, DOI: 10.1016/j.ahj.2014.06.028.
Chabaud et al., "Stereoselective synthesis of (3S,4S)-tert-butyl-N-Boc-3-ethyl-4-hydroxy-I-prolinate and (3S,4R)-tert-butyl-N-Boc-3-ethyl-4-hydroxy-I-prolinate", Tetrahedron, vol. 61, Issue 15, Apr. 11, 2005, pp. 3725-3731, https://doi.org/10.1016/j.tet.2005.02.006.
Chalfant et al., "The structural requirements for ceramide activation of serine-threonine protein phosphatases", The Journal of Lipid Research, vol. 45, Mar. 2004, pp. 496-506, doi: 10.1194/jlr.M300347-JLR200, First Published on Dec. 1, 2003.
Chen et al., "Azacyclic FTY720 Analogues That Limit Nutrient Transporter Expression but Lack S1P Receptor Activity and Negative Chronotropic Effects Offer a Novel and Effective Strategy to Kill Cancer Cells in Vivo", ACS Chemical Biology, Feb. 19, 2016, vol. 11, No. 2, pp. 409-414, Published online Dec. 14, 2015. doi: 10.1021/acschembio.5b00761.
Chen et al., "Crucial role of p53-dependent cellular senescence in suppression of Pten-deficient tumorigenesis", Nature, Aug. 4, 2005, vol. 436, No. 7051, pp. 725-730, doi:10.1038/nature03918.
Chua et al., "FTY720, a fungus metabolite, inhibits in vivo growth of androgen-independent prostate cancer", Int. J. Cancer, 2005, vol. 117, pp. 1039-1048.
Chung, N. et al., "Phytosphingosine as a Specific Inhibitor of Growth and Nutrient Import in *Saccharomyces cerevisiae*", The Journal of Biological Chemistry, Sep. 21, 2001, vol. 276, pp. 35614-35621, First Published on Jul. 23, 2001, doi: 10.1074/jbc.M105653200.
Clemens et al., "Synthesis of 4(5)-phenylimidazole-based analogues of sphingosine-1-phosphate and FTY720: Discovery of potent S1P1 receptors agonists", Bioorganic & Medicinal Chemistry Letters, 2005, vol. 15, pp. 3568-3572.
Cohen et al., "Mechanisms of fingolimod's efficacy and adverse effects in multiple sclerosis", Ann. Neurol., vol. 69, Issue 5, May 2011, pp. 759-777, https://doi.org/10.1002/ana.22426.
Commisso et al., "Macropinocytosis of protein is an amino acid supply route in Ras-transformed cells", Nature, vol. 497, May 30, 2013, pp. 633-637, doi:10.1038/nature12138.
Crooke et al., "Pharmacokinetic properties of several novel oligonucleotide analogs in mice", Journal of Pharmacology and Experimental Therapeutics, May 1996, vol. 277, Issue 2, pp. 923-937.
Davis et al., "Sphingosine 1-Phosphate Analogs as Receipt Antagonists", The Journal of Biological Chemistry, 2005, vol. 280, No. 11, pp. 9833-9841.
Deng et al., "Protein phosphatase 2A inactivates Bcl2's antiapoptotic function by dephosphorylation and up-regulation of Bcl2-p53 binding", Blood, Jan. 8, 2009, vol. 113, No. 2, pp. 422-428.
Digman et al., "The Phasor Approach to Fluorescence Lifetime Imaging Analysis", Biophysical Journal, vol. 94, Issue 2, Jan. 15, 2008, pp. L14-L16, https://doi.org/10.1529/biophysj.107.120154.
Dong et al., "PI(3,5)P2 controls membrane trafficking by direct activation of mucolipin Ca2 in the endolysosome", Nature Communications, vol. 1, Article 38, 2010, 11 pages, first published Jul. 13, 2010, doi:10.1038/ncomms1037.
Dorn et al., "Synthesis, Characterization, and Properties of the Polyphosphinoboranes [RPH-BH2]n (R=Ph, iBu, p-nBuC6H4, p-dodecylC6H4): Inorganic Polymers with a Phosphorus-Boron Backbone", Macromolecules, 2003, vol. 36, No. 2, pp. 291-297, DOI: 10.1021/ma021447q, Online Publication Date Dec. 19, 2002.
Englisch et al., "Chemically Modified Oligonucleotides as Probes and Inhibitors", Angewandte Chemie, International Edition, vol. 30, Issue 6, Jun. 1991, pp. 613-629.
Feun et al., "Arginine deprivation in cancer therapy", Current Opinion in Clinical Nutrition & Metabolic Care, Jan. 2015, vol. 18, Issue 1, pp. 78-82, doi: 10.1097/MCO.0000000000000122.

Forrest et al., "Immune Cell Regulation and Cardiovascular Effects of Sphingosine 1-Phosphate Receptor Agonists in Rodents Are Mediated via Distinct Receptor Subtypes", The Journal of Pharmacology and Experimental Therapeutics, Jan. 26, 2004, vol. 309, No. 2, pp. 758-768.
Fransson et al., "Design, Synthesis, and Antileukemic Activity of Stereochemically Defined Constrained Analogues of FTY720 (Gilenya)", ACS Medical Chemistry Letters, vol. 4, No. 10, 2013, pp. 969-973, DOI: 10.1021/ml4002425, first published Aug. 21, 2013.
Freier et al., "The ups and downs of nucleic acid duplex stability: Structure-stability studies on chemically-modified DNA:RNA duplexes", Nucleic Acids Research, vol. 25, Issue 22, Nov. 1, 1997, pp. 4429-4443, https://doi.org/10.1093/nar/25.22.4429.
Frieden et al., "Expanding the design horizon of antisense oligonucleotides with alpha-L-LNA", Nucleic Acids Research, vol. 31, Issue 21, Nov. 1, 2003, pp. 6365-6372, https://doi.org/10.1093/nar/gkg820.
Gauchot et al., "Asymmetric Aldol Reaction Catalyzed by the Anion of an Ionic Liquid", Journal of Organic Chemistry, 2012, vol. 77, pp. 4917-4923.
Golub et al., "Molecular Classification of Cancer: Class Discovery and Class Prediction by Gene Expression Monitoring", Science, vol. 286, Oct. 15, 1999, pp. 531-537.
Guenther et al., "Ceramide starves cells to death by downregulating nutrient transporter proteins", PNAS, Nov. 11, 2008. vol. 105, No. 45, pp. 17402-17407, https://doi.org/10.1073/pnas.0802781105.
Hammerschmidt et al., "CerS6-Derived Sphingolipids Interact with Mff and Promote Mitochondrial Fragmentation in Obesity", Cell, vol. 177, No. 6, May 30, 2019, pp. 1536-1552.e23.
Hanessian et al., "Constrained Azacyclic analogues of the immunomodulatory agent FTY720 as molecular probes for sphingosine 1-phosphate receptors", Bioorganic & Medicinal Chemistry Letters, vol. 17, Issue 2, Jan. 15, 2007, pp. 491-494.
Hanessian et al., "Synthesis of a Conformationally Constrained Analog of N-Acetylmuramyl Dipeptide (MDP)", Synlett, 1991, Issue 4, pp. 222-224, DOI: 10.1055/s-1991-20684.
Hu et al., "A facile new procedure for the deprotection of allyl ethers under mild conditions", Canadian Journal of Chemistry, 2000, vol. 78, No. 6, pp. 838-845, https://doi.org/10.1139/v00-073.
Huwiler et al., "Stimulation by extracellular ATP and UTP of the mitogen-activated protein kinase cascade and proliferation of rat renal mesangial cells", Br J Pharmacol, Dec. 1994, vol. 113, No. 4, pp. 1455-1463.
Jain et al., "Metabolite Profiling Identifies a Key Role for Glycine in Rapid Cancer Cell Proliferation", Science, May 25, 2012, vol. 336, Issue 6084, pp. 1040-1044, DOI: 10.1126/science.1218595.
Jefferies et al., "A selective PIKfyve inhibitor blocks PtdIns(3,5)P2 production and disrupts endomembrane transport and retroviral budding", EMBO reports, 2008, vol. 9, pp. 164-170, first published online Jan. 11, 2008, DOI 10.1038/sj.embor.7401155.
Kabanov et al., "A new class of antivirals: antisense oligonucleotides combined with a hydrophobic substituent effectively inhibit influenza virus reproduction and synthesis of virus-specific proteins in MDCK cells", FEBS Letters, vol. 259, Issue 2, Jan. 1, 1990, pp. 327-330.
Kanai et al., "The PX domains of p47phox and p40phox bind to lipid products of PI(3)K", Nature Cell Biology, vol. 3, Jul. 2001, pp. 675-678, doi:10.1038/35083070.
Kerr et al., "Inhibition of the PtdIns(5) kinase PIKfyve disrupts intracellular replication of *Salmonella*", The EMBO Journal, 2010, vol. 29, pp. 1331-1347, first published online Published online Mar. 18, 2010, DOI 10.1038/emboj.2010.28.
Kim et al., "Synthesis of (3R)-Carboxy Pyrrolidine (a β-Proline Analogue) and its Oligomer", Bioorganic & Medicinal Chemistry Letters, 2000, vol. 10, pp. 2417-2419.
Kim et al., "Targeting cancer metabolism by simultaneously disrupting parallel nutrient access pathways", The Journal of Clinical Investigation, vol. 126, No. 11, Nov. 1, 2016, pp. 4088-4102.
Kiuchi et al., "Synthesis and Immunosuppressive Activity of 2-Substituted 2-Aminopropane-1,3-diols and 2-Aminoethanols1,2", J. Med. Chem., 2000, vol. 43, No. 15, pp. 2946-2961, DOI: 10.1021/jm000173z, Published Online Jul. 11, 2000.

(56) References Cited

OTHER PUBLICATIONS

Kono et al., "Sphingosine-1-phosphate receptor 1 reporter mice reveal receptor activation sites in vivo", J Clin Invest., May 1, 2014, vol. 124, No. 5, pp. 2076-2086, Published online Mar. 25, 2014, doi: 10.1172/JCI71194.

Koshkin et al., "LNA (Locked Nucleic Acids): Synthesis of the adenine, cytosine, guanine, 5-methylcytosine, thymine and uracil bicyclonucleoside monomers, oligomerisation, and unprecedented nucleic acid recognition", Tetrahedron, vol. 54, Issue 14, Apr. 2, 1998, pp. 3607-3630.

Koyrakh et al., "The Heart Rate Decrease Caused by Acute RTY720 Administration is Mediated by the G Protein-Gated Potassium Channel IKACh", American Journal of Transplantation, 2005, vol. 5, pp. 529-536.

Kucznierz et al., "Tetrahydro-isoquioline-Based Factor Xa Inhibitors", J. Med. Chem., 1998, vol. 41, pp. 4983-4994.

Kumar et al., "Design, synthesis, biophysical and primer extension studies of novel acyclic butyl nucleic acid (BuNA)", Organic & Biomolecular Chemistry, Issue 35, Jul. 9, 2013, pp. 5853-5865.

Kumar et al., "The first analogues of LNA (Locked Nucleic Acids): Phosphorothioate-LNA and 2'-thio-LNA", Bioorganic & Medicinal Chemistry Letters, vol. 8, Issue 16, Aug. 18, 1998, pp. 2219-2222.

Lala et al., "Role of nitric oxide in tumor progression: Lessons from experimental tumors", Cancer and Metastasis Reviews (1998), 17(1), 91-106.

Lamontagne et al., Antagonism of Sphingosine-1-Phosphate Receptors by FTY720 Inhibits Angiogenesis and Tumor Vascularization, Cancer Res., Jan. 1, 2006, vol. 66, p. 221-231.

Lee et al., "FTY720: A Promising Agent for Treatment of Metastatic Hepatocellular Carcinoma", Clinical Cancer Research, Dec. 2005, vol. 11, Issue 23, pp. 8458-8466, DOI: 10.1158/1078-0432.CCR-05-0447.

Letsinger et al., "Cholesteryl-conjugated oligonucleotides: synthesis, properties, and activity as inhibitors of replication of human immunodeficiency virus in cell culture", PNAS, Sep. 1, 1989, vol. 86, No. 17, pp. 6553-6556.

Leumann, "DNA Analogues: From Supramolecular Principles to Biological Properties", Bioorganic & Medicinal Chemistry, vol. 10, Issue 4, Apr. 2002, pp. 841-854.

Lim et al., "(R)-FTY720 methyl ether is a specific sphingosine kinase 2 inhibitor: Effect on sphingosine kinase 2 expression in HEK 293 cells and actin rearrangement and survival of MCF-7 breast cancer cells", Cellular Signalling, vol. 23, Issue 10, Oct. 2011, pp. 1590-1595, https://doi.org/10.1016/j.cellsig.2011.05.010.

Maddocks et al., "Serine starvation induces stress and p53-dependentmetabolic remodelling in cancer cells", Nature, vol. 493, Jan. 24, 2013, pp. 542-546, first published Dec. 16, 2012, doi:10.1038/nature11743.

Maddry et al., "Carbohydrate Modifications in Antisense Research", Chapters 3-4, ACS Symposium Series 580, 1994, pp. 40-65.

Manoharan et al., "Chemical Modifications to Improve Uptake and Bioavailability of Antisense Oligonucleotides", Annals of the New York Academy of Sciences, vol. 660, Issue 1, Oct. 1992, pp. 306-309.

Manoharan et al., "Cholic acid-oligonucleotide conjugates for antisense applications", Bioorganic & Medicinal Chemistry Letters, vol. 4, Issue 8, Apr. 21, 1994, pp. 1053-1060.

Manoharan et al., "Introduction of a lipophilic thioether tether in the minor groove of nucleic acids for antisense applications", Bioorganic & Medicinal Chemistry Letters, vol. 3, Issue 12, Dec. 1993, pp. 2765-2770.

Manoharan et al., "Lipidic nucleic acids", Tetrahedron Letters, vol. 36, Issue 21, May 22, 1995, pp. 3651-3654.

Manoharan et al., "Oligonucleotide Conjugates: Alteration of the Pharmacokinetic Properties of Antisense Agents", Nucleosides and Nucleotide, vol. 14, Issue 3-5, 1995, pp. 969-973.

McCartney et al., "Phosphatidylinositol 3,5-bisphosphate: Low abundance, high significance", Prospects & Overviews, vol. 36, Issue 1, Jan. 2014, pp. 52-64, https://doi.org/10.1002/bies.201300012, First Published Oct. 28, 2013.

McCracken et al., "Nutrient transporters: the Achilles' heel of anabolism", Trends in Endocrinology & Metabolism, vol. 24, Issue 4, Apr. 2013, pp. 200-208, https://doi.org/10.1016/j.tem.2013.01.002.

Mishra et al., "Improved leishmanicidal effect of phosphorotioate antisense oligonucleotides by LDL-mediated delivery", Biochimica et Biophysica Acta (BBA)—Gene Structure and Expression, vol. 1264, Issue 2, Nov. 7, 1995, pp. 229-237.

Mitsumori et al., "Direct Asymmetric anti-Mannich-Type Reactions Catalyzed by a Designed Amino Acid", J. Am. Chem. Soc., 2006, vol. 128, pp. 1040-1041.

Najera et al., "Pyroglutamic acid: a versatile building block in asymmetric synthesis", Tetrahedron: Asymmetry, vol. 10, Issue 12, Jun. 18, 1999, pp. 2245-2303, https://doi.org/10.1016/S0957-4166(99)00213-X.

Neviani et al., "FTY720, a new alternative for treating blast crisis chromic myelogenous leukemia and Philadelphia chromosome-positive acute lymphocytic leukemia", The Journal of Clinical Investigation, Sep. 2007, vol. 117, No. 9, pp. 2408-2421.

Nishina et al., "Chimeric Antisense Oligonucleotide Conjugated to α-Tocopherol", Molecular Therapy—Nucleic Acids, vol. 4, 2015, e220, 10 pages, https://doi.org/10.1038/mtna.2014.72.

Nishina et al., "Efficient In Vivo Delivery of siRNA to the Liver by Conjugation of α-Tocopherol", Molecular Therapy, vol. 16, Issue 4, Apr. 2008, pp. 734-740, https://doi.org/10.1038/mt.2008.14.

Oberhauser et al., "Effective incorporation of 2'-O-methyl-oligoribonuclectides into liposomes and enhanced cell association through modification with thiocholesterol", Nucleic Acids Research, vol. 20, Issue 3, Feb. 11, 1992, pp. 533-538, https://doi.org/10.1093/nar/20.3.533.

Palm et al., "The Utilization of Extracellular Proteins as Nutrients Is Suppressed by mTORC1", Cell, vol. 162, Issue 2, Jul. 16, 2015, pp. 259-270, https://doi.org/10.1016/j.cell.2015.06.017.

Pate et al., "Wnt signaling directs a metabolic program of glycolysis and angiogenesis in colon cancer", The EMBO Journal, 2014, vol. 33, pp. 1454-1473, first published online Published online May 13, 2014, DOI 10.15252/embj.201488598.

Pchejetski et al., "FTY720 (Fingolimod) Sensitizes Prostate Cancer Cells to Radiotherapy by Inhibition of Sphingosine Kinase-1", Cancer Research, Nov. 2010, vol. 70, Issue 21, pp. 8651-8661, DOI: 10.1158/0008-5472.CAN-10-1388.

Perryman et al., "Effects of stereochemistry, saturation, and hydrocarbon chain length on the ability of synthetic constrained azacyclic sphingolipids to trigger nutrient transporter down-regulation, vacuolation, and cell death", Bioorganic & Medicinal Chemistry (2016), 24(18), pp. 4390-4397.

Pieters et al., "L-Asparaginase treatment in acute lymphoblastic leukemia", Cancer, vol. 117, Issue 2, Jan. 15, 2011, pp. 238-249, First published Sep. 7, 2010, https://doi.org/10.1002/cncr.25489.

Reed, "Bcl-2-family proteins and hematologic malignancies: history and future prospects", Blood, Apr. 1, 2008, vol. 111, No. 7, pp. 3322-3330.

Romero Rosales et al., "Sphingolipid-based drugs selectively kill cancer cells by down-regulating nutrient transporter proteins", Biochem. J., Jul. 18, 2011, vol. 439, pp. 299-311.

Rosen et al., "Design, Synthesis, and Properties of (4S)-7-(4-Amino-2-substituted-pyrrolidin-1-yl)quinolone-3-carboxulic Acids", J. Med. Chem., 1988, vol. 31, pp. 1598-1611.

Rutherford et al., "The mammalian phosphatidylinositol 3-phosphate 5-kinase (PIKfyve) regulates endosome-to-TGN retrograde transport", Journal of Cell Science, vol. 119, Issue 19, 2006, pp. 3944-3957, http://dx.doi.org/10.1242/jcs.03153.

Saison-Behmoaras et al., "Short modified antisense oligonucleotides directed against Ha-ras point mutation induce selective cleavage of the mRNA and inhibit T24 cells proliferation", The EMBO Journal, vol. 10, Issue 5, May 1991, pp. 1111-1118.

Sanghvi, "Heterocyclic Base Modifications in Nucleic Acids and Their Applications in Antisense Oligonucleotides", Chapter 15, Antisense Research and Applications, CRC Press, 1993, p. 273-288.

Sanna et al., "Sphingosine 1-Phosphate (S1P) Receptor Subtypes S1P1 and S1P3, Respectively, Regulate Lymphocyte Recirculation and Heart Rate", The Journal of Biological Chemistry, Apr. 2, 2004, vol. 279, No. 14, pp. 13839-13848.

(56) References Cited

OTHER PUBLICATIONS

Schneeberger et al., "Mitofusin 2 in POMC Neurons Connects ER Stress with Leptin Resistance and Energy Imbalance", Cell, vol. 155, No. 1, Sep. 26, 2013, pp. 172-187.
Schwarzenböck et al., "Choline PET and PET/CT in Primary Diagnosis and Staging of Prostate Cancer", Theranostics, 2012, vol. 2, No. 3, pp. 318-330, published online Mar. 15, 2012, doi: 10.7150/thno.4008.
Shea et al., "Synthesis, hybridization properties and antiviral activity of lipid-oligodeoxynucleotide conjugates", Nucleic Acids Research, vol. 18, Issue 13, Jul. 11, 1990, pp. 3777-3783, https://doi.org/10.1093/nar/18.13.3777.
Singh et al., "LNA (locked nucleic acids): synthesis and high-affinity nucleic acid recognition", Chemical Communications, 1998, Issue 4, pp. 455-456.
Singh et al., "Synthesis of 2'-Amino-LNA: A Novel Conformationally Restricted High-Affinity Oligonucleotide Analogue with a Handle", J. Org. Chem., 1998, vol. 63, No. 26, pp. 10035-10039, DOI: 10.1021/jo9814445, Online Publication Date Nov. 26, 1998.
Srivastava et al., "Five- and Six-Membered Conformationally Locked 2',4'-Carbocyclic ribo-Thymidines: Synthesis, Structure, and Biochemical Studies", J. Am. Chem. Soc., 2007, vol. 129, No. 26, pp. 8362-8379, DOI: 10.1021/ja071106y, Online Publication Date Jun. 7, 2007.
Stringari et al., "In Vivo Single-Cell Detection of Metabolic Oscillations in Stem Cells", Cell Reports, vol. 10, Issue 1, Jan. 6, 2015, pp. 1-7, https://doi.org/10.1016/j.celrep.2014.12.007.
Stringari et al., "Metabolic trajectory of cellular differentiation in small intestine by Phasor Fluorescence Lifetime Microscopy of NADH", Scientific Reports, vol. 2, Article 568, 2012, 9 pages, first published Aug. 10, 2012, doi:10.1038/srep00568.
Stringari et al., "Phasor approach to fluorescence lifetime microscopy distinguishes different metabolic states of germ cells in a live tissue", PNAS, Aug. 16, 2011, vol. 108, No. 33, pp. 13582-13587, https://doi.org/10.1073/pnas.1108161108.
Suhalim et al., "Characterization of Cholesterol Crystals in Atherosclerotic Plaques Using Stimulated Raman Scattering and Second-Harmonic Generation Microscopy", Biophysical Journal, vol. 102, Issue 8, Apr. 18, 2012, pp. 1988-1995, https://doi.org/10.1016/j.bpj.2012.03.016.
Sun et al., "A Photoreactive Analogue of the Immunosuppressant FTY720", J. Org. Chem., 2006, vol. 71, No. 5, pp. 2200-2202, DOI: 10.1021/jo0526237, Publication Online Feb. 9, 2006.
Svinarchuk et al., "Inhibition of HIV proliferation in MT-4 cells by antisense oligonucleotide conjugated to lipophilic groups", Biochimie, vol. 75, Issues 1-2, 1993, pp. 49-54.
Tigyi et al., "FTY720 S-ene-phosphonate is a novel pan-antagonist of the S1P receptors that inhibits lymphocyte egress", FASEB Journal, Apr. 2010, vol. 24, No. 1, Supplement, 2 pgs. (Abstract).
Toumi et al., "Total Synthesis of Paliurine F", Angew. Chem. Int. Ed., 2007, vol. 46, pp. 572-575.
Tuveson et al., "Endogenous oncogenic K-rasG12D stimulates proliferation and widespread neoplastic and developmental defects", Cancer Cell, vol. 5, Issue 4, Apr. 2004, pp. 375-387, https://doi.org/10.1016/S1535-6108(04)00085-6.
Valentine et al., "(S)-FTY720-Vinylphosphonate, an analogue of the immunosuppressive agent FTY720, is a pan-antagonist of sphingosine 1-phosphate GPCR signaling and inhibits autotaxin activity", Cellular Signalling, vol. 22, Issue 10, Oct. 2010, pp. 1543-1553, https://doi.org/10.1016/j.cellsig.2010.05.023.
Van Huis et al., "Exploration of 4,4-disubstituted pyrrolidine-1,2-dicarboxamides as potent, orally active Factor Xa inhibitors with extended duration of action", Bioorganic & Medicinal Chemistry, vol. 17, Issue 6, Mar. 15, 2009, pp. 2501-2511, https://doi.org/10.1016/j.bmc.2009.01.063.
Vicinanza, M. et al., "PI(5)P Regulates Autophagosome Biogenesis", Molecular Cell, vol. 57, Issue 2, Jan. 22, 2015, pp. 219-234, https://doi.org/10.1016/j.molcel.2014.12.007.
Wang et al., "Up-regulation of lysosomal TRPML1 channels is essential for lysosomal adaptation to nutrient starvation", PNAS, Mar. 17, 2015, vol. 112, No. 11, pp. E1373-E1381; published online Mar. 2, 2015, https://doi.org/10.1073/pnas.1419669112.
Watanabe et al., "Design and Stereoselective Synthesis of Four Peptide Nucleic Acid Monomers with Cyclic Structures in Backbone", Journal of Heterocyclic Chemistry, 2011, vol. 48, pp. 1132-1139.
Watts et al., "Structure-Reactivity Studies of Simple 4-Hydroxyprolinamide Organocatalysts in the Asymmetric Michael Addition Reaction of Aldehydes to Nitroolefins", Adv. Synth. Catal., 2012, vol. 354, pp. 1035-1042.
Welsch et al., "Genetic, Biochemical, and Transcriptional Responses of *Saccharomyces cerevisiae* to the Novel Immunomodulator FTY720 Largely Mimic Those of the Natural Sphingolipid Phytosphingosine", The Journal of Biological Chemistry, Aug. 27, 2004, vol. 279, pp. 36720-36731, First Published on Jun. 9, 2004, doi: 10.1074/jbc.M406179200.
White, E., "Exploiting the bad eating habits of Ras-driven cancers", Genes & Dev., 2013, vol. 27, pp. 2065-2071, doi: 10.1101/gad.228122.113.
Woo et al., "Asymmetric synthesis from α-amino acids; some reactions of (S)-pyroglutamate", Tetrahedron Letters, vol. 32, Issue 47, Nov. 18, 1991, pp. 6949-6952.
Wu et al., "Lipid metabolism in prostate cancer", Am J Clin Exp Urol., 2014, vol. 2, No. 2, pp. 111-120, Published Online Jul. 15, 2014.
Yan et al., "Design and Synthesis of Conformationally Constrained 3-(N-Alkylamino)Propylphosphonic Acids as Potent Agonists of Sphingosine-1-Phosphate (S1p) Receptors", Bioorganic & Medicinal Chemistry Letters, 2004, Letters 14, 4861-4866.
Zhang et al., "Modulation of synaptic function by VAC14, a protein that regulates the phosphoinositides PI(3,5)p2 and PI(5)P", The EMBO Journal, 2012, vol. 31, pp. 3442-3456, Published online Jul. 27, 2012, DOI 10.1038/emboj.2012.200.
Zhang et al., "Rationally designed 4-phenoxy substituted prolinamide phenols organocatalyst for the direct aldol reaction in water", Tetrahedron Letters, 2009, vol. 50, pp. 1173-1176.
Zhou et al., "Fine Tuning of Electrostatics around the Internucleotidic Phosphate through Incorporation of Modified 2',4'-Carbocyclic-LNAs and -ENAs Leads to Significant Modulation of Antisense Properties", J. Org. Chem., 2009, vol. 74, No. 1, pp. 118-134, DOI: 10.1021/jo8016742, Online Publication Date Dec. 4, 2008.
Zhu et al., "Asymmetric Synthesis of Conformationally Constrained Fingolimod Analogues—Discovery of an Orally Active Sphingosine 1-Phosphate Receptor Type-1 Agonist and Receptor Type-3 Antagonist", J. Med. Chem., vol. 50, No. 25, 2007, pp. 6428-6435, DOI: 10.1021/jm7010172, published online Nov. 10, 2007.
Zolov et al., "In vivo, Pikfyve generates PI(3,5)P2, which serves as both a signaling lipid and the major precursor for PI5P", PNAS, Oct. 23, 2012, vol. 109, No. 43, pp. 17472-17477, https://doi.org/10.1073/pnas.1203106109.
Extended European Search Report for European Application No. 19819948.1, Search completed Jan. 5, 2022, dated Jan. 19, 2022, 8 Pgs.
Chung et al., "Sphingolipids Signal Heat Stress-induced Ubiquitindependent Proteolysis", The Journal of Biological Chemistry, vol. 275, No. 23, Apr. 10, 2000, pp. 17229-17232.
Grisar et al., "(2-Piperidine)- and (2-Pyrrolidine)ethanones and -ethanols as Inhibitors of Blood Platelet Aggregation", Journal of Medicinal Chemistry, Jan. 1, 1976, vol. 19, No. 10, pp. 1195-1201.
Gutierrez et al., "Phenothiazines induce PP2A-mediated apoptosis in T cell acute lymphoblastic leukemia", The Journal of Clinical Investigation, vol. 124, No. 2, Feb. 2014, pp. 644-655.
Hait et al., "The phosphorylated prodrug FTY720 is a histone deacetylase inhibitor that reactivates ERa expression and enhances hormonal therapy for breast cancer", Oncogenesis, vol. 4, Jun. 8, 2015, 11 pgs.
Karver et al., "Synthesis and Evaluation of a Series of 1,2,4,5-Tetrazines for Bioorthogonal Conjugation", Bioconjugate Chemistry, vol. 22, No. 11, Sep. 28, 2011, pp. 2263-2270, https://doi.org/10.1021/bc200295y.
Kastrinsky et al., "Reengineered tricyclic anti-cancer agents", Bioorganic & Medicinal Chemistry, vol. 23, No. 19, Oct. 1, 2015, pp. 6528-6534.

(56) References Cited

OTHER PUBLICATIONS

Kubiniok et al., "Dynamic Phosphoproteomics Uncovers Signaling Pathways Modulated by Anti-oncogenic Sphingolipid Analogs", Molecular & Cellular Proteomics, vol. 18, No. 3, Mar. 2019, Online Publication: Nov. 27, 2018, pp. 408-422.

Mukhopadhyay et al., "Direct interaction between the inhibitor 2 and ceramide via sphingolipid-protein binding is involved in the regulation of protein phosphatase 2A activity and signaling", The FASEB Journal, vol. 23, No. 3, Mar. 2009, pp. 751-763, doi: 10.1096/fj.08-120550.

Murata et al., "Interaction of sphingosine 1-phosphate with plasma components, including lipoproteins, regulates the lipid receptor-mediated actions", Biochemical Journal, vol. 352, No. 3, Dec. 2000, pp. 809-815.

Saddoughi et al., "Sphingosine analogue drug FTY720 targets I2PP2A/SET and mediates lung tumour suppression via activation of PP2A-RIPK1-dependent necroptosis", EMBO Molecular Medicine, vol. 5, No. 1, Nov. 25, 2012, pp. 105-121.

Sangodkar et al., "Activation of tumor suppressor protein PP2A inhibits KRAS-driven tumor growth", The Journal of Clinical Investigation, vol. 127, No. 6, Jun. 1, 2017, Electronic Publication: May 15, 2017, pp. 2081-2090, doi: 10.1172/JCI89548.

Seckute et al., "Expanding room for tetrazine ligations in the in vivo chemistry toolbox", Current Opinion in Chemical Biology, vol. 17, No. 5, Oct. 2013, pp. 761-767, https://doi.org/10.1016/j.cbpa.2013.08.004.

Skrzypek et al., "Inhibition of Amino Acid Transport by Sphingoid Long Chain Bases in *Saccharomyces cerevisiae*", The Journal of Biological Chemistry, vol. 273, No. 5, Jan. 30, 1998, pp. 2829-2834.

Zhang et al., "FTY720 for cancer therapy (Review)", Oncology Reports, vol. 30, No. 6, Oct. 1, 2013, pp. 2571-2578, DOI: 10.3892/or.2013.2765.

International Preliminary Report on Patentability for International Application PCT/US2020/052742, Report dated Mar. 15, 2022, dated Apr. 7, 2022, 6 pgs.

International Preliminary Report on Patentability for International Application PCT/US2020/060513, Report dated May 17, 2022, dated May 27, 2022, 8 pgs.

International Search Report and Written Opinion for International Application No. PCT/US2021/073013, Search completed Mar. 29, 2022, dated Apr. 11, 2022, 14 pgs.

International Search Report and Written Opinion for International Application No. PCT/US2021/072140, Search completed Dec. 17, 2021, dated Jan. 26, 2022, 13 pgs.

Beider et al., "The Sphingosine-1-Phosphate Modulator FTY720 Targets Multiple Myeloma via the CXCR4/CXCL12 Pathway", Clinical Cancer Research, Oct. 3, 2016, vol. 23, Issue 7, pp. 1733-1747.

Cai et al., "PIKfyve, a Class III PI Kinase, Is the Target of the Small Molecule IL-12/IL-23 Inhibitor Apilimod and a Player in Toll-like Receptor Signaling", Chemistry & Biology, vol. 20, No. 7, Jul. 25, 2013, pp. 912-921.

Chaudhry et al., "A pipeline for multidimensional confocal analysis of mitochondrial morphology, function, and dynamics in pancreatic β-cells", American Journal of Physiology-Endocrinology and Metabolism, vol. 318, No. 2, Feb. 1, 2020, pp. E87-E101.

Chaurasia et al., "Targeting a ceramide double bond improves insulin resistance and hepatic steatosis", Science, vol. 365, No. 6451, Jul. 26, 2019, pp. 386-392.

Chavez et al., "A Ceramide-Centric View of Insulin Resistance", Cell Metabolism, vol. 15, No. 5, May 2, 2012, pp. 585-594.

Chen et al., "Control of hyperglycemia in male mice by leflunomide mechanisms of action", Journal of Endocrinology, vol. 237, No. 1, Apr. 2018, pp. 43-58.

Choi et al., "Sphingolipids in High Fat Diet and Obesity-Related Diseases", Mediators of Inflammation, vol. 2015, No. 520618, Nov. 16, 2015, 12 pgs.

Filippi et al., "Dynamin-Related Protein 1-Dependent Mitochondrial Fission Changes in the Dorsal Vagal Complex Regulate Insulin Action", Cell Reports, vol. 18, No. 10, Mar. 7, 2017, pp. 2301-2309.

Frangioudakis et al., "Saturated- and n-6 Polyunsaturated-Fat Diets Each Induce Ceramide Accumulation in Mouse Skeletal Muscle: Reversal and Improvement of Glucose Tolerance by Lipid Metabolism Inhibitors", Endocrinology, vol. 151, No. 9, Sep. 1, 2010, pp. 4187-4196, https://doi.org/10.1210/en.2010-0250.

Galloway et al., "Decreasing mitochondrial fission alleviates hepatic steatosis in a murine model of nonalcoholic fatty liver disease", American Journal of Physiology-Gastrointestinal and Liver Physiology, vol. 307, No. 6, Sep. 2014, pp. G632-G641.

Galloway et al., "Mitochondrial Morphology in Metabolic Diseases", Antioxidants & Redox Signaling, vol. 19, No. 4, Jun. 29, 2013, pp. 415-430.

Guenther et al., "Loss of TSC2 confers resistance to ceramide and nutrient deprivation", Oncogene, vol. 33, No. 14, Apr. 22, 2013, pp. 1776-1787.

Holland et al., "Inhibition of Ceramide Synthesis Ameliorates Glucocorticoid-, Saturated-Fat-, and Obesity-Induced Insulin Resistance", Cell Metabolism, vol. 5, No. 3, Mar. 7, 2007, pp. 167-179.

Jheng et al., "Mitochondrial Fission Contributes to Mitochondrial Dysfunction and Insulin Resistance in Skeletal Muscle", Molecular and Cellular Biology, vol. 32, No. 2, Jan. 2012, pp. 309-319.

Kasumov et al., "Quantification of ceramide species in biological samples by liquid chromatography electrospray ionization tandem mass spectrometry", Analytical Biochemistry, vol. 401, No. 1, Jun. 1, 2010, pp. 154-161.

Li et al., "Reducing Plasma Membrane Sphingomyelin Increases Insulin Sensitivity", Molecular and Cellular Biology, vol. 31, No. 20, Oct. 2011, pp. 4205-4218.

Mancini et al., "Mitofusin 2 in Mature Adipocytes Controls Adiposity and Body Weight", Cell Reports, vol. 26, No. 11, Mar. 12, 2019, pp. 2849-2858.e4.

Murakami et al., "Improved High-Fat Diet-Induced Glucose Intolerance by an Oral Administration of Phytosphingosine", Bioscience, Biotechnology, and Biochemistry, vol. 77, No. 1, Jan. 23, 2013, pp. 194-197, https://doi.org/10.1271/bbb.120644.

Raichur et al., "The role of C16:0 ceramide in the development of obesity and type 2 diabetes: CerS6 inhibition as a novel therapeutic approach", Molecular Metabolism, vol. 21, Mar. 2019, pp. 36-50.

Santoro et al., "DRP1 Suppresses Leptin and Glucose Sensing of POMC Neurons", Cell Metabolism, vol. 25, No. 3, Mar. 7, 2017, pp. 647-660.

Schrepfer et al., "Mitofusins, from Mitochondria to Metabolism", Molecular Cell, vol. 61, No. 5, Mar. 3, 2016, pp. 683-694.

Sebastian et al., "Mitofusin 2 (Mfn2) links mitochondrial and endoplasmic Yeticulum function with insulin signaling and is essential for normal glucose homeostasis", Proceedings of the National Academy of Sciences, vol. 109, No. 14, Apr. 3, 2012, pp. 5523-5528.

Serasinghe et al., "Mitochondrial Division Is Requisite to RAS-Induced Transformation and Targeted by Oncogenic MAPK Pathway Inhibitors", Molecular Cell, vol. 57, No. 3, Feb. 5, 2015, pp. 521-536.

Smith et al., "Mitochondrial fission mediates ceramide-induced metabolic disruption in skeletal muscle", Biochemical Journal, vol. 456, No. 3, Dec. 15, 2013, pp. 427-439.

Summers et al., "Metabolic Messengers: ceramides", Nature Metabolism, vol. 1, No. 11, Oct. 24, 2019, pp. 1051-1058.

Turner et al., "A selective inhibitor of ceramide synthase 1 reveals a novel Yole in fat metabolism", Nature Communications, vol. 9, No. 3165, Aug. 21, 2018, 14 pgs.

Turner et al., "Distinct patterns of tissue-specific lipid accumulation during the induction of insulin resistance in mice by high-fat feeding", Diabetologia, vol. 56, Apr. 26, 2013, pp. 1638-1648.

Turpin et al., "Obesity-Induced CerS6-Dependent C16:0 Ceramide Production Promotes Weight Gain and Glucose Intolerance", Cell Metabolism, vol. 20, No. 4, Oct. 7, 2014, pp. 678-686.

Turpin-Nolan et al., "CerS1-Derived C18:0 Ceramide in Skeletal Muscle Promotes Obesity-Induced Insulin Resistance", Cell Reports, vol. 26, No. 1, Jan. 2, 2019, pp. 1-10.e7.

Ussher et al., "Inhibition of De Novo Ceramide Synthesis Reverses Diet-Induced Insulin Resistance and Enhances Whole-Body Oxygen Consumption", Diabetes, vol. 59, No. 10, Oct. 1, 2010, pp. 2453-2464.

(56) References Cited

OTHER PUBLICATIONS

Wang et al., "Disruption of mitochondrial fission in the liver protects mice from diet-induced obesity and metabolic deterioration", Diabetologia, vol. 58, No. 10, Oct. 2015, pp. 2371-2380.

Yu et al., "Mitochondrial fusion exploits a therapeutic vulnerability of pancreatic cancer", JCI Insight, vol. 4, No. 16, e126915, Aug. 22, 2019, 16 pgs.

Zhao et al., "Partial Leptin Reduction as an Insulin Sensitization and Weight Loss Strategy", Cell Metabolism, vol. 30, No. 4, Oct. 1, 2019, pp. 706-719.e6.

Generic constrained
C-aryl analogue A

Antileukemic O-arylmethyl
(2R, 4S) and (2S, 4R)
pyrrolidine analogues B 20  21

Untreated

Treated

Key aa – amino acid
C – carbohydrate
g – glucose
l – lipid
LDL – low density lipoprotein
n – nucleotide
NA – Nucleic Acid
O – Organelle
P – Protein
X – Blocked Note: compound # is without hundreds place; thus, compound 104 = 4 and compound 125 = 25

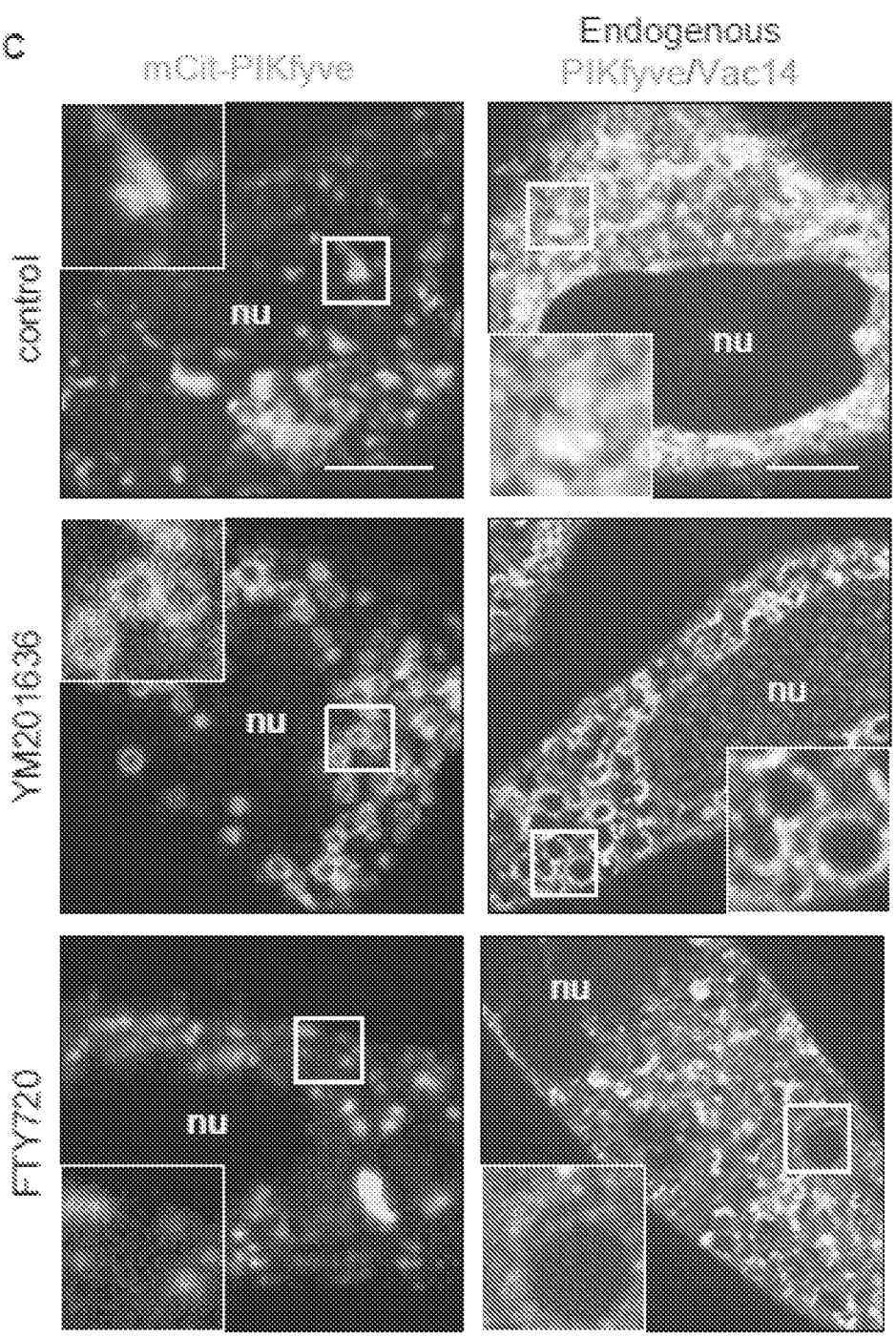

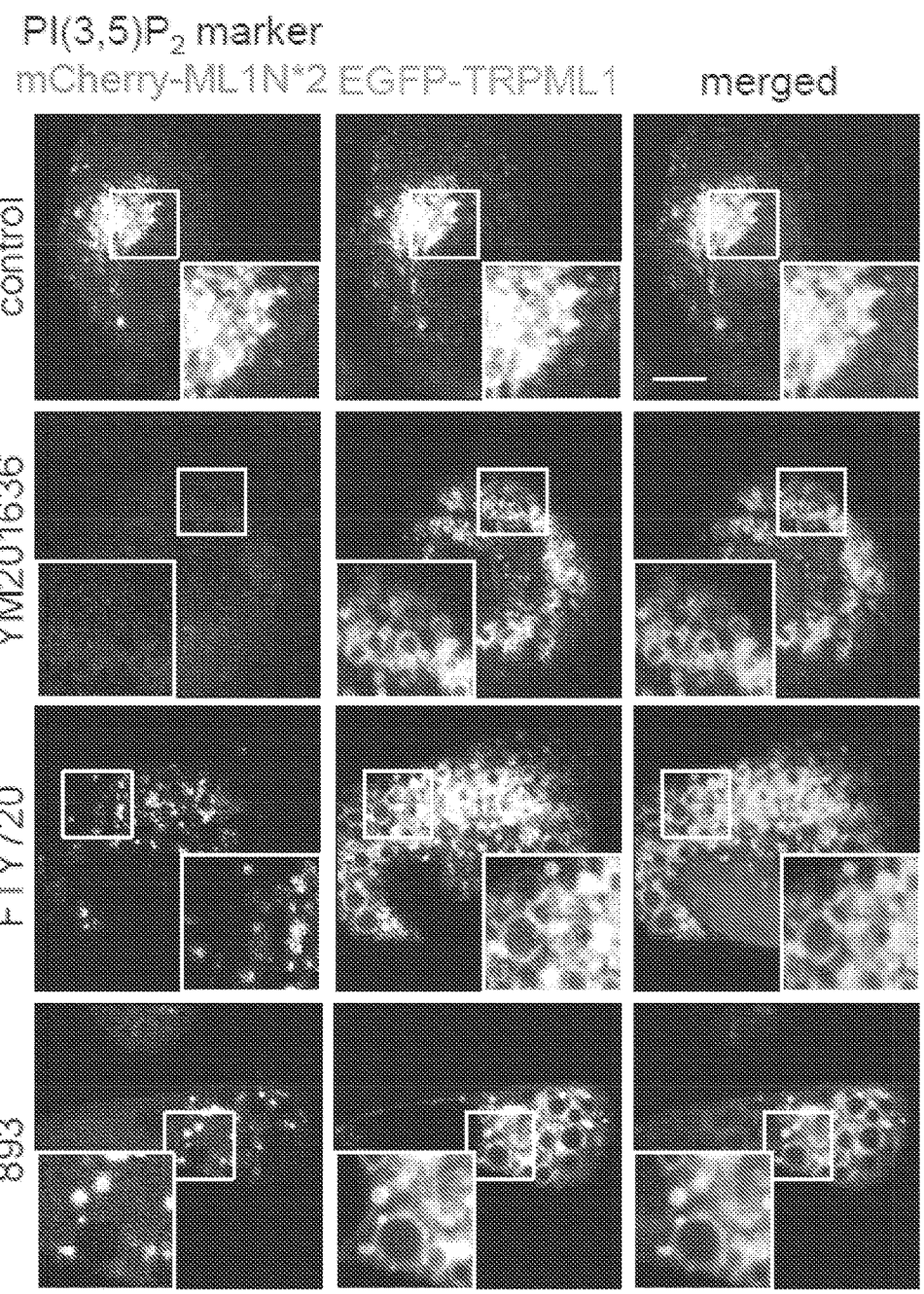

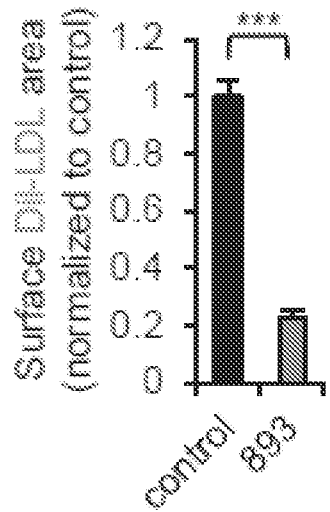

FIG. 65H
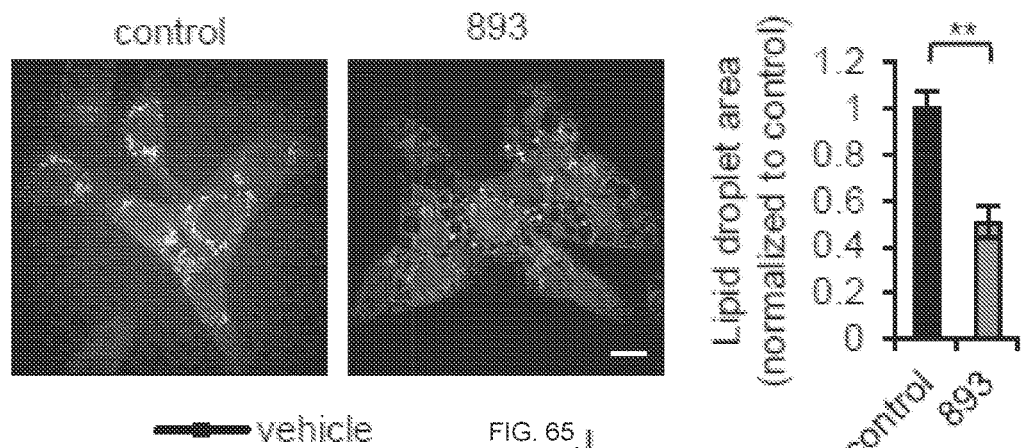
FIG. 65I
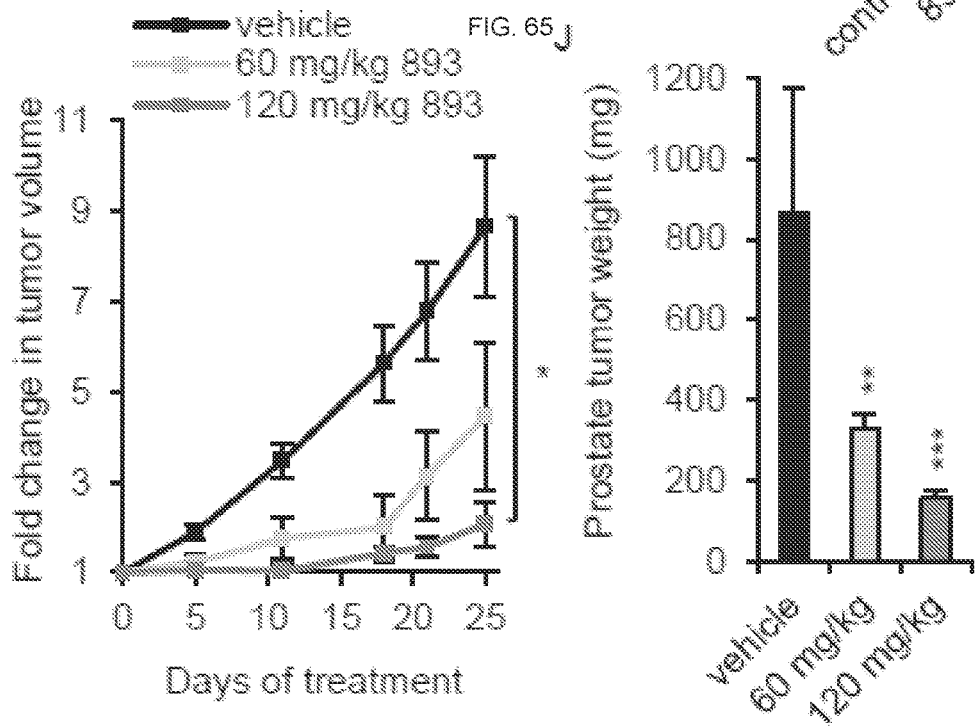
FIG. 65J

SYNTHETIC SPHINGOLIPID-LIKE MOLECULES, DRUGS, METHODS OF THEIR SYNTHESIS AND METHODS OF TREATMENT

CROSS REFERENCE TO RELATED APPLICATIONS

This application is a continuation of U.S. patent application Ser. No. 15/760,199, entitled "Synthetic Sphingolipid-Like Molecules, Drugs, Methods of Their Synthesis and Methods of Treatment" to Edinger et al., filed Mar. 14, 2018, which is a national stage of PCT Patent Application No. PCT/US2016/053815, entitled "Synthetic Sphingolipid-Like Molecules, Drugs, Methods of Their Synthesis and Methods of Treatment" to Edinger et al., filed Sep. 26, 2016, which claims priority to U.S. Provisional Patent Application No. 62/232,377, entitled "Sphingolipid Drugs Active Against Solid Tumors" to Edinger et al., filed Sep. 24, 2015, each of which is herein incorporated by reference in its entirety.

STATEMENT REGARDING FEDERALLY SPONSORED RESEARCH OR DEVELOPMENT

This invention was made with Governmental support under Grant Nos. T32CA009054 awarded by the National Cancer Institute, W81XWH-11-1-0535 awarded by the Department of Defense, and R01 GM089919 and R21 CA178230 awarded by the National Institutes of Health. The government has certain rights in the invention.

FIELD OF THE INVENTION

The invention is generally directed to synthetic sphingolipid-like molecules, medicaments formed from these molecules, methods of synthesis of these molecules, and methods for the treatment of disorders or neoplasms using such therapeutics.

BACKGROUND

Sphingolipids are a class of molecules that are fatty acid derivatives of sphingosine. These molecules are typically found in the membranes of cells and can trigger many different signaling cascades. One common sphingolipid is sphingosine, which can be phosphorylated to form sphingosine-1 phosphate (S1P), the chemical structure of which is provided in FIG. 1.

S1P receptors are found on the surface of many cell types. S1P receptors are activated by S1P binding. There are five types of S1P receptors, each of which triggers distinct signal transduction pathways. S1P binding to S1P receptors may activate different cellular functions, including cell proliferation and differentiation, cell survival, cell invasion, lymphocyte trafficking, and cell migration.

FTY720, the chemical structure of which is provided in FIG. 2, is an immunosuppressant prodrug that functions by stimulating S1P receptors. In its active, phosphorylated state, FTY720 binds four of the five S1P receptors. The binding of FTY720-phosphate to S1P1 causes receptor activation followed by persistent down-regulation of the receptor and subsequent sequestering of lymphocytes in secondary lymphoid organs. Currently, FTY720 is marketed to treat relapsing-remitting multiple sclerosis (MS). Previous publications describe broad classes of FTY720 analogs for use in selectively binding different S1P receptor isoforms.

SUMMARY OF THE INVENTION

In many embodiments the invention is directed to small molecules in the nature of azacyclic constrained analogs of sphingolipid-like molecules, methods of synthesis, medicaments formed from these small molecules, and methods for the treatment of disorders using such therapeutics are disclosed.

In some embodiments, aspects of the invention are directed to compounds having the following molecular formula:

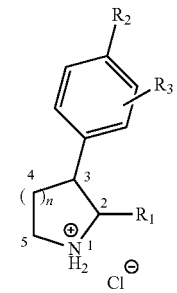

wherein:
  $R_1$ is an optional functional group selected from an alkyl chain, $(CH_2)_nOH$, (CHOH-alkyl, CHOH-alkyne, $(CH_2)_nOMe$, $(CH_2)_nPO(OH)_2$ and esters thereof, $CH=CHPO(OH)_2$ and esters thereof, $(CH_2CH_2)_nPO(OH)_2$ and esters thereof, and $(CH_2)_nOPO(OH)_2$ and esters thereof, $(CH_2)_nPO_3$ and esters thereof, wherein Me is an alkyl, alkene or alkyne;
  $R_2$ is an aliphatic chain $(C_6$-$C_{14})$;
  R3 is a mono-, di-, tri- or tetra-aromatic substituent comprising hydrogen, halogen, alkyl, alkoxy, azide $(N_3)$, ether, $NO_2$, or cyanide (CN);
  n is an independently selected whole integer selected from 1 to 3; and
  wherein the phenyl can be moved between positions 3 to 5 about the heterocycle amine.

In other embodiments, the compound has the specific molecular formula:

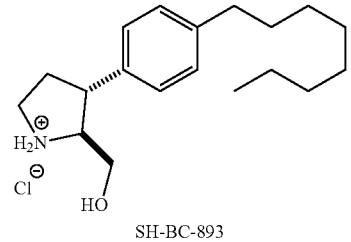

SH-BC-893

In even other embodiments, the compound's stereochemistry is (2R, 3R), (2R, 3S), (2R, 4R), (2R, 4S), (2S, 3R), (2S, 3S), (2S, 4R), or (2S, 4S).

In more embodiments, the compound is capable of having a cytotoxic effect on human neoplastic cells as defined by a reduction of viability percentage of the human neoplastic cells.

In even more embodiments, the cytotoxic effect is achieved with an appropriate local 50% inhibitory concentration ($IC_{50}$), as defined by the concentration of the compound that reduces the viability percentage of the human neoplastic cells equal to 50%.

In yet, even more embodiments, the human neoplastic cells are derived from colon cancer, prostate cancer, lung cancer, pancreatic cancer, breast cancer, or leukemia.

In still yet, even more embodiments, the human neoplastic cells are characterized as slow-growing, fast-growing, aggressive, malignant, Ras-positive, PTEN-negative, benign, metastatic, nodular, or autochthonous.

In many other embodiments, the compound is capable of exerting bioenergetic stress on human cells as characterized by a decrease of at least one nutrient available to the human cells, and wherein the at least one nutrient is any one of glucose, amino acids, nucleotides, or lipids.

In yet, many other embodiments, the bioenergetic stress results in greater percentage of cell death in the neoplastic cells relative to non-neoplastic cells.

In many more embodiments, the compound is capable of inhibiting an increase in tumor diameter, an increase in tumor bioluminescence, an increase in tumor volume, an increase in tumor mass, or an increase in neoplastic cell proliferation rate.

In yet, many more embodiments, the compound is not capable of activating sphinogosine-1 phosphate (S1P) receptors 1, 2, 3, 4, and 5 in human cells.

In some embodiments, aspects of the invention are directed to medicaments for the treatment of a human disorder comprising:

a pharmaceutical formulation containing a therapeutically effective amount of one or more azacyclic constrained sphingolipid-like small molecule compounds comprising:

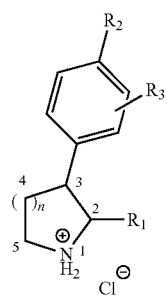

wherein:
$R_1$ is an optional functional group selected from an alkyl chain, $(CH_2)_nOH$, (CHOH-alkyl, CHOH-alkyne, $(CH_2)_nOMe$, $(CH_2)_nPO(OH)_2$ and esters thereof, $CH=CHPO(OH)_2$ and esters thereof, $(CH_2CH_2)_nPO(OH)_2$ and esters thereof, and $(CH_2)_nOPO(OH)_2$ and esters thereof, $(CH_2)_nPO_3$ and esters thereof, wherein Me is an alkyl, alkene or alkyne;
$R_2$ is an aliphatic chain ($C_6$-$C_{14}$);
$R_3$ is a mono-, di-, tri- or tetra-aromatic substituent comprising hydrogen, halogen, alkyl, alkoxy, azide ($N_3$), ether, $NO_2$, or cyanide (CN);
n is an independently selected whole integer selected from 1 to 3; and
wherein the phenyl can be moved between positions 3 to 5 about the heterocycle amine.

In other embodiments, the azacyclic constrained sphingolipid-like small molecule compounds includes:

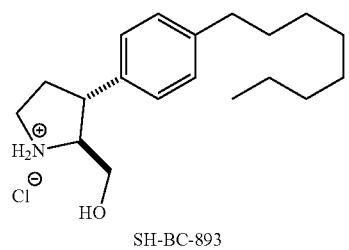

SH-BC-893

In even other embodiments, the human disorder is colon cancer, prostate cancer, lung cancer, pancreatic cancer, breast cancer, leukemia, or obesity.

In even more embodiments, the one or more azacyclic constrained sphingolipid-like small molecule compounds is capable of having a cytotoxic effect on human neoplastic cells, as defined by a reduction of viability percentage of the human neoplastic cells.

In yet, even more embodiments, the cytotoxic effect is achieved with an appropriate local 50% inhibitory concentration ($IC_{50}$), as defined by the concentration of the one or more azacyclic constrained sphingolipid-like small molecule compounds that reduces the viability percentage of the human neoplastic cells equal to 50%.

In still yet, even more embodiments, the human disorder is characterized as slow-growing, fast-growing, aggressive, malignant, Ras-positive, PTEN-negative, benign, metastatic, nodular, or autochthonous.

In many other embodiments, the one or more azacyclic constrained sphingolipid-like small molecule compounds are capable of exerting bioenergetic stress on human cells, as characterized by a decrease of at least one nutrient available to the human cells, and wherein the at least one nutrient is glucose, amino acids, nucleotides, or lipids.

In yet, many other embodiments, the bioenergetic stress results in greater percentage of cell death in the neoplastic cells relative to the non-neoplastic cells.

In still yet, many other embodiments, the pharmaceutical formulation is capable of inhibiting an increase in tumor diameter, an increase in tumor bioluminescence, an increase in tumor volume, an increase in tumor mass, or an increase in neoplastic cell proliferation rate.

In many more embodiments, the one or more azacyclic constrained sphingolipid-like small molecule compounds are not capable of activating sphinogosine-1 phosphate (S1P) receptors 1, 2, 3, 4, and 5.

In yet, many more embodiments, the one or more azacyclic constrained sphingolipid-like small molecule compounds are not capable of inducing bradycardia at the effective dose in a human subject when taken into the body of the human subject.

In still yet, many more embodiments, the medicament is combined at least one FDA-approved compound for the treatment of a neoplasm.

In other particular embodiments, the at least one FDA-approved compound is methotrexate, gemcitabine, tamoxifen, taxol, docetaxel, or enzalutamide.

In some embodiments, aspects of the invention are directed to method of treatment of a human disorder comprising:

administering a pharmaceutical formulation to a human subject, the pharmaceutical formulation containing a therapeutically effective amount of one or more azacyclic constrained sphingolipid-like small molecule compounds comprising:

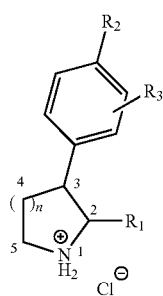

wherein:

R₁ is an optional functional group selected from an alkyl chain, (CH2)nOH, (CHOH-alkyl, CHOH-alkyne, (CH2)nOMe, (CH2)nPO(OH)2 and esters thereof, CH=CHPO(OH)2 and esters thereof, (CH2CH2)nPO(OH)2 and esters thereof, and (CH2)nOPO(OH)2 and esters thereof, (CH2)nPO3 and esters thereof, wherein Me is an alkyl, alkene or alkyne;

R2 is an aliphatic chain (C6-C14);

R3 is a mono-, di-, tri- or tetra-aromatic substituent comprising hydrogen, halogen, alkyl, alkoxy, azide (N3), ether, NO2, or cyanide (CN);

n is an independently selected whole integer selected from 1 to 3; and wherein the phenyl can be moved between positions 3 to 5 about the heterocycle amine.

In other embodiments, azacyclic constrained sphingolipid-like small molecule compounds includes:

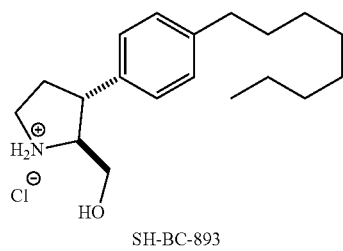

SH-BC-893

In even other embodiments, the method of treatment includes diagnosing the human subject with at least one disorder.

In even more embodiments, the at least one disorder is colon cancer, prostate cancer, lung cancer, pancreatic cancer, breast cancer, leukemia, or obesity.

In yet, even more embodiments, the pharmaceutical formulation does not stimulate bradycardia in the human subject.

In still yet, even more embodiments, the pharmaceutical formulation inhibits an increase in tumor diameter, an increase in tumor bioluminescence, an increase in tumor volume, an increase in tumor mass, or an increase in neoplastic cell proliferation rate.

In many other embodiments, the human disorder is characterized as slow-growing, fast-growing, aggressive, malignant, Ras-positive, PTEN-negative, benign, metastatic, nodular, or autochthonous.

In yet, many other embodiments the method of treatment is combined with an FDA-approved standard of care.

In many more embodiments, the pharmaceutical formulation is combined with at least one FDA-approved compound.

In yet, many more embodiments, the at least one FDA-approved compound is methotrexate, gemcitabine, tamoxifen, taxol, docetaxel, or enzalutamide.

BRIEF DESCRIPTION OF THE DRAWINGS

The description and claims will be more fully understood with reference to the following figures and data graphs, which are presented as exemplary embodiments of the invention and should not be construed as a complete recitation of the scope of the invention.

FIGS. 56A to 56E provide microscope-captured images characterizing vacuolation induced by small molecule analogs in accordance with embodiments of the invention.

FIGS. 56F and 57A to 57D provide western-blot data and microscope-captured images detailing the ability of small molecule analogs to disrupt PIKfyve localization but not activity in accordance with embodiments of the invention.

FIGS. 65A to 65J provide graphical data and microscope-captured images detailing the ability of small molecule analogs to starve prostate cancer cells and limit prostate tumor growth in accordance with embodiments of the invention.

DETAILED DESCRIPTION

Turning now to the drawings and data, molecules capable of treating disorders, including neoplasms and cancer, from a variety of therapeutic mechanisms including triggering cellular nutrient transporter down-regulation and blocking lysosomal fusion reactions, medicaments formed from these molecules, methods of synthesis of these molecules, and methods for the treatment of disorders using such therapeutics are disclosed. In some embodiments, the molecules are constrained azacyclic sphingolipid-like compounds. Additional embodiments of the small molecules are diastereomeric 3- and 4-C-aryl pyrrolidines. Embodiments can exist in a pure compound form or in the form of pharmaceutically effective salts. In other embodiments, formulations and medicaments are provided that are directed to the treatment of disorders. In some such embodiments these formulations and medicaments target cancers, such as, for example, leukemia, prostate, colon, lung, pancreatic and breast cancer, and potentially other diseases, including diseases where oncogenic Ras mutations or PTEN loss are associated with the neoplastic cells. Other embodiments, the disorders targeted are related to eating disorders, such as, for example, obesity. Therapeutic embodiments contain a therapeutically effective dose of one or more small molecule compounds, present either as pharmaceutically effective salt or in pure form. Embodiments allow for various formulations, including, but not limited to, formulations for oral, intravenous, or intramuscular administration. Other additional embodiments provide treatment regimens for disorders using therapeutic amounts of the small molecules.

In addition to embodiments of medicaments and treatments, embodiments are directed to the ability of the azacyclic constrained sphingolipid-like molecules to induce changes in cellular bioenergetics in cells. Embodiments of the mechanism will induce bioenergetic stress due to a decrease in access to nutrients. Accordingly, the stress will cause death of neoplastic cells in some embodiments; in other embodiments, the stress will not cause toxicity in normal, healthy cells. Many embodiments of the invention are directed to the ability of these molecules to decrease nutrient transporters on a cell surface, low-density lipoprotein degradation, macropinosome degradation, and autophagy.

Definitions

For the purposes of this description, the following definitions are used, unless otherwise described.

Figure 1:
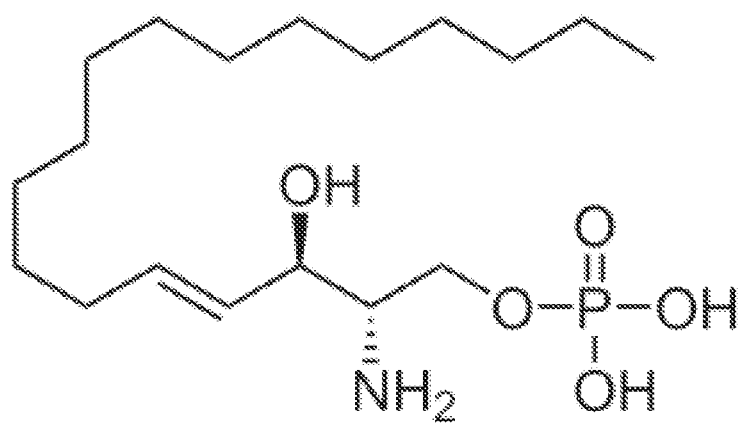
FIG. 1 provides a molecular structure of sphingosine-1-phosphate in accordance with the prior art.

"Sphingosine-1 phosphate (S1P)" is a phosphorylated biochemical molecule that is derived from fatty acids, and involved in several cell signal responses. A structure of the molecule is shown in FIG. 1.

"S1P receptors" are a class of G protein-coupled receptors targeted by S1P. Five subtypes exist, including S1P receptor 1, S1P receptor 2, S1P receptor 3, S1P receptor 4, and S1P receptor 5.

"Protein phosphatase 2 (PP2A)" is an enzyme with serine/threonine phosphatase activity with broad substrate specificity and diverse cellular functions. The enzyme is known to affect various signal transduction pathways, including several oncogenic signaling cascades.

Figure 2:
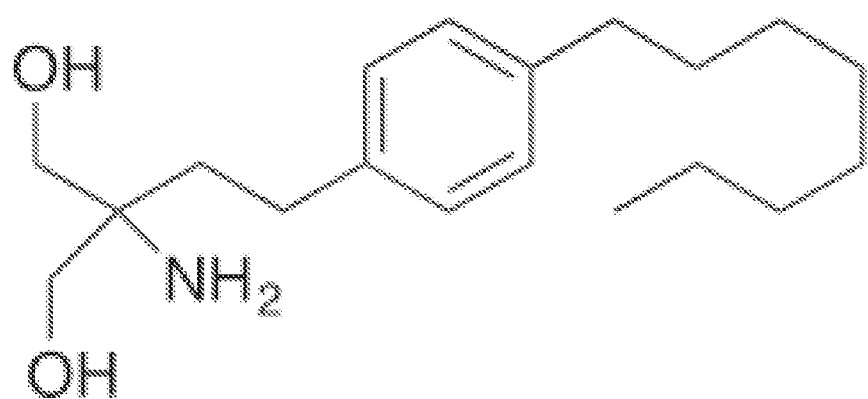
FIG. 2 provides a molecular structure of FTY720 in accordance with the prior art.

"FTY720" (2-Amino-2-[2-(4-octylphenyl)ethyl]propane 1,3-diol hydrochloride), shown diagrammatically in FIG. 2, is a synthetic immunomodulatory agent bearing an aminodiol functionality on an aromatic moiety bearing a hydrophobic aliphatic chain. The molecule is also known as fingolimod and is marketed under the trade name Gilenya™ for the treatment of relapsing-remitting multiple sclerosis.

Terms of Art

"Acyl" means a —R—C=O group.

"Alcohol" means a compound with an —OH group bonded to a saturated, alkane-like compound, (ROH).

"Alkyl" refers to the partial structure that remains when a hydrogen atom is removed from an alkane.

"Alkyl phosphonate" means an acyl group bonded to a phosphate, $RCO_2PO_3^{2-}$.

"Alkane" means a compound of carbon and hydrogen that contains only single bonds.

"Alkene" refers to a hydrocarbon that contains a carbon-carbon double bond, $R_2C=CR_2$.

"Alkyne" refers to a hydrocarbon structure that contains a carbon-carbon triple bond.

"Alkoxy" refers to a portion of a molecular structure featuring an alkyl group bonded to an oxygen atom.

"Aryl" refers to any functional group or substituent derived from an aromatic ring.

"Amine" molecules are compounds containing one or more organic substituents bonded to a nitrogen atom, $RNH_2$, $R_2NH$, or $R_3N$.

"Amino acid" refers to a difunctional compound with an amino group on the carbon atom next to the carboxyl group, $RCH(NH_2)CO_2H$.

"Azide" refers to Ns.

"Cyanide" refers to CN.

"Ester" is a compound containing the —$CO_2R$ functional group.

"Ether" refers to a compound that has two organic substituents bonded to the same oxygen atom, i.e., R—O—R'.

"Halogen" or "halo" means fluoro (F), chloro (Cl), bromo (Br), or iodo (I).

"Hydrocarbon" means an organic chemical compound that consists entirely of the elements carbon (C) and hydrogen (H).

"Phosphate", "phosphonate", or "PO" means a compound containing the elements phosphorous (P) and oxygen (O).

"R" in the molecular formula above and throughout are meant to indicate any suitable organic molecule.

C-Aryl Azacyclic Constrained Pyrrolidine Molecules

Figure 3:
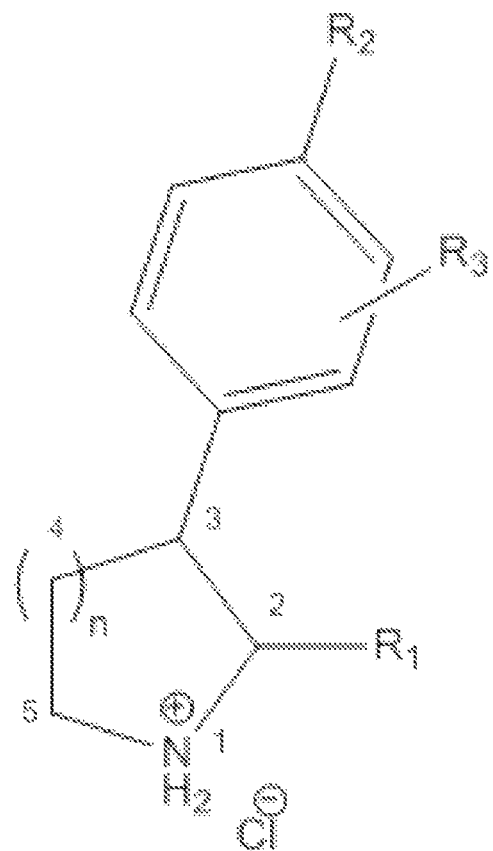
FIGS. 3 and 4 provide molecular structures of therapeutic small molecule analogs in accordance with various embodiments of the invention.

Compounds in accordance with embodiments of the invention are based on diastereomeric 3- and 4-C-aryl 2-hydroxymethyl pyrrolidines. A chemical compound in accordance with embodiments of the invention is illustrated in FIG. 3 and pictured below. Embodiments comprise the molecule as illustrated in FIG. 3, phosphates of such molecules, phosphonates of such molecules, or a pharmaceutically acceptable salt thereof, wherein:

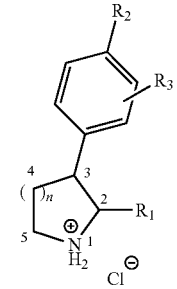

$R_1$ is an optional functional group selected from an alkyl chain, $(CH_2)_nOH$, CHOH-alkyl, CHOH-alkyne, $(CH_2)_n$OMe, $(CH_2)_nPO(OH)_2$ and esters thereof, CH=CHPO$(OH)_2$ and esters thereof, $(CH_2CH_2)_nPO(OH)_2$ and esters thereof, and $(CH_2)_nOPO(OH)_2$ and esters thereof, $(CH_2)_n$PO$_3$ and esters thereof, where Me is an alkyl, alkene or alkyne;

$R_2$ is an aliphatic chain ($C_6$-$C_{14}$);

$R_3$ is a mono-, di-, tri- or tetra-aromatic substituent comprising hydrogen, halogen, alkyl, alkoxy, azide ($N_3$), ether, NO2, or cyanide (CN);

n is an independently selected integer selected from 1, 2, or 3; and wherein the phenyl can be moved about the five carbon ring, e.g., from ring positions 3 to 4 to 5, etc.

Figure 4:
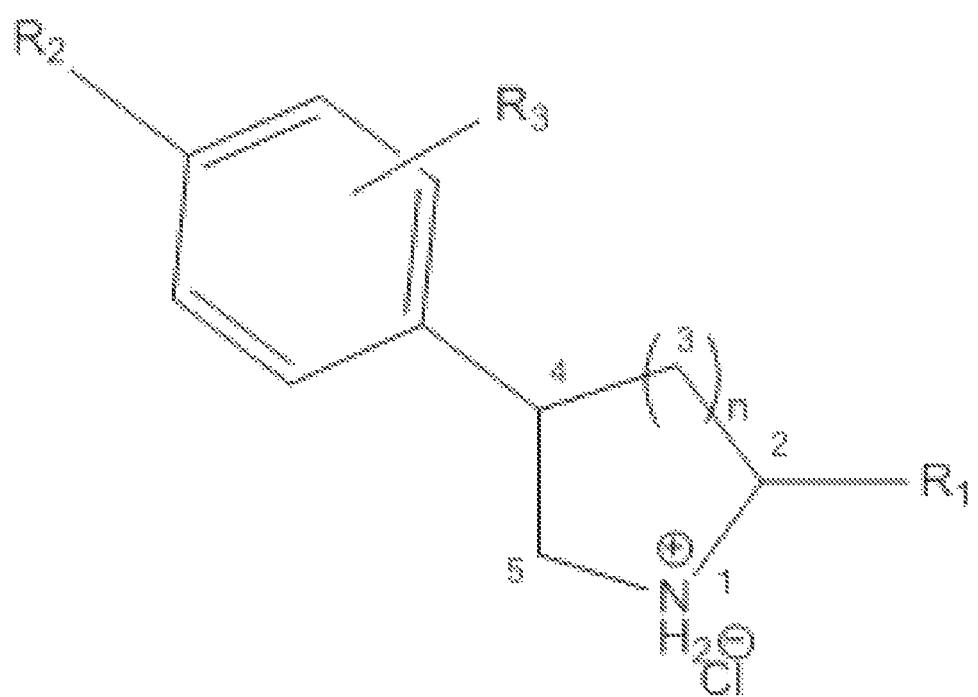
Figure 5:
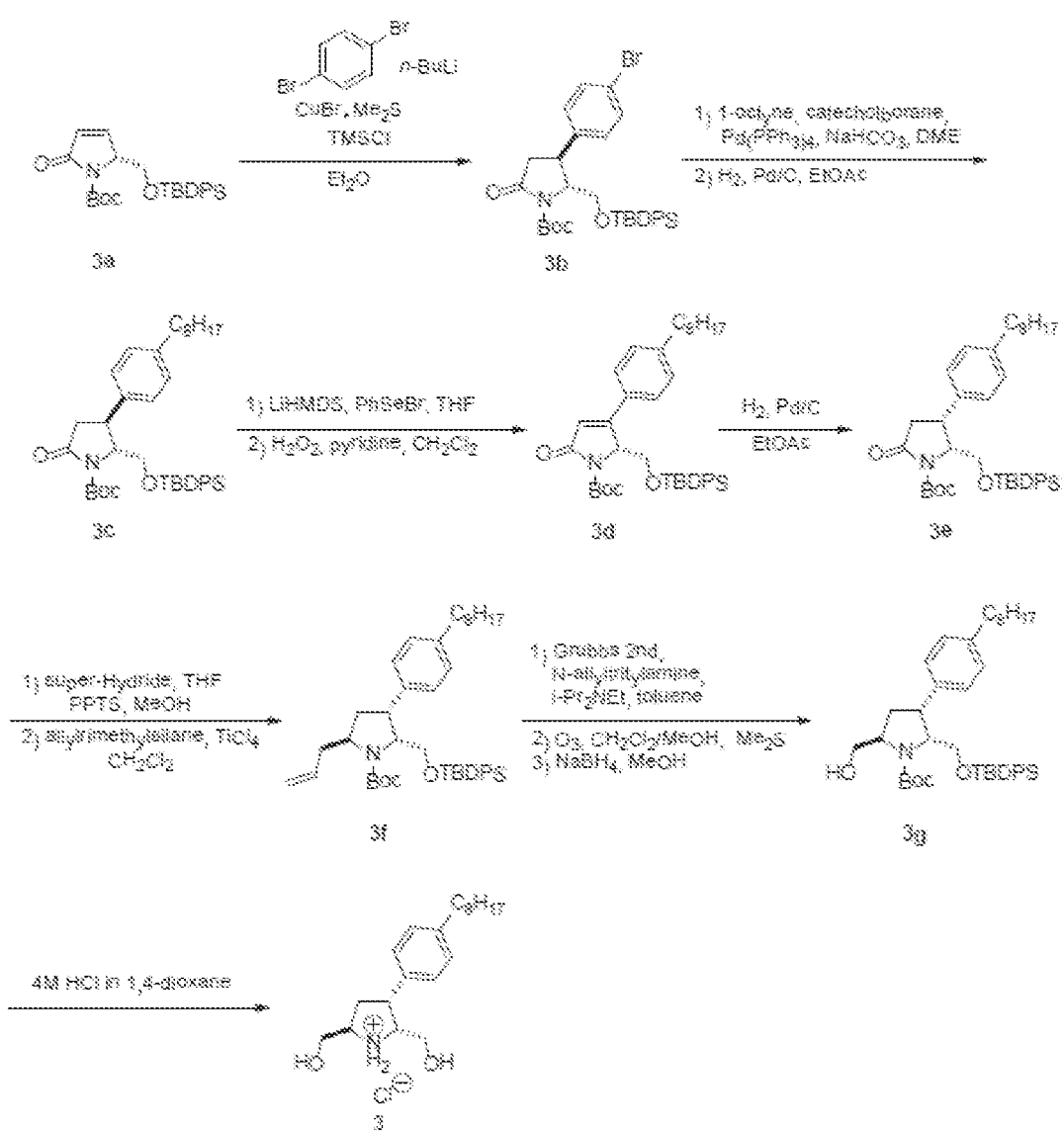
FIGS. 5 to 22 provide reaction pathways for the production of therapeutic small molecule analogs in accordance with various embodiments of the invention.

In further embodiments the C-aryl group can be moved to position 3 or 4, where the position not occupied by the C-aryl group is now H (i.e., $CH_2$), as shown in FIG. 4, and reproduced below.

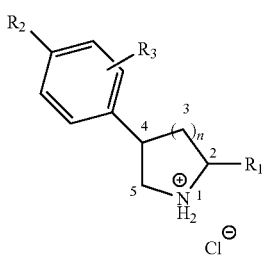

In additional embodiments, alkyl, CH$_2$OH, or (CH$_2$)$_n$OH groups can be added to position 5.

In still other embodiments, the R$_2$ and R$_3$ substituents can have different combinations around the phenyl ring with regard to their position.

In still other embodiments, R$_2$ may be an unsaturated hydrocarbon chain.

In still other embodiments, the R$_1$ may be an alkyl having 1 to 6 carbons.

It will be understood that compounds in this invention may exist as stereoisomers, including phosphate, phosphonates, enantiomers, diastereomers, cis, trans, syn, anti, solvates (including hydrates), tautomers, and mixtures thereof, are contemplated in the compounds of the present invention. (See, e.g., FIGS. 3a to 3b, 5a, 6a, 7c, and 9 for example.)

In many embodiments where the compound is a phosphate or phosphonate, R$_1$ may be, for example, (CH$_2$)$_n$PO(OH)$_2$ and esters thereof, CH=CHPO(OH)$_2$ and esters thereof, (CH$_2$CH$_2$)$_n$PO(OH)$_2$ and esters thereof, and (CH$_2$)nOPO(OH)$_2$ and esters thereof.

The claimed inventions can also be related to pharmaceutically acceptable salts. A "pharmaceutically acceptable salt" retains the desirable biological activity of the compound without undesired toxicological effects. Salts can be salts with a suitable acid, including, but not limited to, hydrochloric acid, hydrobromic acid, sulfuric acid, phosphoric acid, nitric acid and the like; acetic acid, oxalic acid, tartaric acid, succinic acid, malic acid, benzoic acid, pamoic acid, alginic acid, methanesulfonic acid, naphthalenesulphonic acid, and the like. Also, incorporated cations can include ammonium, sodium, potassium, lithium, zinc, copper, barium, bismuth, calcium, and the like; or organic cations such as tetraalkylammonium and trialkylammonium cations. Also useful are combinations of acidic and cationic salts. Included are salts of other acids and/or cations, such as salts with trifluoroacetic acid, chloroacetic acid, and trichloroacetic acid.

Other azacyclic constrained sphingolipid-like molecules, as well as modified azacyclic constrained sphingolipid-like molecules, suitable for practice of the present invention will be apparent to the skilled practitioner. Some molecules may include any diastereomeric C-aryl pyrrolidine compound. Furthermore, these molecules may employ several mechanisms of action to inhibit neoplasm growth, without inducing toxic S1P receptor activity, even if the molecules are not structurally identical to the compounds shown above.

Synthesis of C-Aryl Constrained Pyrrolidine Molecules

Embodiments include diastereomeric C-aryl pyrrolidines starting with appropriately substituted pyrrolone or 1-Bromo-4-octylbenzene. Some listed embodiments of the azacyclic constrained sphingolipid-like small molecule compounds originate from similar reactions.

Compound 3: Synthesis of compounds 3 and 4 begin with different stereoisomers of a pyrrolone 3a (3a, from FIG. 5) (versus (2S, 4R) for compound 4). Compound 3 is a precursor for compounds 6, 9, and 10. To synthesize intermediate (2R,3S)-tert-Butyl 3-(4-bromophenyl)-2-((tert-butyldiphenylsilyloxy)methyl)-5-oxopyrrolidine-1-carboxylate (3b), 1,4-dibromobenzene (9.44 g, 40 mmol) is dissolved in anhydrous Et$_2$O (86 mL) under Argon. The solution is cooled to −20° C. and n-BuLi (2.5 M in hexane, 16 mL, 40 mmol) is added dropwise. After addition, the solution is stirred at −20° C. for 1 hour. Then CuBr-DMS (4.11 g, 20.0 mmol) is added to the mixture in one portion. The cuprate mixture is stirred for 1 more hour at −20° C. and then cooled to −78° C. In another dried flask, 3a (1.8 g, 4.0 mmol) is dissolved in anhydrous Et$_2$O (22 mL) under Argon and also cooled to −78° C. TMSCl (1.02 mL, 8 mmol) is added to the latter solution. This solution is transferred dropwise by canula to the cuprate mixture. This mixture is stirred at −78° C. for 1 hour and warmed to room temperature overnight. The reaction is quenched and washed three times with a 1:1 solution of saturated NH$_4$Cl and 0.5 M NH$_4$OH followed by a brine wash. The organic layers are dried over MgSO$_4$, filtered, and concentrated under reduced pressure. The residue is then purified by flash chromatography (hexane:EtOAc, 10:1 to 6:1) to give 3b.

To synthesize compound 3c (2R,3S)-tert-Butyl 2-((tert-butyldiphenylsilyloxy)methyl)-3-(4-octylphenyl)-5-oxopyrrolidine-1-carboxylate, the following steps are followed. A solution of 1-octyne (398 μL, 2.70 mmol) and catecholborane (1.0 M in THF, 2.70 mL, 2.70 mmol) is heated at 70° C. for 2 hours under Argon atmosphere. The reaction mixture is allowed to cool down to room temperature. A solution of compound 3b (1.1 g, 1.8 mmol) in DME (21.9 mL) is added to the reaction mixture followed by Pd(PPh$_3$)$_4$ (62 mg, 0.054 mmol) and 1N aqueous solution of NaHCO$_3$ (16.8 mL). The reaction mixture is refluxed with vigorous stirring for 4 hours. The mixture is cooled down to room temperature and a brine solution is added. The mixture is extracted 3 times with Et$_2$O and the combined organic layers are dried over NaSO$_4$ and filtrated. The solvent is removed under reduced pressure and the residue is purified by flash chromatography (hexane:EtOAc, 8:1 to 6:1) to give a slightly yellow oil. This oil is then dissolved in EtOAc (30 mL) and Pd/C (10%, 192 mg, 0.18 mmol) is added. The air is pumped out of the flask and replaced by H$_2$. Upon completion as indicated by TLC (overnight), the reaction mixture is filtered through Celite. The solvent is removed under reduced pressure to give hydrogenation product compound 3c (0.80 g, 69% over two steps) as a slightly yellow oil.

To synthesize intermediate compound 3d ((R)-tert-Butyl 2-((tert-butyldiphenylsilyloxy)methyl)-3-(4-octylphenyl)-5-oxo-2,5-dihydro-1H-pyrrole-1-carboxylate), the following steps are performed: A solution of 3c (257 mg, 0.40 mmol) in anhydrous THF (4.0 mL) under argon atmosphere is cooled to −78° C. LiHMDS (1M in THF, 0.44 mL, 0.44 mmol) is added dropwise to the solution. The mixture is stirred at −78° C. for 1 hour. In another flask under argon atmosphere, a solution of PhSeBr (104 mg, 0.44 mmol) in anhydrous THF (1 mL) is also cooled down to −78° C. The phenylselenyl bromide solution is then transferred dropwise by canula to the reaction mixture. This mixture is stirred at −78° C. for 2 hours, no more starting material is visible on TLC. The reaction is quenched with saturated solution of NH$_4$Cl, diluted with CH$_2$Cl$_2$ and the two phases are separated. The aqueous phase is extracted twice with CH$_2$Cl$_2$ and the combined organic phases are dried over MgSO$_4$, filtrated. The solvent is removed under reduced pressure. The residue is dissolved in CH$_2$Cl$_2$ (2 mL) in a flask and cooled to −78° C. Hydrogen peroxide solution (30% (w/w) in H$_2$O, 204 μL) and pyridine (160 μL, 2.2 mmol) were added sequentially to the solution. This solution is allowed to warm to room temperature and stirred for 1 hour. The reaction is quenched with saturated solution of $NH_4Cl$, extracted three times with $CH_2Cl_2$. The organic layers were combined, dried over $NaSO_4$ and filtered. The solvent is removed under reduced pressure and the residue purified by flash chromatography (hexane:EtOAc, 6:1) to give the 3d (192 mg, 75% over two steps) as a yellow oil.

Intermediate compound 3e ((2R,3R)-tert-Butyl 2-((tert-butyldiphenylsilyloxy)methyl)-3-(4-octylphenyl)-5-oxopyrrolidine-1-carboxylate) is synthesized from 3d using the following steps. Pd/C (10%, 28 mg, 0.027 mmol) is added to a solution of 3d (170 mg, 0.27 mmol) in EtOAc (30 mL). The air is pumped out of the flask and replaced by $H_2$. Upon completion as indicated by TLC (overnight), the reaction mixture is filtered through Celite. The solvent is removed under reduced pressure and the residue purified by flash chromatography (hexane:EtOAc, 6:1) to give the hydrogenation product compound 3e (150 mg, 88%) as a slightly yellow oil.

The intermediate compound 3f ((2R, 3R, 5S)-tert-Butyl 5-allyl-2-((tert-butyldiphenylsilyloxy)methyl)-3-(4-octylphenyl)pyrrolidine-1-carboxylate) is synthesized by at least the following steps: compound 3e (105 mg, 0.16 mmol) and anhydrous THF (2.7 mL) are added to a dried flask under argon atmosphere, the solution is then cooled to −78° C. Lithium triethylborohydride (1.0 M in THF, 80 µL, 0.080 mmol) is added dropwise and the mixture is stirred for 1 hour at −78° C. In another dried flask, pyridinium p-toluenesulfonate (22.0 mg, 0.088 mmol) is dissolved in anhydrous MeOH (1.80 mL) under Argon and also cooled to −78° C. This solution is transferred dropwise by canula to the reaction mixture. The pH is verified to be slightly acidic (pH~6), otherwise more pyridinium p-toluenesulfonate should be added. The mixture is allowed to warm to room temperature and stirred overnight. The reaction is quenched with saturated solution of $NaHCO_3$, extracted three times with $CH_2Cl_2$. The organic layers are combined, dried over $NaSO_4$ and filtered. The solvent is removed under reduced pressure to give the crude O-methyl aminal product as a yellow oil (48 mg). This oil is then dissolved in anhydrous $CH_2Cl_2$ (0.34 mL) under argon atmosphere and the solution is cooled to −78° C. Allyltrimethylsilane (59 µL, 0.365 mmol) and Titanium tetrachloride (1.0 M in $CH_2Cl_2$, 80 µL, 0.080 mmol) are added sequentially to the solution. The orange mixture is stirred for 1 hour at −78° C., quenched with water and extracted three times with $CH_2Cl_2$. The organic layers are combined, dried over $NaSO_4$ and filtered. The solvent is removed under reduced pressure and the residue purified by flash chromatography (hexane:EtOAc, 6:1) to give the hydrogenation product 3f (20 mg, 41% over two steps) as a slightly yellow oil.

The next intermediate compound 3g, or (2R,3R,5R)-tert-Butyl 2-((tert-butyldiphenylsilyloxy)methyl)-5-(hydroxymethyl)-3-(4-octylphenyl)pyrrolidine-1-carboxylate, is synthesized by the following. Compound 3f (57 mg, 0.085 mmol) is dissolved in anhydrous toluene (1.8 mL) in a dried flask equipped with a condenser under argon atmosphere. N-allyltritylamine (51 mg, 0.17 mmol) and Grubb's catalyst 2nd generation (14.4 mg, 0.017 mmol) are then sequentially added to the solution of compound 3f. The mixture is refluxed for 3 days, cooled to room temperature and quenched with brine. This mixture is extracted three times with $CH_2Cl_2$. The organic layers are combined, dried over $NaSO_4$ and filtered. The solvent is removed under reduced pressure and the residue purified by flash chromatography (hexane:EtOAc, 40:1 to 20:1) to give the disubstituted alkene isomer (40 mg, 70%) as a yellow oil. This oil (40 mg, 0.06 mmol) is dissolved in a solution (6 mL) of MeOH and $CH_2Cl_2$ (1:1) and cooled to −78° C. Ozone is bubbled through the solution until a deep blue color persists. No more alkene starting material is observed by TLC. Argon is then bubbled through the solution to remove the residual ozone until no more blue color is observed. Dimethyl sulfide (0.4 mL) is added carefully and the reaction is allowed to warm to room temperature slowly and stirred overnight. The solvent is removed under reduced pressure. The residue is dissolved in MeOH (1.96 mL) and cooled to 0° C. Sodium borohydride (6.8 mg, 0.180 mmol) is added and the reaction was stirred at 0° C. for 4 hours. No more aldehyde starting material is observed by TLC. The reaction is quenched with saturated solution of $NH_4Cl$, extracted three times with $CH_2Cl_2$. The organic layers are combined, dried over $NaSO_4$ and filtered. The solvent is removed under reduced pressure and the residue purified by flash chromatography (hexane:EtOAc, 8:1 to 4:1) to give the 3 g (23.8 mg, 75% over two steps) as a yellow oil (23.8 mg, 42% over three steps).

Finally, synthesis of compound 3 ((2R,3R,5R)-2,5-Bis(hydroxymethyl)-3-(4-octylphenyl)pyrrolidinium chloride) ends with the following steps: HCl (4M in 1,4-dioxane, 1.6 mL, 6.4 mmol) is added to a flask with 3 g (21 mg, 0.032 mmol) and the solution is stirred at room temperature until completion is shown by TLC (24 to 48 hours). The solvent is removed under reduced pressure and 1,4-dioxane (2 mL) is added to the flask and evaporated to remove the residual HCl. The crude mixture is purified by flash chromatography ($CH_2Cl_2$:EtOH, 4:1 to 1:1) to give a yellow oil. This oil is dissolved in water, filtered through a plastic syringe filter (pore size: 0.45 µm), lyophilized to give compound 3 (10.0 mg, 88%) as a yellow solid.

Figure 6:
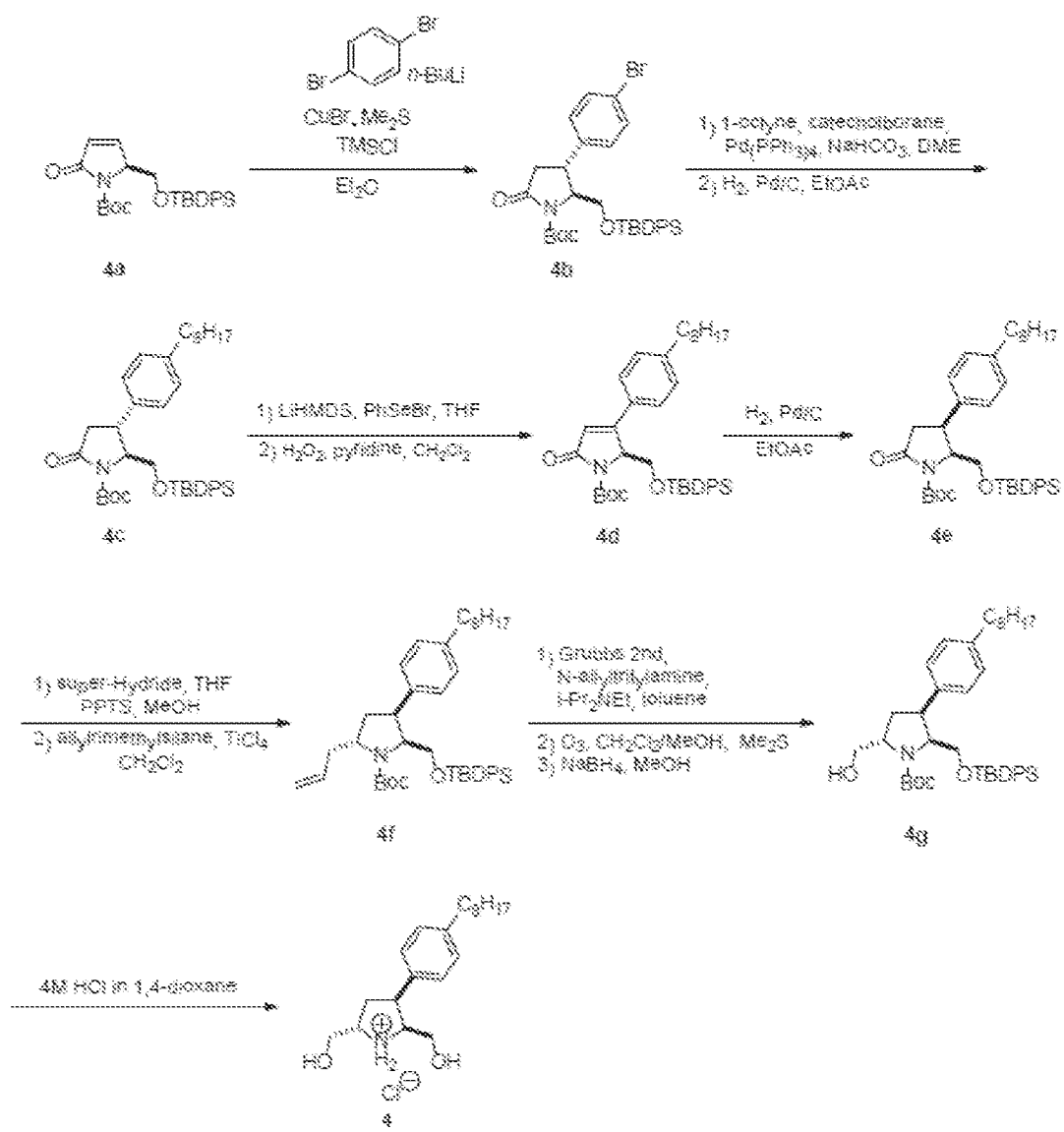

Compound 4: Compound 4 was obtained according to the procedure for synthesizing compound 3, as illustrated in FIG. 6. The initial molecule, compound 4a, is a stereoisomer of compound 3a.

Figure 7:
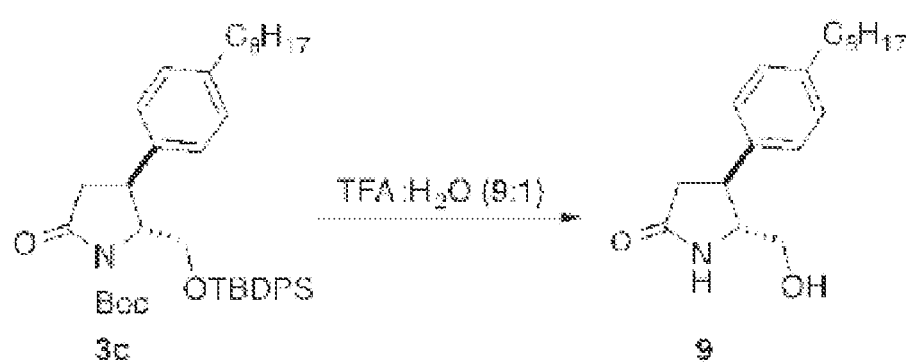

Compound 9: Synthesis of compound 9 ((4S,5R)-5-(hydroxymethyl)-4-(4-octylphenyl)Pyrrolidin-2-one) begins with compound 3c, as illustrated in FIG. 7. A solution (9:1) of trifluoroacetic acid (6.2 mmol, 0.48 mL) and $H_2O$ (0.05 mL) is added to a flask with 3c (40 mg, 0.062 mmol) at 0° C. After 15 mins, the solution is warmed to room temperature and stirred overnight. No more starting material is observed by TLC. The solvent is removed under reduced pressure. The residue is dissolved in $CH_2Cl_2$, extracted three times with saturated solution of $NaHCO_3$. The organic layer is washed with brine, dried over $MgSO_4$ and filtered. The solvent is removed under reduced pressure and the residue is purified by flash chromatography ($CH_2Cl_2$:MeOH:$NH_4OH$, 100:8:1) to give 9 (12.0 mg, 63%) as a white solid.

Figure 8:
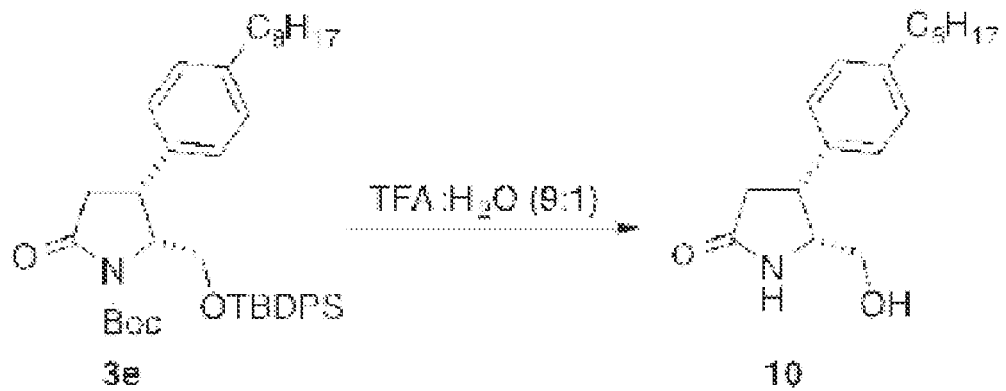

Compound 10: Synthesis of compound 10 is obtained according to the procedure for synthesizing compound 9. As shown in FIG. 8, the synthesis process for compound 10 begins with compound 3e.

Figure 9:
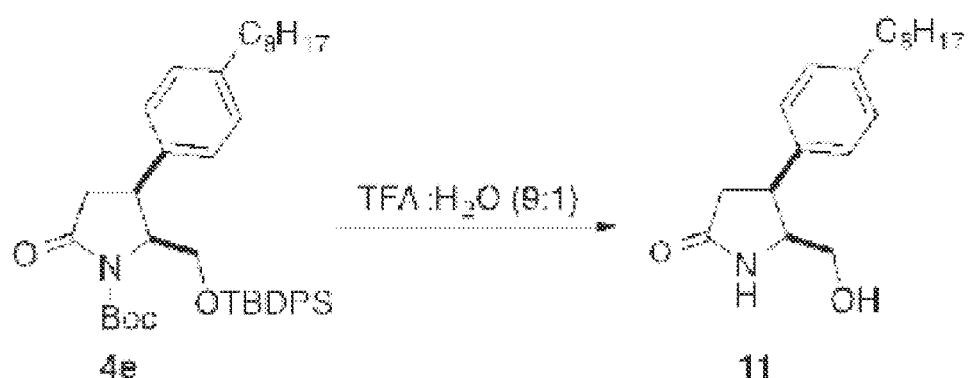

Compound 11: Synthesis of compound 11 is obtained according to the procedure for synthesizing compound 9. As shown in FIG. 9, the synthesis process for compound 11 begins with compound 4e.

Figure 10:
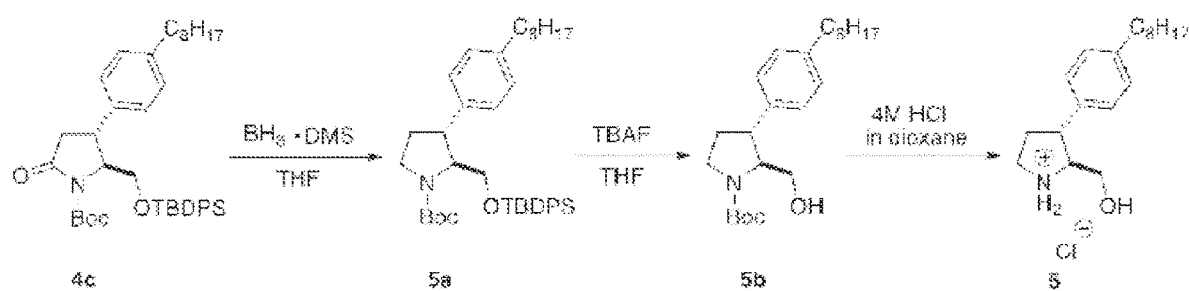

Compound 5: As illustrated in FIG. 10, synthesis of compound 5 begins with compound 4c. The first intermediate, 5a ((2S,3R)-tert-Butyl 2-((tert-butyldiphenylsilyloxy)methyl)-3-(4-octylphenyl)pyrrolidine-1-carboxylate) synthesized in the following manner. A solution of compound 4c (120 mg, 0.187 mmol) in anhydrous THF (2.4 mL) is cooled to 0° C. Borane dimethyl sulfide complex (2M in THF, 0.37 mL, 0.748 mmol) is added and the reaction is allowed to warm to room temperature and is stirred overnight. No more starting material is observed by TLC. The solvent is removed under reduced pressure. After the residue is co-evaporated twice with MeOH (2 mL), it is dissolved in $CH_2Cl_2$, extracted three times with saturated solution of $NaHCO_3$. The organic layer is washed with brine, dried over $MgSO_4$ and filtered. The solvent is removed under reduced pressure and the residue was purified by flash chromatography (hexane:EtOAc, 8:1) to give 5a (94.6 mg, 81%) as a slightly yellow oil.

Synthesis of the next intermediate, compound 5b ((2S,3R)-tert-Butyl 2-(hydroxymethyl)-3-(4-octylphenyl)pyrrolidine-1-carboxylate), begins by cooling a solution of 5a (271 mg, 0.432 mmol) in anhydrous THF (14.3 mL) to 0° C. tetrabutylammonium fluoride solution (1M in THF, 0.756 mL, 0.756 mmol) is added and the reaction is allowed to warm to room temperature and is stirred overnight. No more starting material is observed by TLC. The reaction is quenched with saturated solution of $NaHCO_3$ extracted three times with $CH_2Cl_2$. The organic layers are washed with brine, dried over $MgSO_4$ and filtered. The solvent is removed under reduced pressure and the residue is purified by flash chromatography (hexane:EtOAc, 6:1 to 4:1) to give 5b (155 mg, 92%) as a colorless oil.

In the final step in synthesizing compound 5 ((2S,3R)-2-(hydroxymethyl)-3-(4-octylphenyl)Pyrrolidinium chloride), HCl (4M in 1,4-dioxane, 0.98 mL, 3.9 mmol) is added to a flask with compound 5b (15 mg, 0.039 mmol) and the solution is stirred at room temperature until completion is shown by TLC (24 to 48 hours). The solvent is removed under reduced pressure and 1,4-dioxane (2 mL) is added to the flask and evaporated to remove the residual HCl. The crude mixture is purified by flash chromatography ($CH_2Cl_2$:EtOH, 7:1 to 4:1) to give a yellow oil. This oil is dissolved in water, filtered through a plastic syringe filter (pore size: 0.45 μm), lyophilized to give compound 5 (11.0 mg, 88%) as a yellow solid.

Figure 11:
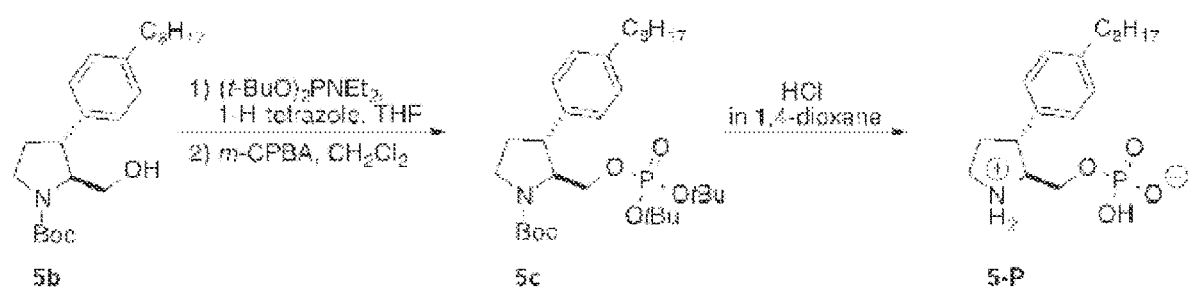

Compound 5-P: As illustrated in FIG. 11, synthesis of compound 5-P begins with compound 5b. In the initial step, compound 5c (tert-Butyl (2S,3R)-2-(((di-tert-butoxyphosphoryl)oxy)methyl)-3-(4-octylphenyl)pyrrolidine-1-carboxylate) is synthesized from intermediate compound 5b. Di-tert-butyl N,N-diethylphosphoramidite (31 μL, 28 mg, 0.104 mmol) and 1H-tetrazole (15 mg, 0.212 mmol) are sequentially added to a solution of compound 5b (14 mg, 0.036 mmol) in anhydrous THF (0.45 mL) under argon atmosphere at room temperature. The mixture is stirred over night at this temperature and then cooled to −78° C. A solution of m-CPBA (72%, 25 mg, 0.104 mmol) in $CH_2Cl_2$ (0.45 ml) is added to the mixture and the reaction is warmed back to room temperature. After 0.5 h, the reaction is quenched with aqueous saturated solution of $NaHCO_3$ and extracted three times with EtOAc. The organic layers are washed with brine, dried over $MgSO_4$ and filtered. The solvent is removed under reduced pressure and the residue is purified by flash chromatography (hexane:EtOAc, 4:1 to 2:1) to give compound 5c (10 mg, 48%) as a colorless oil.

In the next step, compound 5-P (((2S,3R)-3-(4-octylphenyl)pyrrolidin-1-ium-2-yl)Methyl hydrogen phosphate) is synthesized from compound 5c. HCl (4M in 1,4-dioxane, 0.34 mL, 1.35 mmol) is added to a flask with 5b (5 mg, 0.009 mmol) and the solution is stirred at room temperature for 24 hours. The solvent is removed under reduced pressure and 1,4-dioxane (2 mL) is added to the flask and evaporated to remove the residual HCl. The crude mixture is purified by flash chromatography (i-PrOH:$NH_4OH$:$H_2O$, 8:2:1 to 8:4:1) to give 5-P (2.5 mg, 78%) as a white solid.

Figure 12:
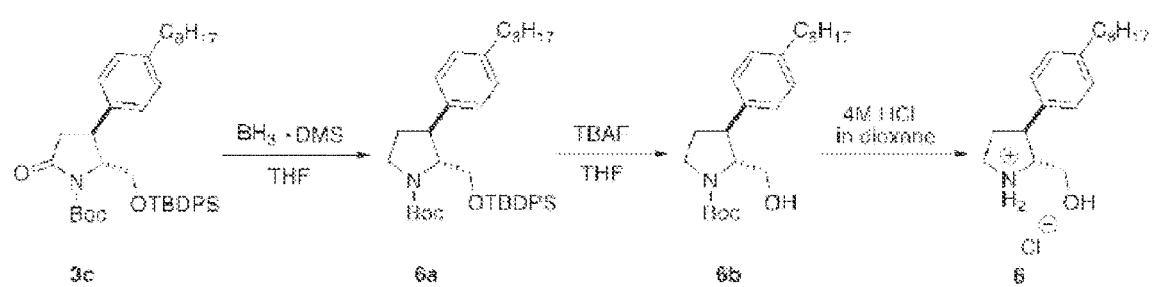

Compound 6: Compound 6 is obtained according to the procedure for synthesizing compound 5. The starting molecule for the synthesis of compound 6 is intermediate compound 3c, as illustrated in FIG. 12.

Figure 13:
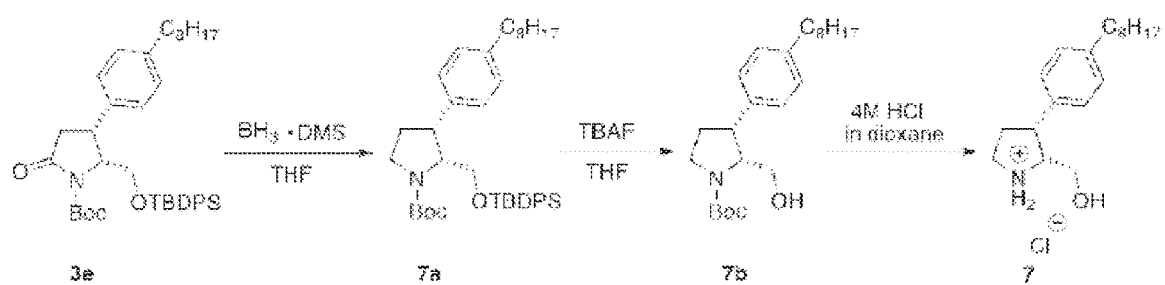

Compound 7: The starting molecule for the synthesis of compound 7 is intermediate compound 3e, as illustrated in FIG. 13. Compound 7 is obtained according to the procedure for synthesizing compound 5, with a difference in the synthesis of intermediate compound 7b ((2R,3R)-tert-Butyl 2-(hydroxymethyl)-3-(4-octylphenyl)pyrrolidine-1-carboxylate). To synthesize intermediate compound 7b, a solution of compound 7a (22 mg, 0.035 mmol) in anhydrous THF (1.14 mL) is cooled to 0° C. Tetrabutylammonium fluoride solution (1M in THF, 61 μL, 0.061 mmol) is added and the reaction is allowed to warm to room temperature and stirred overnight. Starting material is not all consumed indicated by TLC. The reaction is then heated to 40° C. for 48 hours, quenched with saturated solution of $NaHCO_3$ extracted three times with $CH_2Cl_2$. The organic layers are washed with brine, dried over $MgSO_4$ and filtered. The solvent is removed under reduced pressure and the residue is purified by flash chromatography (hexane:EtOAc, 6:1 to 4:1) to give 7b (12.5 mg, 92%) as a colorless oil.

Figure 14:
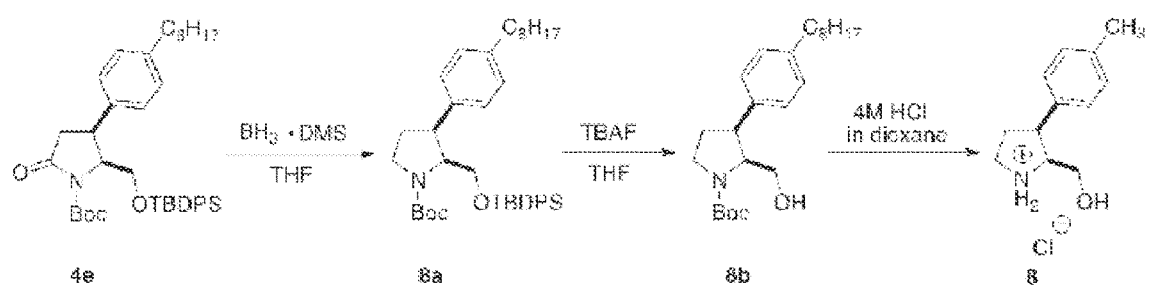

Compound 8: Compound 8 is obtained according to the procedure for synthesizing compounds 5 and 7. The starting molecule for the synthesis of compound 6 is intermediate compound 4e, as illustrated in FIG. 14.

Figure 15:
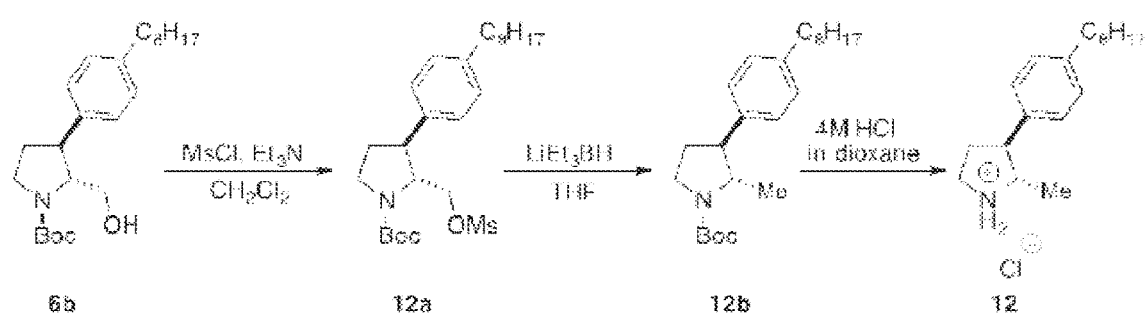

Compound 12: Synthesis of compound 12 begins with intermediate compound 6b, as illustrated in FIG. 15. To synthesize intermediate compound 12a, triethylamine (22 μL, 0.154 mmol) is added to a solution of compound 6b (30 mg, 0.077 mmol) in anhydrous $CH_2Cl_2$ (0.30 mL) and the solution is then cooled to 0° C. Methanesulfonyl chloride (9.0 μL, 0.116 mmol) is added to the solution and the reaction is allowed to warm to room temperature and stirred overnight. The reaction is poured into water and extracted three times with EtOAc. The organic layers are washed with brine, dried over $MgSO_4$ and filtered. The solvent is removed under reduced pressure and the residue is purified by flash chromatography (hexane:EtOAc, 3:1 to 2:1) to give 12a (34.0 mg, 94%) as a colorless oil.

To synthesize intermediate compound 12b, a solution of compound 12a (29 mg, 0.062 mmol) in anhydrous THF (0.06 mL) is cooled to 0° C. Lithium triethylborohydride (1.0 M solution in THF, 248 μL, 0.248 mmol) is added to the solution and the reaction is allowed to warm to room temperature and stirred for 5 h. The reaction is poured into water and extracted three times with EtOAc. The organic layers were washed with brine, dried over $MgSO_4$ and filtered. The solvent is removed under reduced pressure and the residue is purified by flash chromatography (hexane:EtOAc, 14:1) to give 12b (20.7 mg, 89%) as a colorless oil.

Finally, to synthesize compound 12, HCl (4M in 1,4-dioxane, 0.68 mL, 2.7 mmol) is added to a flask with 12b (10 mg, 0.027 mmol) and the solution is stirred at room temperature overnight. The solvent is removed under reduced pressure and 1,4-dioxane (1 mL) is added to the flask and evaporated to remove the residual HCl. The crude mixture is purified by flash chromatography ($CH_2Cl_2$:EtOH, 9:1 to 3:1) to give a yellow oil. This oil was dissolved in water, filtered through a plastic syringe filter (pore size: 0.45 μm), lyophilized to give 12 (8.0 mg, 96%) as a yellow solid.

Figure 16:
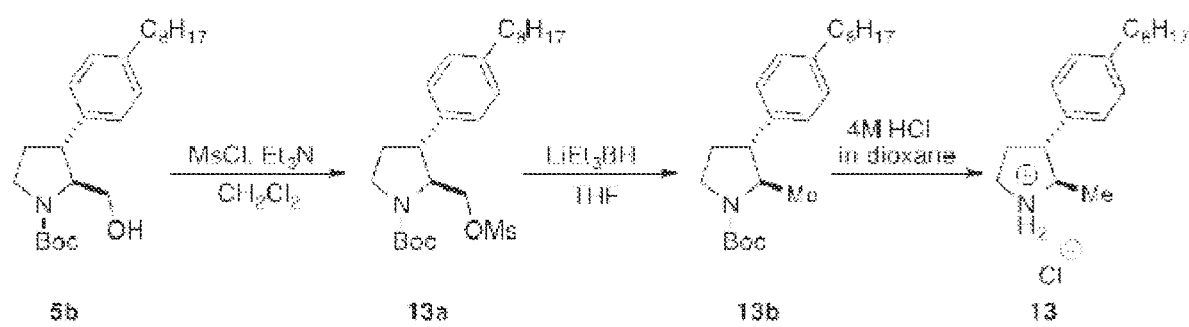

Compound 13: Compound 13 is obtained according to the procedure for synthesizing compound 12. The starting molecule for the synthesis of compound 13 is intermediate compound 5b, as illustrated in FIG. 16.

Figure 17:
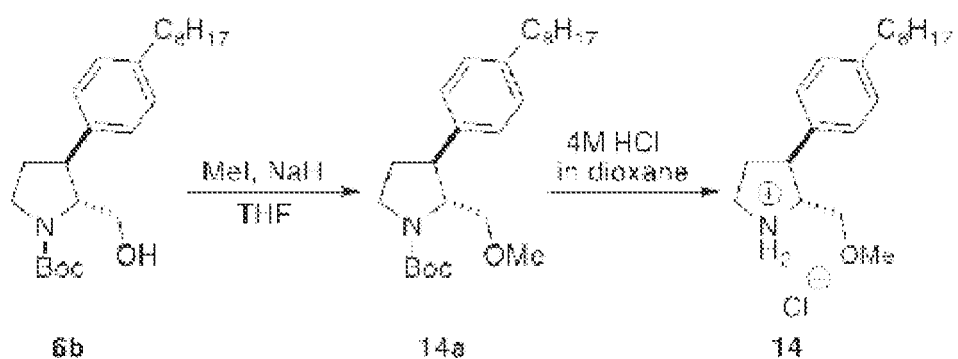

Compound 14: FIG. 17 illustrates the process of synthesizing compound 14. The synthesis of compound 14 begins with intermediate compound 6b. A solution of compound 6b (35 mg, 0.090 mmol) in anhydrous THF (0.75 mL) is cooled to 0° C. Sodium hydride (60% dispersion in mineral oil, 7.2 mg, 0.180 mmol) is added to the solution followed by Methyl iodide (26 mg, 12 µL, 0.180 mmol). The reaction is allowed to warm to room temperature and stirred overnight. The mixture is poured into water and extracted three times with EtOAc. The organic layers are washed with brine, dried over $MgSO_4$ and filtered. The solvent is removed under reduced pressure and the residue is purified by flash chromatography (hexane:EtOAc, 4:1) to give 14a (33 mg, 92%) as a colorless oil.

To synthesize compound 14, HCl (4M in 1,4-dioxane, 0.75 mL, 3.0 mmol) is added to a flask with compound 14a (12 mg, 0.030 mmol) and the solution is stirred at room temperature overnight. The solvent is removed under reduced pressure and 1,4-dioxane (1 mL) is added to the flask and evaporated to remove the residual HCl. The crude mixture is purified by flash chromatography ($CH_2Cl_2$:EtOH, 9:1 to 4:1) to give a yellow oil. This oil is dissolved in water, filtered through a plastic syringe filter (pore size: 0.45 µm), lyophilized to give 12 (9.9 mg, 98%) as a yellow oil.

Figure 18:
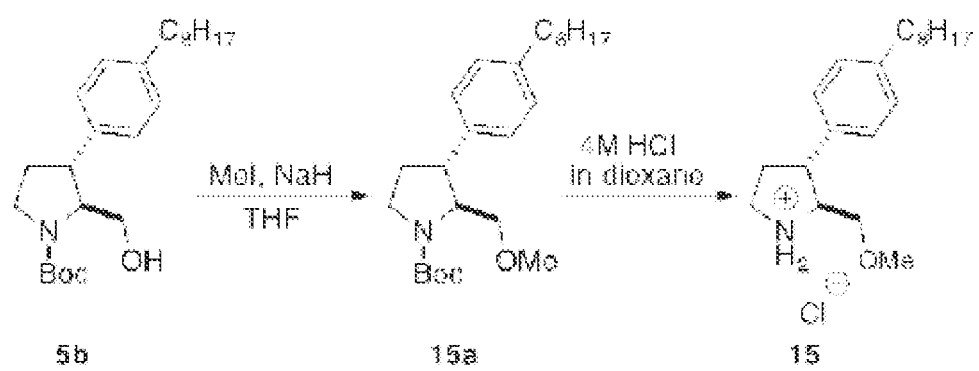

Compound 15: Compound 15 is obtained according to the procedure for synthesizing compound 14. The starting molecule for the synthesis of compound 15 is intermediate compound 5b, as illustrated in FIG. 18.

Figure 19:
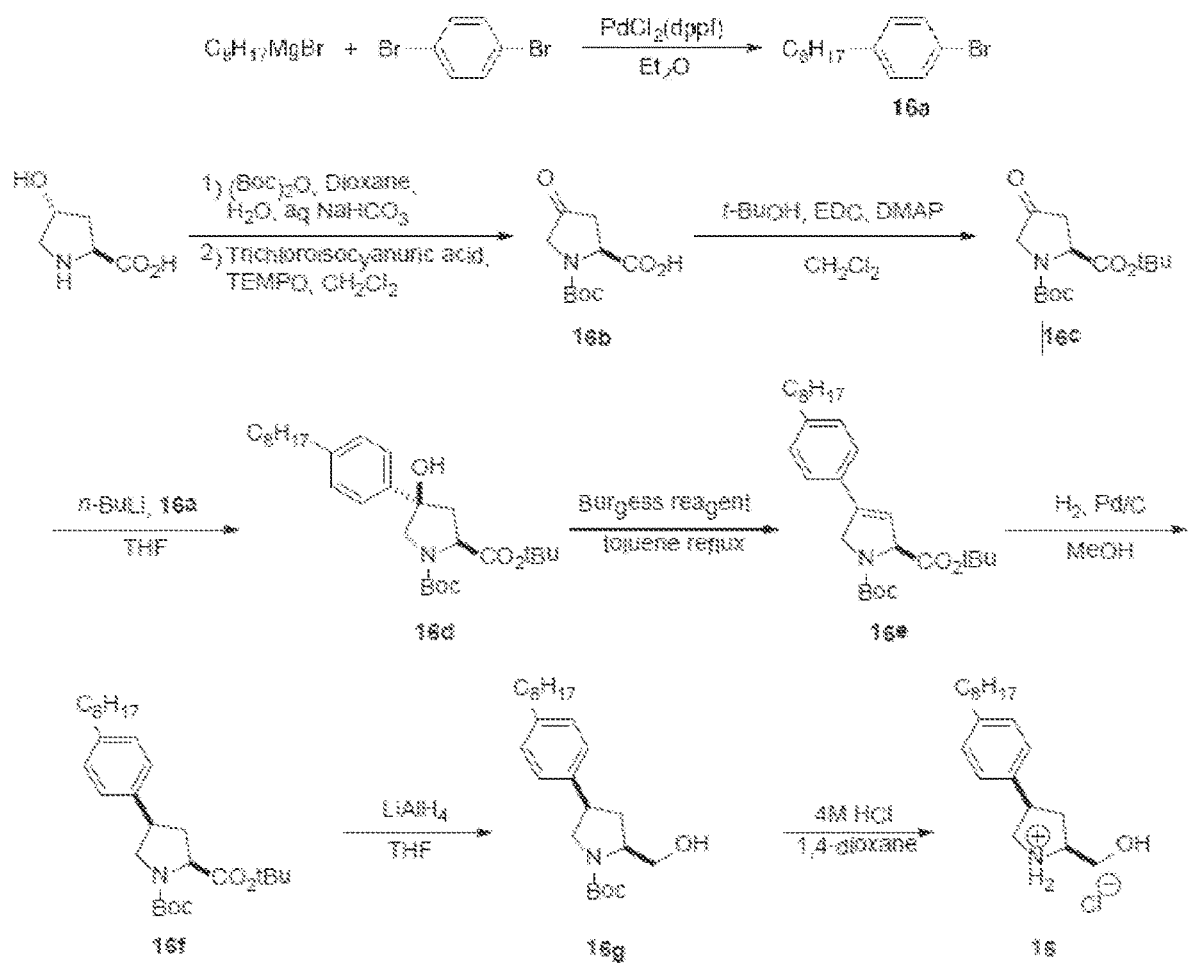

Compound 16: FIG. 19 illustrates the process of synthesizing compound 16. Compound 16a is synthesized according to a procedure to generate p-dodecyl$C_6H_4$Br reported by Ian Manners. (Dorn, H., et al. *Macromolecules*, 2003, 36, 291-297.) Compounds 16b, 16c are all known compounds and spectral data were in agreement with the proposed structures and matched those reported in the literature (Barraclough, P., et al., 1995, 51, 4195-4212; Van Huis, C. A., et al. *J. J. Bioorg. Med. Chem.* 2009, 17, 2501-2511.)

To synthesize intermediate compound 16a, octylmagnesium bromide solution (2.0 M in diethyl ether, 10.6 mL, 21.2 mmol) is added dropwise to a diethyl ether solution (12.5 mL) of 1,4-dibromobenzene (5 g, 21.2 mmol) and $PdCl_2$ (dppf) at 0° C. under argon. After stirring 48 h at room temperature, the mixture is refluxed for 2.5 h, exposed to air, poured into water and extracted three times with diethyl ether. The combined organic layers are washed with brine, dried over $MgSO_4$ and filtered. The solvent is removed under reduced pressure and the residue is purified by preparative thin-layer chromatography (20×20 cm, 1000 µm, 4 plates in hexane) to give compound 16a (4.4 g, 77%) as a colorless oil. The product contained a minor impurity and is used as such in the subsequent reaction.

To synthesize intermediate compound 16b, saturated $NaHCO_3$ solution (200 mL) is added to a solution of trans-4-hydroxy-L-proline (5 g, 38.0 mmol) in dioxane and water (1:1, 100 mL). The solution is cooled to 0° C. and $(Boc)_2O$ (9.2 g, 9.7 mL, 41.8 mmol) was added drop wise. The reaction is stirred at room temperature overnight. The pH is maintained at 3 by addition of 2M HCl and the reaction mixture is extracted with EtOAc. The organic layers are combined, dried over $MgSO_4$ and filtered. The solvent is removed under reduced pressure to give crude product (8.0 g, 91%) as a colorless oil. This crude oil (1.5 g, 6.5 mmol) is dissolved in $CH_2Cl_2$ (32 mL), and trichloroisocyanuric acid (1.5 g, 6.5 mmol) is added in one portion. The mixture is then cooled to 0° C. and TEMPO (51 mg, 0.325 mmol) is added to the reaction. The mixture is stirred at 0° C. for 0.5 h, then warmed to room temperature, stirred for another 0.5 h. No more starting material is visible on TLC. Water (5 mL) is then added to the mixture. After stirring for 10 min, the organics are removed in vacuo, diluted with ethyl acetate (20 mL), filtered through Celite. The filtrate is acidified with HCl solution (1M, 40 mL), washed with water (10 mL) four times, brine (10 mL), dried over $MgSO_4$ and filtered. The solvent is removed under reduced pressure to give compound 16b (1.35 g, 91%) as a white solid, which is directly used in next step without purification.

To synthesize intermediate compound 16c, a solution of intermediate compound 16b (1.35 g, 5.9 mmol) in anhydrous $CH_2Cl_2$ (27 mL) is cooled to 0° C. tert-Butyl alcohol (1.7 mL, 17.7 mmol) and DMAP (72 mg, 0.59 mmol) are added to the solution. After stirring for 5 min, 1-ethyl-3-(3-dimethylaminopropyl)carbodiimide hydrochloride (1.19 g, 6.2 mmol) is added to the solution. The reaction is allowed to warm to room temperature and stirred overnight. The mixture is quenched by saturated $NaHCO_3$ solution and extracted three times with $CH_2Cl_2$. The organic layers are washed with brine, dried over $MgSO_4$ and filtered. The solvent is removed under reduced pressure and the residue is purified by flash chromatography (hexane:EtOAc, 8:1) to give 16c (0.96 g, 57%) as a slightly yellow oil.

To synthesize intermediate compound 16d, n-BuLi (2.5 M in hexane, 146 µL, 0.364 mmol) is added dropwise to a solution of 1-bromo-4-octylbenzene (16a) (94 mg, 0.350 mmol) in THF (0.53 mL) at −78° C. After stirring for 0.5 h, 16c (40 mg, 0.14 mmol) in THF (0.1 mL) is added to the mixture, and the solution is stirred for an additional 2 h at −78° C. The reaction is then warmed to −40° C. and stirred overnight. The reaction mixture is quenched at −40° C. with saturated $NH_4Cl$ solution and allowed to warm to room temperature. The organic layer is separated and the aqueous layer is extracted three times with $CH_2Cl_2$. The combined organic layers are washed with brine, dried over $MgSO_4$ and filtered. The solvent is removed under reduced pressure and the residue is purified by flash chromatography (hexane:EtOAc, 12:1 to 8:1) to give compound 16d (21 mg, 32%) as a slightly yellow oil.

To synthesize intermediate compound 16e, Burgess' reagent (15 mg, 0.064 mmol) is added to a solution of 16e (15 mg, 0.032 mmol) in toluene (0.3 mL). The mixture is heated to reflux under argon for 4 h, then cooled to room temperature and diluted with EtOAc. The mixture is washed with water, brine, dried over $MgSO_4$ and filtered. The solvent is removed under reduced pressure and the residue was purified by flash chromatography (hexane:EtOAc, 12:1 to 8:1) to give compound 16e (10 mg, 67%) as a slightly yellow oil.

To synthesize intermediate compound 16f, Pd/C (10%, 4.6 mg, 0.004 mmol) is added to a solution of 16e (20 mg, 0.044 mmol) in MeOH (1.0 mL). The air is pumped out of the flask and replaced by $H_2$. Upon completion as indicated by TLC (overnight), the reaction mixture is filtered through Celite. The solvent is removed under reduced pressure and the residue purified by flash chromatography (hexane:EtOAc, 12:1 to 8:1) to give the hydrogenation product compound 16f (19 mg, 95%) as a white solid, m.p. (82.5-83.5° C.).

To synthesize intermediate compound 16g, a mixture of Lithium aluminum hydride (1.3 mg, 0.033 mmol) in anhydrous THF (1.0 mL) is cooled to 0° C. 16f (15 mg, 0.033 mmol) in THF (1.0 mL) is then added slowly to the mixture. After stirring at 0° C. for 1 h, the reaction is quenched by water, diluted with $CH_2Cl_2$ and washed with water and brine, dried over $MgSO_4$ and filtrated. The solvent is removed under reduced pressure and the residue is purified by flash chromatography (hexane:EtOAc, 4:1) to give compound 16g (11.4 mg, 90%) as a slightly yellow oil.

Finally, synthesize compound 16, HCl (4M in 1,4-dioxane, 1.2 mL, 4.621 mmol) is added to a flask with 16 g (9 mg, 0.023 mmol) and the solution is stirred at room temperature until completion is shown by TLC (1-5 h). The solvent is removed under reduced pressure and 1,4-dioxane (2 mL) is added to the flask and evaporated to remove the residual HCl. The crude mixture is purified by flash chromatography ($CH_2Cl_2$:EtOH, 8:1 to 4:1) to give a yellow oil. This oil is dissolved in water, filtered through a plastic syringe filter (pore size: 0.45 µm), lyophilized to give compound 5 (7.0 mg, 93%) as a slightly yellow solid.

Figure 20:
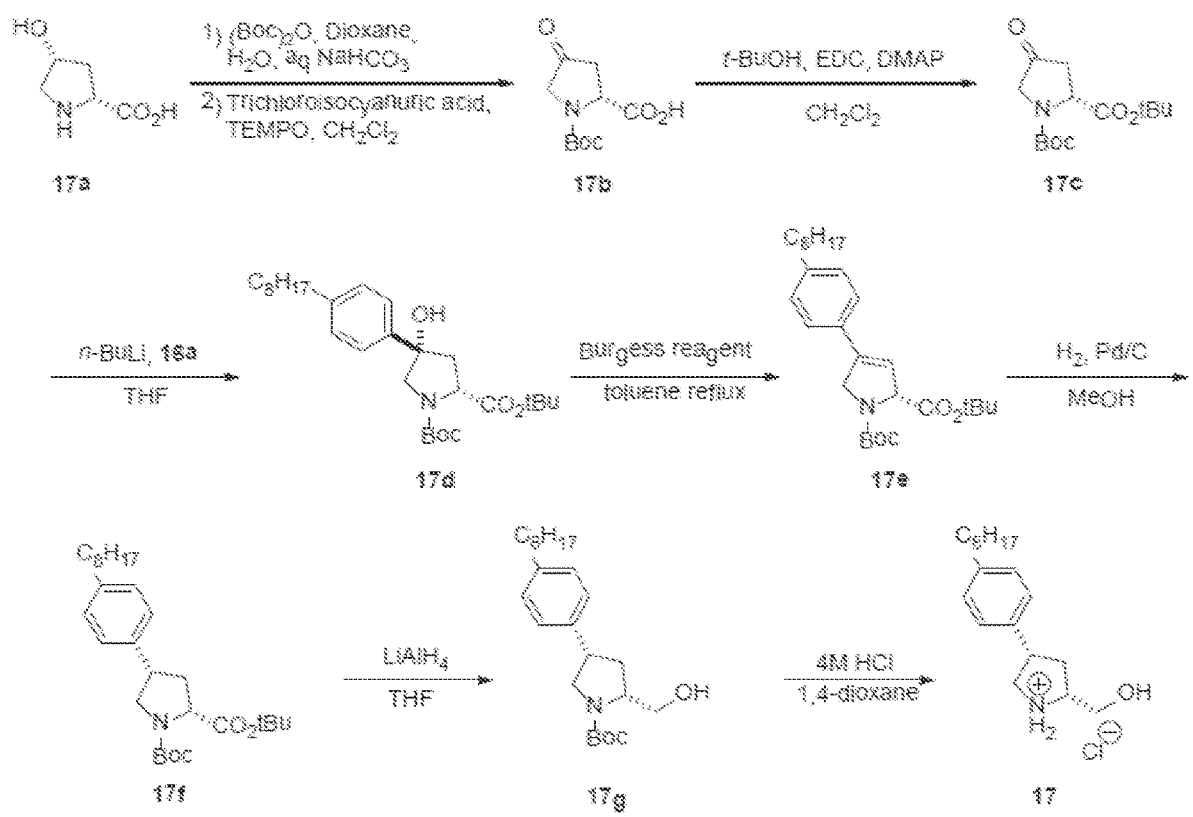

Compound 17: Compound 17 was obtained according to the procedure for synthesizing compound 16, as illustrated in FIG. 20. Compound 17b is a known compound and spectral data were in agreement with the proposed structures and matched those reported in the literature (Chabaud, P., et al., *Tetrahedron*, 2005, 61, 3725-3731.)

Figure 21:
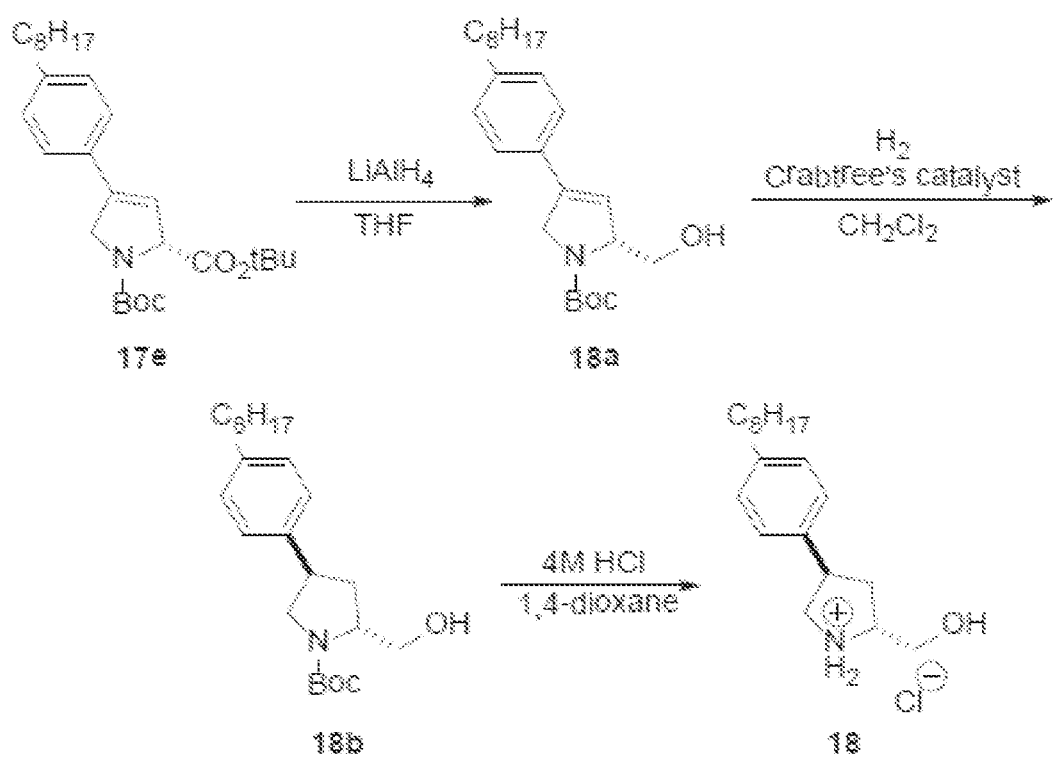

Compound 18: The synthesis of compound 18 is illustrated in FIG. 21. Compound 18a is synthesized according to the procedure for synthesizing compound 16g.

To synthesize intermediate compound 18b, Crabtree's catalyst (5.0 mg, 0.006 mmol) is added to a solution of compound 18a (16 mg, 0.041 mmol) in anhydrous $CH_2Cl_2$ (0.8 mL). This light orange mixture is then subjected to a hydrogen pressure of 70 psi for 72 h. The solvent is removed under reduced pressure and the residue purified by flash chromatography (hexane:EtOAc, 10:1 to 8:1) to give the trans hydrogenation product 18b (11.6 mg, 72%) as a slightly yellow oil.

Finally, to synthesize compound 18, HCl (4M in 1,4-dioxane, 0.75 mL, 3.0 mmol) is added to a flask with 18b (11.6 mg, 0.030 mmol) and the solution is stirred at room temperature until completion is shown by TLC (1-2 h). The solvent is removed under reduced pressure and 1,4-dioxane (2 mL) is added to the flask and evaporated to remove the residual HCl. The crude mixture is purified by flash chromatography ($CH_2Cl_2$:EtOH, 8:1 to 4:1) to give a yellow oil. This oil is dissolved in water, filtered through a plastic syringe filter (pore size: 0.45 µm), lyophilized to give 18 (8.5 mg, 88%) as a slightly yellow solid.

Figure 22:
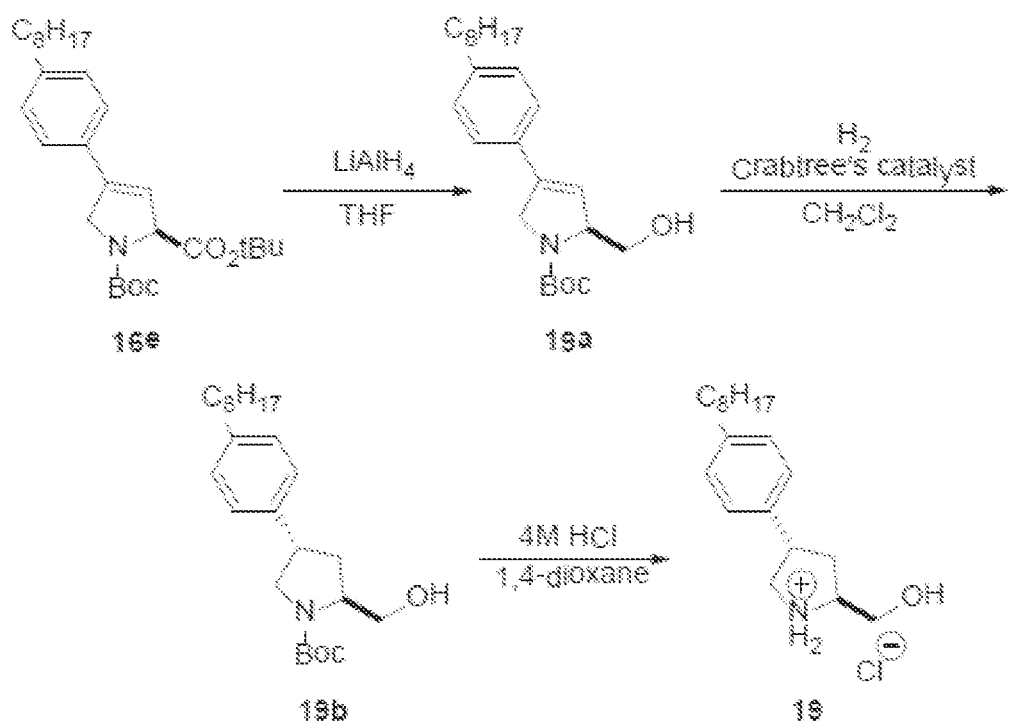

Compound 19: The synthesis of compound 19 is illustrated in FIG. 22. Compound 19 was obtained according to the procedure for synthesizing compound 18. Compound 19a was obtained according to the procedure for synthesizing 16 g.

Medicament Formulations and Treatments Thereof

In embodiments, the small molecule azacyclic constrained sphingolipid-like molecules are formulated into therapeutic medicaments for treatments. Many embodiments are directed to methods of treatment with medicaments containing the azacyclic constrained sphingolipid-like molecules. In some embodiments, the medicament targets disorders that are exemplified by proliferative growth or excess nutrient consumption, such as, for example, neoplasms, cancers, or obesity. Other embodiments will have medicaments that modify nutrient transport. Even other embodiments will have medicaments that activate the PP2A enzyme. In even other embodiments, the medicaments are capable of mis-localizing the enzyme Phosphoinositide Kinase, FYVE Finger-Containing (PIKfyve).

In many such embodiments, the modes of administration for the therapeutics include, but are not limited to, oral, transdermal, transmucosal (e.g., sublingual, nasal, vaginal or rectal), or parenteral (e.g., subcutaneous, intramuscular, intravenous, bolus or continuous infusion). The actual amount of drug needed will depend on factors such as the size, age and severity of disease in the afflicted individual. The actual amount of drug needed will also depend on the effective inhibitory concentration ranges of the various azacyclic constrained sphingolipid-like compounds. Different analogous compounds have different effective inhibitory concentration ranges, as shown and described in greater detail in Tables 1 to 6, below.

In some embodiments, the azacyclic constrained sphingolipid-like compounds are administered in a therapeutically effective amount as part of a course of treatment. As used in this context, to "treat" means to ameliorate at least one symptom of the disorder to be treated or to provide a beneficial physiological effect. For example, one such amelioration of a symptom could be inhibition of neoplastic proliferation. Assessment of neoplastic proliferation can be performed in many ways, including, but not limited to assessing changes in tumor diameter, changes in tumor bioluminescence, changes in tumor volume, changes in tumor mass, or changes in neoplastic cell proliferation rate.

A therapeutically effective amount can be an amount sufficient to prevent reduce, ameliorate or eliminate the symptoms of diseases or pathological conditions susceptible to such treatment, such as, for example, cancers like leukemia, prostate, colon, lung, pancreatic, or breast cancer, or diseases where oncogenic Ras mutations afford multiple metabolic advantages to transformed cells. In some embodiments, a therapeutically effective amount is an amount sufficient to reduce the transport of nutrients, such as, for example, glucose or amino acids, into cells.

Dosage, toxicity and therapeutic efficacy of the compounds can be determined, e.g., by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit high therapeutic indices are preferred. While compounds that exhibit toxic side effects may be used, care should be taken to design a delivery system that targets such compounds to the site of affected tissue in order to minimize potential damage to non-neoplastic cells and, thereby, reduce side effects.

Data obtained from cell culture assays or animal studies can be used in formulating a range of dosage for use in humans. If the medicament is provided systemically, the dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration or within the local environment to be treated in a range that includes the $IC_{50}$ (i.e., the concentration of the test compound that achieves a half-maximal inhibition of neoplastic growth) as determined in cell culture. Such information can be used to more accurately determine useful doses in humans. Levels in plasma may be measured, for example, by liquid chromatography coupled to mass spectrometry.

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a composition depends on the composition selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the compositions described herein can include a single treatment or a series of treatments. For example, several divided doses may be administered daily, one dose, or cyclic administration of the compounds to achieve the desired therapeutic result. A single azacyclic constrained sphingolipid-like small molecule compound may be administered, or combinations of various azacyclic constrained sphingolipid-like small molecule compounds may also be administered.

It is also possible to add agents that improve the solubility of these compounds. For example, the claimed compounds can be formulated with one or more adjuvants and/or pharmaceutically acceptable carriers according to the selected route of administration. For oral applications, gelatin, flavoring agents, or coating material can be added. In general, for solutions or emulsions, carriers may include aqueous or alcoholic/aqueous solutions, emulsions or suspensions, including saline and buffered media. Parenteral vehicles can include sodium chloride and potassium chloride, among others. In addition, intravenous vehicles can include fluid and nutrient replenishers, electrolyte replenishers and the like.

Preservatives and other additives, like antimicrobial, antioxidant, chelating agents, and inert gases, can also be present. (See generally, Remington's Pharmaceutical Sciences, 16th Edition, Mack, (1980), the disclosure of which is incorporated herein by reference.)

Anti-Proliferative Activity of Immunosuppressant Compound FTY720

FTY720, the chemical structure of which is illustrated in FIG. 2, is a well-known immunosuppressant. When employed as an immunosuppressant, FTY720 is a prodrug that requires in vivo phosphorylation. Once phosphorylated, FTY720 acts as a functional antagonist by activating and then down-regulating S1P receptors to sequester lymphocytes to secondary lymphoid tissues. By sequestering the lymphocytes, FTY720 suppresses the immune system by removing these immune cells out of the blood circulation.

FTY720 is also a potent anti-proliferative agent. (Lee, T. K., et al. (2005) *Clin. Cancer Res.* 11, 8458-8466; Azuma, H., et al. (2002) *Cancer Res.* 62, 1410-1419; Chua, C. W., et al. (2005) *Int. J. Cancer,* 117, 1039-1048; Azuma, H., et al. (2003) *J. Urol.* 169, 2372-2377; Neviani, P., et al. (2007) *J. Clin. Invest.* 117, 2408-2421; the disclosures of which are incorporated herein by reference). In recent years, scientists have begun to propose FTY720 for use as an anticancer agent (See, e.g., Byrd, J. C. et al., US 2013/0123366, the disclosure of which is incorporated herein by reference.) Although effective in animal models, FTY720 cannot be used in human cancer patients because the active, phosphorylated form triggers profound bradycardia through actions on S1P receptor 1 and S1P receptor 3. (Camm, J., et al. (2014) *Am. Heart J.* 168, 632-644; Cohen, J. A., (2011) *Ann. Neurol.* 69, 759-777; Sanna, M. G., et al. (2004) *J. Biol. Chem.* 279, 13839-13848, the disclosure of which are incorporated herein by reference). This S1P receptor activation has eliminated the utility of FTY720 as an anticancer drug.

FTY720 is a successful, FDA-approved drug registered under the name fingolimod (brand name Gilenya) for the treatment of multiple sclerosis (MS). At the dose used to treat MS, FTY720 has been shown to be well tolerated. For the treatment of cancer, however, elevated doses of FTY720 are required to be effective. This requisite amount of FTY720 has been shown to cause bradycardia via the activation of S1P receptors 1 and 3. (See, e.g., Lee, T. K. et al., *Clin. Cancer Res.* 2005, 11, 8458-8466; Azuma, H. et al., *Cancer Res.* 2002, 62, 1410-1419; Chua, C. W. et al., *Int. J. Cancer* 2005, 117, 1039-1048; Azuma, H. et al., *J. Urol.* 2003, 169, 2372-2377; Neviani, P. et al., *J. Clin. Invest.* 2007, 117, 2408-2421. Sanna, M. G., et al., *J. Biol. Chem.* 2004, 279, 13839-13848; and Koyrakh, L., et al., *Am. J. Transplant.* 2005, 5, 529-536; the disclosures of which are incorporated herein by reference.) Thus, despite FTY720's potential to treat cancer, the dose-limiting bradycardia side-effect renders it untenable for cancer treatment. Recently, scientists published that FTY720 can treat neoplastic cells independent of S1P receptor activation. (Romero Rosales, K., et al. (2011). *Biochem. J.* 439, 299-311, the disclosure of which are incorporated herein by reference.) It was found that FTY720 induces a starvation-like death secondary to the down-regulation of plasma membrane transporters for amino acids and glucose through a mechanism that involves protein phosphatase 2A activation (PP2A). This suggests that sphingolipid-like molecules that do not activate S1P receptors but retain the ability to reduce nutrient transporter expression may be safe and effective anti-cancer agents.

It is well known in the field that all living cells express transporters to provide themselves with nutrients, such as glucose and amino acids, from the extracellular environment. Thus, inhibition of nutrient transporters of neoplastic cells would also likely have an effect on non-neoplastic, healthy cells. This effect could be detrimental or even toxic to healthy cells. Nevertheless, targeting the nutrient transporter systems of neoplastic cells remained an intriguing, although risky, experimental hypothesis to attack cancer and other neoplasms.

One treatment possibility to target neoplastic nutrient transporters is to use competitive inhibitors (e.g., phloretin). Competitive inhibitors of nutrient transport, however, are poor anti-cancer drug candidates as they must reach millimolar concentrations to be effective. Targeting the evolutionarily conserved pathways that regulate nutrient transporter trafficking, on the other hand, may be feasible. For example, yeast down-regulate amino acid transporters when treated with the sphingolipid phytosphingosine, triggering an adaptive growth arrest (Chung, N., et al. J. *Biol. Chem.* 276, 35614-21 (2001), the disclosure of which is incorporated herein by reference). Ceramide, a naturally occurring sphingolipid, and the FDA-approved drug FTY720, also down-regulate nutrient transporters and induce starvation in mammalian cells (Guenther, G. G. et al. *Proc. Natl. Acad. Sci. U. S. A* 105, 17402-7 (2008); Romero Rosales, K. et al. *Biochem. J.* 439, 299-311 (2011). Welsch, C. A., et al. J. *Biol. Chem.* 279, 36720-36731 (2004); Azuma, H. et al. *Cancer Res.* 62, 1410-1419 (2002); Pchejetski, D. et al. *Cancer Res.* 70, 8651-8661 (2010). Neviani, P. et al. J. *Clin. Invest.* 117, (2007); Chua, C. W. et al. *Int. J. Cancer* 117, 1039-48 (2005). Lee, T. K. et al. *Clin. Cancer Res.* 11, 8458-8466 (2005); the disclosures of which are incorporated herein by reference). Although transporter loss slows tumor growth, activation of macropinocytosis and autophagy pathways would provide resistance to sphingolipid-induced starvation, particularly in tumors with activated Ras where both these pathways are up-regulated. (Commisso, C. et al., *Nature* 497, 633-7 (2013); White, E. *Genes Dev.* 27, 2065-2071 (2013); the disclosures of which are incorporated herein by reference). Hence, desirable anti-neoplastic compounds targeting nutrient uptake have been difficult to discover as the mechanism is complicated and the compounds may need to target multiple nutrient transporter pathways to slow neoplastic growth, which may include down-regulating expression of nutrient transporters as well as blocking micropinocytosis and autophagy pathways as well as other mechanisms of nutrient acquisition.

Other Sphingolipid-Like Compounds

In a previous study, a series of 2,3,5-trisubstituted pyrrolidines were prepared as constrained azacyclic analogues of FTY720 represented by a generic pyrrolidine core scaffold A (FIG. 23) (Hanessian, S., et al. (2007) *Bioorg. Med. Chem. Lett.* 17, 491-494, the disclosure of which is incorporated herein by reference). These phosphorylated versions of (2R,3R,5R)-2,5-bis-hydroxymethyl-3-(4-octyl)phenyl pyrrolidine (compound 1) and the corresponding enantiomer (compound 2) exhibited a remarkable selectivity for S1P4 and S1P5 over S1P1 and S1P3 compared to FTY720 phosphate. This observation affirmed that chemical modification of the conformationally flexible aminodiol portion of FTY720 could lead to selective affinities towards S1P receptors (Clemens, J. J., et al. (2005) *Bioorg. Med. Chem. Lett.* 15, 3568-3572; Davis, M. D., et al. (2005) *J. Biol. Chem.* 280, 9833-9841; Zhu, R., et al. (2007) *J. Med. Chem.* 50, 6428-6435; Forrest, M., et al. (2004) *J. Pharmacol. Exp. Ther.* 309, 758-768; the disclosures of which are incorporated herein by reference).

Figure 24:
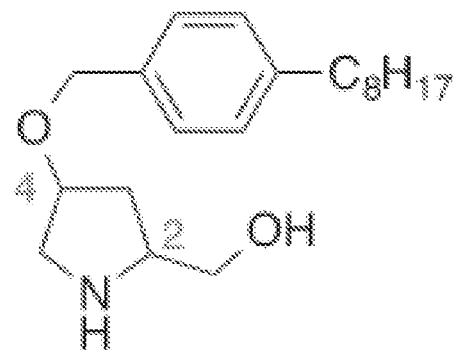
Figure 24:
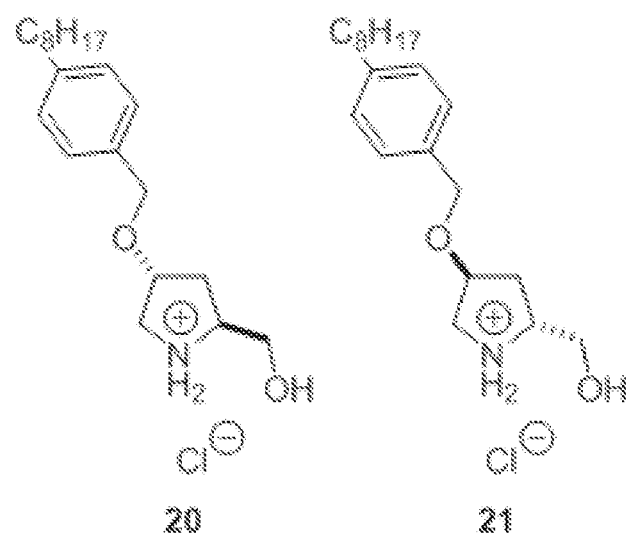

Another study reported on synthetically more accessible constrained analogues of FTY720 in a series of stereochemically distinct 2-hydroxymethyl 4-O-arylmethyl pyrrolidines which exhibited remarkable anti-leukemic activity in BCR-Abl-expressing cell lines as exemplified by the (2R,4S)-analogue B (FIG. 24) (Fransson, R., et al. (2013) *ACS. Med. Chem. Lett.* 4, 969-973, the disclosure of which is incorporated herein by reference). A stereochemical dependence was shown, since the enantiomeric (2S,4R)-diastereomer was six times less active. However, this series of constrained FTY720 analogues exhibited much weaker activity against other types of cancer cell lines including many derived from solid tumors.

Mechanism of C-Aryl Constrained Pyrrolidine Compounds

Accordingly, in sharp contrast to previous studies, safe and effective anticancer agents based on C-aryl constrained pyrrolidine analog series that do not implicate FTY720's S1P receptor-related, dose-limiting toxicity are presented as embodiments of the invention. In particular embodiments, it has been discovered that C-aryl pyrrolidines as constrained azacyclic sphingolipid-like molecules, are promising inhibitors of neoplastic growth. Embodiments are thus directed to C-aryl pyrrolidines as constrained azacyclic sphingolipid-like molecules as potent inhibitors of proliferation that do not activate S1P receptors. Furthermore, embodiments of the invention, particularly compound SH-BC-893, are novel anti-neoplastic sphingolipid-like compounds that lack the pharmacologic liabilities of ceramide and FTY720. Embodiments of the invention affect anticancer activity by simultaneously blocking lysosomal fusion reactions that are essential for LDL, macropinosome, and autophagosome degradation and down-regulating glucose and amino acid transporters from the cell surface.

Figure 25:
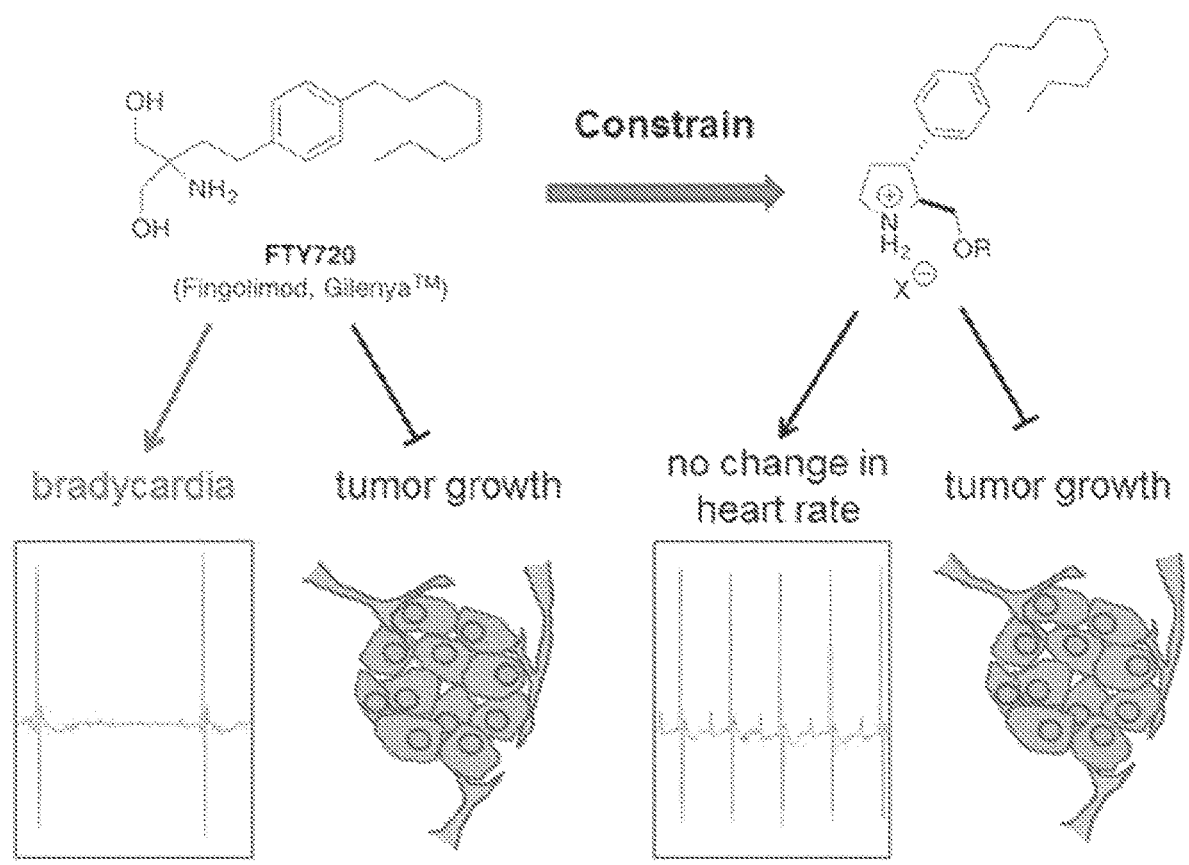
FIGS. 25 to 27 provide schematics describing aspects of therapeutic small molecule analogs' mechanism of action in accordance with various embodiments of the invention.

Prior art molecules, such as FTY720, have been found to inhibit neoplastic growth and cause severe bradycardia (FIG. 25). C-aryl azacyclic constrained sphingolipid-like compounds, on the other hand, inhibit neoplastic growth but do not stimulate bradycardia symptoms. It is now known that activation of S1P receptors at high doses of FTY720 stimulates the bradycardia phenotype. Certain sphingolipid-like molecules with constrained pyrrolidines do not activate S1P receptors and thus, these molecules do not cause bradycardia (FIGS. 25 and 34-36). As such, embodiments of the invention are directed to constrained pyrrolidine moieties of sphingolipid-like molecules that prevent the activation of S1P receptors.

Figure 26:
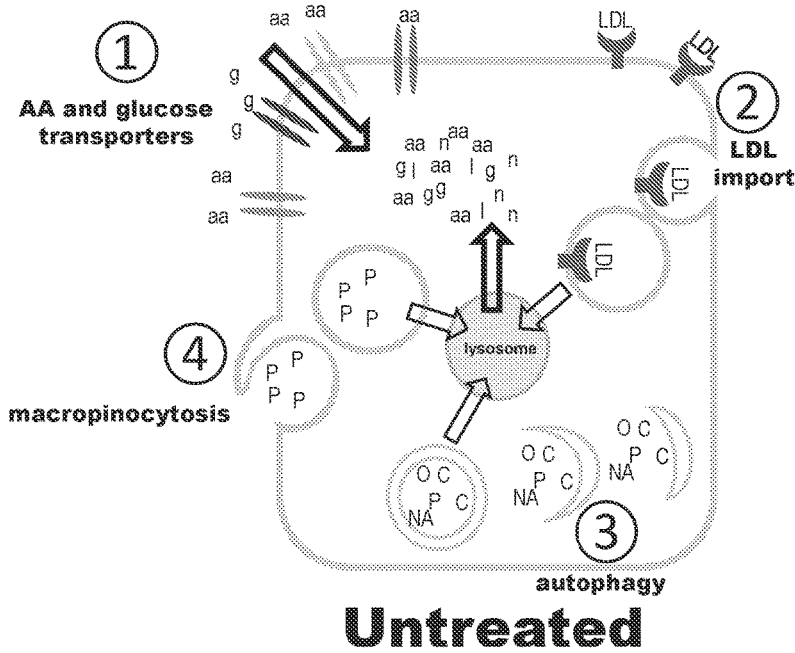
Figure 26:
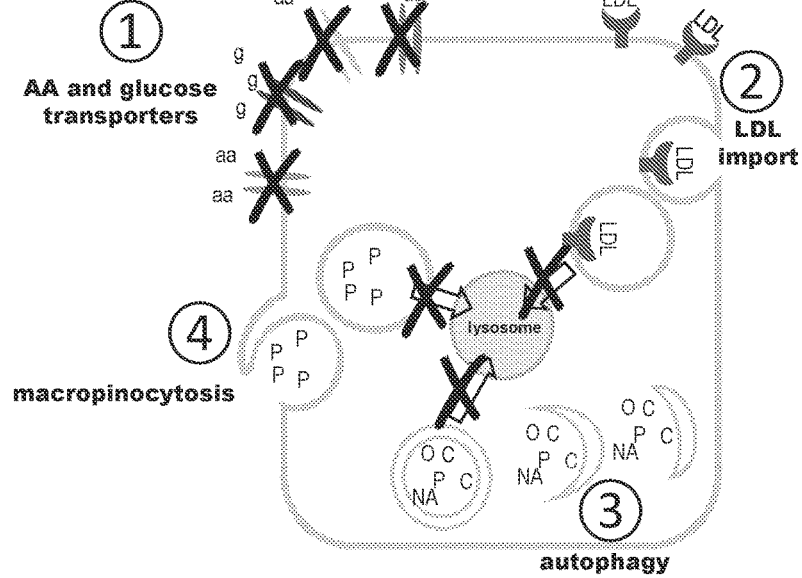

C-aryl azacyclic constrained sphingolipid-like compounds and FTY720 inhibit and kill neoplasms independent of S1P activation by a bioenergetic mechanism. In this mechanism, the sphingolipid-like compounds starve the neoplastic cells to death by preventing access to key nutrients and biofuels, such as glucose and amino acids (FIG. 26). Accordingly, many embodiments of the invention are directed to azacyclic constrained sphingolipid-like compounds that starve neoplastic cells of key nutrients and amino acids.

Neoplastic cells are able to acquire nutrients by several different pathways. These pathways include nutrient passage across the cell membrane by amino acid or glucose transport channels (1), low-density lipoprotein (LDL) import via LDL receptors (2), autophagy (3), and macropinocytosis (4) (FIG. 26). Thus, multiple embodiments of the invention are directed to constrained sphingolipid-like molecules as a treatment that prevents nutrient access by nutrient transporters, LDL endocytosis, autophagy, or macropinocytosis.

Figure 27:
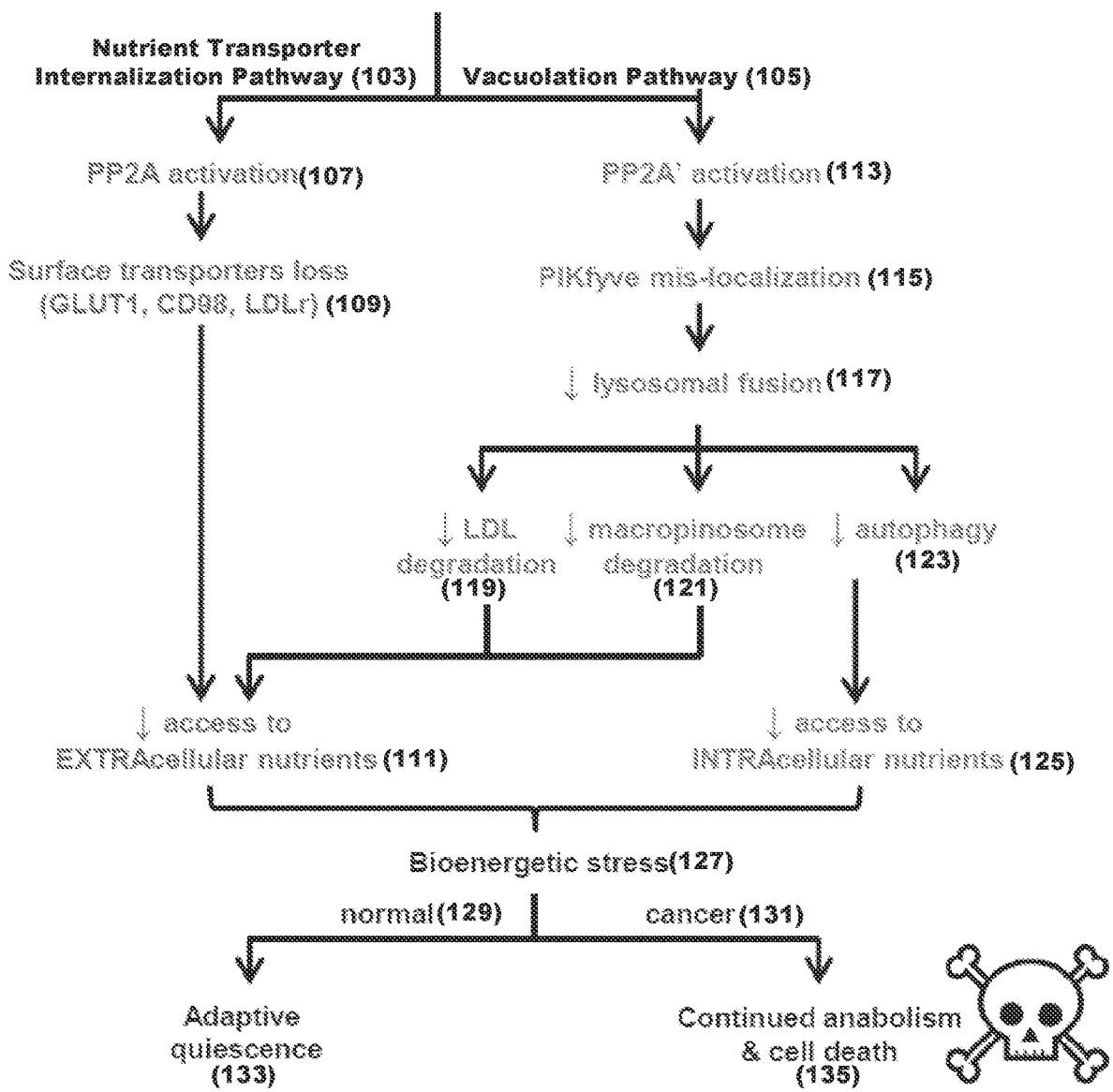

A detailed graphic of the bioenergetic mechanism is depicted in FIG. 27. As shown, azacyclic constrained sphingolipid-like molecules (101) can stimulate two parallel pathways: the Nutrient Transporter Internalization Pathway (103) and/or the Vacuolation Pathway (105). Overall, both pathways eventually lead to a decrease in intracellular nutrients (111) & (125) that causes treated cells to experience bioenergetic stress (127). Different cell types, however, react to the stress differently. Healthy, normal cells (129) become quiescent (133), and simply adapt to the lower nutrient rate. Transformed, neoplastic cells (131), however, are "addicted" to high levels of nutrients and thus unable to adapt to the bioenergetics stress. These neoplastic cells continue to attempt to synthesize macromolecules despite the lack of nutrients, eventually undergoing cell death when reserves are depleted (133).

The Nutrient Transporter Internalization Pathway (103) and Vacuolation Pathway (105) each begin with an azacyclic constrained sphingolipid-like molecule activating a PP2A complex (107) & (113). Because these pathways are distinct, it is believed that the activated PP2A complex is different for the two pathways. PP2A is a heterotrimeric complex with more than 90 isoforms, and thus it's very possible that sphingolipid-like molecules could stimulate different PP2A complexes that, in turn, trigger two distinct pathways.

In the Nutrient Transport Internalization Pathway (103), PP2A activation (107) directly leads to loss of nutrient transporters from the cell surface (109). This loss of transporters reduces the availability of nutrients, such as glucose and amino acids, from the extracellular space (111). The reduction of available nutrients contributes, at least in part, to the bioenergetic stress (127).

In the parallel Vacuolation Pathway (105), PP2A activation (113) can cause the kinase PIKfyve to mis-localize (115). Thus, PIKfyve does not associate with the cell's multivesicular bodies, decreasing lysosomal fusion (117) with LDL vesicles, macropinosomes, and autophagosomes. Consequently, the lack of lysosomal fusion decreases LDL degradation (119), macropinosome degradation (121), and autophagy (123), which, in turn, decreases the cell's access to the respective extracellular (111) and intracellular (125) nutrients. Again, the reduction of available nutrients contributes to the bioenergetic stress (127).

By understanding the bioenergetic stress mechanism, one would be able to discern that C-aryl azacyclic constrained sphingolipid-like compounds are capable of treating any and all cancer types and classes. One hallmark that is consistent among all neoplasms is an inflexible commitment to anabolism. Thus, it is expected that any cancer class, including, but not limited to neoplasms that are characterized as slow-growing, fast-growing, aggressive, malignant, Ras-positive, PTEN-negative, benign, metastatic, nodular, autochthonous, solid tumors or blood cancers, are sensitive to azacyclic constrained sphingolipid-like compounds. As such, it is expected that the molecules are effective against almost all cancerous tissue, including, but not limited to, leukemia, prostate cancer, colon cancer, pancreatic cancer, or breast cancer. Furthermore, the described sphingolipid-like compounds should overcome complications of neoplastic heterogeneity across, and within, patients. Overcoming heterogeneity will also reduce drug resistance common to many current treatments that are specific to a tumor genotype.

In addition to neoplastic disorders, the bioenergetic stress model would predict that C-aryl azacyclic constrained sphingolipid-like compounds could treat certain metabolic disorders. In particular, disorders of excessive nutrient acquisition, such as, for example, obesity, could be treated with these compounds. It would be expected that by limiting nutrient uptake in cells, a patient would lose excessive weight. It is fully expected that the C-aryl azacyclic constrained sphingolipid-like compounds are effective in human patients. As described in the exemplary embodiments infra, the sphingolipid-like compounds are effective on multiple human neoplastic cell lines, cell-line xenografts in mice, and autochthonous tumors in mice. Because of the success in each of these models as well as in patient-derived cancer organoids and patient-derived cancer xenografts in mice, it is expected these molecules will also eventually be successful in human clinical trials. Furthermore, it is expected that these compounds can be combined with and improve the efficacy of other cancer treatments or medicaments, including, but not limited to an FDA-approved standard of care, methotrexate, gemcitabine, tamoxifen, taxol, docetaxel, and enzalutamide.

In accordance with the bioenergetic mechanism, many embodiments of the invention are directed to azacyclic constrained sphingolipid-like compounds capable of killing neoplastic cells due to increased stress. In other embodiments, the sphingolipid-like compounds are not toxic to normal, healthy cells. In more embodiments, the sphingolipid-like compounds stimulate the Nutrient Transport Internalization Pathway and/or the Vacuolation pathway. Embodiments of the invention are directed to sphingolipid-like compounds capable of reducing cellular access to extracellular or intracellular nutrients. More specific embodiments are directed to these compounds capable of decreasing the amount of surface nutrient transporters, LDL degradation, macropinosome degradation, or autophagy. Furthermore, other embodiments are directed to PP2A activation, PIKfyve mislocalization, or a decrease of lysosomal fusion.

In sum, the C-aryl azacyclic constrained sphingolipid-like compounds described herein fight cancer and neoplasms without the lethal side-effects inherent to other approaches in the field, and which make the use of FTY720 as an anticancer agent effectively untenable. Accordingly, presented below are embodiments of small molecule azacyclic constrained sphingolipid-like molecules, therapeutics based on such small molecules, and treatment regimens incorporating such therapeutics for use in treating cancer and other disorders.

EXEMPLARY EMBODIMENTS

Biological data supports the use of the aforementioned azacyclic constrained sphingolipid-like compounds in a variety of embodiments to treat disease. Previous studies have established that chemical modifications to the flexible aminodiol portion of FTY720 influence the selective binding to S1P receptors. (Clemens, J. J. et al., Davis et al., Zhu et al., and Forrest et al., cited above.) It is noted that embodiments of azacyclic constrained analogs of FTY720, in accordance with the disclosure, kill and/or inhibit the growth of neoplastic cells with reduced risk of lethal side effects like bradycardia. Accordingly, embodiments using these compounds to treat various diseases avoid the pitfalls associated with prior approaches. As will be discussed, data supports the proposition that small molecule azacyclic constrained sphingolipid-like molecules embodiments according to the disclosure are superior to existing FTY720-related molecules and related treatment methods.

The expected therapeutic efficacy of the azacyclic constrained sphingolipid-like small molecule embodiments stems from its demonstrated biological activity in preliminary studies using PC3 and DU15 prostate cancer cells. Additional studies demonstrated biological activity of the azacyclic constrained sphingolipid-like small molecule embodiments using SW-620 and SW-480 colon cancer cells, A-549 lung cancer cells, PANC-1 pancreatic cancer cells, MDA-MB-231 breast cancer cells, and Sup-1315 leukemia cells. As discussed below, minor chemical and structural modifications, including changes to charge on the nitrogen in the pyrrolidine and loss of phosphorylation sites, have varying effects on the activity of the molecules. Changes to charge on the nitrogen in the pyrrolidine (lactam) led to a loss of activity. Loss of phosphorylation sites had a slight effect on activity. Thus, non-lactam analogs still show therapeutic advantages over the FTY720 control. Embodiments of azacyclic constrained sphingolipid-like compounds slow tumor growth and kill cancer cells at least by blocking lysosomal fusion reactions that are essential for macropinosome and autophagosome degradation and down-regulating glucose and amino acid transporters from the cell surface.

Figure 28:
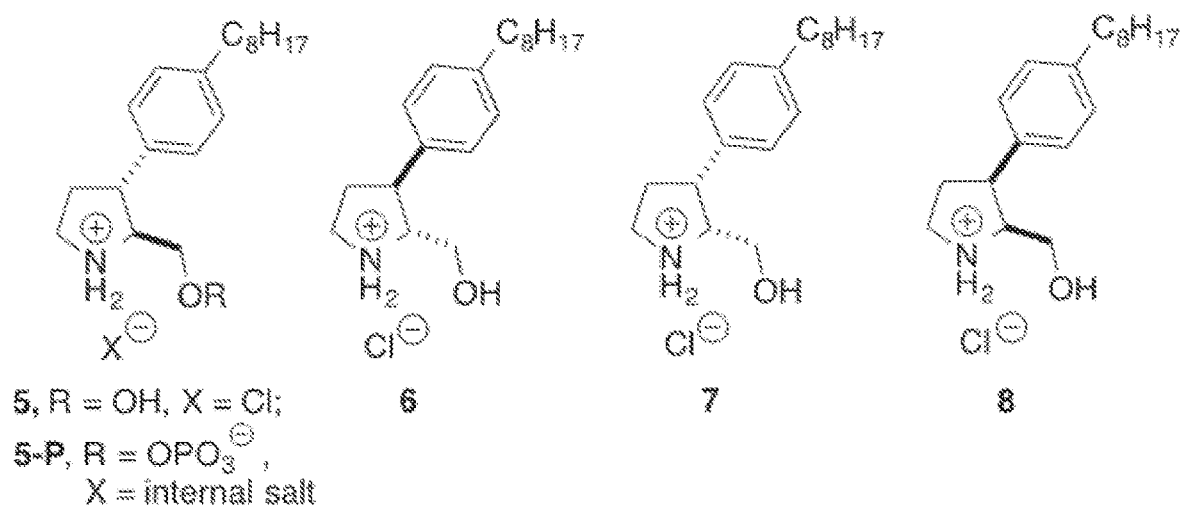
FIG. 28 provides molecular structures of therapeutic small molecule analogs in accordance with various embodiments of the invention.
Figure 29:
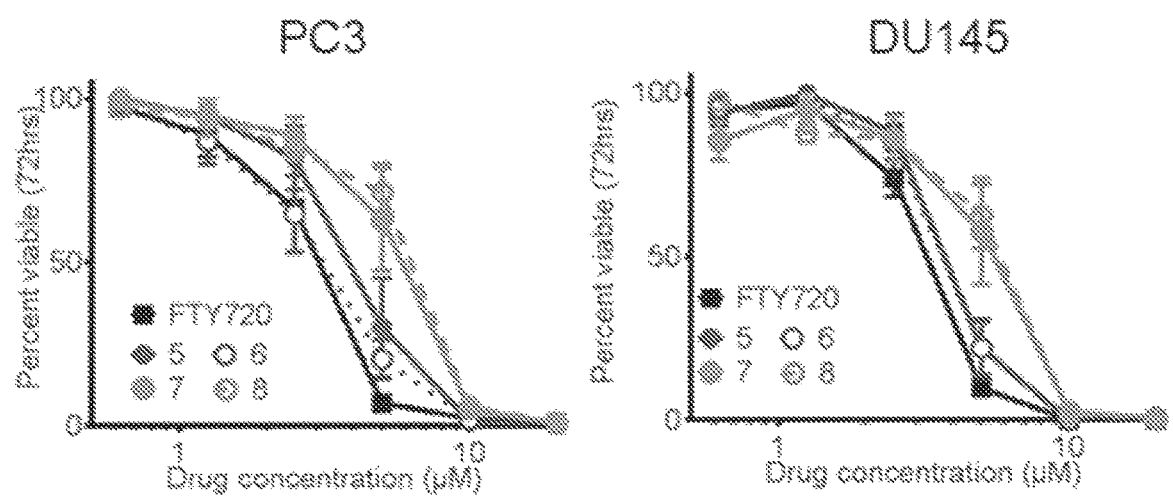
FIG. 29 provides data plots summarizing studies of the influence of the stereochemistry influence of aryl relative to hydroxymethyl on the ability of therapeutic small molecule analogs to kill prostate cancer cells in accordance with various embodiments of the invention.

Optimization of Azacyclic Constrained Sphingolipid-Like Compounds and Effects on Cancer Cells:

In a first embodiment, cell culture assays were carried out to demonstrate the killing capabilities of different small molecules. Previously presented compounds 1-4 (FIG. 23), compounds 5-8 (FIG. 28), and control compound FTY720 (FIG. 2) were used to treat the well-established PC3 and DU145 prostate cancer lines (FIG. 29 and Table 1). A Cell Titer Glo assay was performed to measure proliferation of the cancer lines. As indicated in Table 1, compounds 1-8 are each able to retain its anticancer activity.

TABLE 1

IC$_{50}$ values (µM) in prostate cancer cell lines.
(Mean ± SEM, n ≥ 3)

|        | PC3        | DU145      |
|--------|------------|------------|
| FTY720 | 2.6 ± 0.2  | 3.1 ± 0.2  |
| 1      | 7.0 ± 0.3  | 7.3 ± 0.8  |
| 2      | 6.1 ± 1.0  | 5.7 ± 0.4  |
| 3      | 4.9 ± 0.6  | 5.3 ± 0.2  |
| 4      | 3.4 ± 0.6  | 4.0 ± 0.6  |
| 5      | 4.0 ± 0.7  | 3.8 ± 0.4  |
| 6      | 3.0 ± 0.4  | 3.7 ± 0.4  |
| 7      | 5.5 ± 0.7  | 5.3 ± 0.7  |
| 8      | 6.5 ± 0.3  | 5.4 ± 0.3  |
| 9      | >20        | >20        |
| 10     | >20        | >20        |
| 11     | >20        | >20        |
| 12     | 4.1 ± 0.4  | 5.0 ± 0.1  |
| 13     | 4.4 ± 0.6  | 5.1 ± 0.6  |
| 14     | 1.9 ± 0.3  | 5.6 ± 0.1  |
| 15     | 6.3 ± 0.3  | 5.9 ± 0.3  |
| 16     | 6.3 ± 0.1  | 4.9 ± 0.1  |
| 17     | 6.6 ± 0.1  | 5.8 ± 0.2  |
| 18     | 14.4 ± 0.9 | 17.6 ± 2.3 |
| 19     | 9.8 ± 1.3  | 10.6 ± 1.0 |
| 20     | 8.0 ± 0.9  | 6.1 ± 0.5  |

Compounds 5-8 are truncated versions of compounds 1-4, which do not contain the 5-hydroxymethyl group. This structural version did not diminish the activity of compounds 1-4, since compounds 5 and 6 were as active as FTY720 in prostate cancer cell lines. These findings also suggest that stereochemistry in this series of C-aryl analogues is not important for interaction with the anticancer target.

Figure 30:
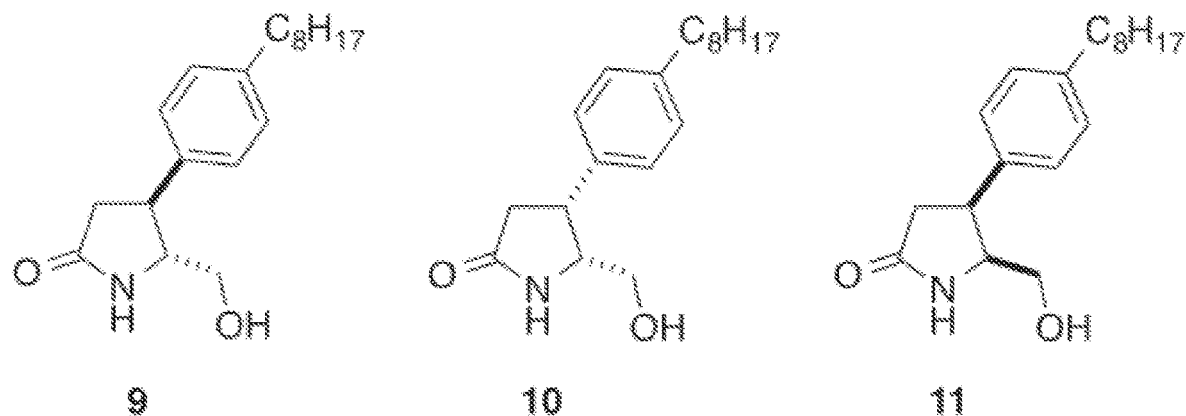
FIG. 30 provides molecular structures of therapeutic small molecule analogs in accordance with various embodiments of the invention.
Figure 31:
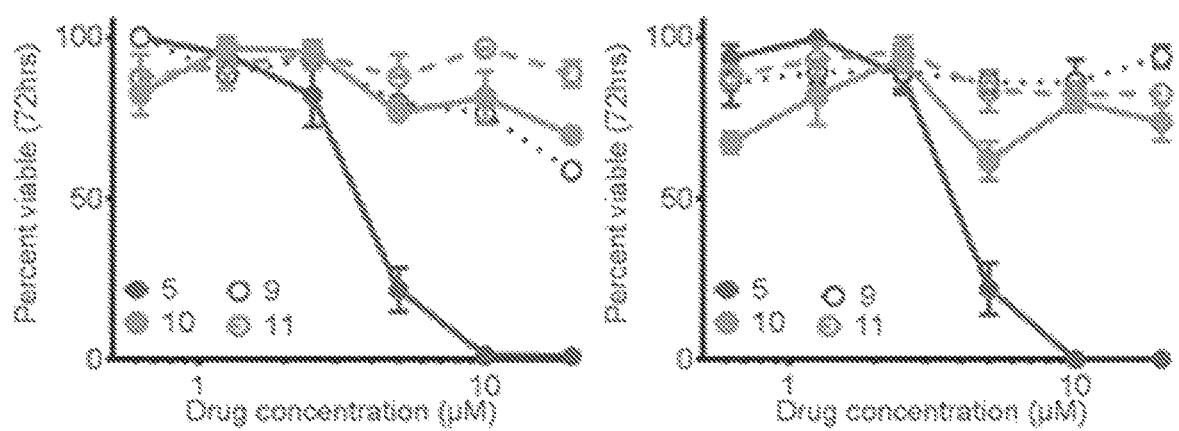
FIG. 31 provides data plots summarizing studies of the effect of charge on the nitrogen of the pyrrolidine ring on the ability of therapeutic small molecule analogs to kill prostate cancer cells in accordance with various embodiments of the invention.

In another exemplary embodiment, further cell culture assays were carried out to determine whether the charge on the nitrogen in the pyrrolidine ring was important for activity. In particular, lactam-ring containing compounds 9-11 (FIG. 30) were compared with corresponding to analogues 6-8 (FIG. 28) in the prostate cancer cell proliferation assay. As indicated in FIG. 31 and Table 1, neutralizing the charge of the nitrogen in the pyrrolidine resulted in dramatic loss of activity, suggesting that electrostatic interaction with target may be critical for compound activity.

Figure 32:
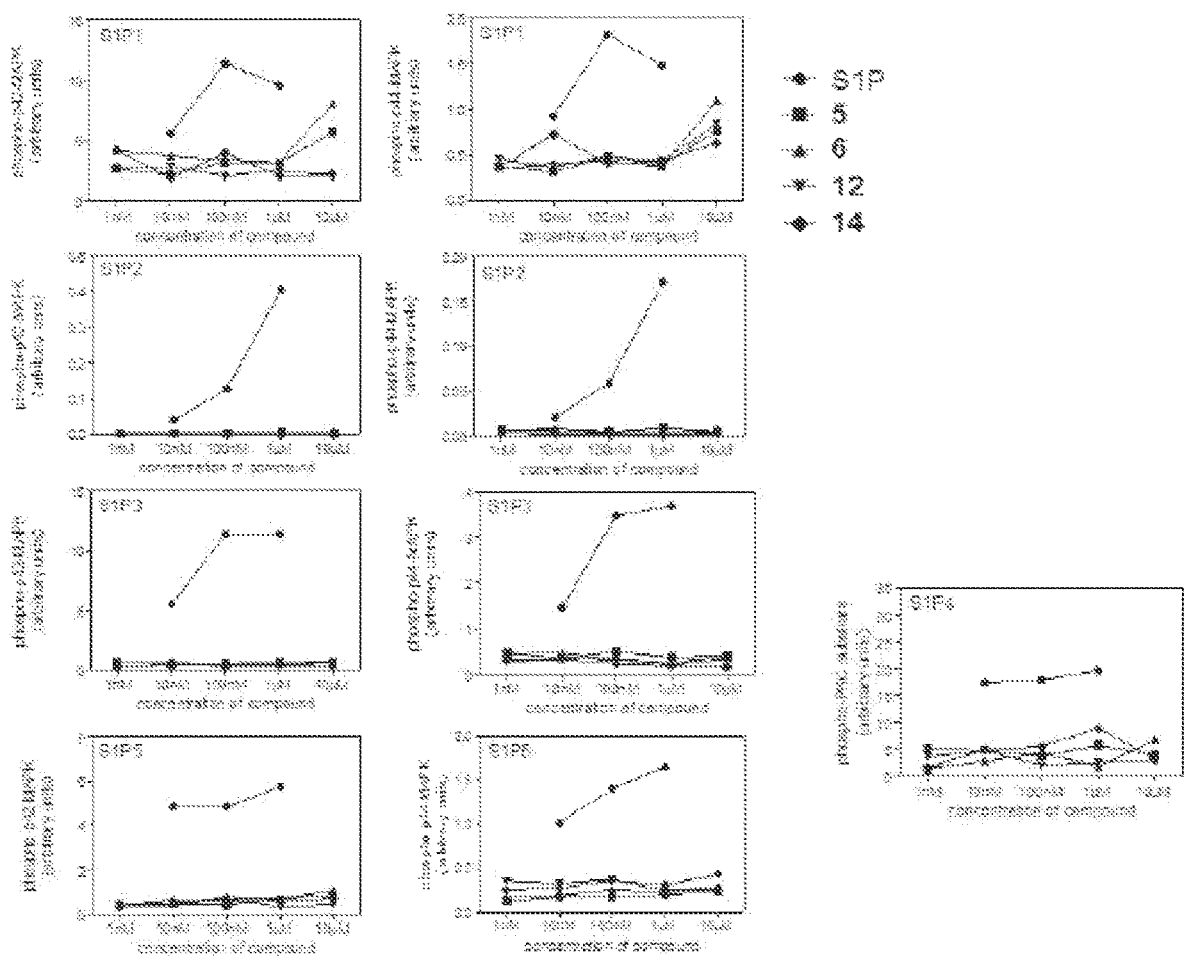
FIG. 32 provides data plots summarizing studies of the effect of therapeutic small molecule analogs on S1P receptor activation in accordance with various embodiments of the invention.

In even another exemplary embodiment, cell culture assays were carried out to demonstrate the effects of phosphorylation on S1P receptor activity. Phosphorylation may have effects on S1P receptor activity that could cause bradycardia. Bradycardia, the dose-limiting toxicity that prevents the use of FTY720 in cancer patients, stems from FTY720-P's actions on S1P receptors 1 and 3. (Camm, J., et al. (2014) *Am. Heart J.* 168, 632-644; Cohen, J. A., Chun, J. (2011) *Ann. Neurol.* 69, 759-777; Sanna, M. G., et al. (2004) *J. Biol. Chem.* 279, 13839-13848; the disclosures of which are incorporated herein by reference). Phosphorylation by sphingosine kinase may make compounds competent to activate S1P receptors. FTY720, for example, when phosphorylated is known to activate S1P receptors 1 and 3. Because compound 5 could be phosphorylated, the activity of compound 5 and its phosphate 5-P (FIG. 28) on S1P receptors was evaluated (FIG. 32). As expected, the positive control S1P activated all its receptors (1-5) at nanomolar concentrations. In contrast, exemplary embodiments of the azacyclic constrained sphingolipid-like molecules in accordance with various embodiments do not or only weakly activate S1P receptors. In particular, cell culture-based assays indicate that analogues 5, 5-P, and 6 failed to activate S1P receptors 2, 3, 4, or 5 (FIG. 32). S1P receptor 1 was weakly activated but only at 1000-fold higher doses (>1 uM) than the S1P control. These results were unexpected, considering other C-aryl constrained sphingolipid-like compounds have been shown to stimulate S1P receptors in previous reports (Hanessian, S., et al. (2007) *Bioorg. Med. Chem. Lett.* 17, 491-494, cited above). These results demonstrate that the current embodiments of sphingolipid-like compounds lack the S1P receptor activity that precludes the use of FTY720 and other sphingolipid-like compounds to treat neoplasms.

Figure 33:
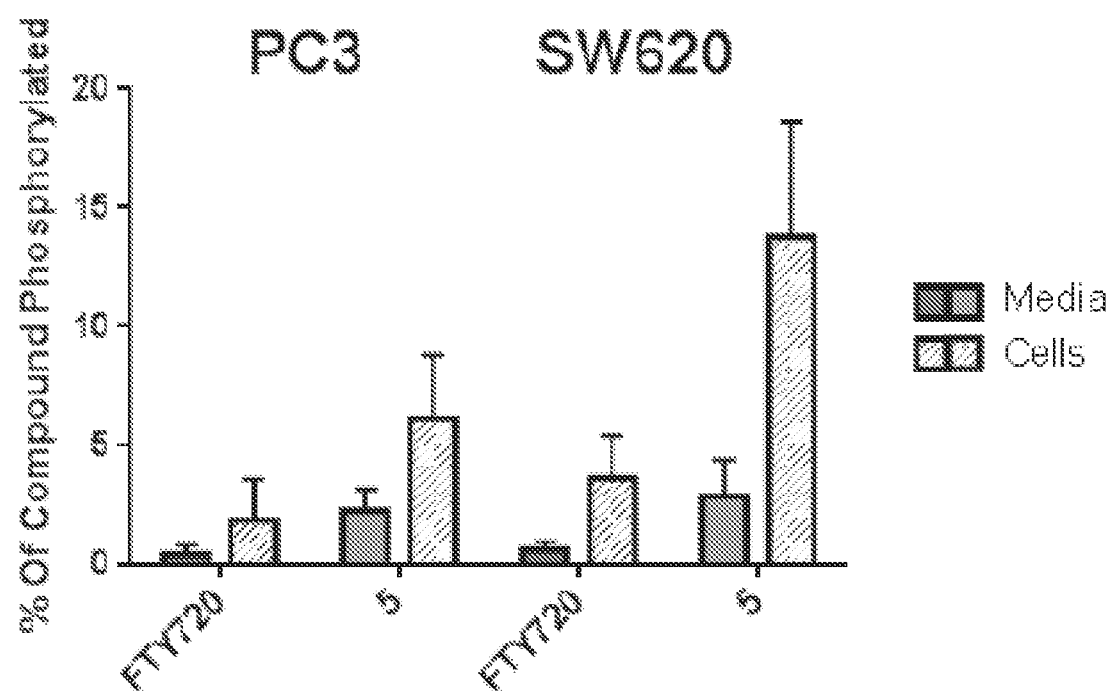
FIG. 33 provides a data plot summarizing studies of the efficiency of phosphorylation of compound 5 relative to FTY720 in intact cells in vitro.
Figure 34:
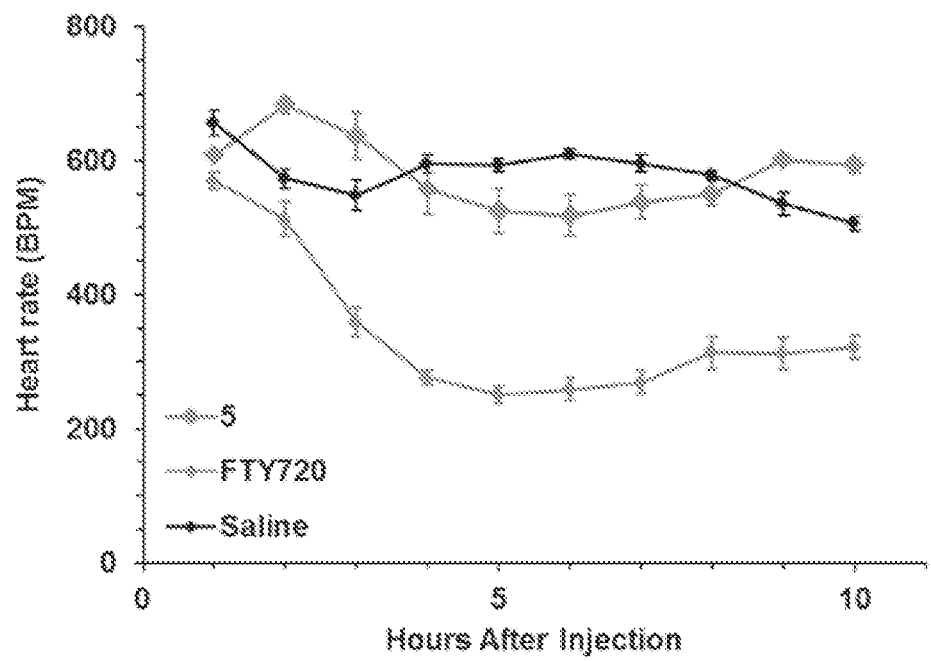
FIGS. 34 and 35 provide a data plot summarizing studies of the effect of therapeutic small molecule analogs on heart rate in accordance with various embodiments of the invention.
Figure 35:
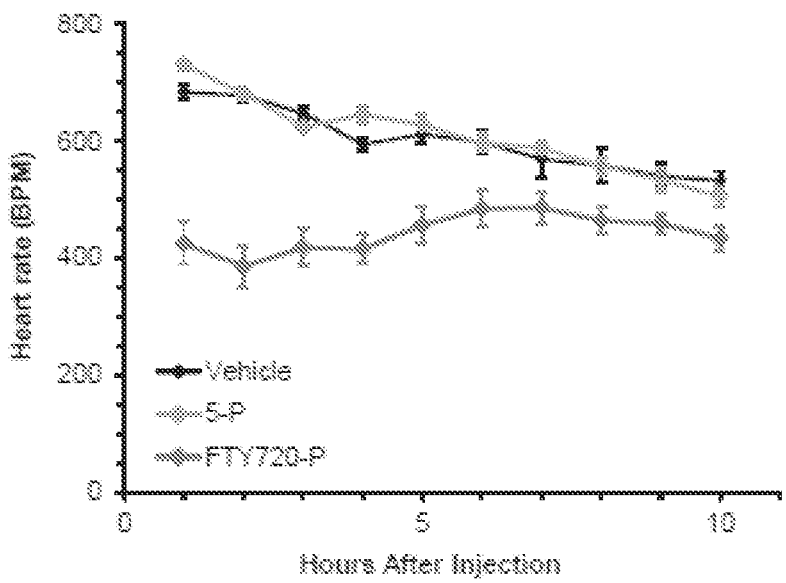

In a further exemplary embodiment, in vitro studies show that analogue 5 is phosphorylated slightly more efficiently than FTY720 in PC3 and SW620 cells and exported into the medium (FIG. 33, phosphorylated compounds in prostate (PC3) or colon cancer (SW620) cells after a 16 h incubation expressed as the percent of total compound recovered by UPLC-MS/MS). This further demonstrates that loss of S1P receptor activation is not the result of inefficient phosphorylation.

In more exemplary embodiments, compounds 5 and 5-P were further examined for their ability to activate multiple S1P receptors in vivo. In particular, mouse heart rate and lymphocyte sequestration were examined. Mouse heart rate decreases causing bradycardia when S1P receptor 3 is activated while in humans this effect may be mediated by S1P receptor 1. In both mice and humans, lymphocytes are sequestered when the S1P receptor 1 is activated. As expected, both the pro-drug FTY720 and the activated drug FTY720-P decreased heart rate approximately 50% and significantly sequestered lymphocytes compared to saline vehicle (FIGS. 34-37). Compounds 5 and 5-P, on the other hand, had no significant effect on heart rate or lymphocyte sequestration compared to saline controls (FIGS. 34-37).

Figure 36:
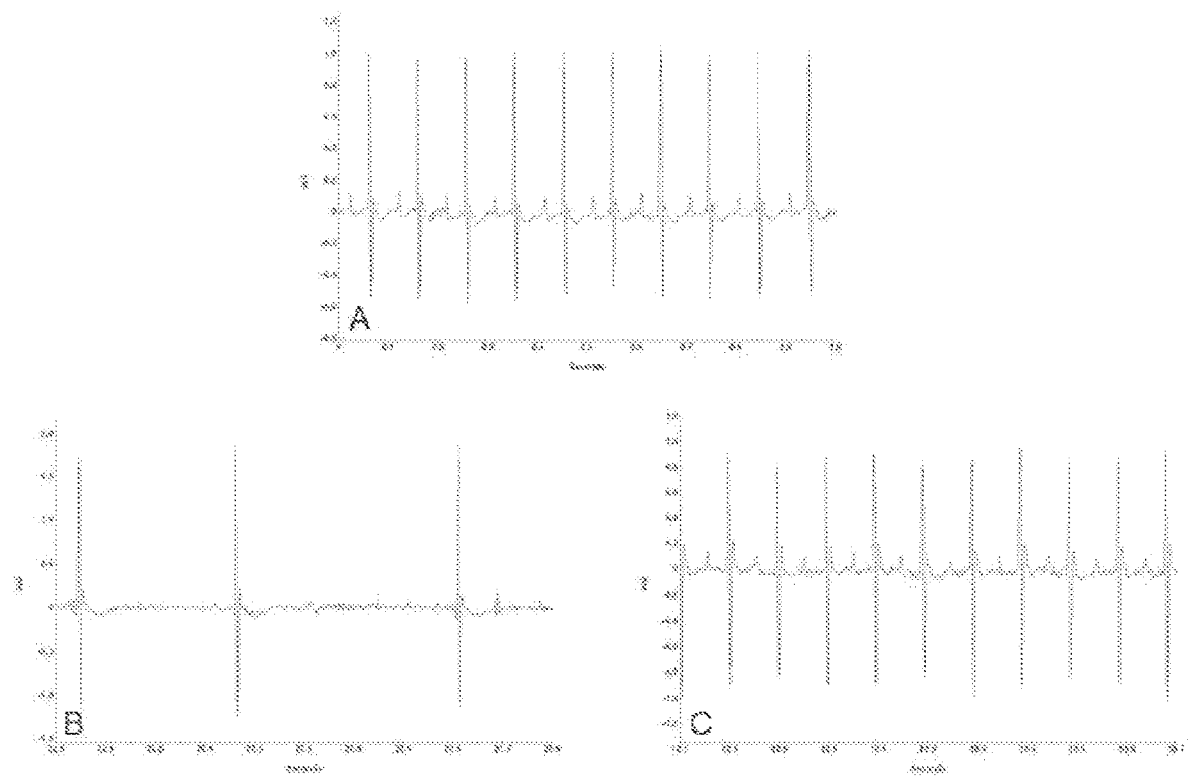
FIG. 36 provides a telemetry reading showing the effect of the therapeutic small molecule analogs on heart rate in accordance with various embodiments of the invention.
Figure 37:
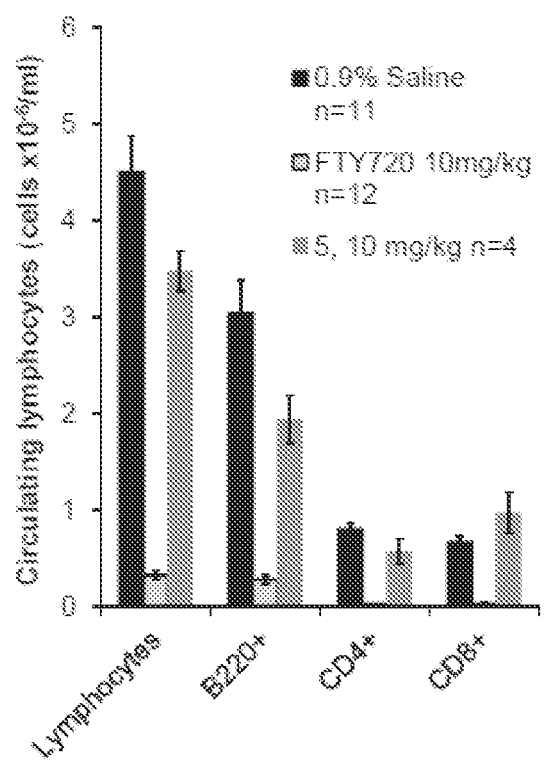
FIG. 37 provides a data plot summarizing studies of the effect of therapeutic small molecule analogs on lymphocyte sequestration in accordance with embodiments of the invention.
Figure 37:
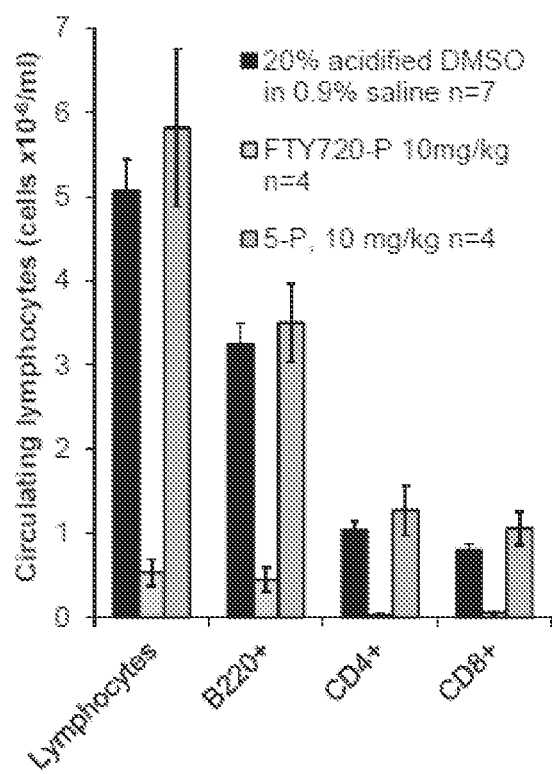

As shown in the telemetry readings detailed in FIG. 36, FTY720 (B) slowed heart rate comparison to compound 5 (C) and the control (A, saline). As shown in A, after administering saline, normal sinus rhythm with clearly discernible P waves, representing atrial depolarization, and QRS complexes, representing ventricular depolarization, at regular intervals is observed. The heart rate in this tracing was approximately 600 beats per minute (BPM). In contrast, as shown in B, upon administration of FTY720, bradycardia of approximately 200 BPM was observed in this tracing. Distinct P waves were no longer present and the R-R rhythm was much more variable, indicating that the lowest heart rates following injection of the drug resulted from a suppression of sinoatrial node conduction rather than merely a reduction in the sinus rhythm. Finally, as shown in C, for exemplary embodiment compound 5, similar to the saline injection, normal sinus rhythm with well-defined and consistent P waves and QRS complexes were present following injection. The heart rate in this tracing was approximately 600 BPM, similar to saline.

Together, this in vivo data demonstrates that exemplary embodiment compound 5 lacks the dose-limiting S1P1 and S1P3 activities that preclude the use of FTY720 in cancer patients. Furthermore, phosphorylation of active compounds such as 5 has no detrimental effect on heart rate in mice, unlike the parent FTY720.

Figure 23:
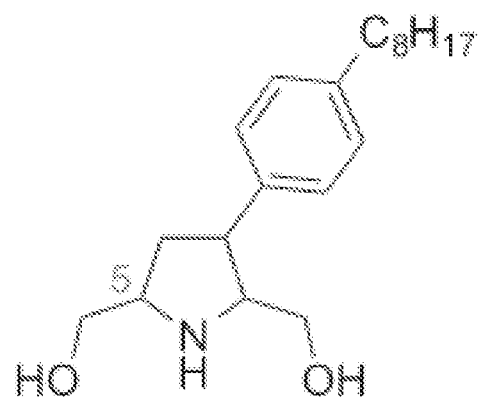
FIGS. 23 and 24 provide molecular structures of therapeutic small molecule analogs in accordance with various embodiments of the invention.
Figure 23:
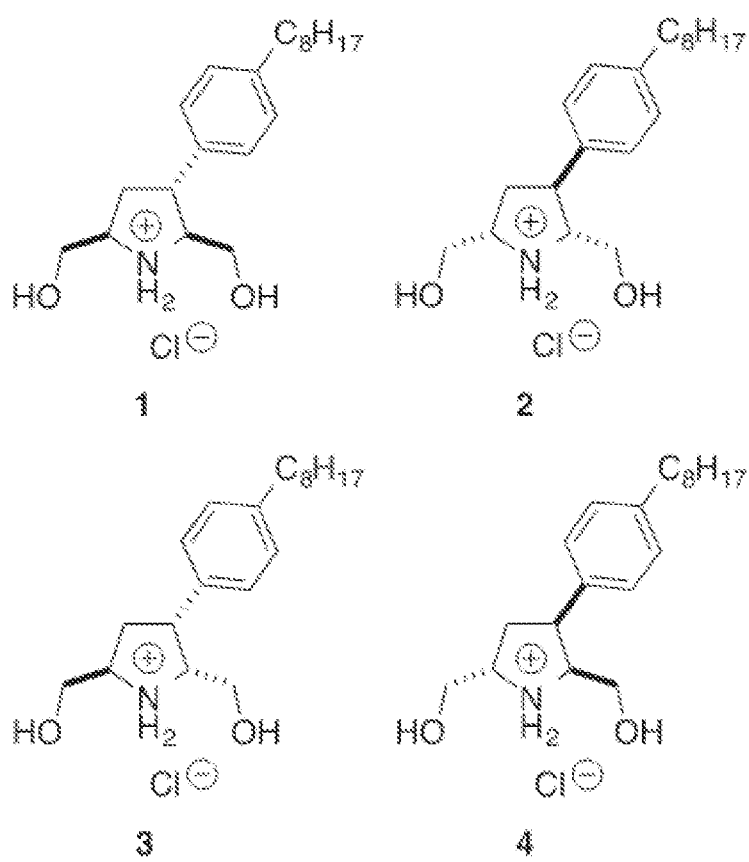
Figure 38:
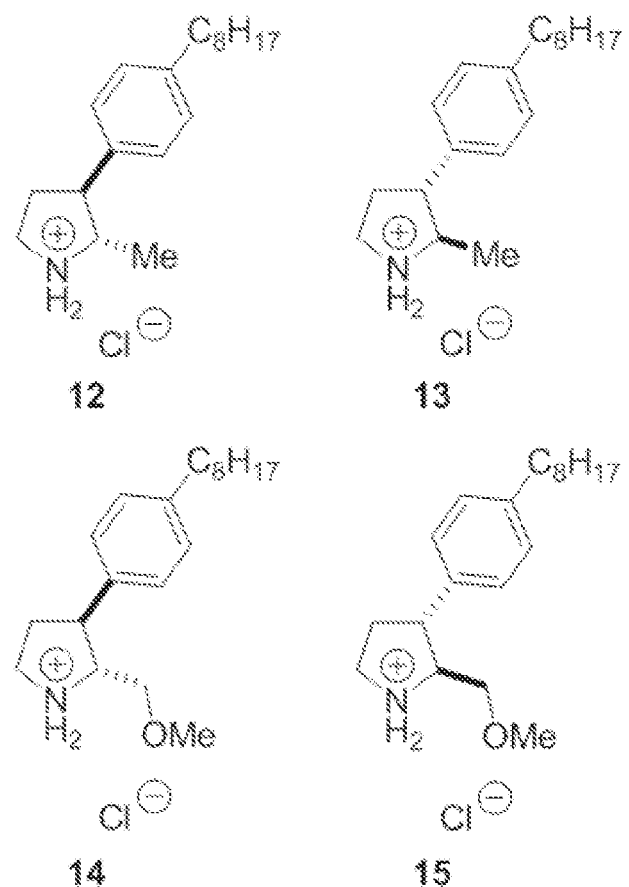
FIGS. 38 and 39 provide molecular structures of therapeutic small molecule analogs in accordance with various embodiments of the invention.

In even another example, the 2-hydroxymethyl moiety was replaced with methyl moieties (compounds 12-15) to remove any possibility of phosphorylation of the molecule (FIG. 38). As expected, compounds 12 and 14 were not able to activate any of the S1P receptors (FIG. 23). However, the replacement with non-phosphorylatable moieties also did not limit compounds 12-15 ability to suppress the proliferation of the cancer cell lines (Table 1). Unexpectedly, these compounds were nearly as potent as the parent 2-hydroxymethyl compounds and FTY720. Thus, these molecules demonstrate that neither the 2-hydroxymethyl moiety nor phosphorylation of the compound is required to inhibit cancer growth.

Figure 39:
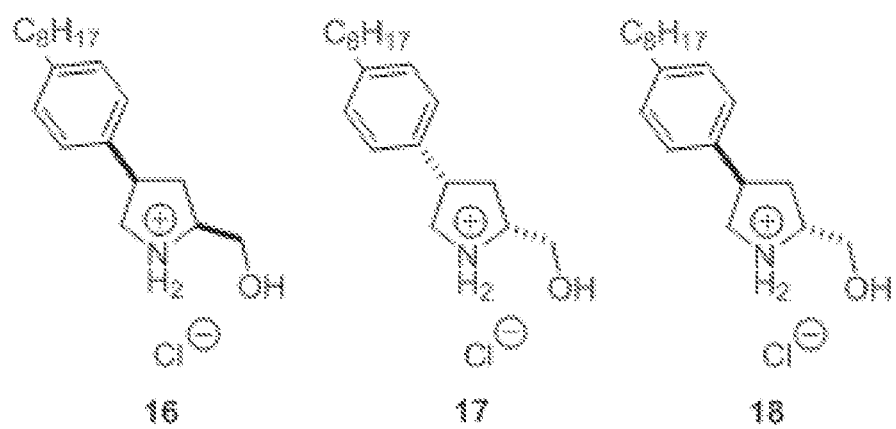
Figure 39:
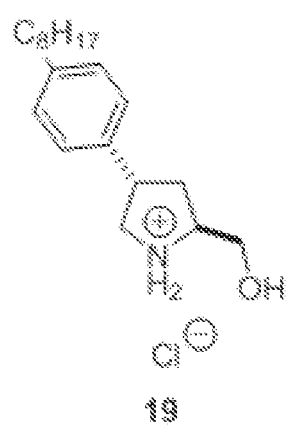

In another exemplary study, the effect of positioning of the C-aryl ring on activity was examined. The position of the C-aryl pyrrolidine in compounds 12-15 were transferred from position 3 to position 4 to create compounds 16-19 (FIG. 39). Evaluation in the cancer cell line proliferation assay demonstrated that 4-C-aryl pyrrolidines 16 and 17 were as active as 3-C-aryl pyrrolidines 12-15 and FTY720 (Table 1). Compounds 18 and 19, however, were active but less potent (Table 1). This result suggests that the relative positions and stereochemistry of substituents on the pyrrolidine core scaffold in this series do not have a major negative effect on anticancer activity.

The Cell Titer Glo proliferation assay, which was used to screen the compounds as depicted in Table 1, does not discriminate well between compounds that are cytostatic and compounds that are cytotoxic. Thus, to determine whether analogues in accordance with embodiments of the invention are cytotoxic, studies were conducted using vital dye exclusion and flow cytometry (Table 2). Compounds 3-6 and 14 were tested and found to be cytotoxic, triggering cell death in PC3 prostate cancer cells with $IC_{50}$s similar to that observed in the Cell Titer Glo assays (Tables 1 & 2).

TABLE 2

$IC_{50}$ (μM) for cell viability in PC3 Prostate Cancer cells as determined by vital dye exclusion and flow cytometry.

| FTY720 | 4.8 ± 0.1 |
|---|---|
| 3 | 8.3 ± 0.2 |
| 4 | 6.4 ± 0.3 |
| 5 | 5.5 ± 0.4 |
| 6 | 5.4 ± 0.6 |
| 14 | 4.6 ± 0.4 |
| 20 | 10.0 ± 0.2 |
| 21 | 10.7 ± 0.6 |

Having observed a suitable potency of some embodiments of the invention, including, at least with compounds 3-6, 14 in prostate cancer cell lines, other cancer cell lines were tested with these compounds. Results from the vital dye exclusion assay demonstrated activity similar to FTY720 in colon (SW-620), lung (A-549), pancreatic (PANC-1), breast (MDA-MB-231), and leukemia (SupB-15) cancer cell lines (Table 3). Table 3 shows $IC_{50}$ values in cancer cell lines in μM (ND means not determined). Compounds that were active in prostate cancer cell lines also killed BCR-Abl-positive leukemia cells with similar potency to FTY720. Unlike the enantiomeric 4-O-arylmethyl ether compounds 20 and 21, 4-C-aryl-2-hydroxymethyl pyrrolidines 16-19 did not show distinct stereochemical differences in their activities toward BCR-Abl positive leukemia cells (Fransson, R., et al. (2013) *ACS. Med. Chem. Lett.* 4, 969-973.) Compounds 4-6, 14, like FTY720, were slightly less active against the lung cancer cell line A-549.

TABLE 3

$IC_{50}$ (μM) values in various cancer cell lines. (Mean ± SEM, n ≥ 3)

| | Colon (SW-620) | Lung (A-549) | Pancreas (PANC-1) | Breast (MDA-MB-231) | Leukemia (SupB-15) |
|---|---|---|---|---|---|
| FTY720 | 2.8 ± 0.1 | 6.0 ± 0.4 | 4.6 ± 0.5 | 4.0 ± 0.1 | 6.8 ± 0.7 |
| 4 | 2.6 ± 0.0 | 4.7 ± 0.6 | 3.5 ± 0.3 | 4.6 ± 0.5 | ND |
| 5 | 2.5 ± 0.1 | 8.9 ± 1.4 | 3.3 ± 0.5 | 2.1 ± 0.2 | 5.1 ± 0.9 |
| 6 | 2.1 ± 0.2 | 8.4 ± 1.2 | 5.0 ± 0.9 | 4.9 ± 0.6 | 5.9 ± 0.1 |
| 14 | 2.7 ± 0.2 | 7.8 ± 1.8 | 4.8 ± 0.6 | 4.0 ± 0.0 | 7.5 ± 0.4 |
| 20 | 7.0 ± 1.2 | 10.7 ± 0.2 | 8.0 ± 1.5 | 9.1 ± 0.3 | 7.7 ± 0.8 |
| 21 | 4.9 ± 0.9 | 9.5 ± 1.1 | 8.8 ± 0.6 | 6.4 ± 0.4 | 2.0 ± 0.2 |

Figure 40:
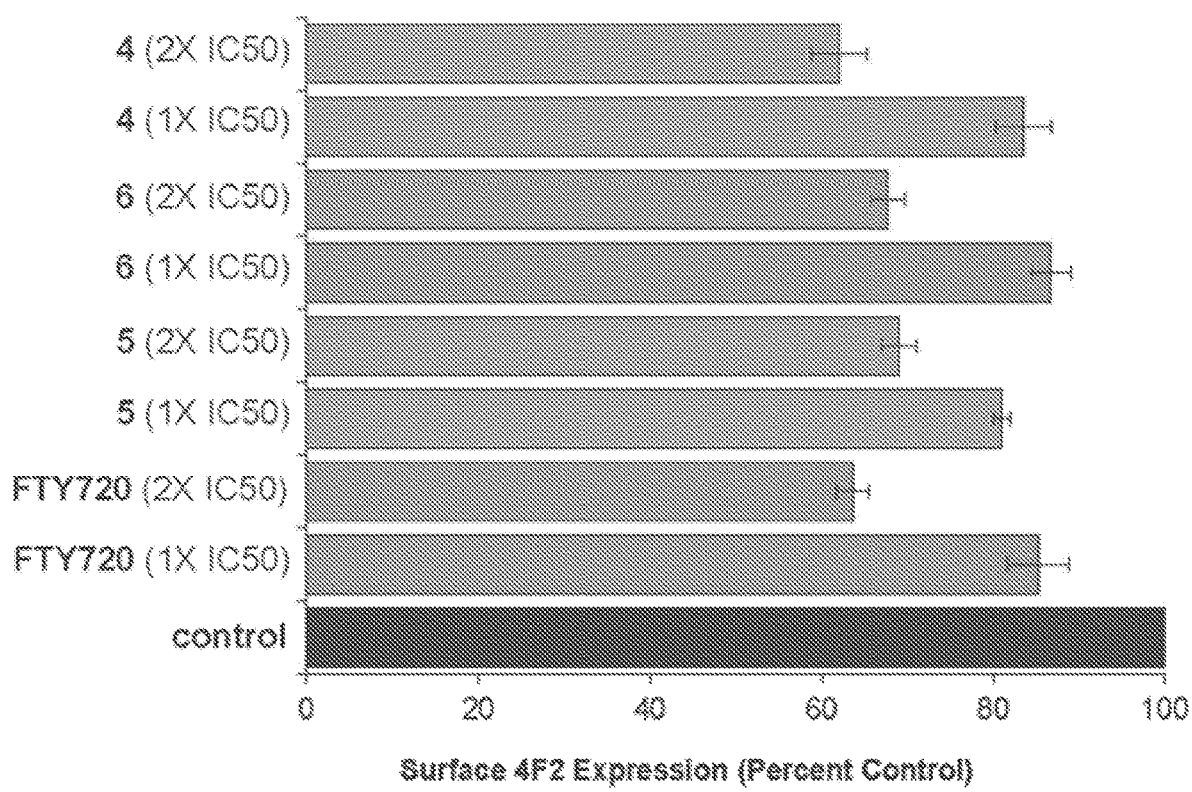
FIG. 40 provides a data plot summarizing studies on the ability of various therapeutic small molecule analogs to effect the expression of nutrient transporters in accordance with various embodiments of the invention.

The broad activity of the embodiments of the inventions described herein is consistent with a bioenergetic mechanism of action against cancer cells that includes nutrient transporter down-regulation, as described supra. Thus, to directly examine the constrained pyrrolidine sphingolipid-like molecules on nutrient transport, the surface-levels of the amino acid transporter associated protein 4F2 cell-surface antigen heavy chain (4F2hc) was examined following treatment with several analogues at their $IC_{50}$ and at twice this dose. Compounds 4, 5, and 6 reduced 4F2hc surface levels with efficacy similar to FTY720 (FIG. 40). These results are consistent with the bioenergetic mechanism for starving and killing neoplastic cells.

Figure 41:
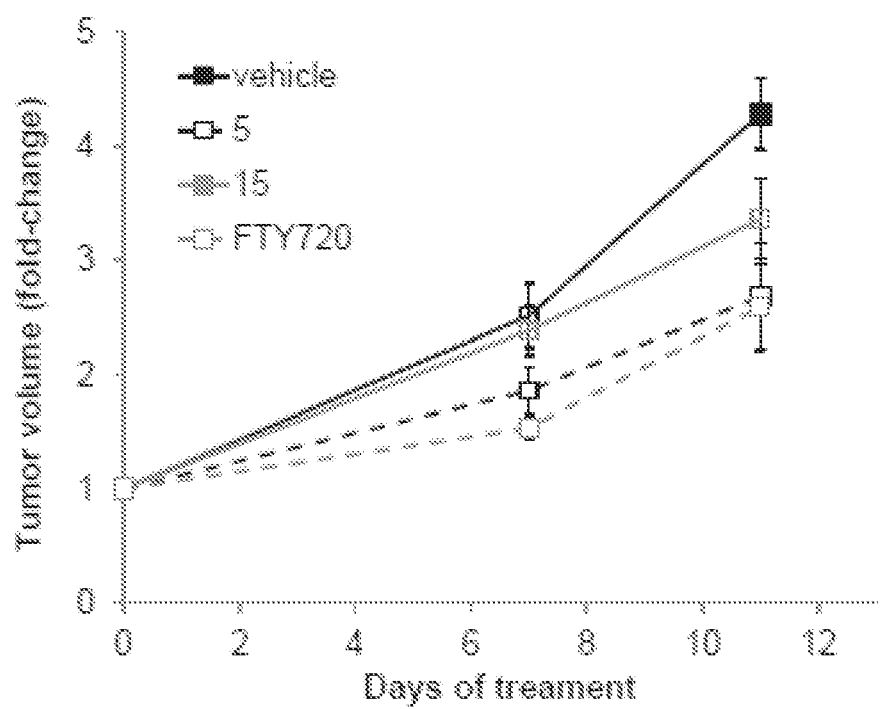
FIG. 41 provides a data plot summarizing studies on the ability of therapeutic small molecule analogs to effect neoplastic activity in a colorectal cancer xenograft model in accordance with various embodiments of the invention.

In even another exemplary study, anti-neoplasm potency of the constrained pyrrolidine sphingolipid-like compounds in xenograft tumor animal studies. Nude mice bearing subcutaneous SW620 xenograft tumors were treated daily with 10 mg/kg FTY720 or 20 mg/kg of compounds 5 or 15 by intraperitoneal injection. All three compounds inhibited tumor growth (FIG. 41). These results suggest that the pyrrolidine sphingolipid-like compounds are capable of treating neoplasms by a bioenergetic mechanism. Furthermore, these compounds retain many of the beneficial abilities of FTY720, such as, for example water solubility, oral bioavailability, and anti-tumor activity but no longer trigger bradycardia. Thus, these compounds are ideal for medicaments and treatments for neoplasms.

Further Optimization of Azacyclic Constrained Sphingolipid-Like Compounds and Effects on Nutrient Transport. Vacuolation, and Cell Death Azacyclic constrained sphingolipid-like compounds were modified and analyzed for their ability to down-regulate nutrient transporter proteins and induce cytoplasmic vacuolation. Modification of the compounds include varying the length of the hydrocarbon chain, the degree of unsaturation, and the presence or absence of an aryl moiety on the appended chains, and stereochemistry at two stereogenic centers. In general, cytotoxicity was positively correlated with nutrient transporter down-regulation and vacuolation. Thus, a molecule that produces maximal vacuolation and transporter loss is expected to have maximal anti-neoplastic activity and thus would be ideal for a medicament and treatment regimen.

Based on the bioenergetic mechanism described supra, sphingolipids and sphingolipid-like molecules may bind to an allosteric regulatory site to activate PP2A. PP2A is a heterotrimeric complex with more than 90 isoforms that control substrate specificity. Accordingly, it is suggested that two distinct PP2A complexes are activated by the sphingolipid-like molecules to induce 2 distinct phenotypes: nutrient transporter down-regulation and vacuolation. The purpose of the modifications to the azacyclic constrained sphingolipid-like compounds is identifying which features maximally induce both down-regulation of nutrient transporters and vacuolation.

In an exemplified study, nutrient transporter down-regulation was monitored by quantifying surface levels of the amino acid transporter-associated protein, CD98, by flow cytometry. Vacuolation was scored in a range from 0 to 84, as determined by a vacuolation assay described in greater detail in the Materials and Methods section below. The $IC_{50}$ was determined by measuring the concentration that killed half of a murine hematopoietic cell line FL5.12 at 48 hours, via the vital dye exclusion assay. This data was obtained for various naturally occurring sphingolipids and synthetic sphingolipid-like compounds.

Figure 42:
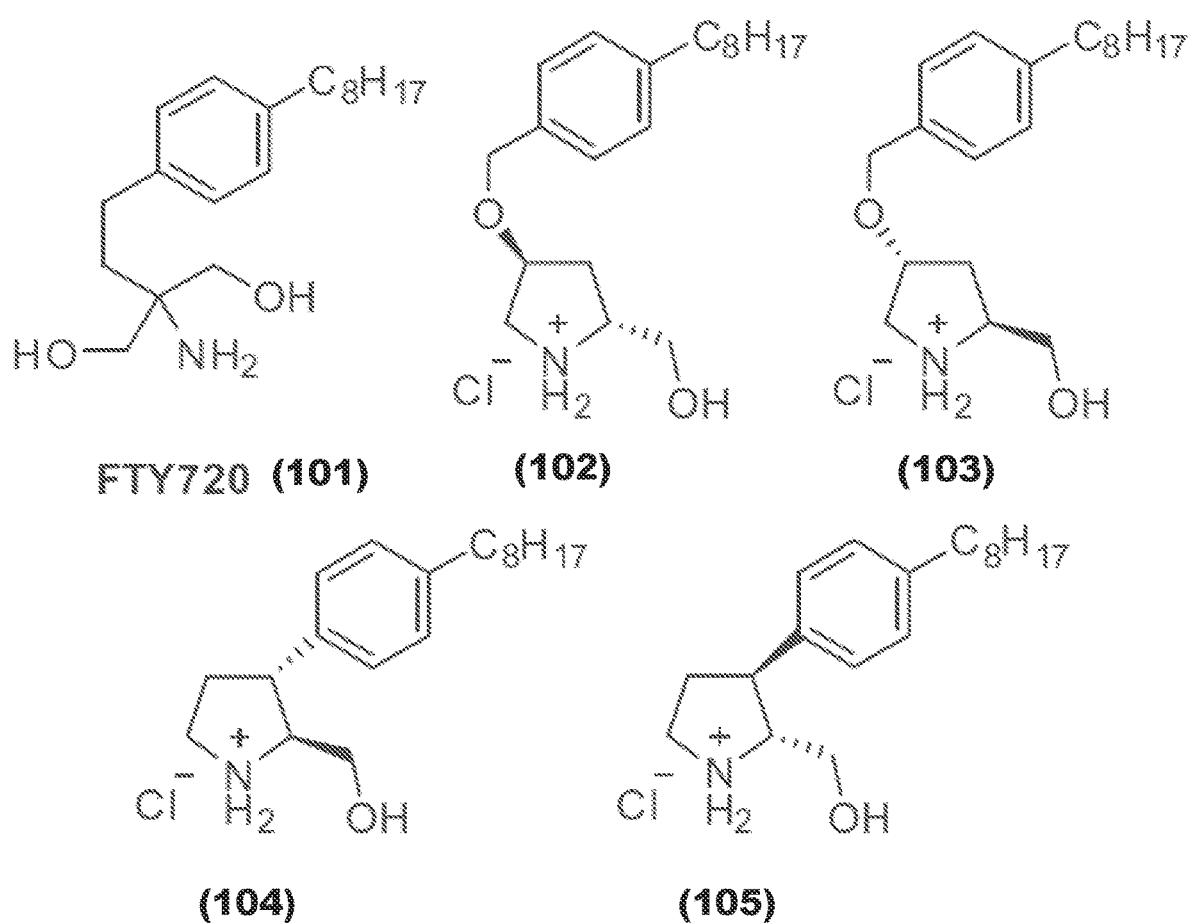
FIGS. 42 and 43 provide molecular structures of therapeutic small molecule analogs in accordance with various embodiments of the invention.
Figure 43:
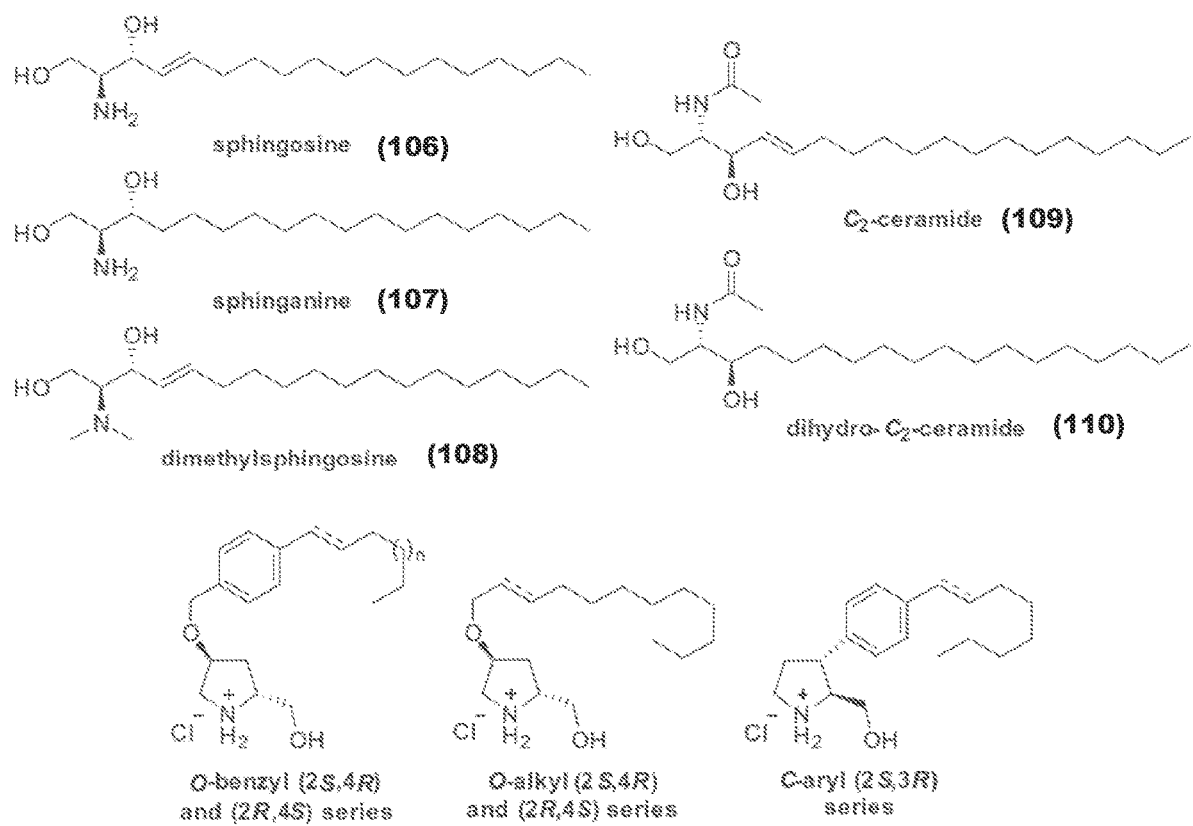
Figure 44:
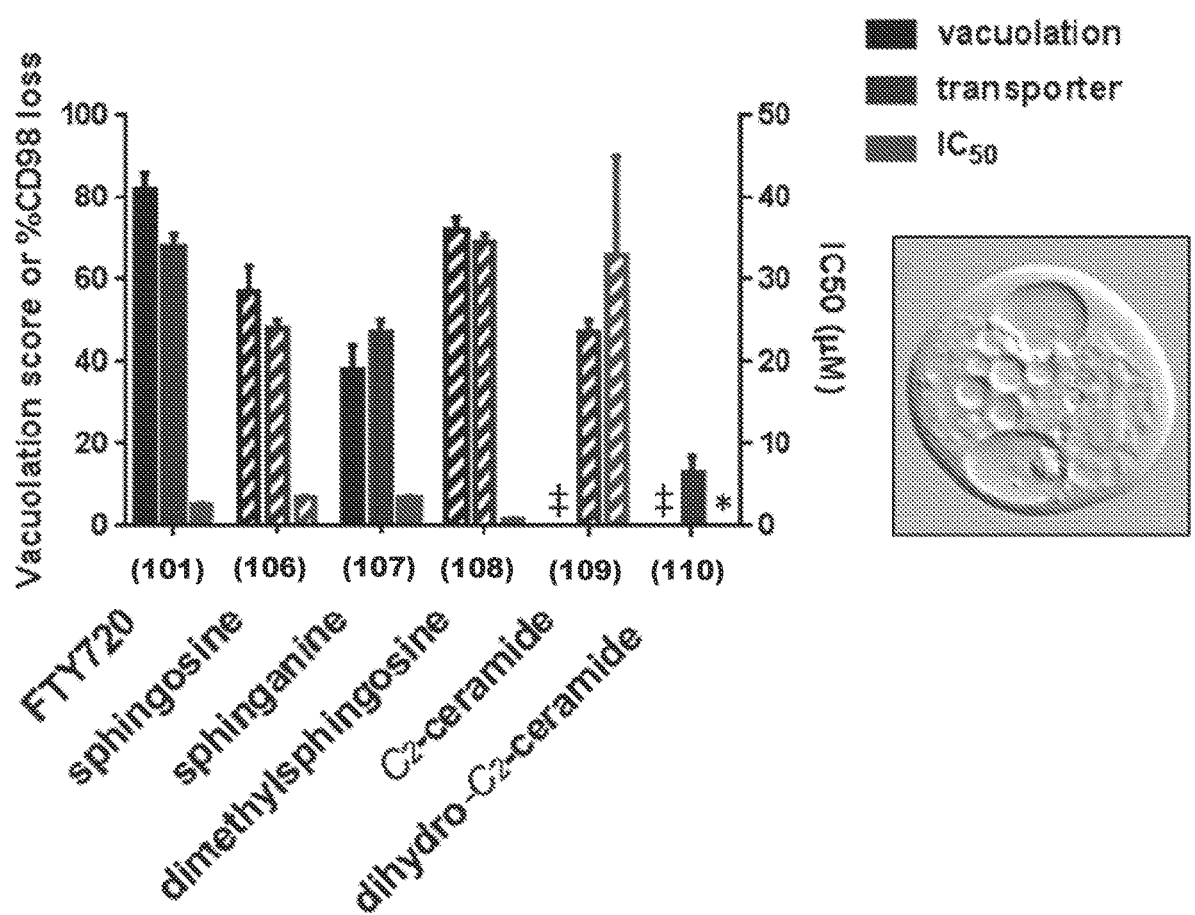
FIG. 44 provides a graphical representation of several sphingolipids capable of inducing vacuolation, CD98 loss, and cell death in accordance with various embodiments of the invention.

The Structure-Activity-Relationship (SAR) strategy, in accordance with embodiments of the invention, was founded on results obtained with the naturally occurring sphingolipids sphingosine (compound 106) and sphinganine (compound 107) and the moderately soluble, short-chain $C_2$-ceramide (compound 109) and dihydro-$C_2$-ceramide (compound 110) that are often used in place of extremely hydrophobic (but physiologic) long-chain ceramides (FIGS. 42 and 43). Sphingosine (106) and sphinganine (107) both triggered nutrient transporter loss and vacuolation and efficiently killed cells with $IC_{50}$s of 3.6 and 3.5 μM, respectively (FIG. 44 and Table 4). $C_2$-Ceramide (109) triggered nutrient transporter loss with reduced potency compared to sphingosine (106) since 50 μM $C_2$-ceramide (109) was required to cause similar transporter loss as 2.5 μM sphingosine (106) (Table 4). $C_2$-Ceramide did not cause vacuolation at any dose. Consistent with previous reports that it does not activate PP2A (Chalfant, C. E. et al., Y. A. J. Lipid Res. 2004, 45, 496, the disclosure of which is incorporated herein by reference), dihydro-C2-ceramide (110) failed to kill cells, did not efficiently trigger CD98 down-regulation, and caused no vacuolation (Table 4 and FIG. 44). While C2-ceramide (109) was much less active than sphingosine (106), dimethylsphingosine (108) was almost 5-fold more potent ($IC_{50}$=0.77 μM) (Table 4 and FIG. 44). Interestingly, saturation of sphingosine reduced vacuolation while transporter loss and cytotoxicity were unaffected. These results suggest that different naturally occurring sphingolipid structures can activate distinct PP2A complexes leading to either down-regulation of nutrient transporters or vacuolation. Some sphingolipids activated both the nutrient transporter down-regulation and the vacuolation pathways, while others only activated one pathway, and even other sphingolipids did not activate either pathway.

TABLE 4

Activities of O-benzyl and C-aryl pyrrolidine analogs.

| Entry | Compound; Stereochemistry | R** | Compound number | $IC_{50}$ (μM) [95% CI] | % CD98 down-regulation | Vacuolation score |
|---|---|---|---|---|---|---|
| 1 | FTY720 | | 101 | 2.4 [2.1-2.7] | 68 ± 3 | 82 ± 4 |
| 2 | Sphingosine | | 106 | 3.6 [3.5-3.7] | 48 ± 2 | 57 ± 6 |
| 3 | Sphinganine | | 107 | 3.5 [3.3-3.7] | 47 ± 3 | 38 ± 6 |
| 4 | Dimethylsphingosine | | 108 | 0.8 [0.7-0.9] | 69 ± 2 | 72 ± 3 |
| 5 | C2-Ceramide | | 109 | 33.0 [23.3-47.0] | 47 ± 3 | 0 |
| 6 | Dihydro-C2- O-Benzyl | | 110 | Cytostatic | 13 ± 40 | |
| 7 | (2R, 4S) | $C_6H_{13}$ | 111 | 2.7 [2.6-2.8] | 30 ± 2 | 0 |
| 8 | (2R, 4S) | $C_6H_{11}$ | 112 | 5.5 [5.3-5.7] | 30 ± 4 | 0 |
| 9 | (2R, 4S) | $C_8H_{17}$ | 102 | 2.0 [1.8-2.2] | 63 ± 3 | 33 ± 2 |
| 10 | (2R, 4S) | $C_8H_{15}$ | 113 | 1.4 [1.3-1.6] | 64 ± 1 | 27 ± 1 |
| 11 | (2R, 4S) | $C_{12}H_{25}$ | 114 | 10.1 [8.7-11.6] | 13 ± 3 | 3 ± 1 |
| 12 | (2R, 4S) | $C_{12}H_{23}$ | 115 | 2.8 [2.4-3.3] | 52 ± 1 | 33 ± 3 |
| 13 | (2R, 4S) | $C_{14}H_{29}$ | 116 | 10.5 [9.7-11.3] | 12 ± 3 | 4 ± 2 |
| 14 | (2R, 4S) | $C_{14}H_{27}$ | 117 | 5.1 [5.0-5.3] | 19 ± 3 | 8 ± 1 |
| 15 | (2S, 4R) | $C_6H_{11}$ | 118 | 5.7 [3.9-8.3] | 9 ± 3 | 5 ± 2 |
| 16 | (2S, 4R) | $C_8H_{17}$ | 103 | 3.0 [2.9-3.2] | 48 ± 2 | 47 ± 2 |
| 17 | (2S, 4R) | $C_8H_{15}$ | 119 | 2.4 [2.3-2.4] | 41 ± 3 | 70 ± 1 |
| 18 | (2S, 4R) | $C_{10}H_{21}$ | 120 | 3.6 [3.4-3.7] | 28 ± 1 | 36 ± 5 |
| 19 | (2S, 4R) | $C_{12}H_{25}$ | 121 | 3.9 [3.7-4.2] | 14 ± 4 | 30 ± 2 |
| 20 | (2S, 4R) | $C_{12}H_{23}$ | 122 | 2.4 [2.3-2.5] | 40 ± 2 | 76 ± 6 |
| 21 | (2S, 4R) | $C_{14}H_{29}$ | 123 | 5.7 [5.5-5.9] | 19 ± 1 | 3 ± 3 |
| 22 | (2S, 4R) C-Aryl series | $C_{14}H_{27}$ | 124 | 7.3 [6.7-8.1] | 20 ± 3 | 1 ± 1 |
| 23 | (2S, 3R) | $C_8H_{17}$ | 104 | 1.9 [1.8-2.1] | 54 ± 1 | 81 ± 3 |
| 24 | (2S, 3R) | $C_8H_{15}$ | 125 | 1.7 [1.6-1.8] | 58 ± 3 | 84 ± 2 |
| 25 | (2R, 3S) | $C_8H_{17}$ | 105 | 1.7 [1.4-2.1] | 47 ± 3 | 53 ± 3 |

Figure 45:
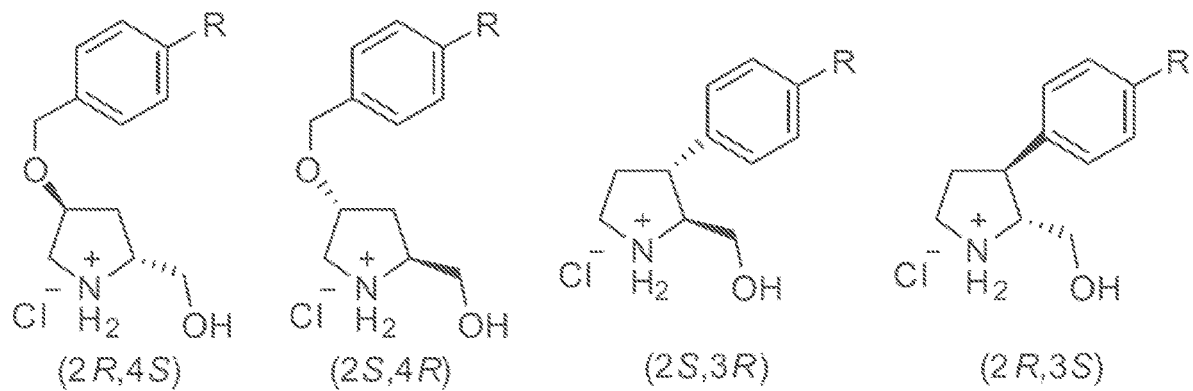
FIG. 45 provides molecular structures of therapeutic small molecule analogs in accordance with various embodiments of the invention.

**See FIG. 45 for Compound structure
$IC_{50}$ values are given with 95% confidence intervals, CD98 and vacuolation scores are means ± SEM. n ≥ 3 in all cases Based on the naturally occurring sphingolipid data, it suggests that sphingolipid-like pyrrolidine analogs containing O-benzyl and C-aryl could also vary in their ability to activate either the nutrient transporter down-regulation or vacuolation pathway. Thus, several variants of the sphingolipid-like molecules were synthesized and tested. The results are included in Tables 4-6 and FIGS. 45-50.

In some particular embodiments, the chain length of the O-benzyl compounds 102 and 103 were generated with C6, C8, C10, C12, or C14 hydrocarbon chains (FIG. 45). These compounds were assayed for cytotoxicity, effects on nutrient transporter levels, and vacuolation (Table 4 and FIG. 46).

Figure 46:
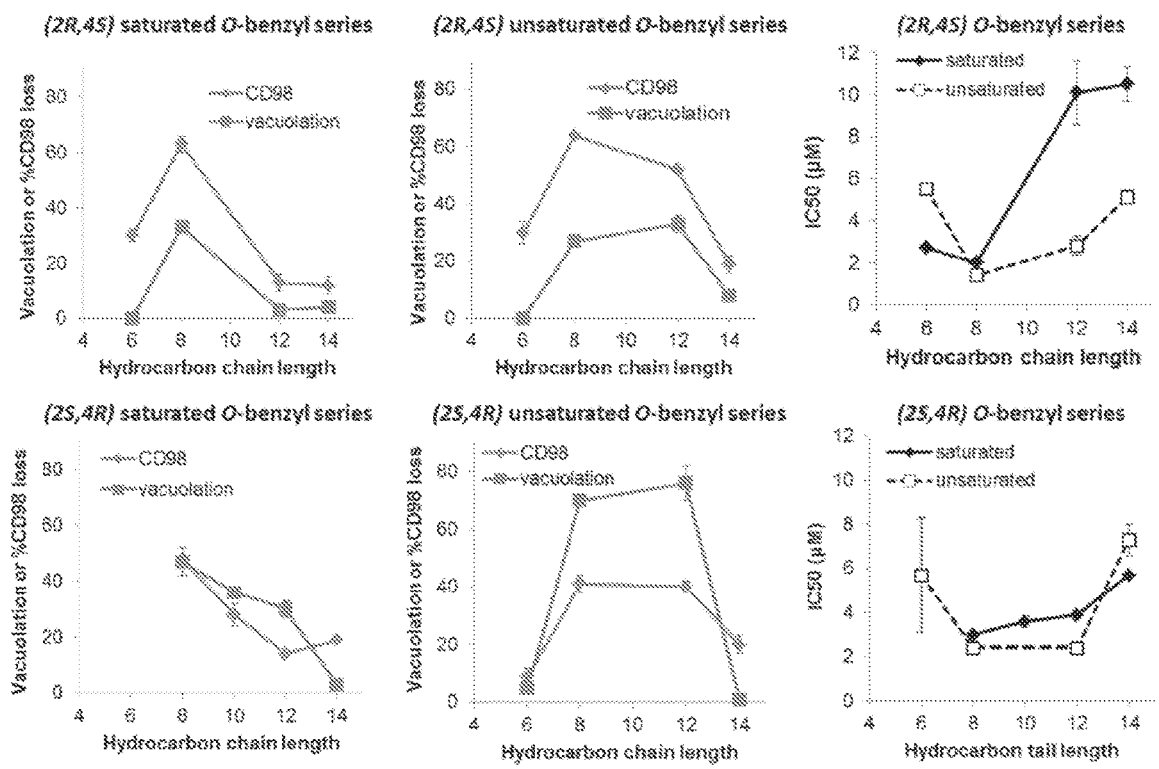
FIG. 46 provides a graphical representation of the effect of chain-tail length on various small molecule analogs in accordance with various embodiments of the invention.

In both stereochemical series, (2R,4S) and (2S,4R), analogs 114 (C12), 116 (C14), 121 (C12), and 123 (C14) that bear a fully saturated chain lost activity in transporter and vacuolation assays (FIG. 46, Table 4). When the hydrocarbon chain was partially unsaturated, as in analogs 115 (C12) and 122 (C12), the longer chain was tolerated (Table 4). The finding that C12 analogs are more active when unsaturated in both stereochemical series as represented by analogs 114 and 115 and the enantiomeric 121 and 122, respectively, suggests that introducing a double bond may permit a better fit of the suboptimally long hydrocarbon chain in a hydrophobic binding site in the target protein. Recall that sphingosine (116) was better at vacuolation than its saturated congener sphinganine (117) (Table 4).

Compounds 117 and 124 contained an unsaturated C14 chain and did not induce robust vacuolation or reduce transporter levels (Table 4 and FIG. 46). Analogs in this O-benzyl series with shorter C6 hydrocarbon chains (compounds 111, 112 and 118) were also less active than the C8 hydrocarbon chain compounds (102, 103, 113 and 119) (Table 4). These results indicate that a C8 hydrocarbon chain length in this series leads to optimal potency in both transporter and vacuolation assays, although a C12 chain, as in compounds 115 and 122, is tolerated provided that the chain is partially unsaturated (Table 4).

Interestingly, in the unsaturated (2S,4R) series corresponding to compound 103, peak vacuolation scores were higher than peak transporter loss scores, while in the unsaturated (2R,4S) series corresponding to 102, these activities were reversed and more transporter loss than vacuolation was observed (FIG. 46). For example, the (2S,4R) unsaturated compound 119 triggers vacuolation twice as well as the (2R,4S) unsaturated enantiomer 113, while the trend is reversed with 113 which induces transporter loss nearly twice as much as 119 (Table 4). These differential activities of enantiomeric compounds in transporter and vacuolation assays are also apparent, but less robust, when the saturated compounds, 102 and 103 are compared. These results suggest that certain enantiomers may have desired properties (e.g., induce greater vacuolation) that may lead to desired clinical outcome.

It is also interesting to note that the unsaturated (2S,4R) analogs of 103 are much more active in vacuolation assays than the matched saturated compounds. Partial unsaturation increases transporter loss as well, but to a lesser degree. Because unsaturation in the hydrocarbon chain increased the activity of all compounds in each assay, it was evaluated whether unsaturation would also enhance the activity of the structurally related C-aryl series as in (2S,3R) 104 (FIGS. 42 & 45). Unsaturated analog 125 was not significantly more active than its saturated counterpart 104 in any of the assays (Table 4). However, compound 104 is much better at inducing vacuolation than the corresponding saturated O-benzyl analog, 103 (Table 4).

Similar to the O-benzyl series, it is observed that there is a stereochemical dependence for optimal activity within the C-aryl series. Thus, the C-aryl analog (2R,3S) 105 does not vacuolate as well as the enantiomeric (2S,3R) 104 with scores of 53 and 81, respectively (Table 4).

In summary, the (2S,4R) stereochemistry in the O-benzyl series represented by 103 leads to better vacuolation, while the enantiomeric (2R,4S) stereochemistry as in 102 promotes nutrient transporter down-regulation. These results could reflect differential affinities for distinct PP2A heterotrimers. The C8 hydrocarbon chain length is favored in both assays, and, at this optimal tail length, unsaturation has only a minor positive effect on activity. Better vacuolation is observed with the C-aryl (2S,3R) and (2R,3S) analogs 104 and 105 compared to the O-benzyl counterparts 103 and 102, respectively.

Figure 47:
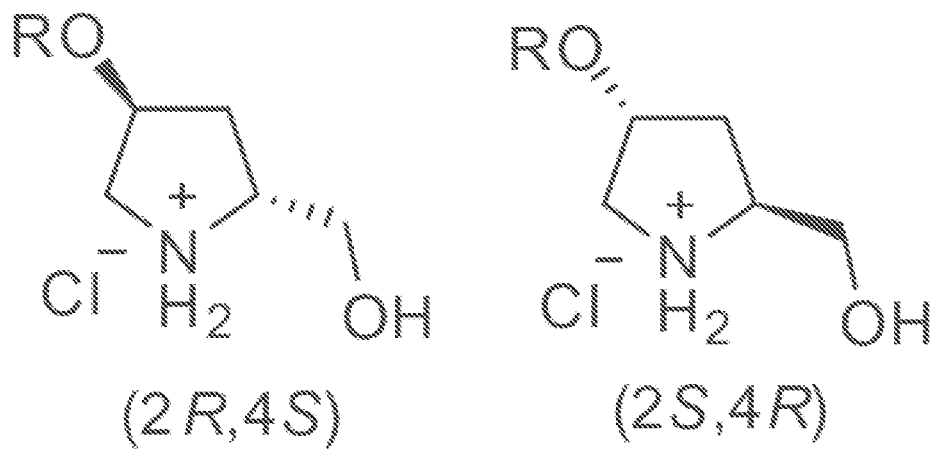
FIG. 47 provides molecular structures of therapeutic small molecule analogs in accordance with various embodiments of the invention.
Figure 48:
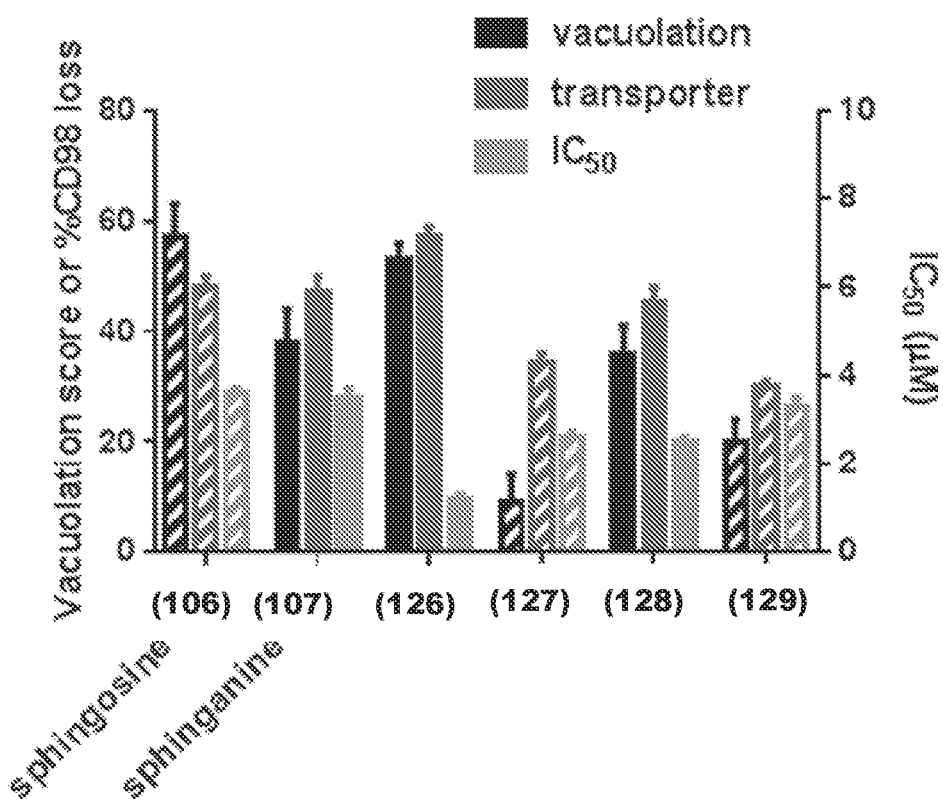
FIG. 48 provides a graphical representation of several small molecule analogs capable of inducing vacuolation, CD98 loss, and cell death in accordance with various embodiments of the invention.

In more embodiments, various alterations were examined for the O-alkyl pyrrolidine analogs and compared to the sphingosine (106) and sphinganine (107) (FIG. 47). Replacing the polar amino diol portion of sphingosine (106) and sphinganine (107) with a pyrrolidine ring did not dramatically alter the $IC_{50}$ values of the enantiomeric analogs 126-129 with the exception that 126 was 3-fold more cytotoxic than the parent compound, sphinganine (Table 5, FIG. 48). CD98 transporter loss and vacuolation were slightly greater with analog 126 than with the parent, consistent with its increased cytotoxicity. However, the unsaturated analog 127 exhibited decreased activity in transporter and vacuolation assays compared to sphingosine without a concomitant increase in the $IC_{50}$. Sphingosine (106) and sphinganine (107) have similar effects on nutrient transporter proteins, however sphingosine (106) vacuolates much better than sphinganine (107) (FIG. 48). Unexpectedly, this relationship was reversed in the constrained analogs, where the enantiomeric fully saturated constrained sphinganine analogs 126 and 128 were 2-4-fold more active in vacuolation assays than the unsaturated sphingosine analogs 127 and 129 (Table 5, FIG. 48).

TABLE 5

Activities of O-alkyl pyrrolidine analogs.

| Entry | Compound; Stereochemistry | R** | Compound number | $IC_{50}$ (µM) [95% CI] | % CD98 down-regulation | Vacuolation score |
|---|---|---|---|---|---|---|
| 1 | FTY720 | | 101 | 2.4 [2.1-2.7] | 68 ± 3 | 82 ± 4 |
| 2 | Sphingosine | | 106 | 3.6 [3.5-3.7] | 48 ± 2 | 57 ± 6 |
| 3 | Sphinganine | | 107 | 3.5 [3.3-3.7] | 47 ± 3 | 38 ± 6 |
| 4 | Dimethylsphingosine | | 108 | 0.8 [0.7-0.9] | 69 ± 2 | 72 ± 3 |
| 5 | C2-Ceramide | | 109 | 33.0 [23.3-47.0] | 47 ± 3 | 0 |
| 6 | Dihydro-C2-ceramide | | 110 | Cytostatic | 13 ± 4 | 0 |
| 7 | (2R, 4S) | $C_{12}H_{25}$ | 126 | 1.2 [1.1-1.3] | 57 ± 2 | 53 ± 3 |
| 8 | (2R, 4S) | $C_{12}H_{23}$ | 127 | 2.6 [2.6-2.7] | 34 ± 2 | 9 ± 5 |
| 9 | (2S, 4R) | $C_{12}H_{25}$ | 128 | 2.5 [2.4-2.6] | 45 ± 3 | 36 ± 5 |
| 10 | (2S, 4R) | $C_{12}H_{23}$ | 129 | 3.3 [3.1-3.5] | 30 ± 1 | 20 ± 4 |

**See FIG. 47 for Compound structure $IC_{50}$ values are given with 95% confidence intervals, CD98 and vacuolation scores are means ± SEM. n ≥ 3 in all cases Stereochemistry had only a modest effect in the O-alkyl series, although the (2R,4S) stereoisomers were slightly better at vacuolation than the (2S,4R) versions (Table 5, FIG. 48). In summary, unlike in the O-benzyl series, constraint had a negative effect on the transporter and vacuolation activities of sphingosine (106) but not sphinganine (107).

Figure 49:
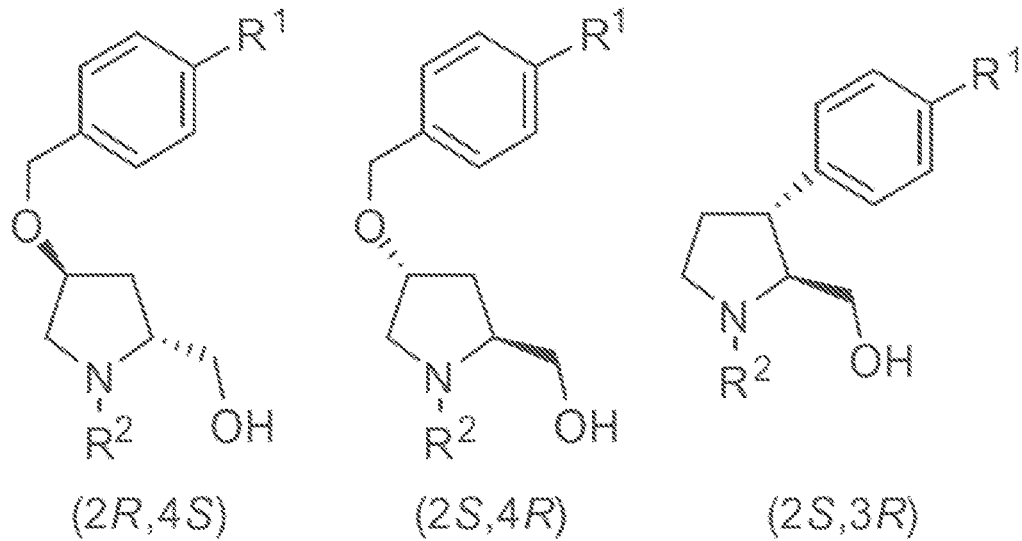
FIG. 49 provides molecular structures of therapeutic small molecule analogs in accordance with various embodiments of the invention.

In even more embodiments, the charge of the pyrrolidine nitrogen of several analogs was neutralized and subsequently assayed (FIG. 49). As expected, given the lack of the basic nitrogen, N-acetyl analog 131 in the O-benzyl series was 10-fold less potent than analog 102, in analogy with the similar difference in potency between C2-ceramide (109) and sphingosine (106) (Table 6). Furthermore, analog 131 exhibited no vacuolation activity at the highest dose tested (Table 6). The effect of N-acetylation on C-aryl compounds such as 104 and 125, which induce vacuolation very efficiently, was also evaluated. Although the loss of transporter activity was not as significant, compounds 134 and 135 also failed to induce vacuolation, (Table 6). Thus, N-acetylated pyrrolidine sphingolipid-like analogs in the C-aryl series may be useful for applications that only produce down-regulation of nutrient transporters but have no effect on vacuolation.

ever, the potency of these compounds was reduced 5-7 fold compared to the parent compounds 103 and 102 in the same series. Moreover, the ability to induce vacuole formation was lost even at the highest concentrations tested (30 µM). These results suggest that although basicity is important, steric effects in the environment of the pyrrolidine nitrogen may play a role in interactions with cellular targets.

Figure 50:
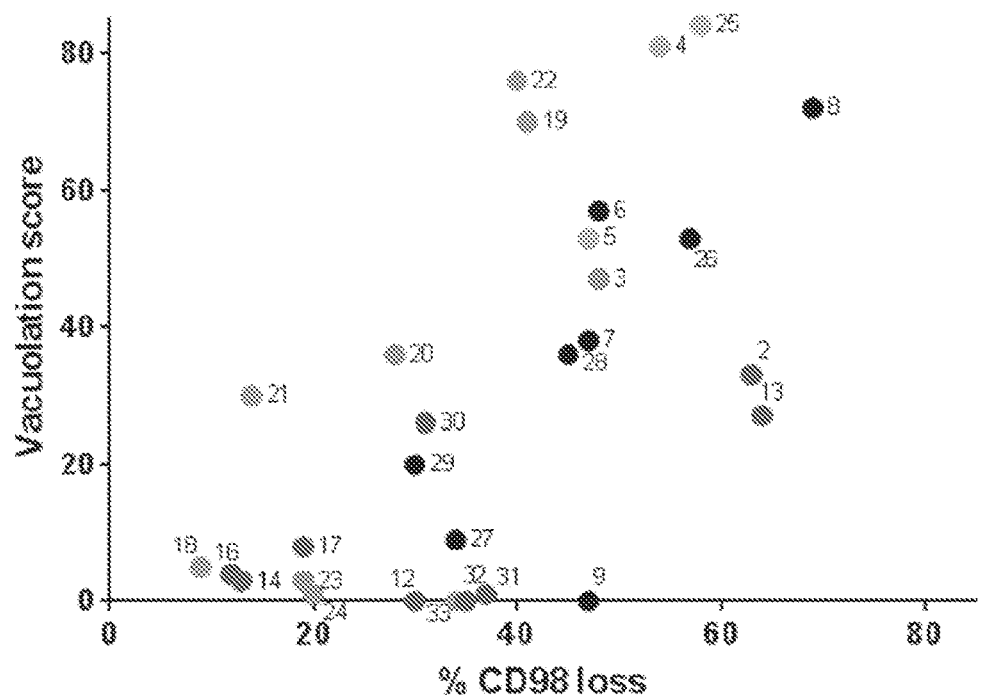
FIG. 50 provides a dot-plot representation of several small molecule analogs capable of inducing vacuolation and CD98 loss in accordance with various embodiments of the invention.

In summary, these SAR studies of constrained azcyclic sphingolipid-like analogs suggest that a compound with an unsaturated C8 hydrocarbon chain in the (2S,4R)—O-benzyl pyrrolidine series, such as, for example, compound 119, will have higher overall activity than saturated, longer or shorter chain analogs having the same stereochemistry (FIG. 50). The (S,R) stereochemistry as in 119 correlates with better vacuolating ability while the enantiomeric (R,S) compounds, as in 102 and 113, are slightly better at triggering nutrient transporter loss (Table 4 and FIGS. 46 and 50). However, in the C-aryl series, this difference in transporter down-regulation between enantiomers becomes negligible (54% vs 47% with compounds 104 and 105, respectively). Of the pyrrolidine analogs tested, the saturated and unsaturated C-aryl analogs 104 and 125, respectively are the most potent inducers of vacuolation and transporter loss leading

TABLE 6

Effect of N-substitution and unsaturation on the activities of O-benzyl and C-aryl pyrrolidine analogs

| Entry | Compound; Stereochemistry | R1** | R2** | Compound number | IC$_{50}$ (µM) [95% CI] | % CD98 down-regulation | Vacuolation score |
|---|---|---|---|---|---|---|---|
| 1 | FTY720 | | | 101 | 2.4 [2.1-2.7] | 68 ± 3 | 82 ± 4 |
| 2 | Sphingosine | | | 106 | 3.6 [3.5-3.7] | 48 ± 2 | 57 ± 6 |
| 3 | Sphinganine | | | 107 | 3.5 [3.3-3.7] | 47 ± 3 | 38 ± 6 |
| 4 | Dimethyl-sphingosine | | | 108 | 0.8 [0.7-0.9] | 69 ± 2 | 72 ± 3 |
| 5 | C2-Ceramide | | | 109 | 33.0 [23.3-47.0] | 47 ± 3 | 0 |
| 6 | Dihydro-C2-ceramide | | | 110 | Cytostatic | 13 ± 4 | 0 |
| | O-Benzyl series | | | | | | |
| 7 | (2R, 4S) | C$_8$H$_{17}$ | H | 102 | 2.0 [1.8-2.2] | 63 ± 3 | 33 ± 2 |
| 8 | (2R, 4S) | C$_8$H$_{15}$ | H | 113 | 1.4 [1.3-1.6] | 64 ± 1 | 27 ± 1 |
| 9 | (2S, 4R) | C$_8$H$_{17}$ | H | 103 | 3.0 [2.9-3.2] | 48 ± 2 | 47 ± 2 |
| 10 | (2R, 4S) | C$_8$H$_{15}$ | Me | 130 | 1.9 [1.8-2.1] | 31 ± 4 | 26 ± 2 |
| 11 | (2R, 4S) | C$_8$H$_{17}$ | Ac | 131 | 29.7 [ND] | 37 ± 3 | 1 ± 1 |
| 12 | (2R, 4S) | C$_8$H$_{17}$ | HN=C—NH2 | 132 | 14.2 [12.5-16.1] | 35 ± 1 | 0 |
| 13 | (2S, 4R) | C$_8$H$_{17}$ | HN=C—NH2 | 133 | 17.3 [15.9-18.9] | 34 ± 3 | 0 |
| | C-Aryl series | | | | | | |
| 14 | (2S, 3R) | C$_8$H$_{17}$ | H | 104 | 1.9 [1.8-2.1] | 54 ± 1 | 81 ± 3 |
| 15 | (2S, 3R) | C$_8$H$_{15}$ | H | 125 | 1.7 [1.6-1.8] | 58 ± 3 | 84 ± 2 |
| 16 | (2S, 3R) | C$_8$H$_{17}$ | Ac | 134 | 39.7 [37.1-42.4] | 40 ± 4 | 0 |
| 17 | (2S, 3R) | C$_8$H$_{15}$ | Ac | 135 | 46.2 [43.5-49.0] | 40 ± 2 | 2 ± 2 |

**See FIG. 49 for Compound structure
IC$_{50}$ values are given with 95% confidence intervals, CD98 and vacuolation scores are means ± SEM. n ≥ 3 in all cases The finding that N-acetylation reduces potency is consistent with previous observations that the positive charge of the nitrogen in the pyrrolidine is critical for enhanced compound activity. Since dimethylsphingosine (108) exhibited the best potency, transporter loss and vacuolation among the sphingolipids tested (Tables 4-6, FIG. 44), it was surmised that the N-methyl analog 130 would represent a good mimic, albeit with a pyrrolidine scaffold. Unexpectedly, the N-methyl analog 130 was not more active than the parent 113, and its ability to induce transporter loss and vacuolation were reduced (Table 6).

To determine whether increasing the basicity of the pyrrolidine nitrogen atom would also increase potency, guanidino analogs 132 and 133 were generated (Table 6). Howto potent cytotoxicity in the low µM range (FIG. 50). Given this profile, these compounds would be predicted to have the high anti-neoplastic activity.

Azacyclic Constrained Sphingolipid-Like Compounds Disrupt Nutrient Acquisition in Neoplastic Cells As explained supra, sphingolipid-like compounds can suppress neoplastic growth by down-regulating nutrient transporters. Neoplastic cells, however, can obtain nutrients by macropinocytosis and autophagy in addition to using cell-surface nutrient transporters. Here, embodiments are provided that azacyclic constrained sphingolipid-like compounds can block a neoplastic cell's access to nutrients by inhibiting macropinocytosis or autophagy. In an embodiment, sphingolipid-like compounds activate PP2A leading to mislocalization of the lipid kinase PIKfyve. In another embodiment, sphingolipid-like compounds trigger cytosolic vacuolation. In even other embodiments, the compounds block lysosomal fusion reactions essential for low-density lipoprotein (LDL), autophagosome, and macropinosome degradation. Embodiments are directed to sphingolipid-like compounds that selectively kill cells expressing activated Ras or lacking the tumor suppressor PTEN. More embodiments are directed to the ability of the compounds to treat neoplasms that do not exhibit a classic Warburg phenotype. Furthermore, some embodiments are directed to the compounds' ability to inhibit neoplastic growth without significantly affecting normal proliferative tissues.

Figure 51A:
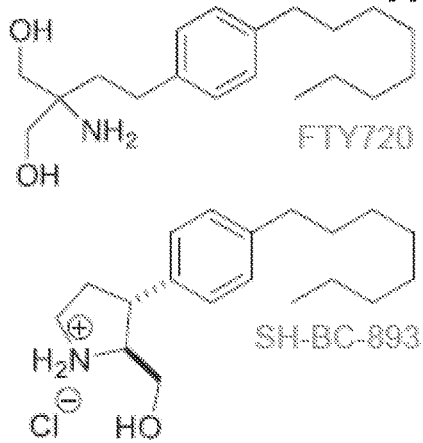
FIGS. 51A to 51G provide molecular structures of therapeutic small molecule analogs, microscope-captured images and graphical data detailing the ability of small molecule analogs to trigger nutrient transporter internalization and metabolic changes but not S1P receptor activation in accordance with embodiments of the invention.
Figure 51B:
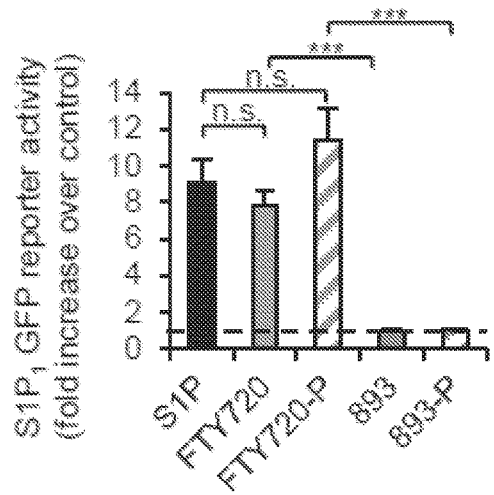
Figure 51C:
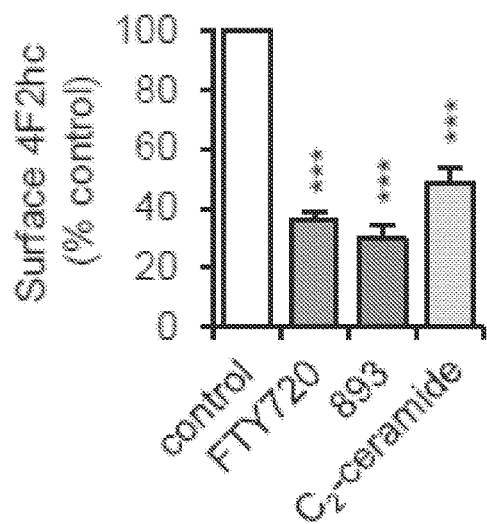
Figure 51D:
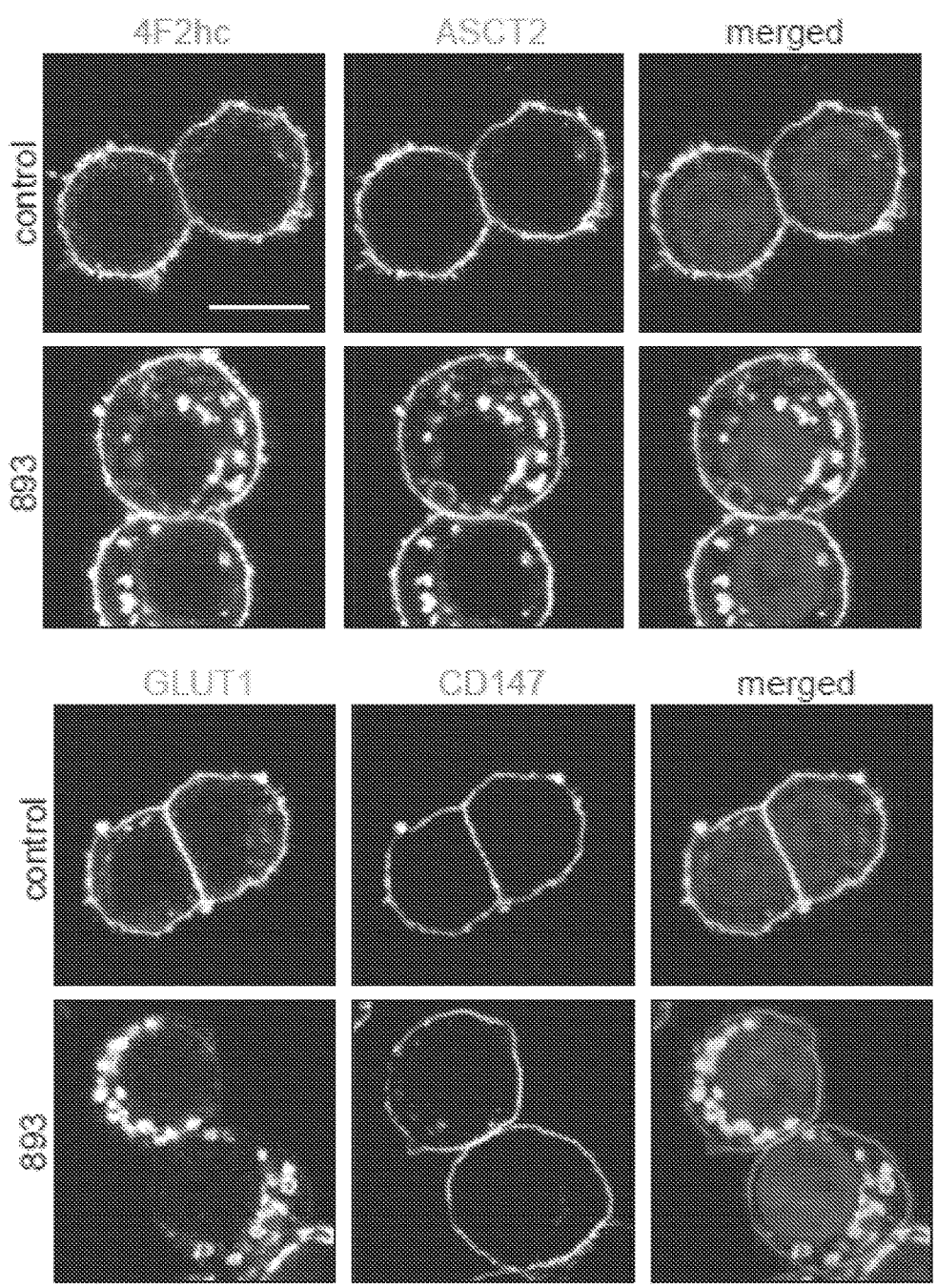
Figure 51E:
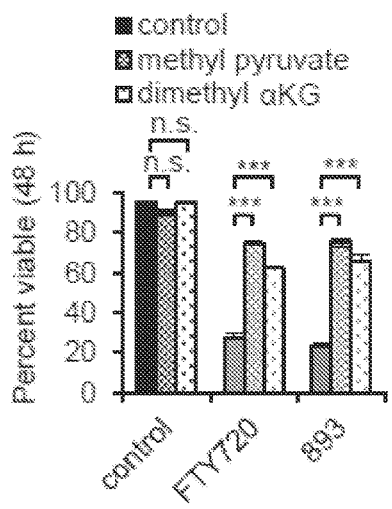

As a proof of principle concerning the ability of C-aryl azacyclic constrained sphingolipid-like compounds, compound SH-BC-893 was examined thoroughly in a series of exemplary embodiment experiments. (The chemical structure of SH-BC-893, also referred to in the in this application as compound 5 and compound 104, and of FTY720 are shown in FIG. 51A). Results are provided below, along with a number of correlated data tables and graphs (Tables 7 and 8 and FIGS. 51-67). In embodiments, SH-BC-893 induces nutrient transporter loss and mimics starvation without the S1P receptor associated toxicity of FTY720. SH-BC-893 lacks the sphingosine-1-phosphate (S1P) receptor activity that prevents the use of FTY720 in cancer patients (FIG. 51B). SH-BC-893 still triggers the selective internalization of amino acid transporters, such as, for example 4F2hc or Alanine-Serine-Cysteine Transporter 2 (ASCT2), and glucose transporters, such as, for example glucose transporter 1 (GLUT1) (FIGS. 51C and 51D). Other surface proteins, such as CD147, a chaperone protein with similar functions to 4F2hc, are not affected. If cells are nutrient-limited, blocking apoptosis via Bcl-XL over-expression did not prevent SH-BC-893-induced cell death (FIGS. 51E, 52A and 52B). In contrast, the transporter-independent, membrane-permeant nutrients methyl pyruvate and dimethyl-α-ketoglutarate rescued SH-BC-893-treated cells (FIG. 51E). These results confirm that SH-BC-893 kills cells by limiting nutrient access.

Cells adapt to nutrient limitation by increasing oxidative phosphorylation. The relative rate of glycolysis and oxidative phosphorylation can be monitored by measuring the fluorescence lifetime of the reduced form of nicotinamide adenine dinucleotide (NADH). A higher ratio of protein-bound to free NADH (increased lifetime) correlates with increased oxidative phosphorylation in multiple cell types both in vitro and in vivo. Oligomycin and rotenone/antimycin A are molecules known in the field to induce glycolysis, whereas 2-deoxy-glucose (2DG) is an inhibitor of glycolysis and subsequently increases oxidative phosphorylation. Starvation of cells by removing access to glucose and amino acids is also known to increase oxidative phosphorylation.

Figure 51F:
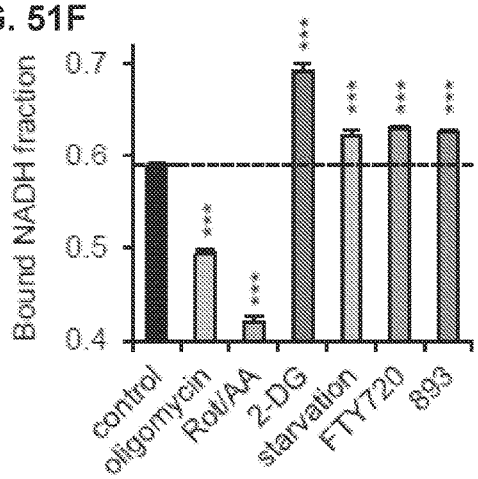
Figure 51G:
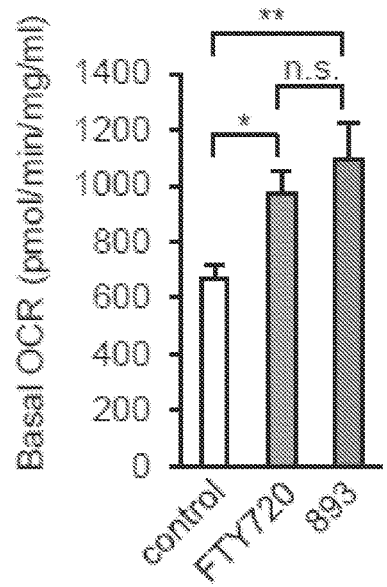
Figure 52A:
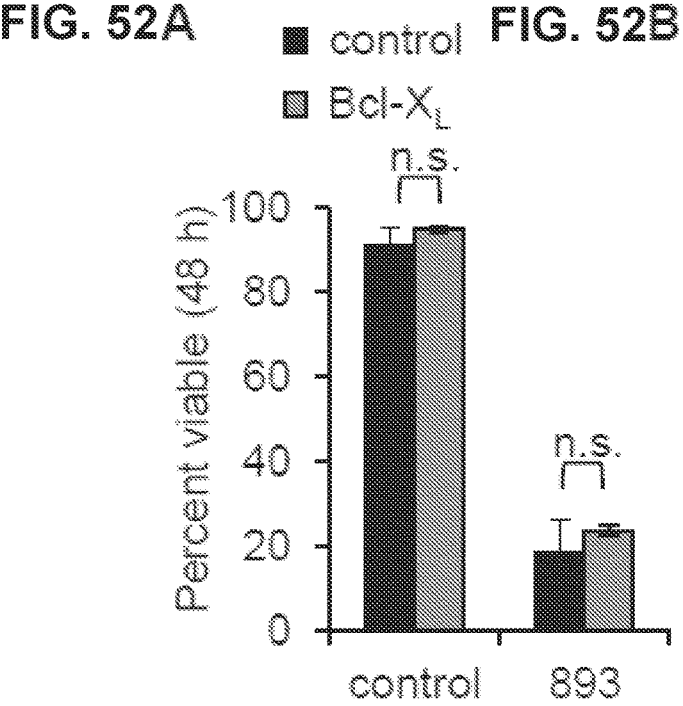
FIGS. 52A and 52B provide graphical data detailing that the induced cell death that caused by small molecule analogs does not occur even in cells resistant to apoptosis in accordance with embodiments of the invention.
Figure 52B:
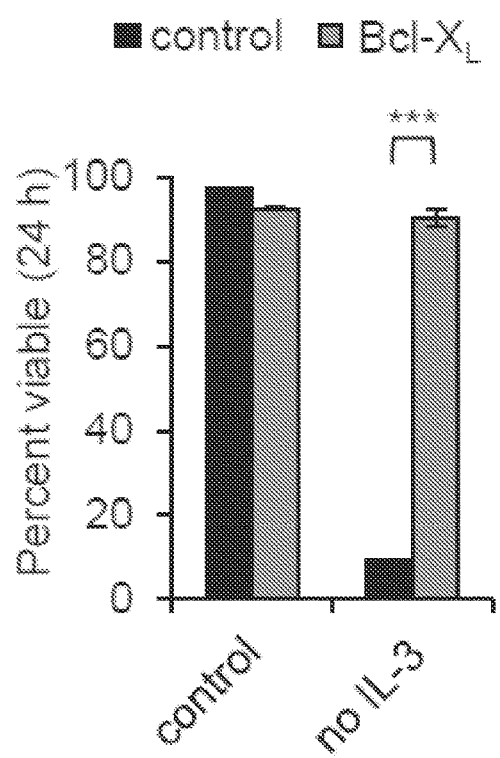

Cells treated with oligomycin or rotenone/antimycin A, as expected, compensated for the loss of oxidative phosphorylation by increasing glycolysis, reducing the bound NADH fraction (FIG. 51F). Conversely, the glycolysis inhibitor 2-DG and starvation increased oxidative phosphorylation and the bound to free NADH ratio. SH-BC-893 mimicked the effect of amino acid and glucose starvation, increasing the bound NADH fraction and cellular oxygen consumption (FIGS. 51F and 51G). Cells responded similarly to the anti-inflammatory drug FTY720. Thus, the metabolic changes triggered by SH-BC-893 parallel those seen in cells with restricted access to key metabolic substrates.

Figure 53A:
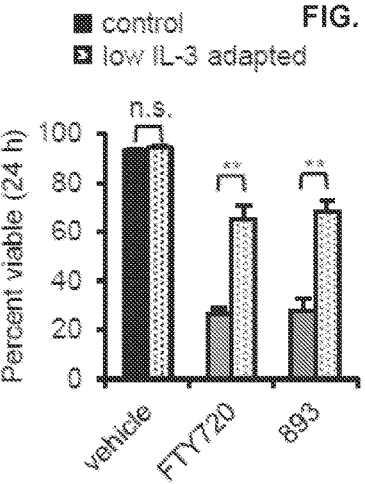
FIGS. 53A to 53I provide graphical data detailing the ability of small molecule analogs to selectively kill cancer cells in accordance with embodiments of the invention.
Figure 53B:
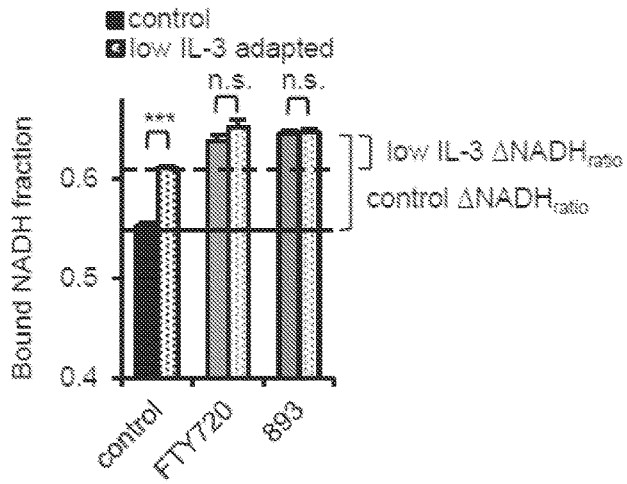
Figure 53C:
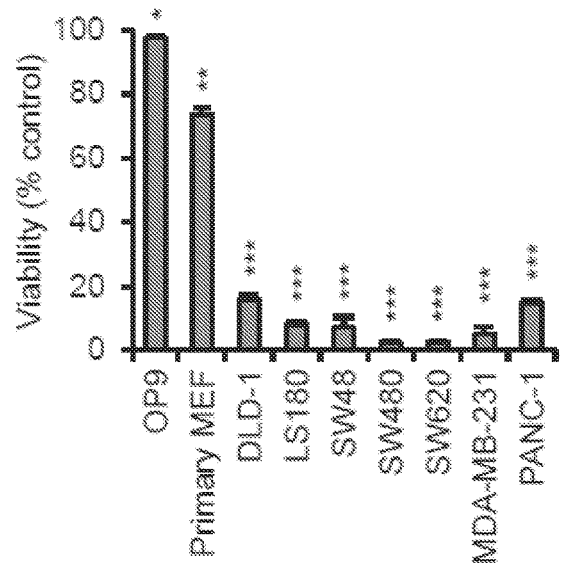
Figure 53D:
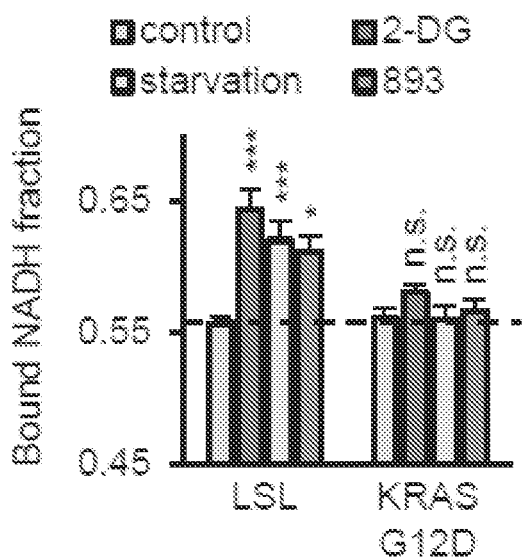
Figure 53E:
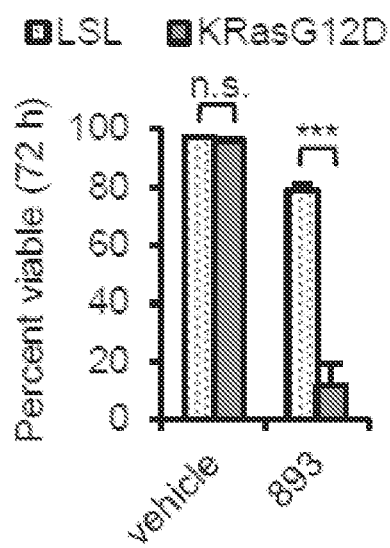
Figure 54A:
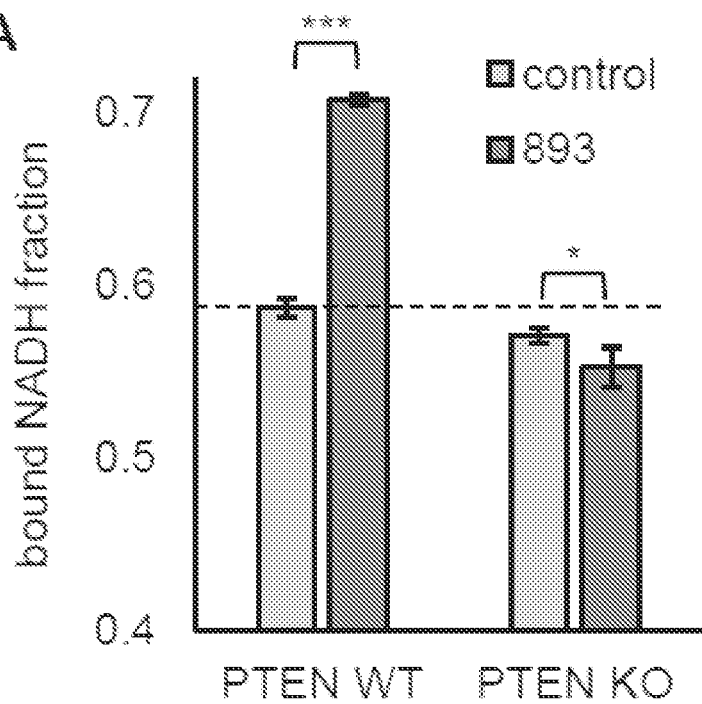
FIGS. 54A to 54F provide graphical data and microscope-captured images detailing the ability of small molecule analogs to selectively kill cells expressing oncogenes or lacking tumor suppressor genes and to inhibit tumor growth in vivo in accordance with embodiments of the invention.
Figure 54:
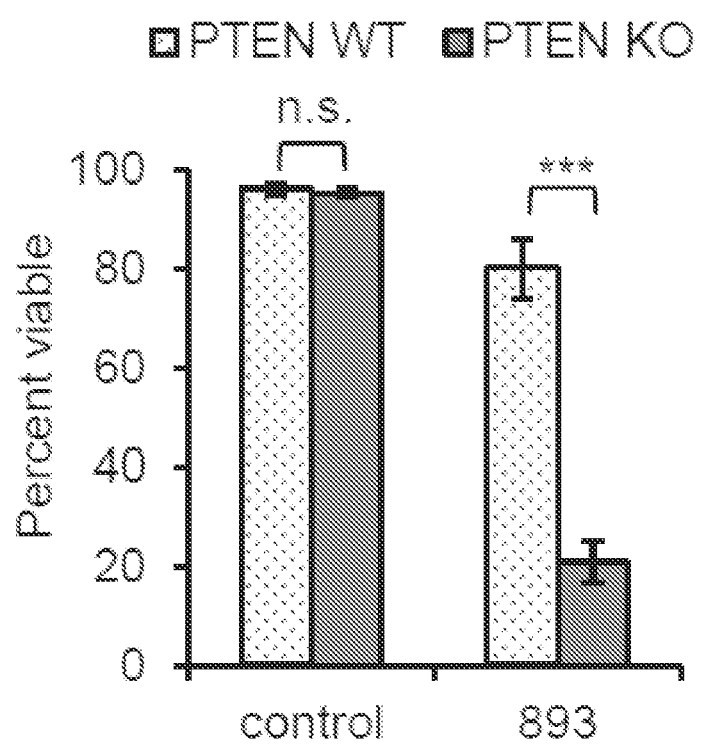
Figure 54C:
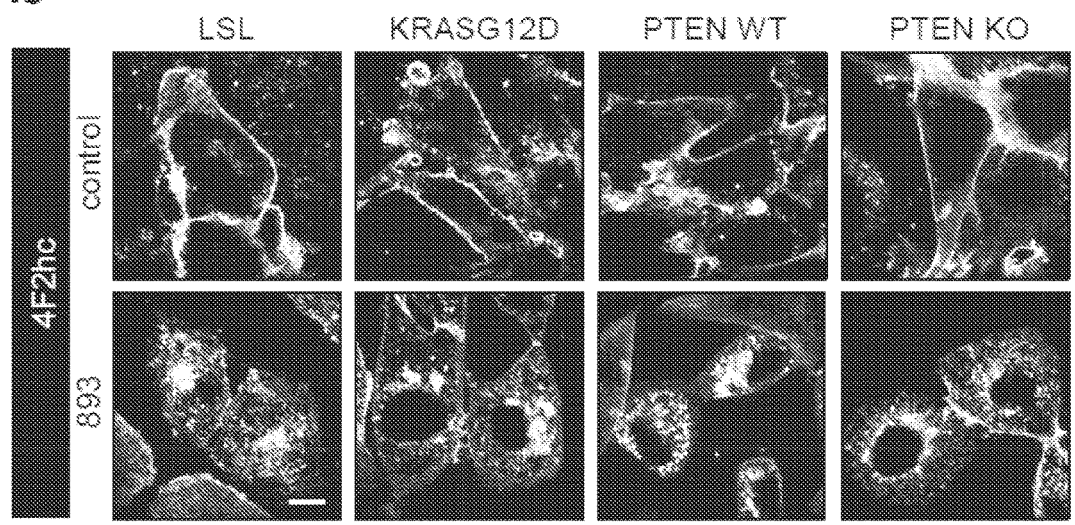
Figure 54D:
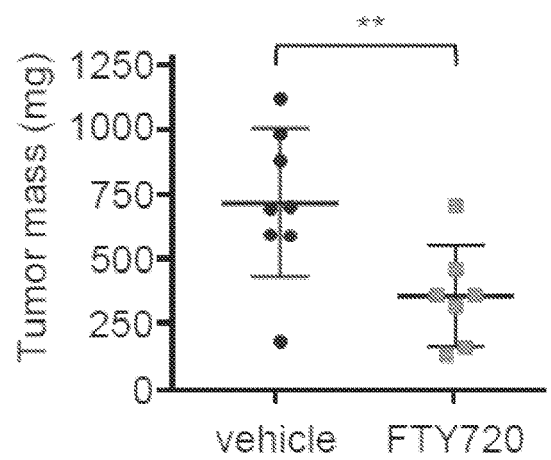

Consistent with the bioenergetic mechanism described supra, cells with a higher anabolic rate should be more sensitive to sphingolipid-like compounds. In exemplary experiments testing this mechanism, murine FL5.12 cells with different anabolic rates were treated with SH-BC-893. The anabolic rate of FL5.12 cells can be titrated by modulating the levels of their required growth factor, IL-3; comparing FL5.12 cells grown in high and low IL-3 allows the impact of elevated growth factor signaling and anabolism to be evaluated in a constant genetic background. High concentrations of IL-3 drive aerobic glycolysis and a rapid doubling time (12 h). Reducing IL-3 levels slows proliferation and increases oxidative phosphorylation without compromising cell viability (FIGS. 53A and 53B). Maintenance in low IL-3 medium reduced the need for metabolic adaptation (FIG. 53B) and protected cells from SH-BC-893-induced death (FIG. 53A), suggesting that cells with low anabolism (e.g. healthy tissue) will be less sensitive to treatment with sphingolipid-like compounds than cells with high anabolism (e.g. neoplastic cells). Indeed, consistent with particular embodiments of the invention, non-transformed murine OP9 bone marrow stromal cells and primary murine embryonic fibroblasts (MEFs) were less sensitive to SH-BC-893 than human cancer cell lines, including DLD-1, LS180, SW48, SW480, SW620, MDA-MB-231, and PANC-1 (FIG. 53C). Many of these cancer cell lines carry activating mutations in Ras. In fact, K-Ras activation following Cre expression in Lox-STOP-Lox-KRasG12D MEFs was sufficient to limit metabolic flexibility and sensitize cells to SH-BC-893 (FIGS. 53D and 53E) (Cell line described in: Tuveson D. A., et al., *Cancer Cell* 5:375-87 2004, the disclosure of which incorporated herein by reference). In other embodiments, loss of the tumor suppressor PTEN produced similar effects (FIGS. 54A and 54B). Importantly, oncogenic mutations did not affect surface nutrient transporter down-regulation in K-Ras G12D-expressing or PTEN-deficient MEFs (FIG. 54C).

Figure 53F:
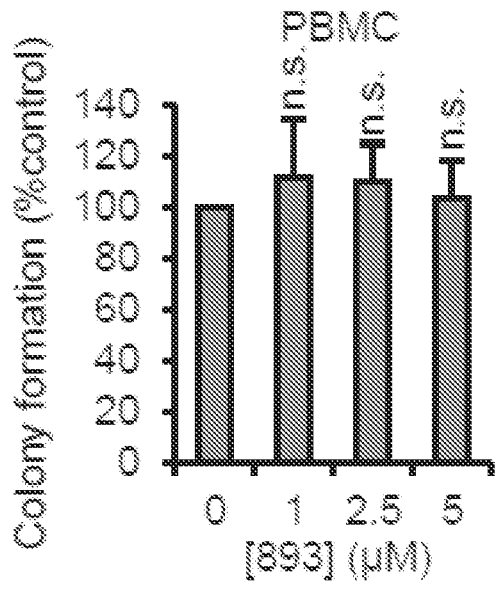
Figure 53F:
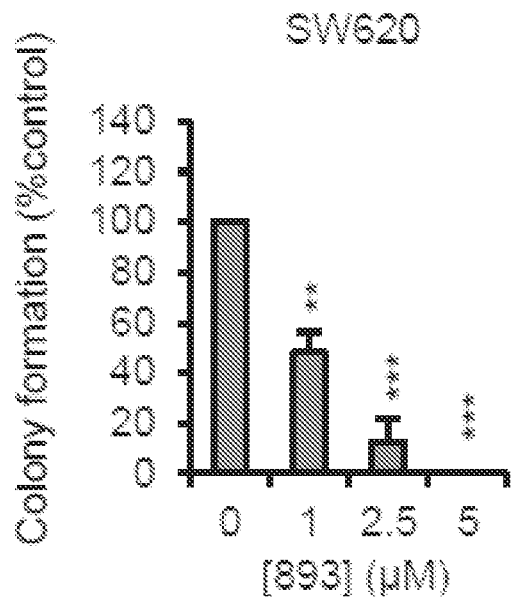
Figure 53G:
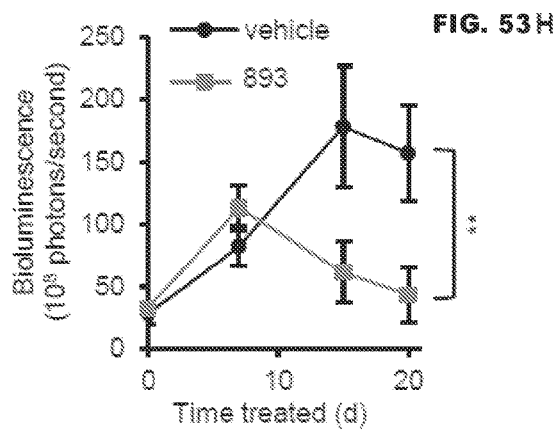
Figure 53H:
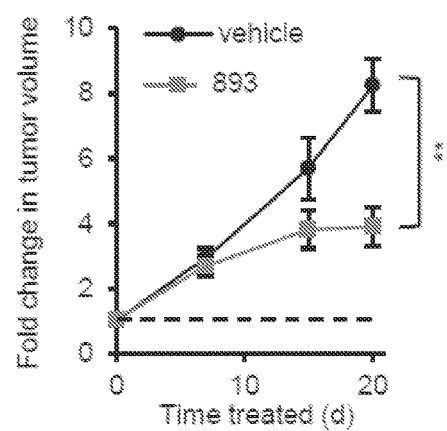
Figure 53I:
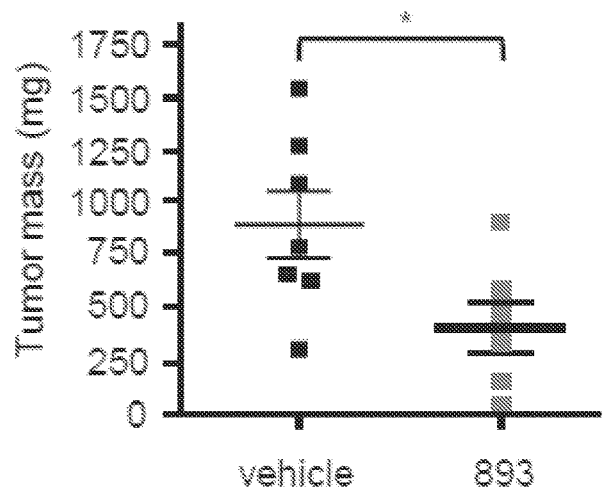

These results indicate that both normal and transformed cells express the SH-BC-893 target but show differential sensitivity to the compound. The difference in sensitivity stems from the inability of neoplastic cells to adapt to decreases of metabolism. Consistent with these results, healthy cells with flexible metabolism, such as normal human peripheral blood mononuclear cells (PBMC), were resistant to SH-BC-893, whereas the colon cancer cells SW620 were highly sensitive in colony formation assays (FIG. 53F). Taken together, these data suggest that constitutive anabolism sensitizes cancer cells to SH-BC-893 and could generate an acceptable therapeutic index.

Figure 54E:
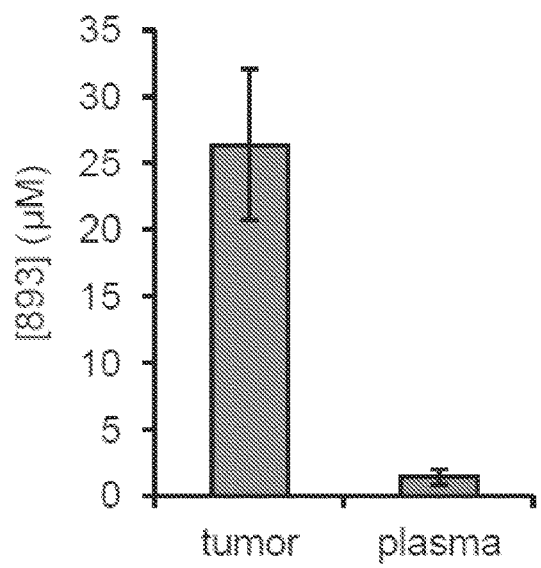
Figure 54F:
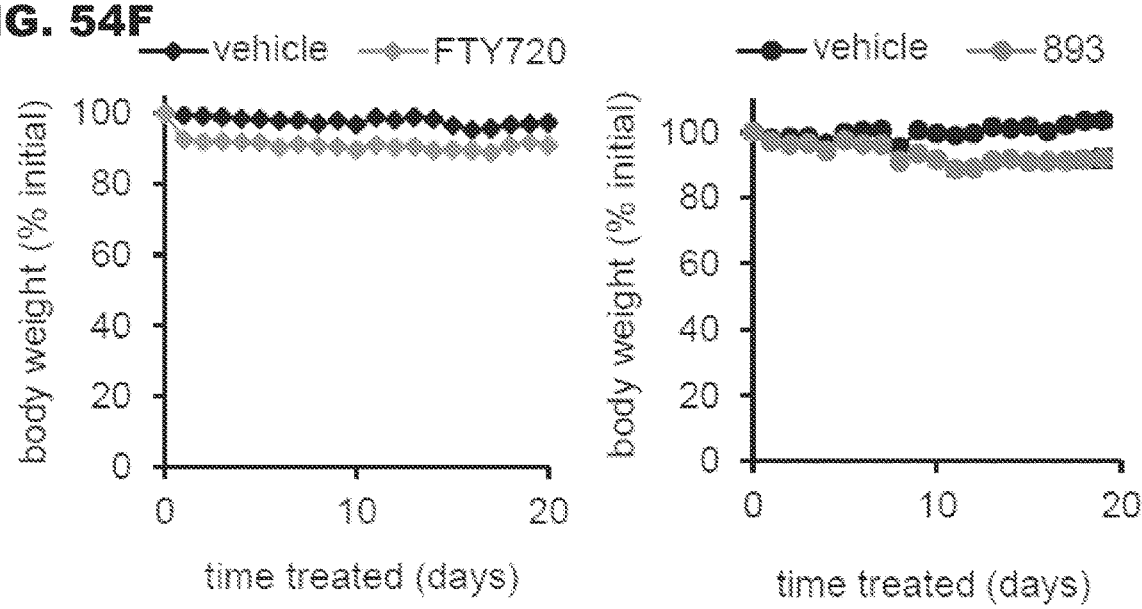

In many embodiments, exemplary experimentation was carried out to determine whether azacyclic constrained sphingolipid-lipid molecules inhibited neoplastic growth in vivo. To carry out this experimentation, luciferase-expressing SW620 xenografts were generated in mice. Results from bioluminescence imaging (BLI), caliper measurements, and tumor mass at sacrifice experiments showed that the SW620 tumors were reduced to a similar degree by SH-BC-893 and FTY720 (FIGS. 53G-I and 54D). SH-BC-893 was present at low micromolar concentrations in both tumors and plasma at sacrifice (FIG. 54E). Mild weight loss occurred in treated mice as expected given that nutrient access would be restricted in both normal and transformed cells (FIG. 54F). These results suggest that sphingolipid-like molecules, such as SH-BC-893, could provide a safe and effective means to target neoplasms, including, for example, Ras-driven cancers or tumors with PTEN loss.

Figure 55A:
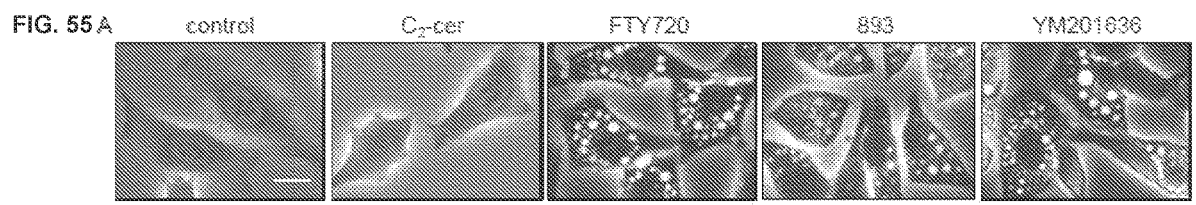
FIGS. 55A to 55F provide microscope-captured images and graphical data detailing the ability of small molecule analogs to induce vacuolation in accordance with embodiments of the invention.
Figure 55B:
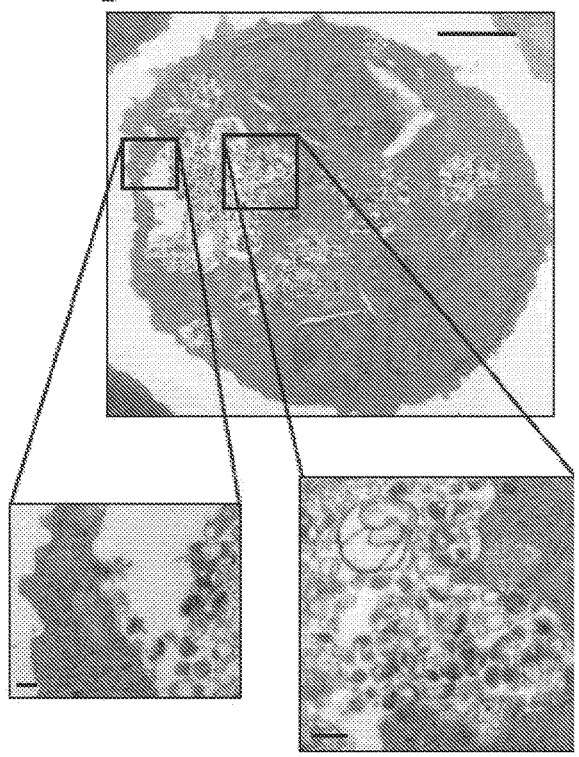
Figure 55C:
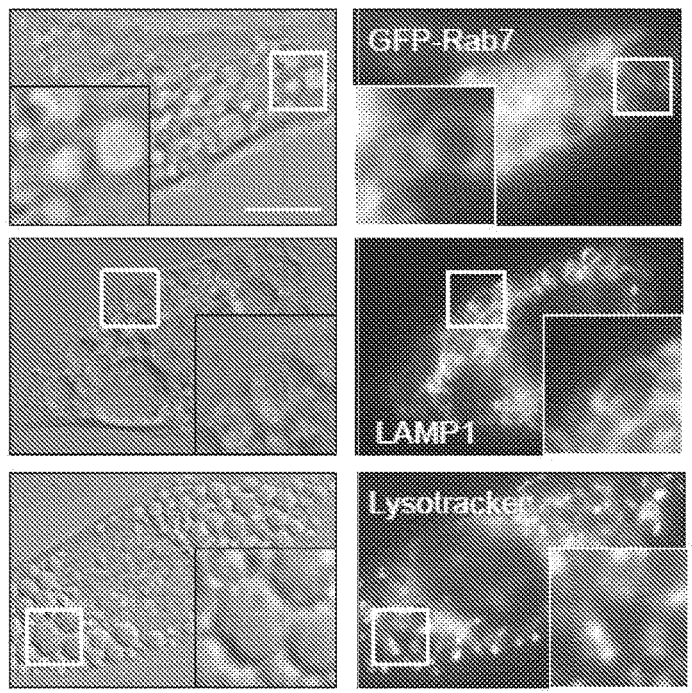
Figure 55D:
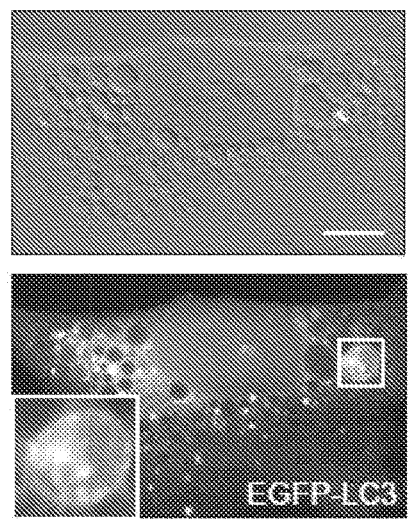
Figure 55:
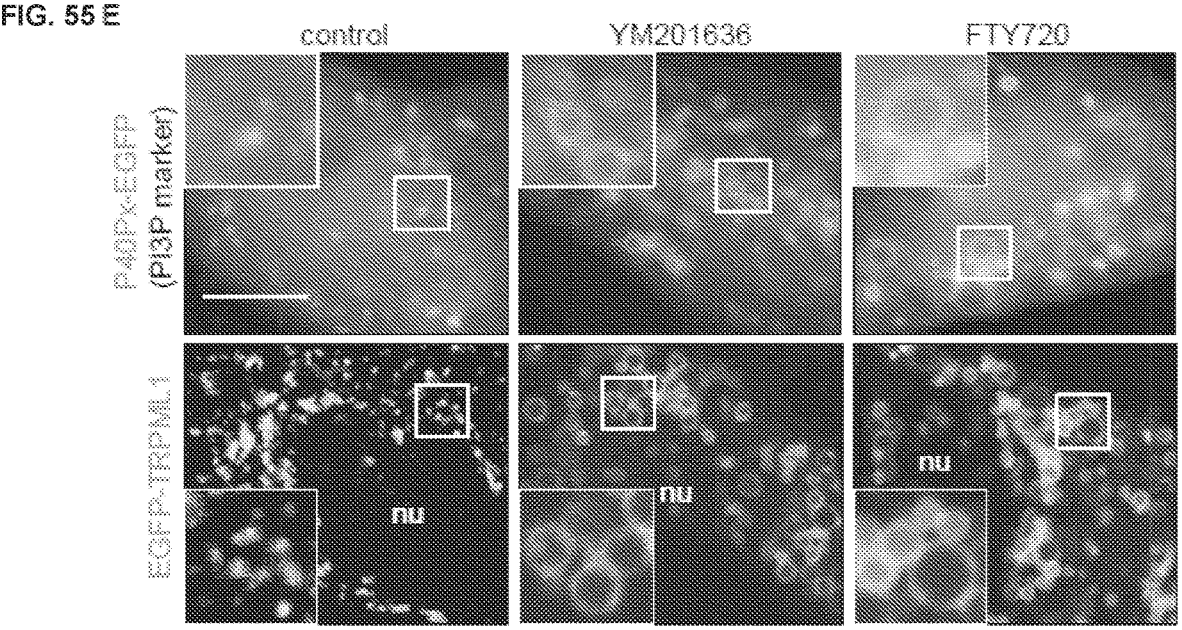
Figure 55:
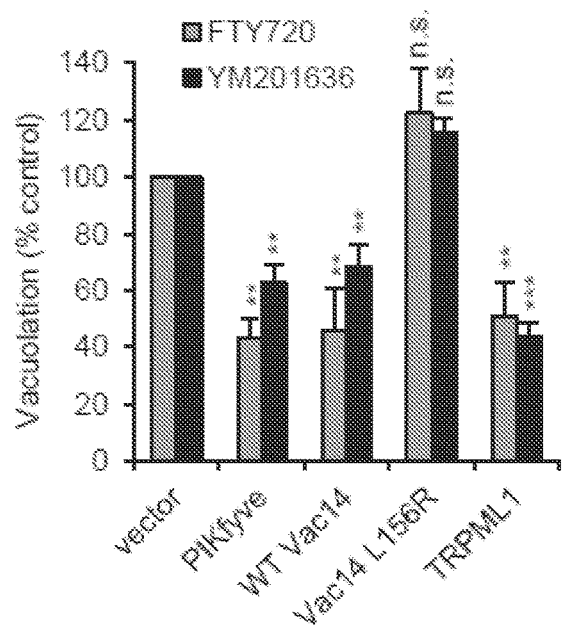
Figure 56A:
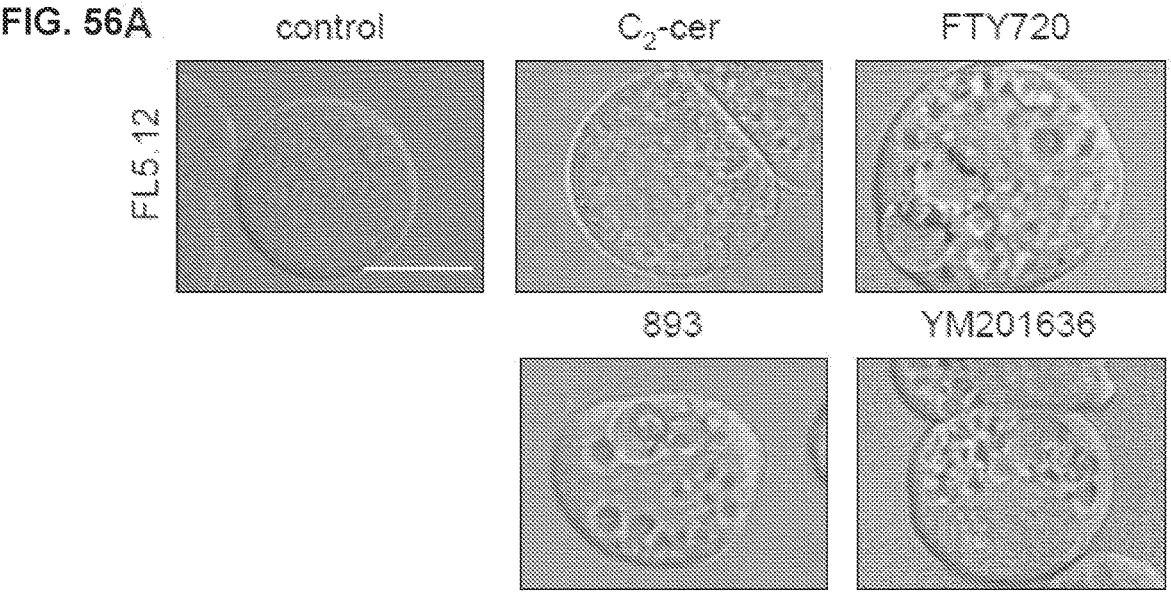
Figure 56B:
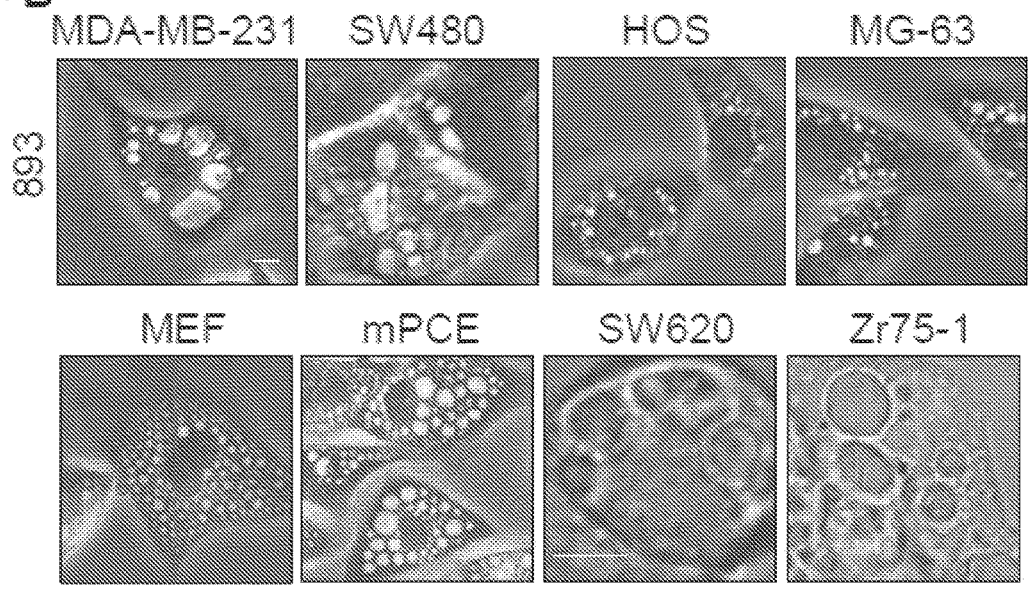
Figure 56:
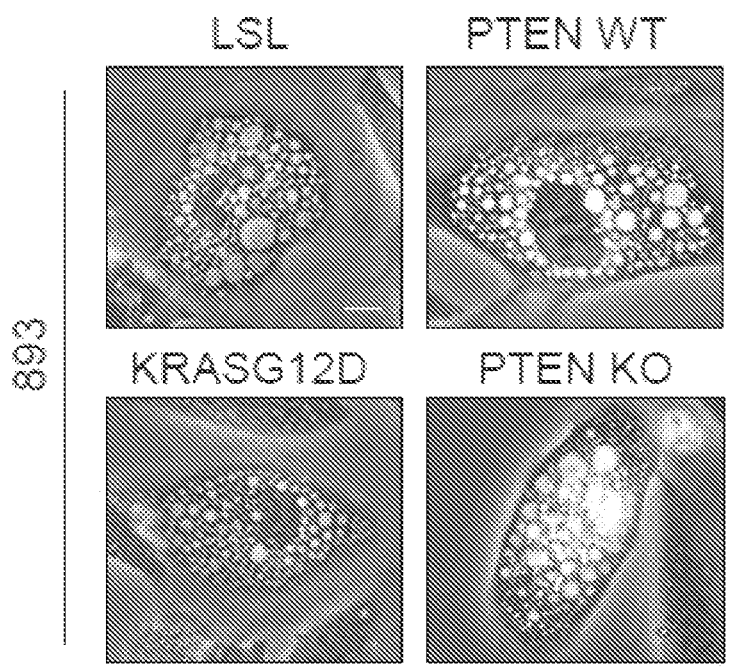
Figure 56:
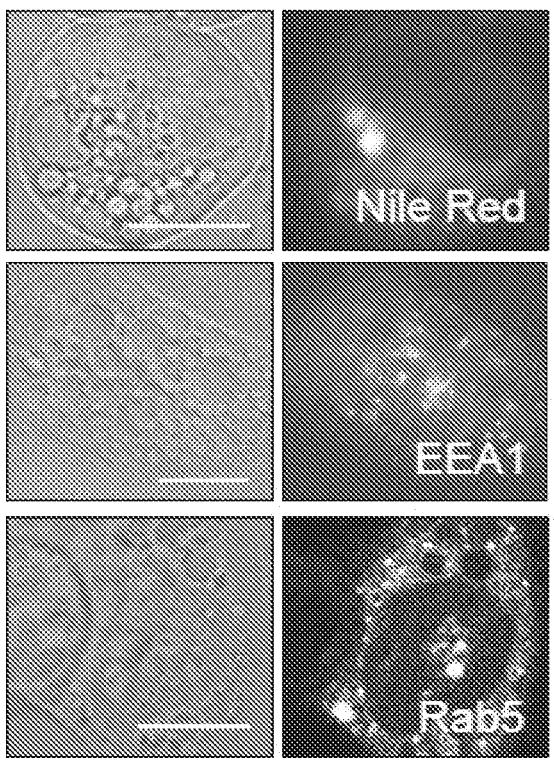
Figure 56E:
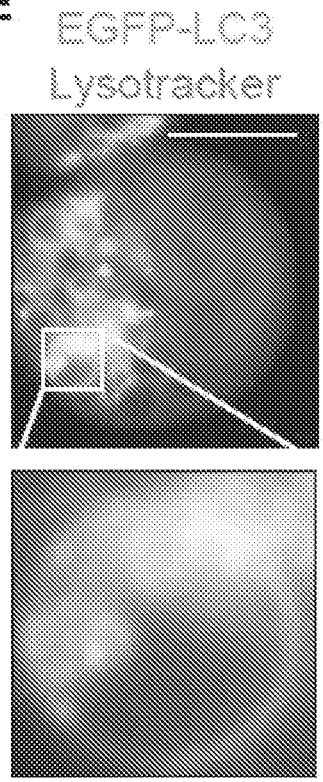
Figure 56:
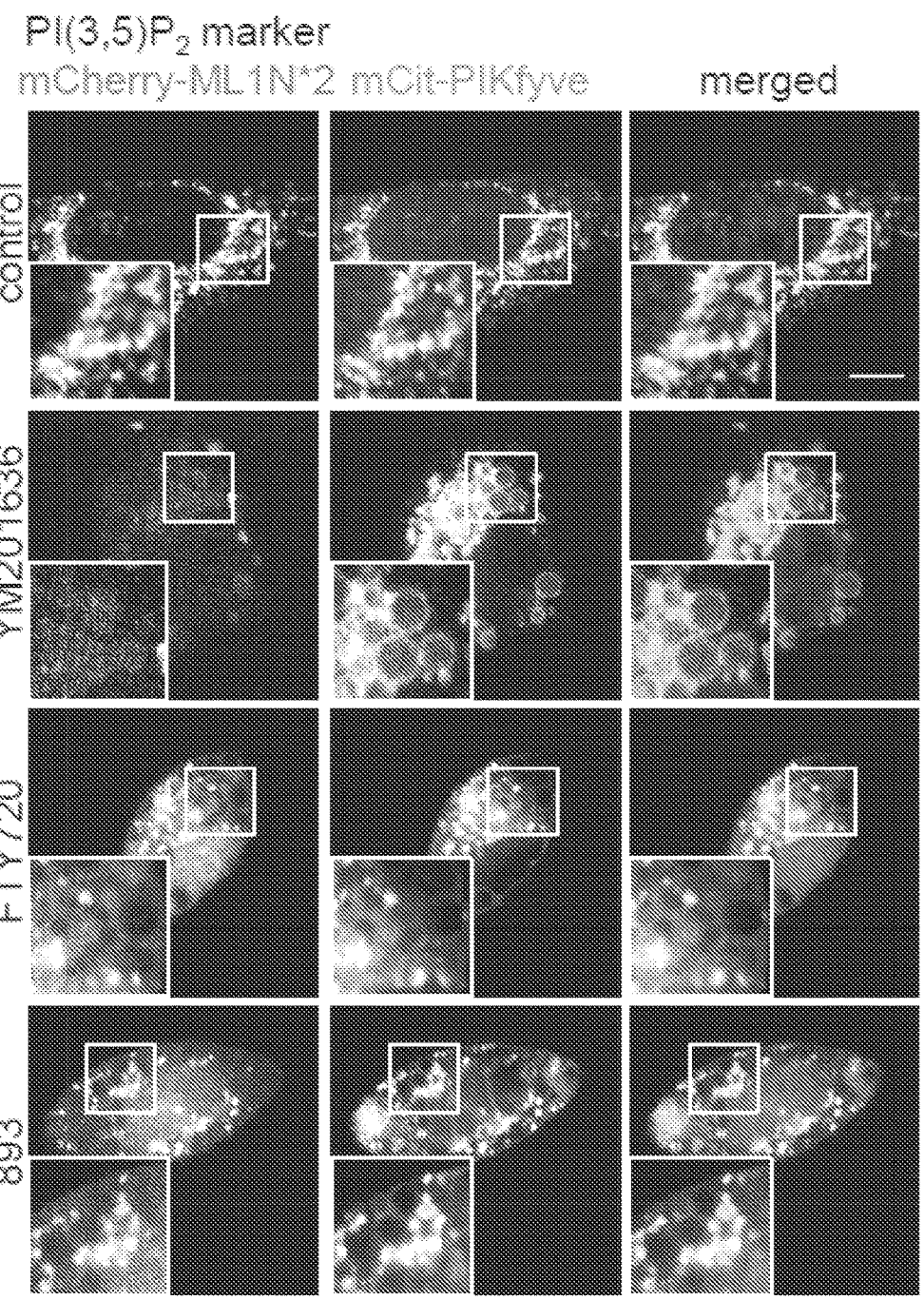

Certain embodiments of the invention are directed to azacyclic constrained sphingolipid-like molecules to inhibit macropinocytosis and autophagy, consistent with the bioenergetic mechanism. This aspect of the mechanism was unexpected because it was initially believed in that these molecules would only reduce nutrient transporter surface expression. However, considering that Ras activation increases macropinocytosis and autophagy, and the finding that SH-BC-893 was very effective against neoplastic cells with activated Ras led to the hypothesis that azacyclic constrained sphingolipid-like molecules might also affect macropinocytosis and autophagy pathways. It was found that SH-BC-893 induced equally striking cytosolic vacuolation in both non-transformed and cancer cells (FIGS. 55A, 56A, 56B and 56C). These vacuoles contained intraluminal vesicles (ILVs) as well as amorphous, partially degraded material suggesting that they originate from multivesicular bodies (MVBs) or another late endocytic compartment (FIG. 55B). Vacuoles were positive for the late endosomal markers Lamp1 and Rab7 (FIG. 55C) and negative for the early endosomal markers EEA1 and Rab5 and the lipid stain Nile Red (FIG. 56D). Acidified puncta, likely lysosomes, were observed within or proximal to vacuoles along with material marked as autophagosomes by GFP-LC3 (FIGS. 55C, 55D and 56E). Taken together, these results suggest that azacyclic constrained sphingolipid-like molecules, like SH-BC-893, enlarge MVBs.

Phosphatidylinositol 3,5-biphosphate (PI(3,5)P2) is the product of the phosphatidylinositol 3-phosphate 5-kinase (PI3P 5-kinase). PIKfyve and regulates membrane fusion and ILV formation in MVBs. Reducing PIKfyve activity with the inhibitor YM201636 produced PI3P-positive, PI(3,5)P2-negative vacuoles phenotypically similar to those generated by SH-BC-893 and FTY720 (FIGS. 55A, 55E, 56A and 56F). The $Ca^{2+}$ channel transient receptor potential cation channel, mucolipin subfamily, member 1 (TRPML1) is found in MVB membranes where it is activated by PI(3,5)P2 generated by PIKfyve.

Cells treated with FTY720 or YM201636 accumulated TRPML1 in vacuolar membranes in (FIG. 55E). Furthermore, over-expression of PIKfyve, its scaffolding protein Vac14, or its effector protein TRMPL1 rescued the vacuolation in cells induced from FTY720 or YM201636 (FIG. 55F). Note, a mutant form of Vac14 that does not associate with PIKfyve did not rescue the cells from FTY720- or YM201636-induced vacuolation (FIG. 55F). Together, these data suggest that sphingolipid-like molecules can enlarge MVBs by interfering with PIKfyve activity.

Figure 57A:
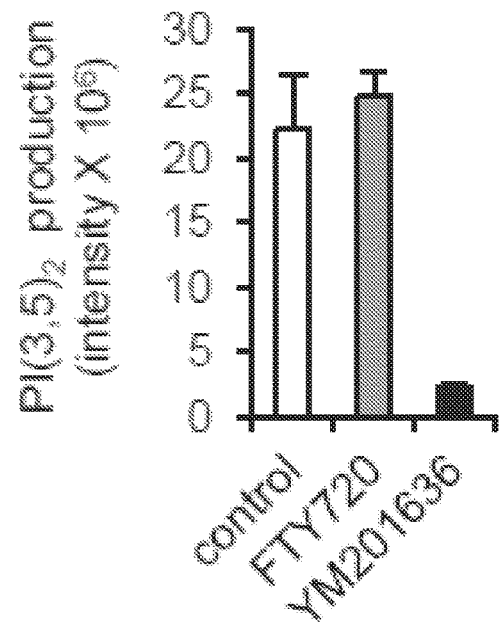
Figure 57B:
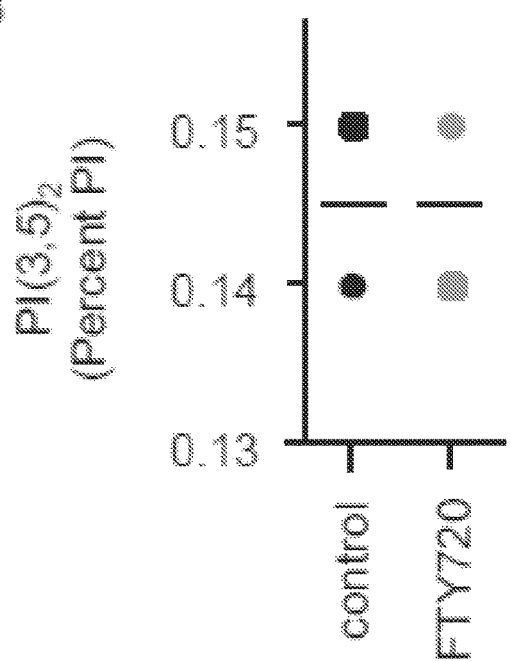

Unlike the inhibitor YM201636, FTY720 unexpectedly did not inhibit PIKfyve kinase activity or reduce PI(3,5)P2 levels (FIGS. 57A and 57B). In certain embodiments of the invention, sphingolipid-like molecules mis-localize PIKfyve preventing its association with TRMPL1 and inducing vacuolation, instead of inhibiting PIKfyve kinase activity. While PIKfyve localized to the limiting membrane of YM201636-induced vacuoles as expected, PIKfyve was present in clumps between vacuoles in FTY720-treated cells (FIGS. 57C and 56F). Validated antibodies recognizing endogenous PIKfyve and Vac14 confirmed this result (FIGS. 57C, 58A and 58B).

Figure 57D:
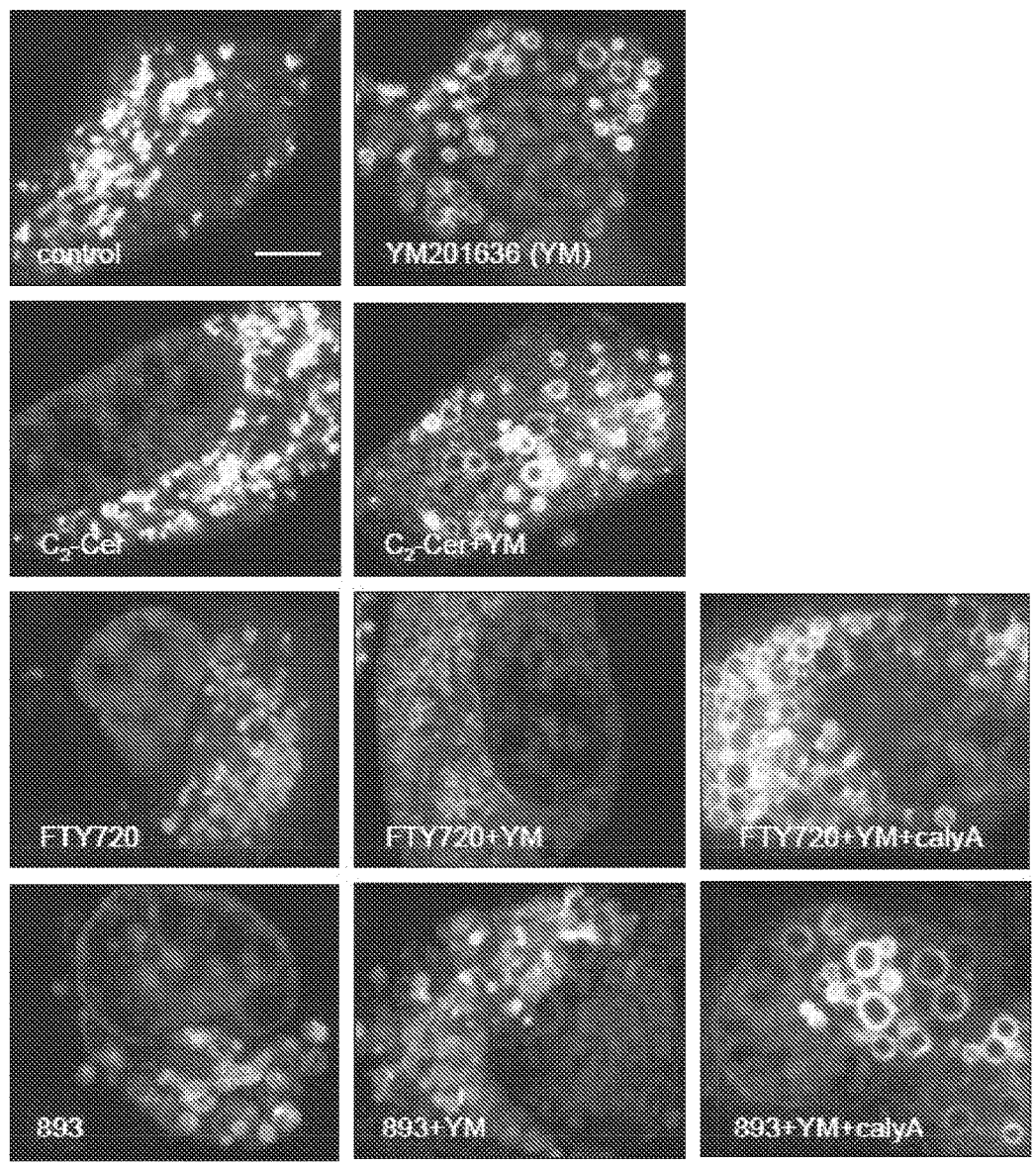
Figure 58:
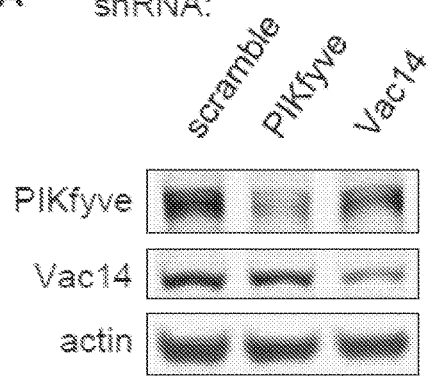
FIGS. 58A to 58D provide graphical data and microscope-captured images detailing the ability of small molecule analogs to disrupt PIKfyve localization but not activity in accordance with embodiments of the invention.
Figure 58C:
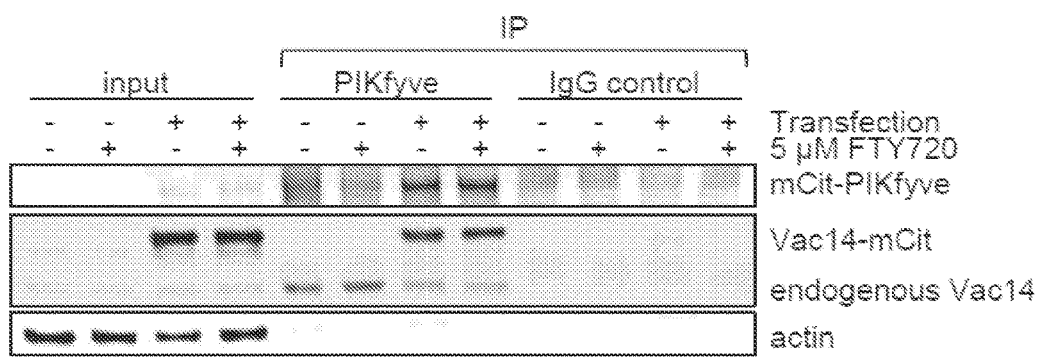
Figure 58:
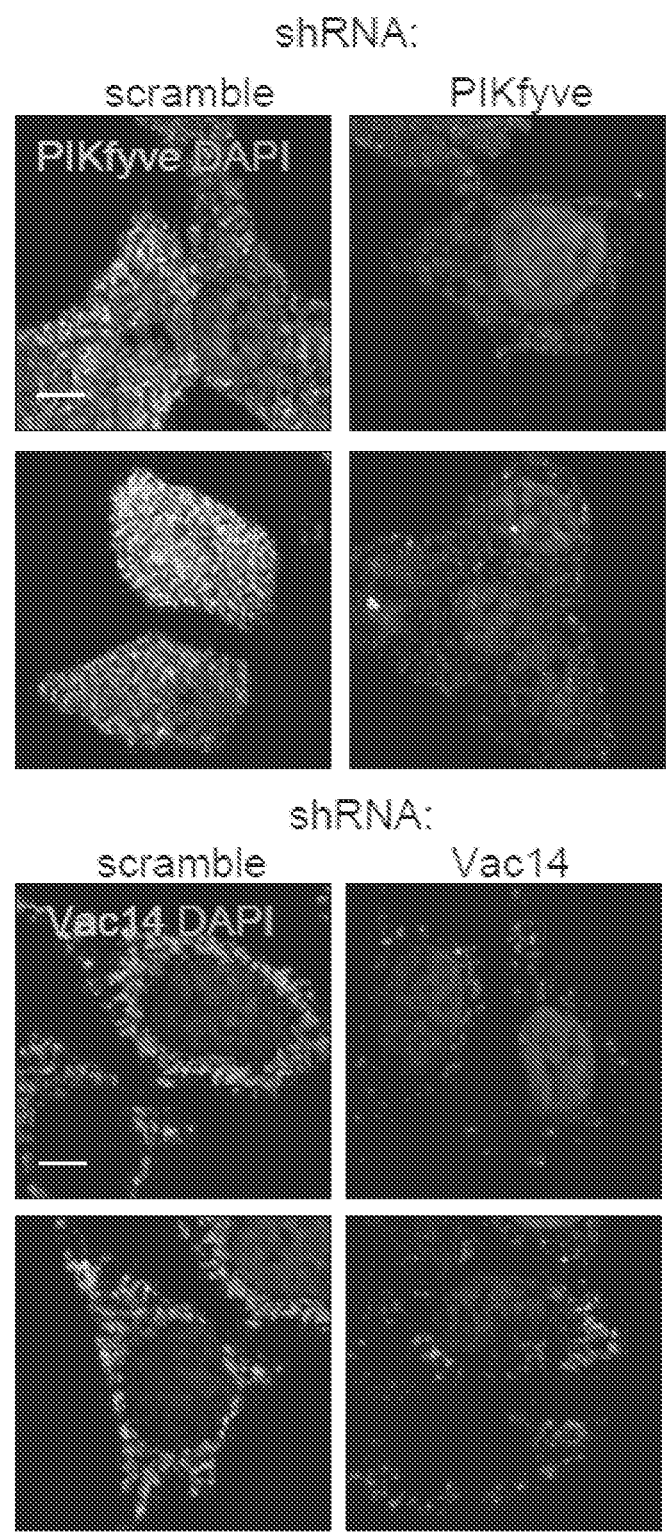

Consistent with their disparate mechanisms of action, YM201636 abolished membrane association of a PI(3,5)P2 probe, while in FTY720 or SH-BC-893 treated cells, the PI(3,5)P2 probe co-localized with PIKfyve to puncta between the vacuoles (FIG. 56F). Moreover, neither PIKfyve (FIG. 57D) nor PI(3,5)P2 (FIG. 58D) co-localized with the PI(3,5)P2 effector protein TRMPL1 on vacuoles in FTY720- or SH-BC-893-treated cells. As TRPML1 was present on both YM201636- and SH-BC-893-induced vacuoles (FIGS. 55E and 58D), PIKfyve and not TRPML1 was mislocalized by FTY720 and SH-BC-893. FTY720 and SH-BC-893 also eliminated PIKfyve from the TRPML1-positive vacuoles in YM201636-treated cells (FIG. 57D). Consistent with its lack of vacuolating activity (FIG. 55A), ceramide did not disrupt PIKfyve-TRMPL1 co-localization in the presence or absence of YM201636 (FIG. 57D). These results indicate that sphingolipid-like molecules induce vacuolation by mis-localizing PIKfyve, which leads to generation of PI(3,5)P2 in a disparate compartment from its transmembrane effector protein, TRPML1.

Figure 59:
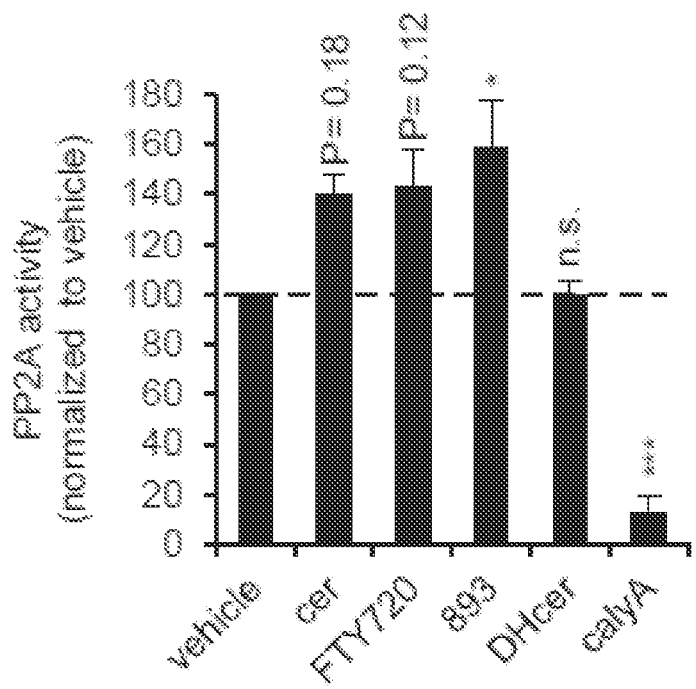
FIGS. 59A to 59C provide graphical data and microscope-captured images detailing the ability of small molecule analogs to activate PP2A as a means to induce nutrient transporter loss and vacuolation in accordance with embodiments of the invention.
Figure 59:
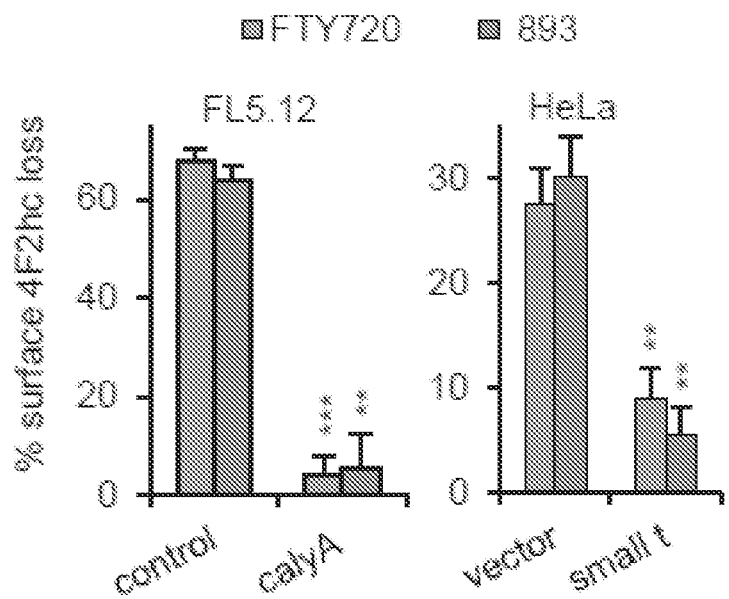
Figure 59C:
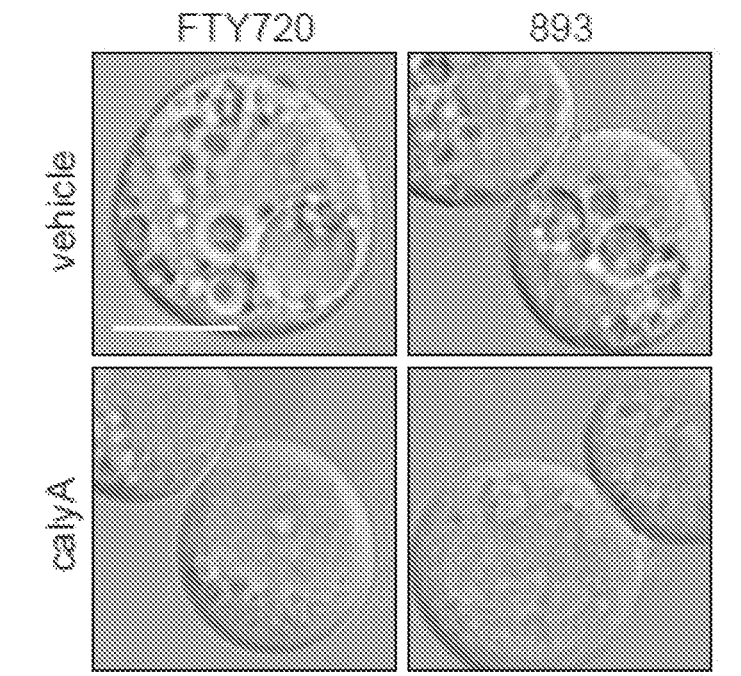
Figure 59C:
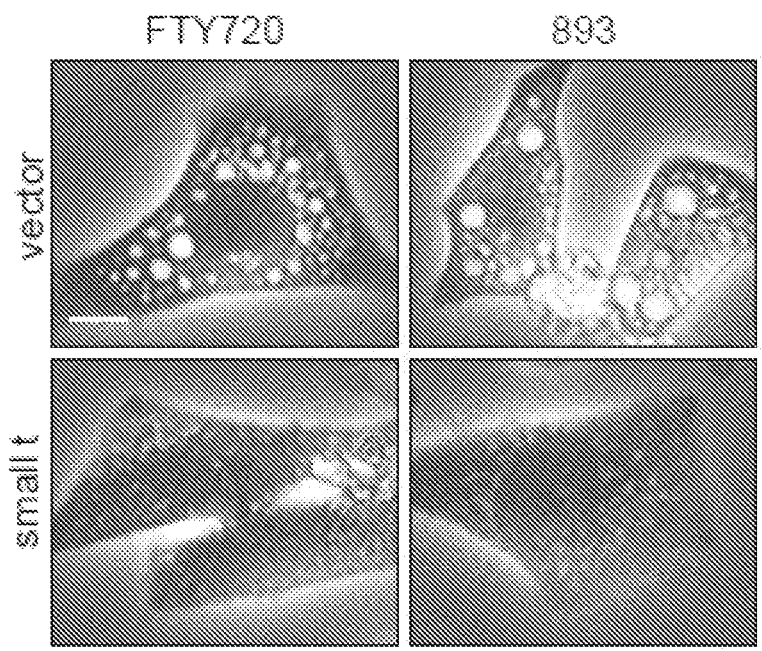
Figure 60:
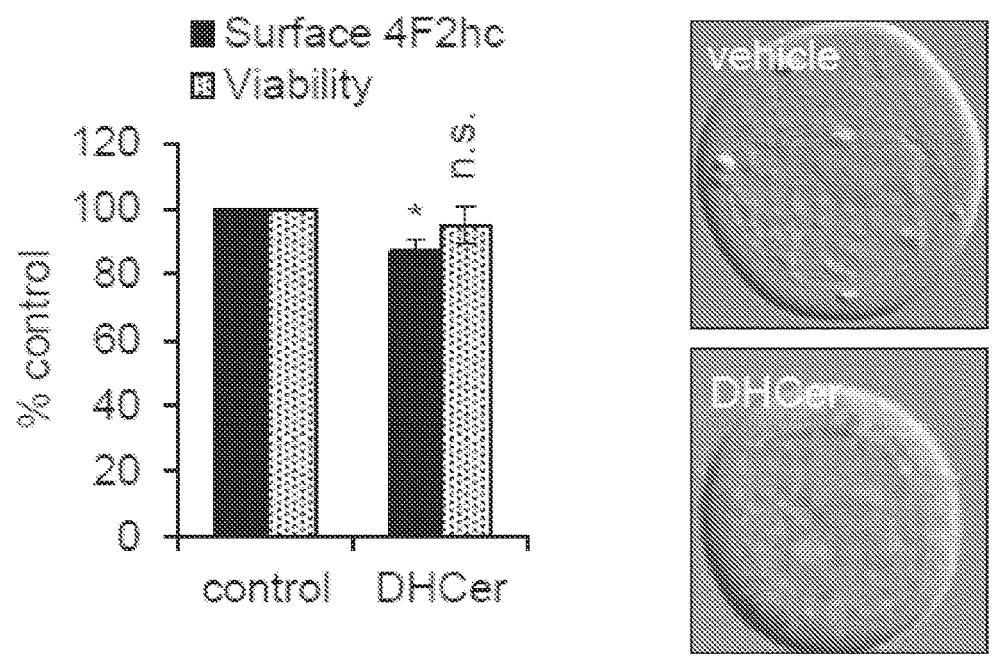
FIGS. 60A to 60E provide graphical data and microscope-captured images detailing the ability of small molecule analogs, but not other sphingolipids, to induce surface nutrient transporter loss and vacuolation via two distinct PP2A-dependent mechanisms in accordance with embodiments of the invention.
Figure 60:
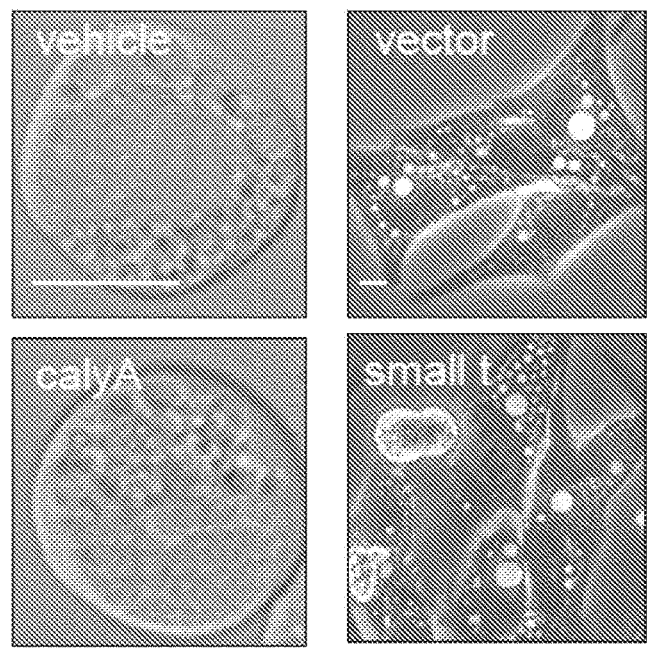
Figure 60C:
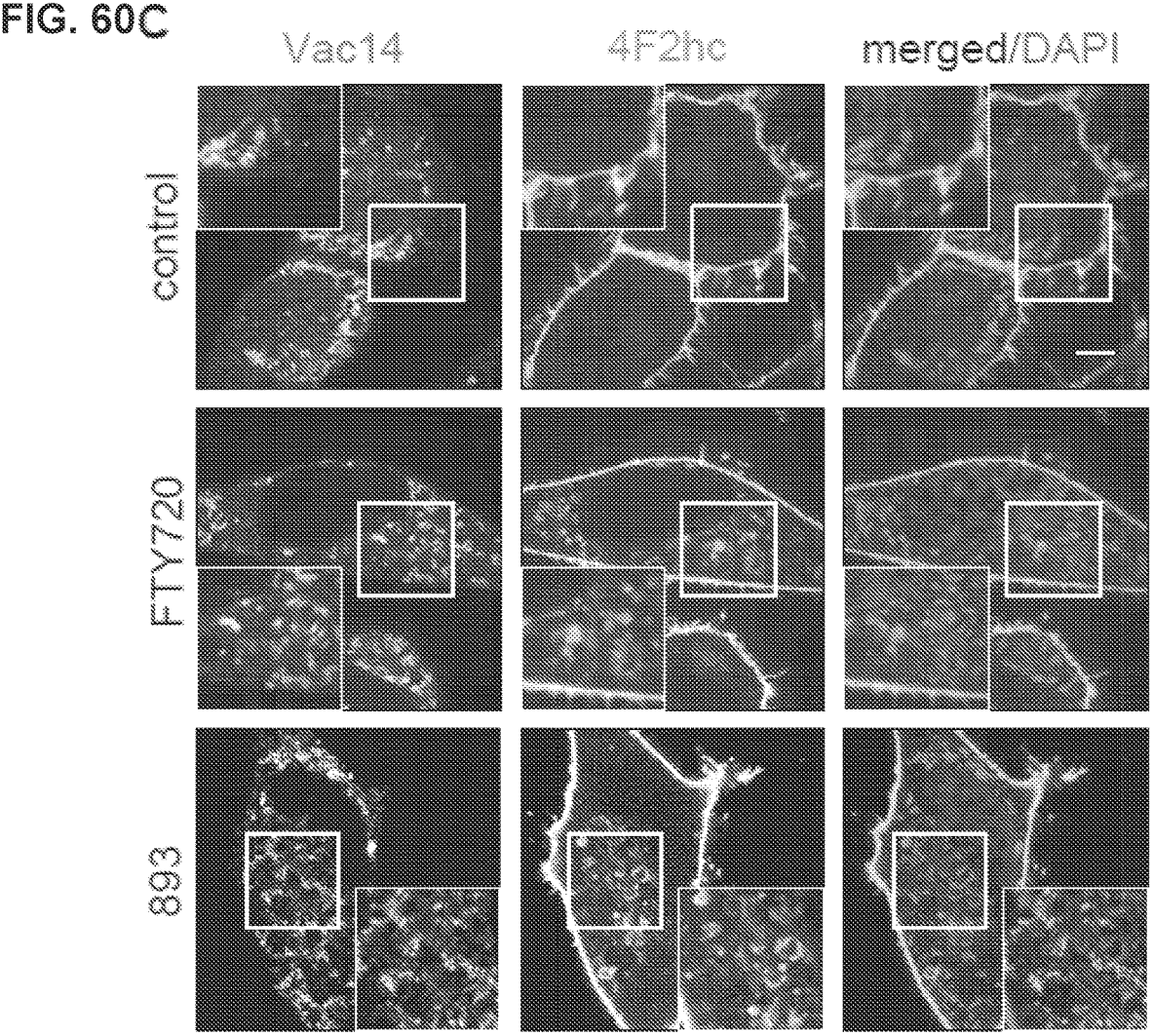
Figure 60D:
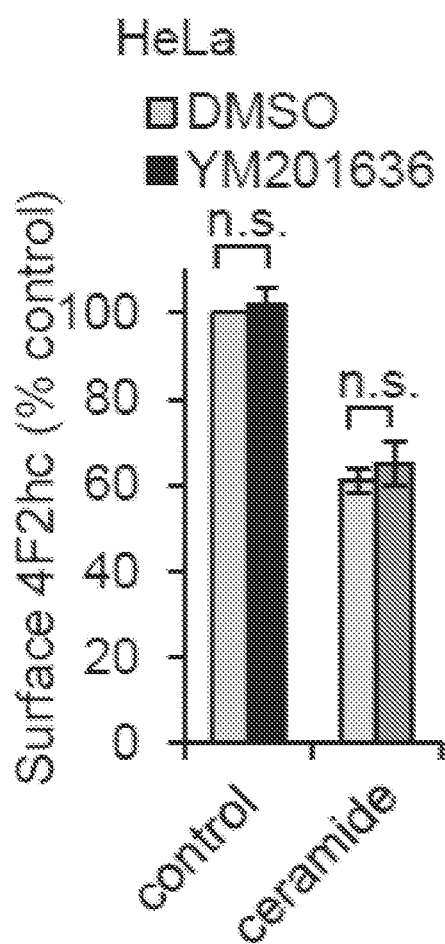
Figure 60E:
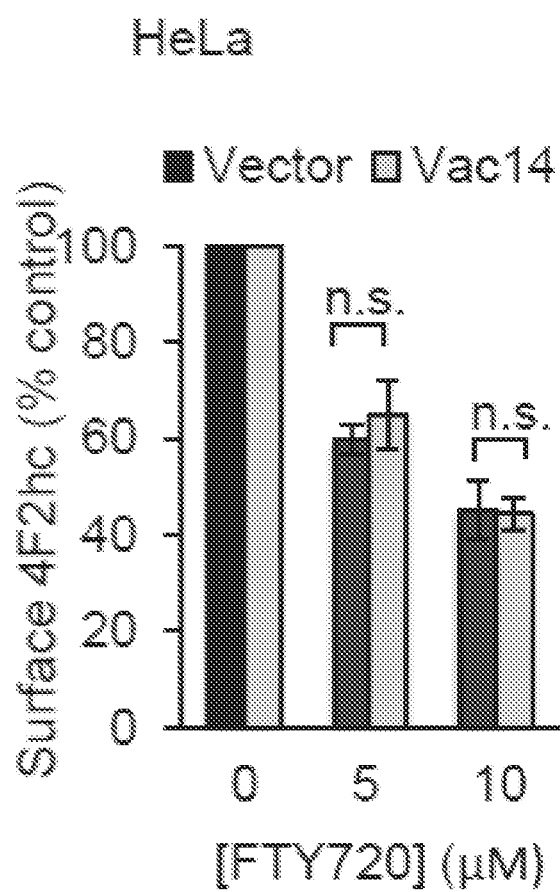

Furthermore, many embodiments of the invention are directed to azacyclic constrained sphingolipid-like molecules inducing internalization of nutrient transporters via a mechanism that activates PP2A. These embodiments reflect that ceramide, FTY720, and SH-BC-893 trigger nutrient transporter loss by activating PP2A (FIGS. 59A and 59B). Dihydroceramide, which differs from ceramide by a single saturated bond does not activate PP2A, does not kill cells, and does not trigger transporter loss or vacuolation (FIGS. 59A and 60A). Thus, activation of PP2A is very peculiar to certain sphingolipid structures. Activation of PP2A by FTY720 and SH-BC-893 also stimulated vacuolation, and as the PP2A inhibitors calyculin A and SV40 small t antigen, each blocked this effect (FIG. 59C). Of note, YM201636-induced vacuolation was unaffected by PP2A inhibition (FIG. 60B). In addition, inhibiting PP2A restored PIKfyve to the proper location within vacuoles in cells treated with FTY720 or SH-BC-893 (FIG. 57D). Because ceramide triggers transporter loss by activating PP2A, but lacks ability to stimulate vacuolation and does not mis-localize PIKfyve, it is suggested that different combinations PP2A heterotrimers or distinct pools of PP2A promote the nutrient-transporter-internalization and vacuolation pathways. Consistent with this suggestion, the data shows that the amino acid and glucose transporters internalized by FTY720 and SH-BC-893 did not co-localize with the PIKfyve complex (FIG. 60C). Moreover, triggering vacuolation with YM201636 did not decrease surface nutrient transporter levels, and preventing vacuolation by over-expressing Vac14 did not interfere with nutrient transporter down-regulation by FTY720 (FIGS. 60D and 60E). Taken together, these data indicate that sphingolipid-like compounds disrupt PIKfyve localization and nutrient transporter trafficking in both normal and transformed cells through two distinct PP2A-dependent mechanisms.

In other embodiments, azacyclic constrained sphingolipid-like molecules inhibit autophagy. In more particular embodiments, the sphingolipid-like molecules inhibit autophagic flux by preventing autophagosome-lysosome fusion due to mis-localization of PIKfyve and PI(3,5)P2. In other particular embodiments, the molecules inhibit autophagic flux by preventing autophagosome formation.

Figure 61A:
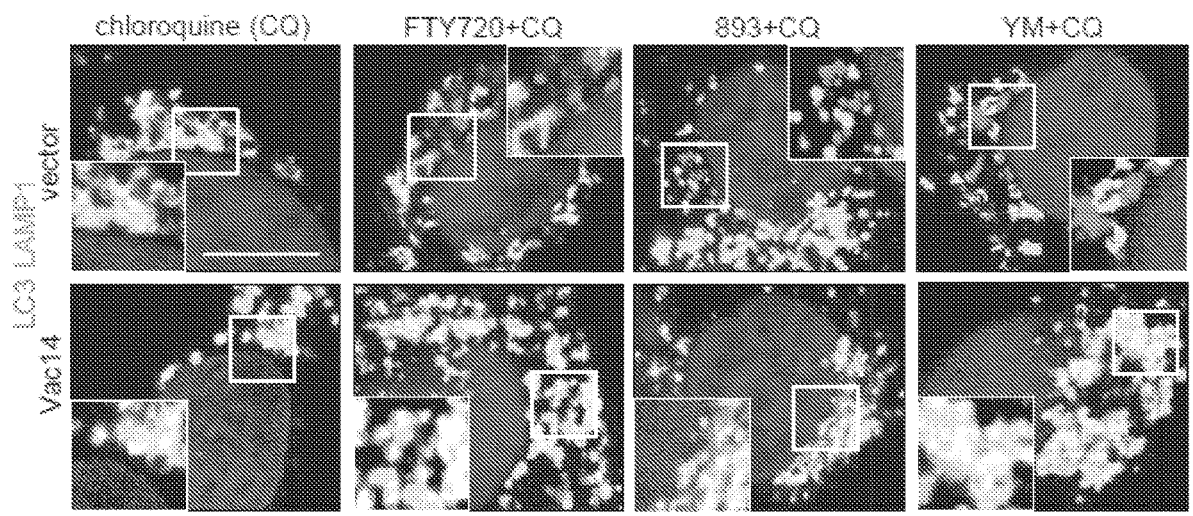
FIGS. 61A to 61H provide graphical data and microscope-captured images detailing the ability of small molecule analogs to reduce autophagic flux and macropinosome degradation in accordance with embodiments of the invention.
Figure 61B:
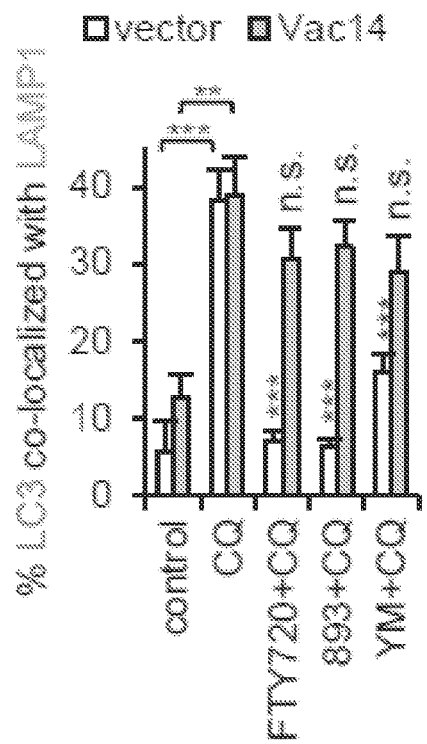
Figure 61C:
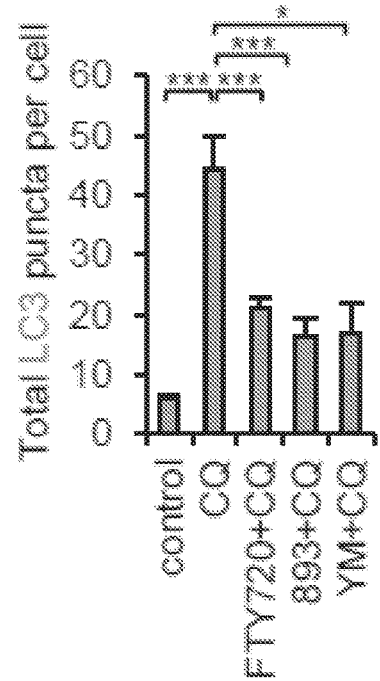
Figure 61D:
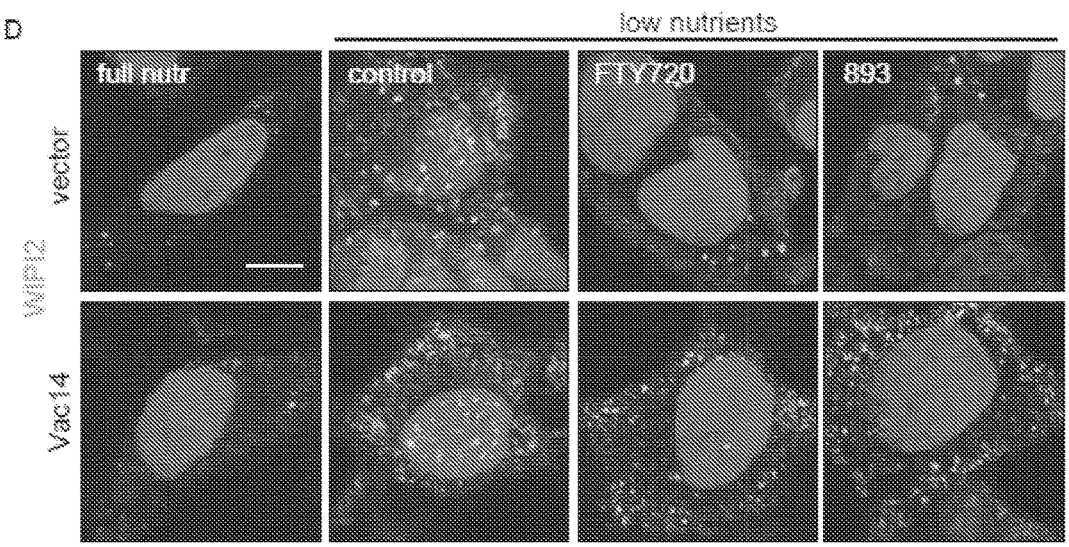
Figure 61E:
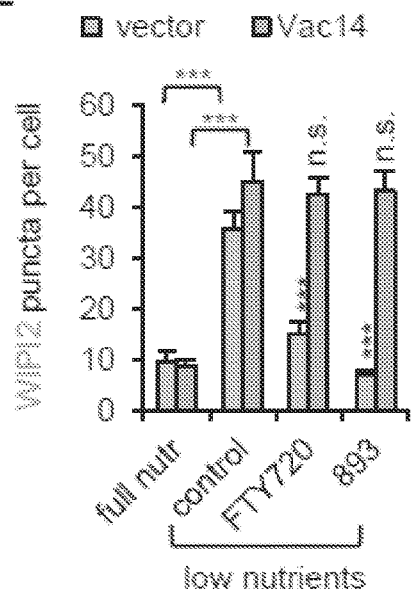
Figure 61F:
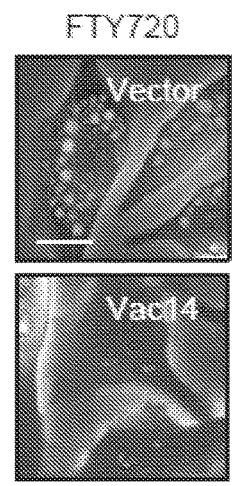
Figure 62A:
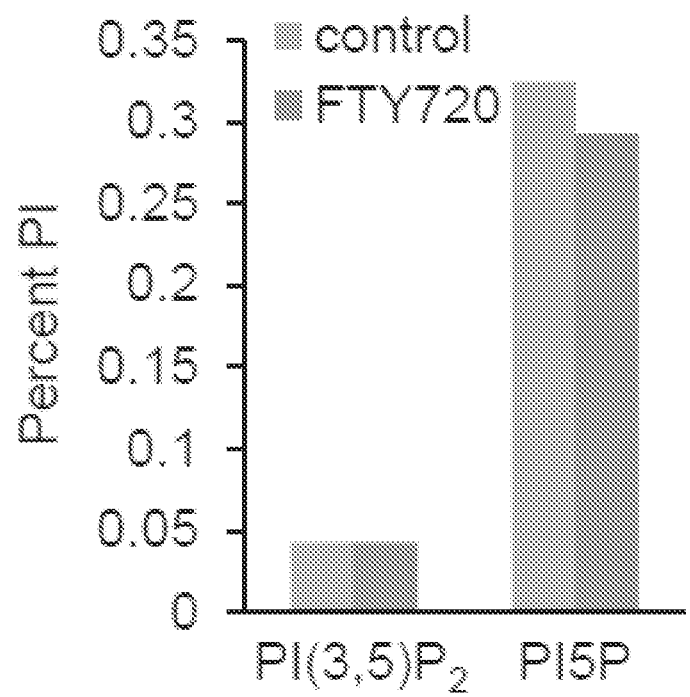
FIGS. 62A and 62B provide graphical data and microscope-captured images detailing the ability of small molecule analogs to alter PIKfyve localization but not activity in accordance with embodiments of the invention.
Figure 62B:
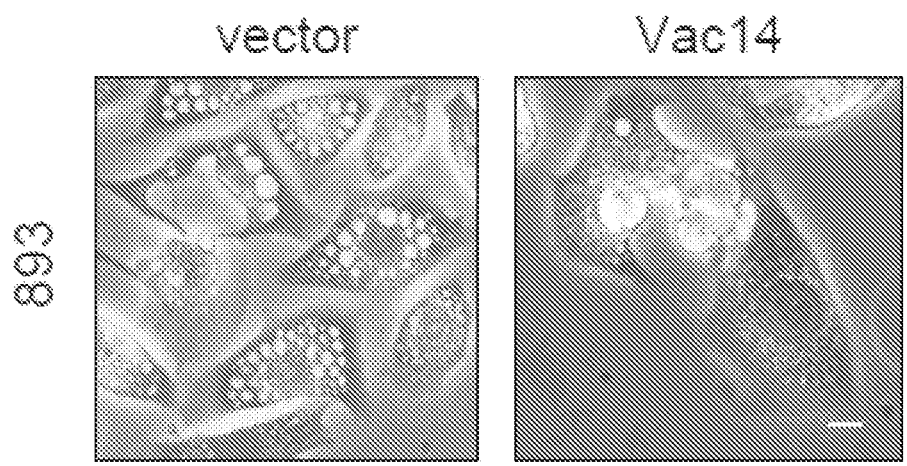
Figure 63:
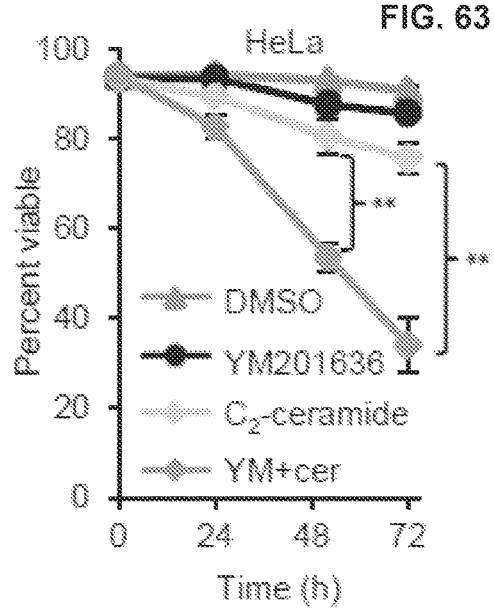
FIGS. 63A to 63F provide graphical data and microscope-captured images detailing that vacuolation enhances the anti-neoplastic effects of small molecule analogs in vitro and in vivo in accordance with embodiments of the invention.
Figure 63:
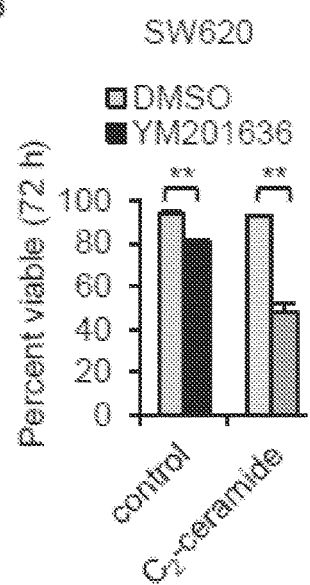
Figure 63:
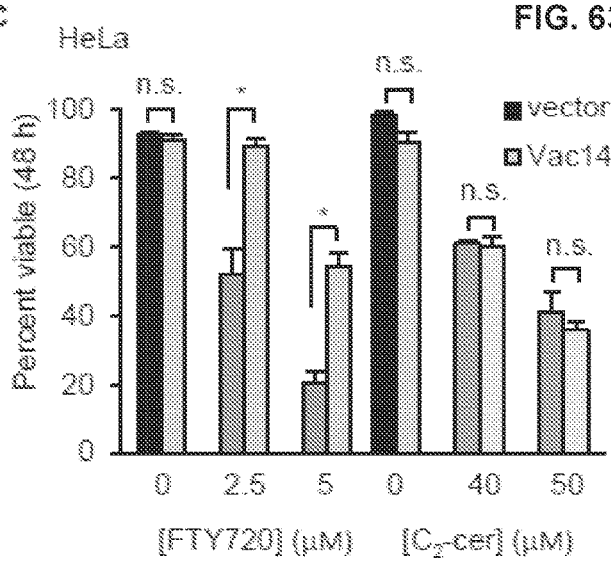
Figure 63:
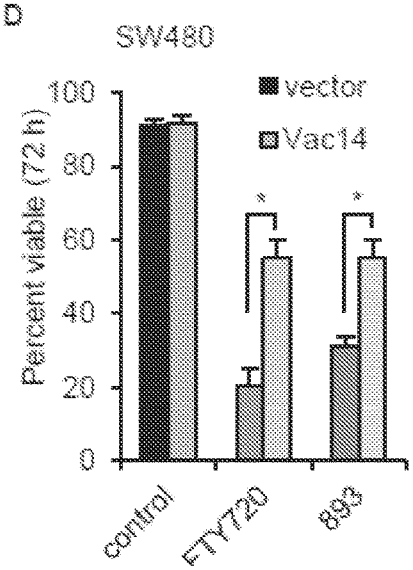
Figure 63:
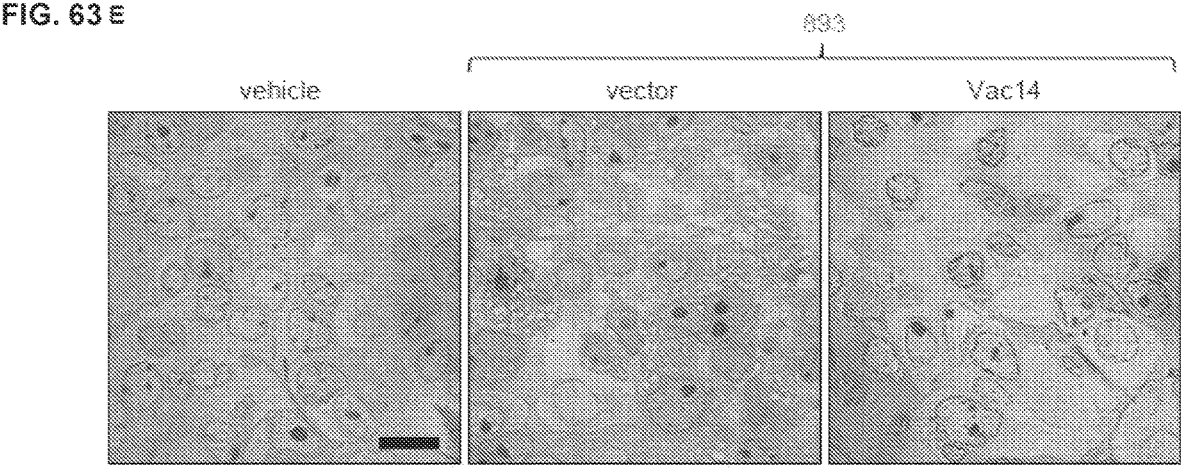
Figure 63:
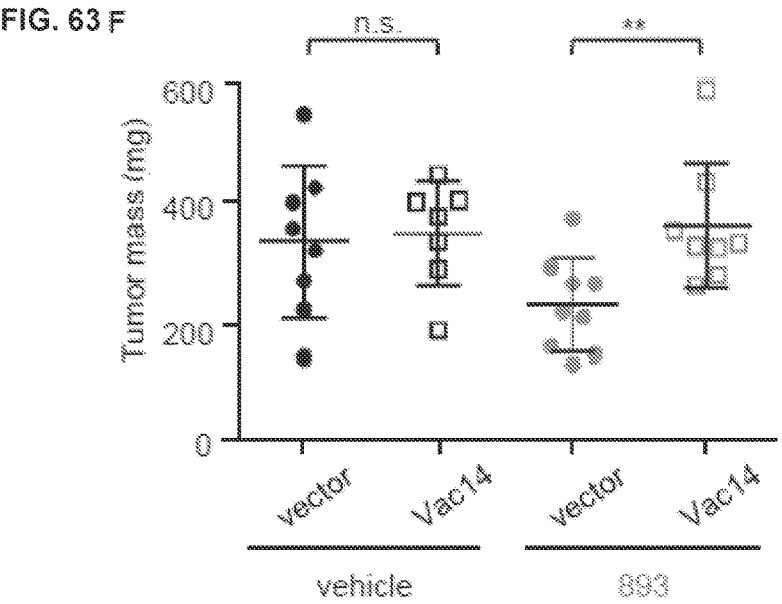

It is known in the art that cells adapt to nutrient stress by increasing autophagic flux. However, autophagosome-lysosome fusion reactions depend upon $Ca^{2+}$ release via TRPML1 channels that are activated by PI(3,5)P2. The lack of PIKfyve and PI(3,5)P2 co-localization with TRPML1 (FIGS. 57D and 58D) suggested that sphingolipid-like drugs, such as SH-BC-893, may limit autophagic flux. Chloroquine (CQ) is molecule that stabilizes the transient autophagosomes. Cells were treated with CG to stabilize autophagolysosomes and subsequently treated with FTY720, SH-BC-893, or YM201636. Each treatment reduced fusion of LC3-positive autophagosomes with LAMP 1-positive lysosomes (FIGS. 61A and 61B). The sphingolipid-like molecules and YM201636 also decreased the total number of LC3 puncta per cell, suggesting that autophagosome formation was reduced (FIG. 61C). Phosphatidylinositol 5-Phosphate (PI(5)P) is essential for autophagosome biogenesis upon glucose depletion. PI(5)P is produced by dephosphorylating PI(3,5)P2, and thus PI(5)P might also be mis-localized in SH-BC-893-treated cells, and thus also contributing to the disruption of autophagosome formation. Indeed, in an experiment that detected nascent autophagomes by identifying the WIPI2 protein, which is known to correlate with autophagosome formation, FTY720 and SH-BC-893 treatment reduced the number of autophagosomes in low-nutrient media without affecting PI5P levels (FIGS. 61D, 61E and 62A). Thus, SH-BC-893 inhibited both autophagosome formation and degradation. As a control, Vac14 over-expression limited vacuolation (FIGS. 55F, 61F, and 62B) and rescued autophagic flux in SH-BC-893-treated cells (FIGS. 61A, 61B, 61D and 61E). Together, these data indicate that azacyclic constrained sphingolipid-like molecules block autophagic flux at multiple levels, including formation and lysosome-fusion, by mis-localizing PIKfyve.

Figure 61G:
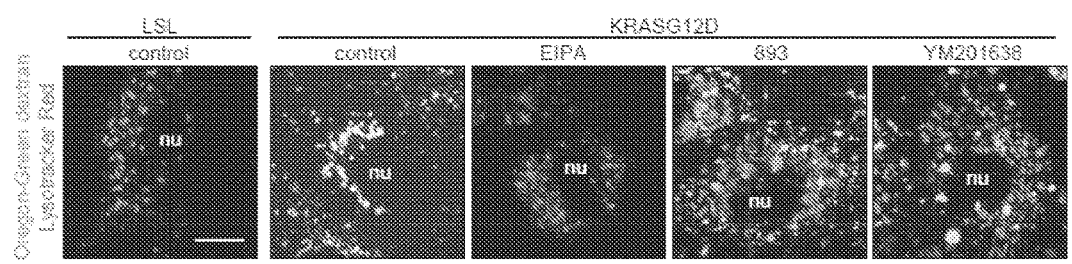
Figure 61H:
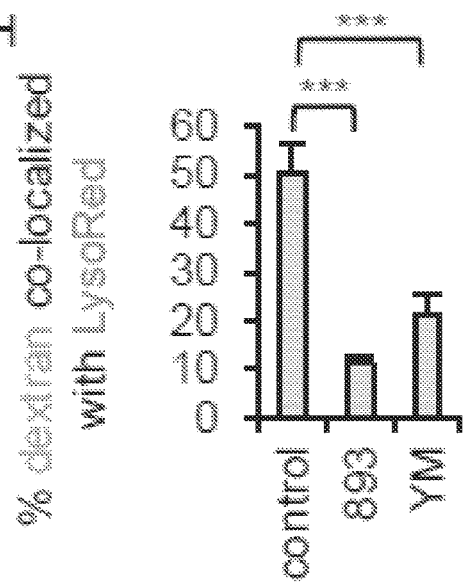

In even other embodiments, sphingolipid-like compounds inhibit micropinocytosis by preventing macropinosome fusion with lysosomes. In cells with activated Ras, macropinocytosis might also confer resistance to nutrient transporter down-regulation. However, PI(3,5)P2 is also required for macropinosome degradation. While K-RasG12D expressing cells efficiently macropinocytosed dextran in an 5-(N-ethyl-N-isopropyl) amiloride (EIPA) sensitive manner, both YM201636 and SH-BC-893 dramatically reduced macropinosome fusion with lysosomes (FIGS. 61G and 61H). Macropinosomes that fail to fuse with lysosomes would not be able to supply nutrients, such as amino acids. Thus, by disrupting PIKfyve localization, sphingolipid-like compounds limit access to lysosome-derived nutrients at the same time it down-regulates transporters for amino acids and glucose.

Figure 64A:
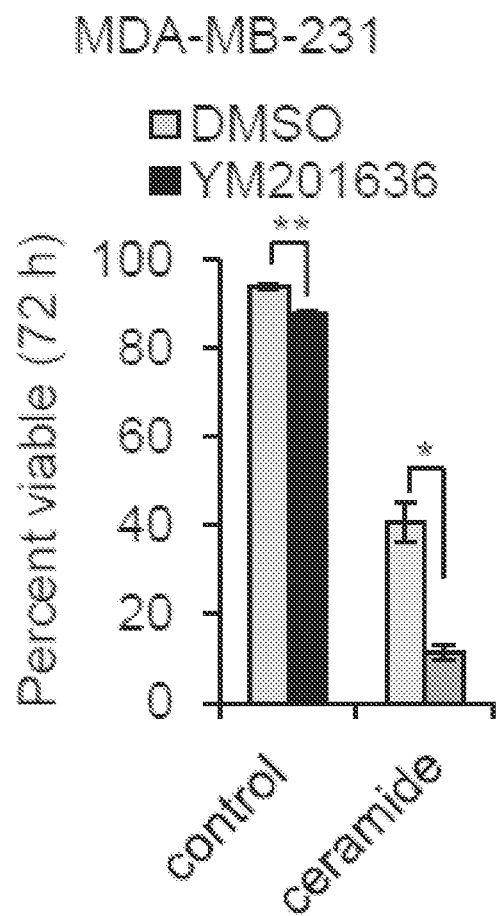
FIGS. 64A and 64B provide graphical data detailing that vacuolation enhances cell death in accordance with embodiments of the invention.
Figure 64B:
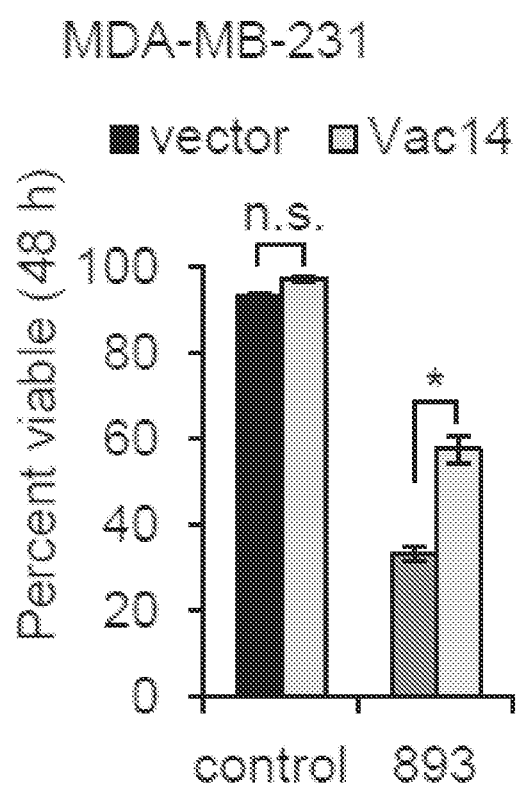

In even more embodiments, azacyclic constrained sphingolipid-like molecules stimulate neoplastic cell death via vacuolation. To assess the relative contribution of vacuolation to SH-BC-893's anti-neoplastic activity, cells were treated with YM201636 (vacuolation only) and ceramide (transporter loss without vacuolation) alone and in combination. YM201636 was minimally cytotoxic alone, but when combined with ceramide, the combination significantly enhanced cell death in multiple cancer cell lines without increasing nutrient transporter loss (FIGS. 60D, 63A, 63B 64A). Moreover, Vac14 over-expressing cells that did not vacuolate (FIGS. 55F and 61F) were resistant to SH-BC-893- and FTY720-induced death. The Vac14 over-expressing cells, however, were not protected from death induced by the non-vacuolating sphingolipid ceramide (FIGS. 63C, 63D and 64B). Taken together, these data suggest that vacuolation contributes to the ability of sphingolipid-like molecules, such as SH-BC-893, to kill cancer cells.

To assess whether vacuolation enhances the anti-neoplastic activity of SH-BC-893 in vivo, mice bearing SW480 xenografts expressing empty vector or Vac14 were treated with vehicle or SH-BC-893. Tumors were harvested while still small in order to limit tumor necrosis that might confound microscopic analysis of SH-BC-893-induced vacuolation. As seen in vitro, Vac14 over-expression conferred resistance to both vacuolation and growth inhibition by SH-BC-893 (FIGS. 63E and 63F). These results demonstrate that vacuolation contributes to the anti-neoplastic effects of SH-BC-893 both in vitro and in vivo.

Accordingly, embodiments of the invention are directed to methods of treatment involving the therapeutic use of azacyclic constrained sphingolipid-like molecules to induce a starvation-like phenotype in slow-growing or autochthonous neoplasms. Even more embodiments of the invention are directed to methods of treatment involving the therapeutic use of sphingolipid-like molecules to kill slow-growing or autochthonous neoplasms. More particular embodiments are direct to the ability of these molecules to be well tolerated or lack toxicity in vivo.

Figure 65A:
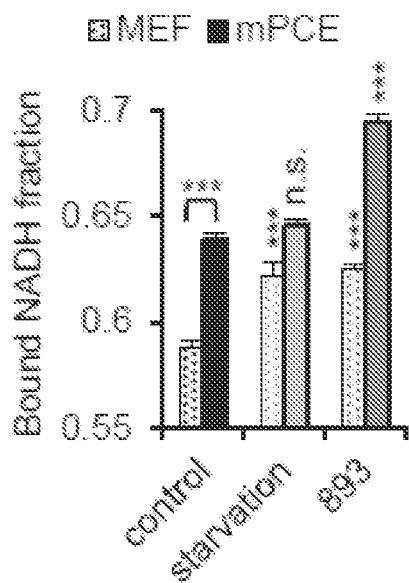
Figure 65B:
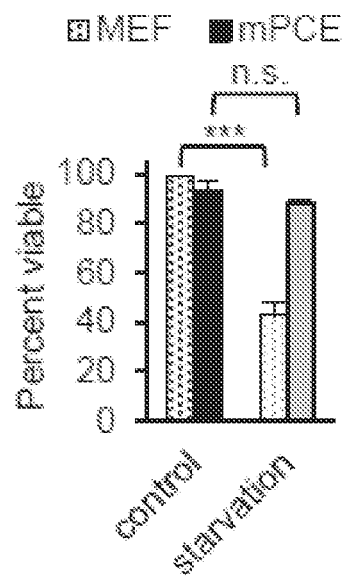
Figure 65C:
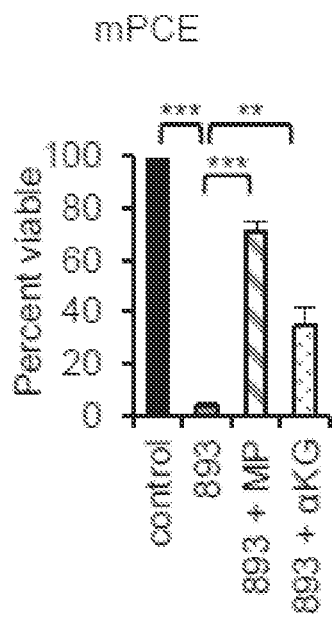
Figure 65D:
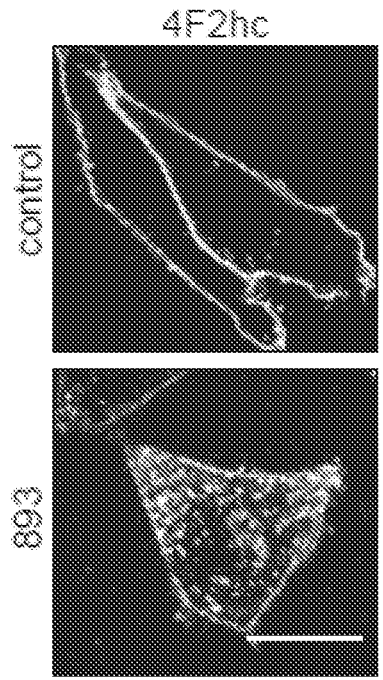
Figure 65E:
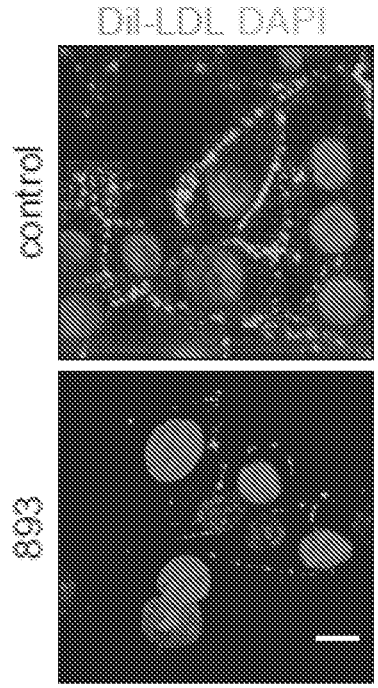
Figure 65F:
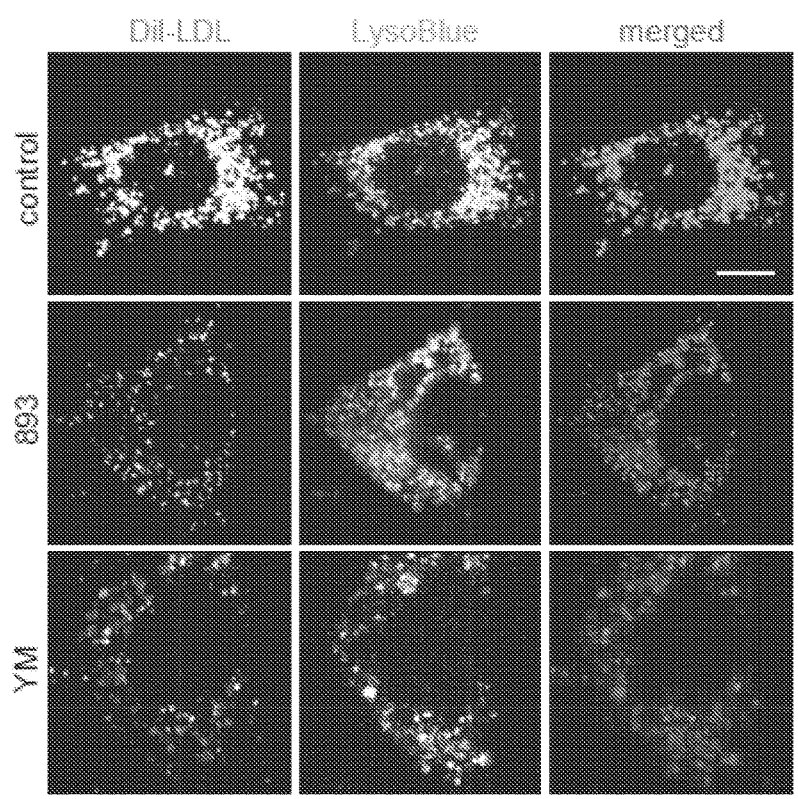
Figure 65G:
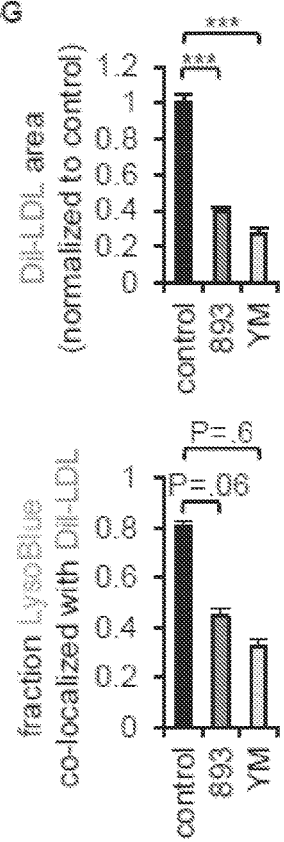
Figure 66A:
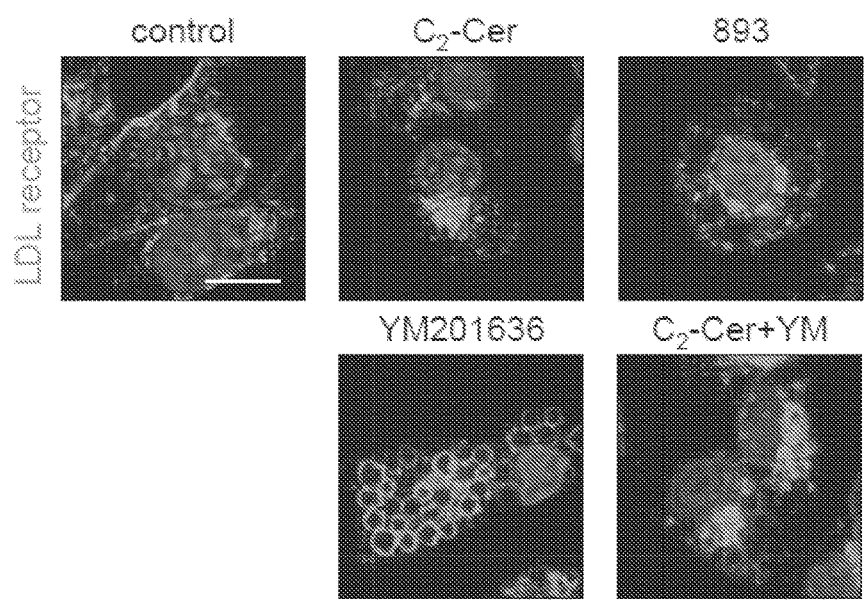
FIGS. 66A to 66C provide western blot data, graphical data and microscope-captured images detailing the ability of small molecule analogs to block uptake of lipids and amino acids in prostate cancer cells in vitro and in vivo, while 66D and E show selective toxicity against neoplastic cells in accordance with embodiments of the invention.
Figure 66B:
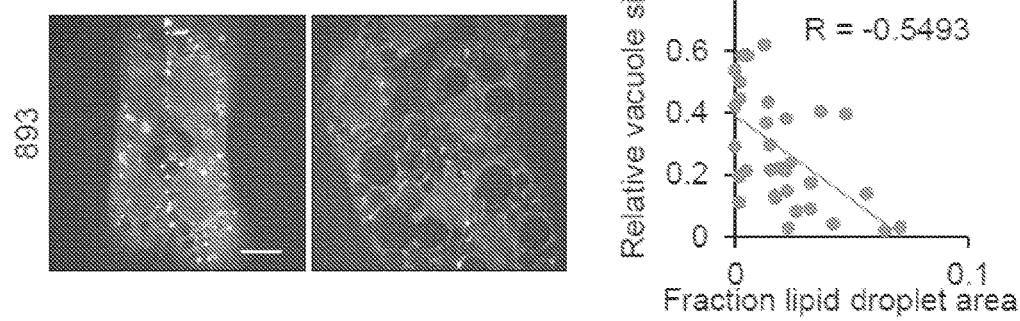
Figure 66:
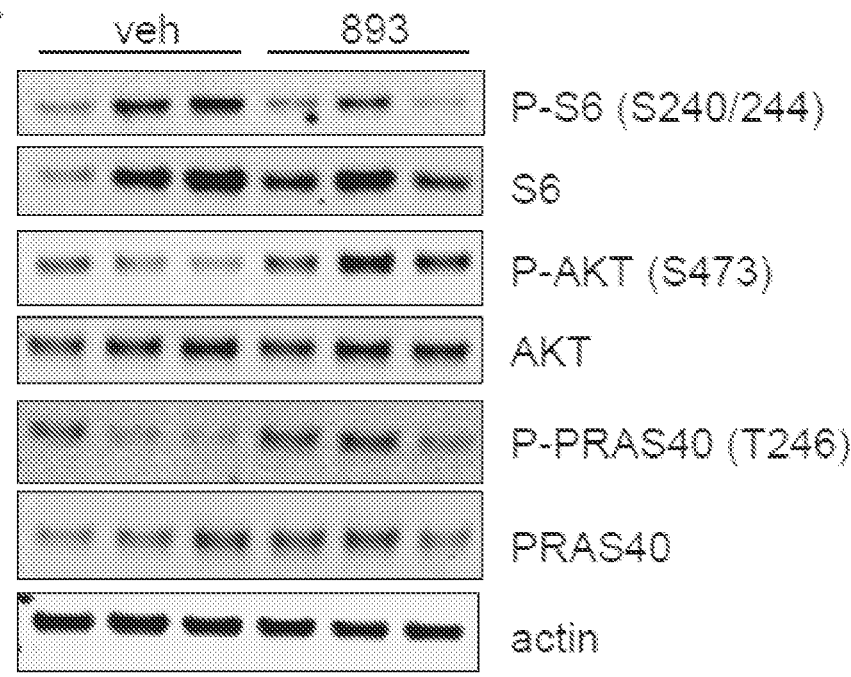
Figure 66:
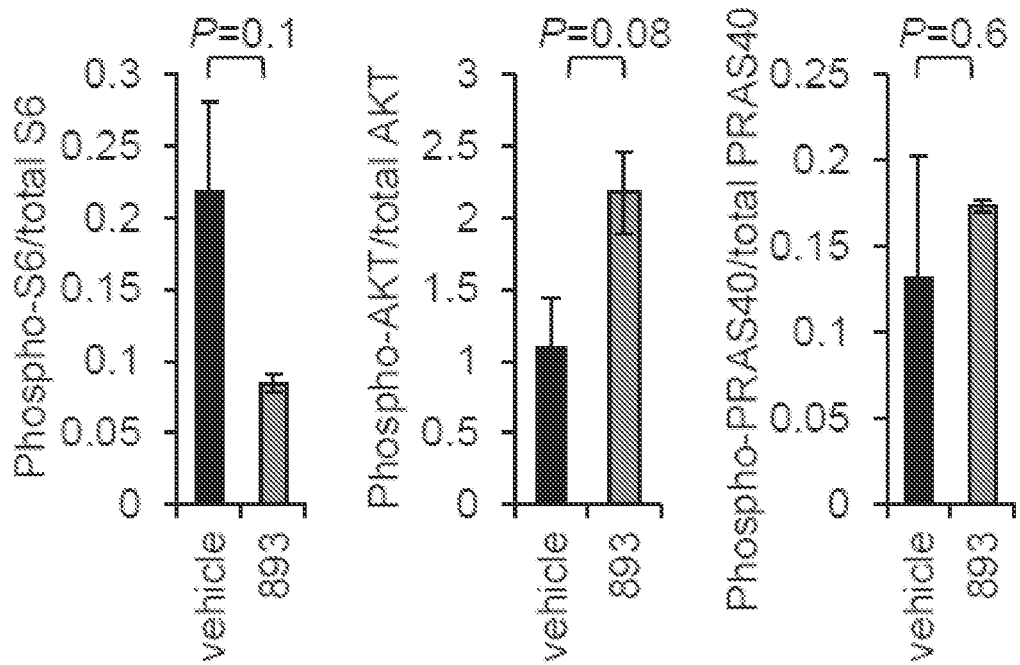
Figure 66:
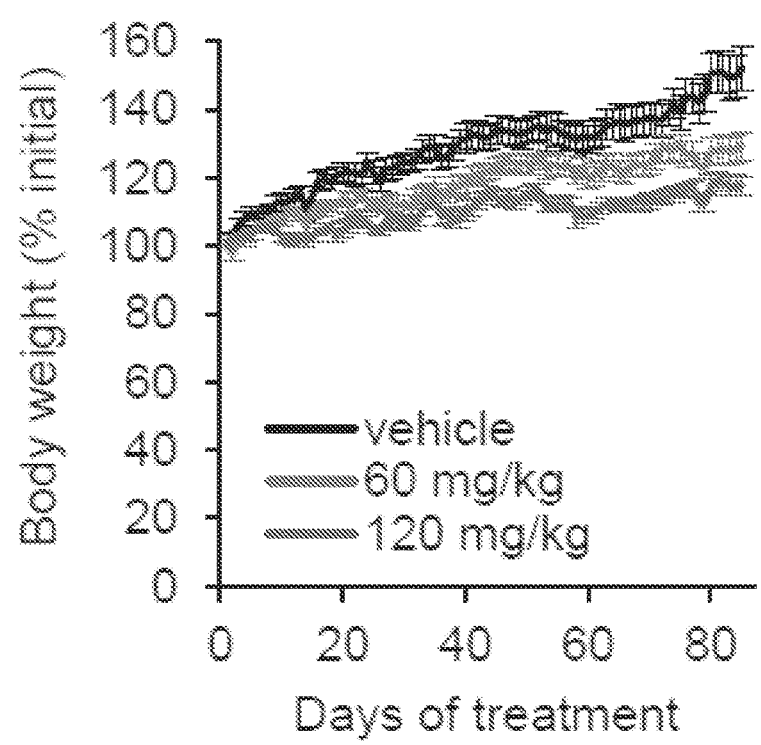
Figure 66:
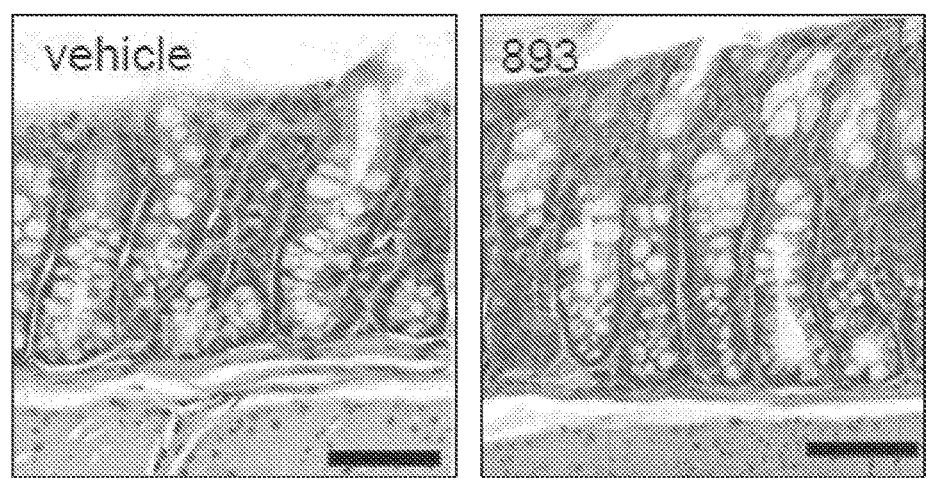

Because the activity of SH-BC-893 was linked to metabolic rate, it was not clear whether slower-growing tumors that do not exhibit the classic Warburg phenotype would also be sensitive. To determine the sensitivity, SH-BC-893 was evaluated in a validated genetically-engineered mouse model for invasive castration-resistant prostate cancer that lacks p53 and PTEN expression exclusively in the prostate (pDKO) (Wu X, et al. *Am J Clin Exp Urol.* 2014; 2(2): 111-20; Schwarzenböck S, et al. *Theranostics.* 2012; 2(3): 318-330; Chen Z, et al. *Nature.* 2005; 436(7051):725-730; the disclosures of which are herein incorporated by reference). Cells derived from the tumors that developed in these mice (mouse prostate cancer epithelial cells, mPCEs) exhibited reduced glycolysis and were not dependent on extracellular glucose and amino acids for survival (FIGS. 65A and 65B). SH-BC-893, however, still produced a phenotype consistent with starvation as the bound NADH fraction increased and cell permeant nutrients protected mPCE cells from death (FIGS. 65A and 65C). Prostate cancer cells depend on exogenous LDL for growth and survival. Accordingly, SH-BC-893 not only vacuolated mPCE cells and down-regulated 4F2hc, but also dramatically decreased surface levels of the LDL receptor (LDLr), LDL uptake, and lipid droplet accumulation (FIGS. 55B, 65D-H, 66A and 66B). Ceramide and YM201636 both reduced surface LDLr levels, but LDLr still accumulated in different intracellular compartments (FIG. 66A). Consistent with their ability to block lysosomal fusion (FIG. 61), both YM201636 and SH-BC-893 reduced LDL co-localization with Lysotracker Blue (FIGS. 65F and 65G). In keeping with the inhibition of LDL degradation in lysosomes, cellular lipid droplet content was inversely correlated with the extent of vacuolation (FIG. 66B). In summary, sphingolipid-like compounds, such as SH-BC-893, starve slow-growing neoplasms, such prostate cancer, by down-regulating nutrient transporters and blocking lysosomal nutrient generation.

Figure 67:
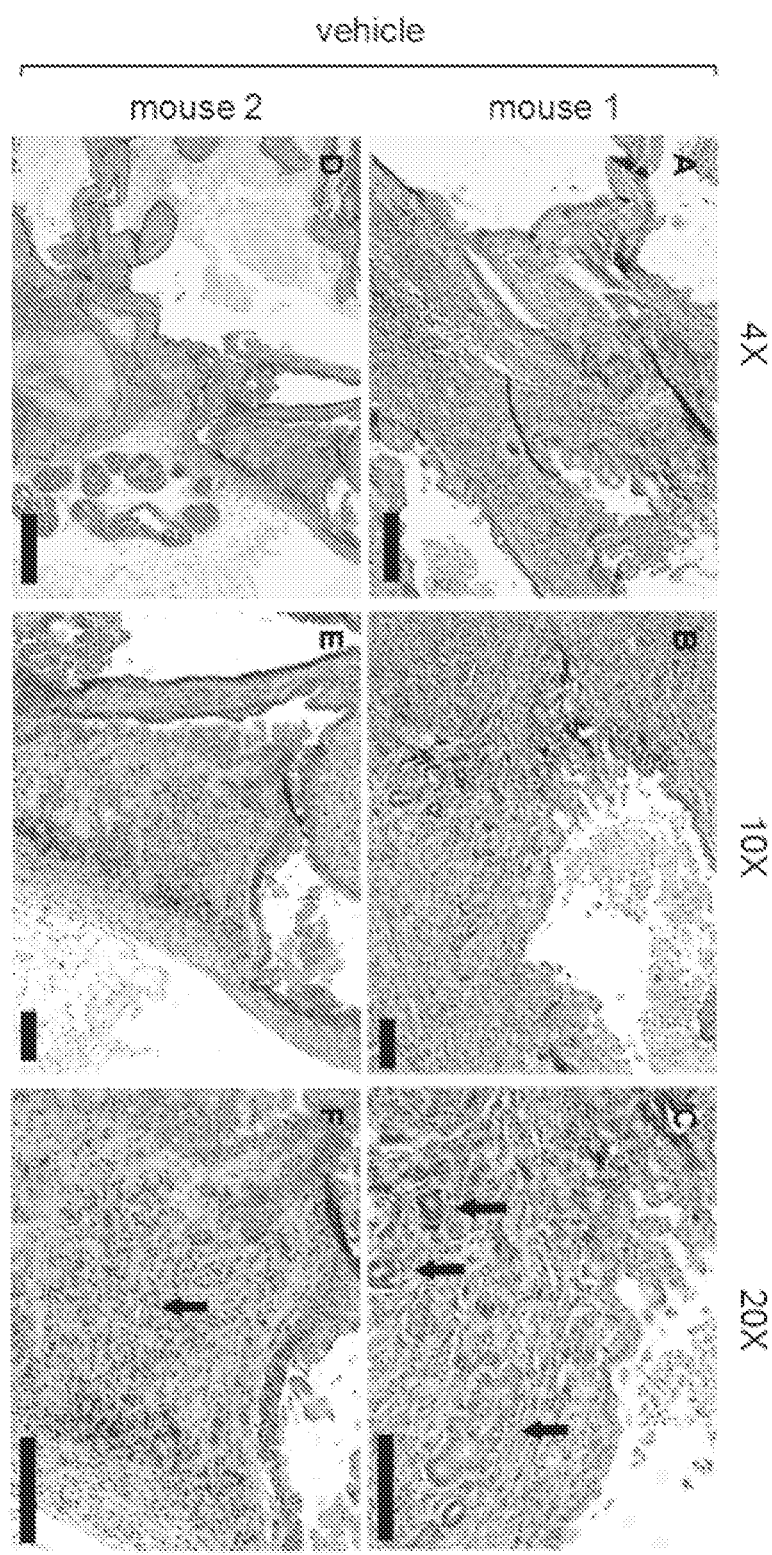
FIG. 67 provides microscope-captured images detailing the ability of small molecule analogs to inhibit prostate cancer progression in accordance with embodiments of the invention.
Figure 67:
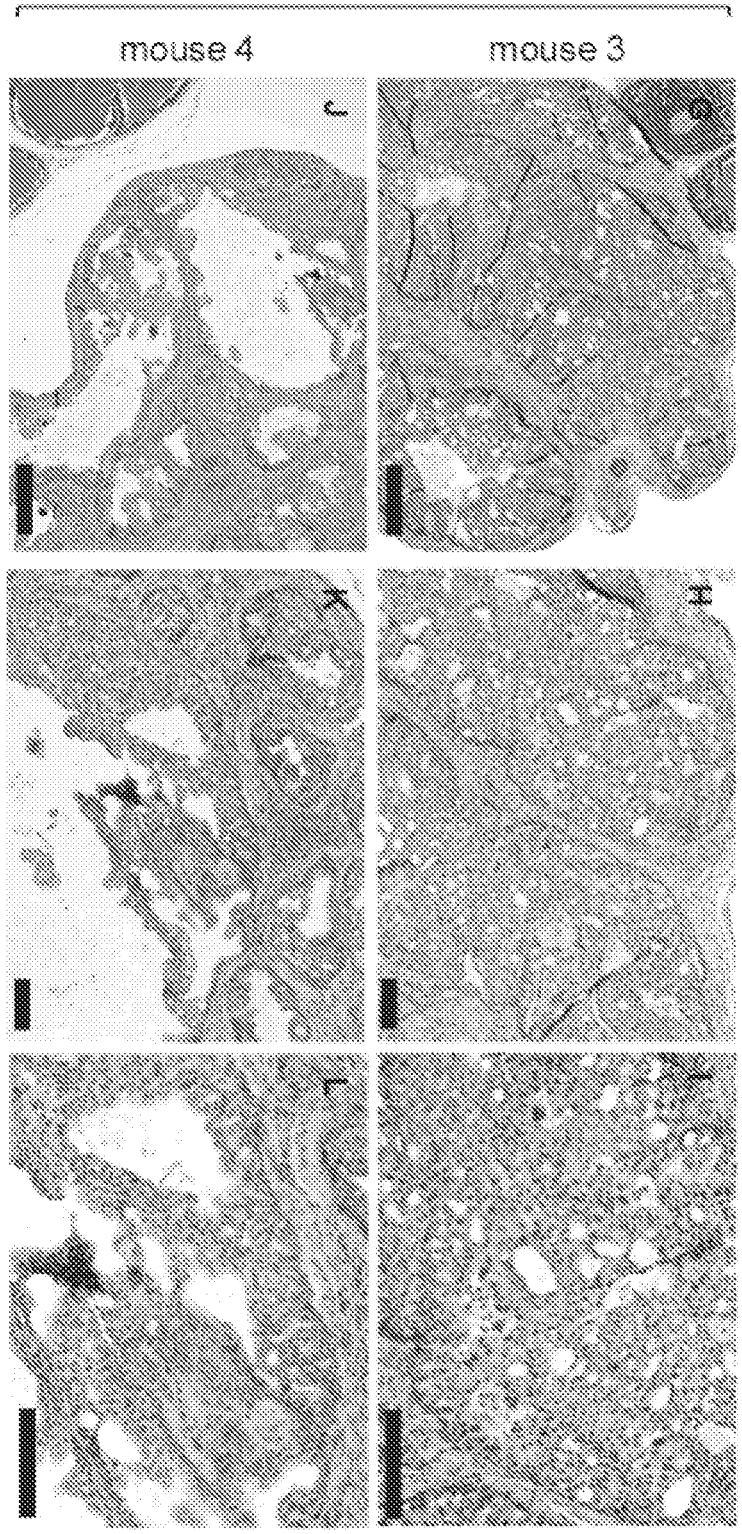

The ability of starvation-inducing sphingolipid-like drugs to affect the growth of slow growing or autochthonous neoplasms was also evaluated. In C57BL/6 mice bearing mPCE subcutaneous isografts, 60 mg/kg SH-BC-893 was given daily by gavage and slowed tumor growth by 60% similar to results with SW620 xenografts dosed with 20 mg/kg i.p. (FIGS. 53G-I and 65I). At 120 mg/kg, SH-BC-893 inhibited prostate tumor growth by more than 90% (FIG. 65I). SH-BC-893 also decreased autochthonous tumor growth in pDKO mice by 62% (60 mg/kg) or 82% (120 mg/kg) (FIG. 65J). Histologically, SH-BC-893 slowed prostate tumor progression, eliminating invasive disease and dramatically reducing cellular pleomorphism, hyperchromasia, and nuclear atypia; SH-BC-893-treated mice exclusively exhibited prostatic intraepithelial neoplasia while adenocarcinoma was present in all vehicle-treated animals (FIG. 67). As expected if amino acid transporters are down-regulated (FIG. 65D), TORC1-dependent ribosomal protein S6 phosphorylation was reduced in SH-BC-893-treated tumors (FIG. 66C). Akt activity was slightly elevated by SH-BC-893 consistent with loss of TORC1-mediated negative feedback. Thus, sphingolipid-like compounds, such as SH-BC- 893, are effective against neoplasms with distinct molecular defects and metabolic characteristics.

SH-BC-893 produces equivalent transporter loss and vacuolation in normal and transformed cells and therefore also limits the access of normal cells to nutrients (FIGS. 51C, 51E, 56B and 56C). As such, SH-BC-893-treated pDKO mice gained less weight than untreated mice (FIG. 66D). However, even mice treated with the highest dose of SH-BC-893 gained weight, and all treated mice exhibited normal behavior and activity levels. Blood chemistry analysis at sacrifice indicated that SH-BC-893 was not toxic to the liver or kidneys at the anti-neoplastic dose (Table 7). The slight elevation in serum creatine phosphokinase in animals treated with 120 mg/kg SH-BC-893 suggests mild muscle catabolism in response to nutrient restriction. Importantly, proliferating normal, healthy tissues were minimally affected by SH-BC-893 as evidenced by normal complete blood counts and histopathology of intestinal crypts in mice treated with 120 mg/kg SH-BC-893 for 11 weeks (Table 8 and FIG. 66E). The lack of toxicity to normal tissues is consistent with the finding that non-transformed cells can adapt to nutrient stress that triggers a bioenergetic crisis in less metabolically flexible tumor cells (FIGS. 53D and 53E). In conclusion, blocking parallel nutrient access pathways by disrupting membrane trafficking is a safe and effective means to target constitutive anabolism in cancer cells with divergent metabolic programs.

Specifically, in cancer cells, to support biosynthesis and proliferation, oncogenic mutations drive glucose and amino acid transporter expression. (McCracken, A. N. & Edinger, A. L. Trends Endocrinol. Metab. 24, 200-8 (2013), the disclosure of which is incorporated herein by reference.) Oncogenic Ras mutations also boost amino acid acquisition through the degradation of extracellular proteins acquired via macropinocytosis. (Palm, W. et al. Ceil 162, 1-12 (2015); Commisso, C. et al. Nature 497, 633-7 (2013); the disclosures of which are incorporated herein by reference). Many cancer cells become "addicted" to this elevated nutrient influx. For example, the degradative enzyme L-asparaginase is an effective therapy for acute lymphoblastic leukemia because these cells cannot synthesize sufficient asparagine to meet their anabolic demand (Pieters, R. et al. Cancer 117, 238-249 (2011), the disclosure of which is incorporated herein by reference). Pre-clinical studies show that other types of cancer exhibit similar dependencies, relying on imported arginine, serine, or glycine for growth and survival. (Feun, L. G., et al. Curr. Opin. Clin. Nutr. Metab. Care 18, 78-82 (2015); Jain, M. et al. Science. 336, 1040-1044 (2012); Maddocks, O. D. K. et al. Nature 493, 542-6 (2013), the disclosures of which are incorporated herein by reference). These results suggest that limiting nutrient uptake may be a broadly effective therapeutic approach for many types of neoplasms and cancers.

TABLE 7

Blood chemistry of pDKO mice treated with SH-BC-893

| | | SH-BC-893 | |
| --- | --- | --- | --- |
| | vehicle | 60 mg/kg | 120 mg/kg |
| Alkaline Phosphatase | 93 ± 5.4 | 77 ± 7.8 | 83 ± 6.2 |
| Serum Glutamic-Pyruvic Transaminase (Ala aminotransferase) | 65 ± 10.4 | 78 ± 25 | 91 ± 17.2 |
| Serum Glutamic Oxaloacetic Transaminase (Asp aminotransferase) | 809 ± 200 | 640 ± 136 | 907 ± 171 |
| Creatine Phosphokinase | 5,017 ± 1199 | 5,340 ± 2366 | 10,441 ± 3014 |
| Albumin | 3 ± 0.2 | 3 ± 0.2 | 3 ± 0.1 |
| Total Protein | 6 ± 0.3 | 5 ± 0.4 | 6 ± 0.2 |
| Globulin | 3 ± 0.13 | 2 ± 0.18 | 2 ± 0.03 |
| Total Bilirubin | 0.2 ± 0.03 | 0.1 ± 0 | 0.2 ± 0.03 |
| Blood Urea Nitrogen | 29 ± 3.1 | 19 ± 1.1 | 23 ± 1.5 |
| Creatine | <0.2 | <0.2 | <0.2 |
| Cholesterol | 187 ± 8.8 | 134 ± 15.8 | 107 ± 7.5 |
| Glucose | 264 ± 43 | 282 ± 24 | 307 ± 28 |
| $Ca^{2+}$ | 11 ± 0.8 | 10 ± 0.7 | 10 ± 0.1 |
| P | 13 ± 0.6 | 11 ± 1.0 | 13 ± 0.1 |
| $HCO^{3-}$ | 19 ± 5.8 | 20 ± 3.2 | 17 ± 2.8 |

Means ± SEM, n = 4; Data acquired at sacrifice

TABLE 8

Blood cell count of pDKO mice treated with SH-BC-893

| | | SH-BC-893 | |
| --- | --- | --- | --- |
| | vehicle | 60 mg/kg | 120 mg/kg |
| White Blood Cells [$10^3$ cells/μL] | 5 ± 1 | 5 ± 1 | 8 ± 1 |
| % neutrophil | 16 ± 5 | 14 ± 3 | 19 ± 5 |
| % lymphocyte | 76 ± 7 | 77 ± 4 | 73 ± 5 |
| Red Blood Cells [M/μL] | 9 ± 0 | 8 ± 1 | 9 ± 1 |
| Hematocrit | 38 ± 3 | 32 ± 5 | 41 ± 3 |

Means ± SEM, n = 4; Data acquired at sacrifice

The relative resistance of non-transformed cells to FTY720-induced death likely stems from the ability of normal cells to become metabolically quiescent under stress.

Experimental Materials and Methods

Biology Procedures in Initial Optimization Study:

Cell culture studies: Sup-1315 cells are maintained at 2-3 million/mL in RPMI 1640 (Mediatech) supplemented with 10% fetal calf serum (FCS, Sigma-Aldrich), 10 mM Hepes (Mediatech), 55 μM β-mercaptoethanol (Sigma-Aldrich), 2 mM L-glutamine (Mediatech), and antibiotics. All adherent cells are maintained at 70-80% confluence. Cell are cultured in the following media: PC3 & A549, Ham's F12K (Corning Cell Gro) supplemented with 10% FCS and antibiotics; DU145 cells, MEM (Corning Cell Gro) supplemented with 10% FCS, 1 mM sodium pyruvate (Mediatech), and antibiotics; SW620 & MDA-MB-231, DMEM (Corning Cell Gro) with 10% FCS, 1 mM sodium pyruvate (Mediatech), and antibiotics; Panc-1 cells, DMEM (Corning Cell Gro) supplemented with 10% FCS and antibiotics. All of the above cell lines are available from the ATCC.

Viability assays: Cell Titer Glo assays (Cell Titer Glo Luminescent Cell Viability Assay kit, cat # G7571, Promega Corporation) are performed in clear bottom 96-well black cell culture plates (cat #655090, Greiner Bio-One, NC, USA). After plating at 1,000 cells/well in volume of 100 µl, cells are left undisturbed for at least 24 h before drug addition. After 72 h, cells are prepared for analysis by adding 10 µl of 0.1% Triton-X100 in PBS with shaking for 1 min at room temperature (RT). Cell Titer-Glo cell lysis reagent (20 µl) is then added followed by 1 min of shaking and a 10 min incubation in the dark at RT. Luminescence is detected using an IVIS imaging system (IVIS Lumina II, Perkin Elmer, USA). $IC_{50}$ values were also determined by flow cytometry 72 h in PC3 cells by vital dye exclusion using DAPI (4', 6 diamidino-2-phenylindole). $IC_{50}$s are determined using GraphPad Prism (GraphPad Software, Inc, La Jolla, Calif.). SupB-15 viability was determined by flow cytometry. Cell Titer Glo assays were performed with the other cell lines.

S1P1-5 activation: Chinese hamster ovary (CHO) cells stably over-expressing the different human S1P receptor subtypes are used. S1P1, S1P4 and S1P5 overexpressing CHO cells are cultured in medium containing alpha-MEM supplemented with 10% FBS, 50 µg/ml gentamycin and 0.5 mg/ml G418. S1P2 and S1P3 overexpressing CHO cells are cultured in RPMI containing 10% FBS, 50 µg/ml gentamycin and 0.5 mg/ml G418. Prior to stimulation, cells are rendered serum-free for 24 h. Stimulation is carried out for 10 min in serum-free DMEM containing 0.1 mg/ml of fatty-acid free BSA in the absence or presence of the various compounds or S1P. Protein lysates are prepared using a buffer containing (50 mM Tris pH 7.4, 150 mM NaCl, 10% glycerol, 1% Triton X-100, 2 mM EDTA, 2 mM EGTA, 40 mM β-glycerophosphate, 50 mM sodium fluoride, 10 mM sodium pyrophosphate, 2 mM dithiothreitol, 0.2 mM sodium orthovanadate). Cells are homogenized by one 5 sec burst in a MSE Ultrasonic Disintegrator, centrifuged and taken for protein determination. Equal amounts of protein are separated by SDS-PAGE (10% polyacrylamide gel), transferred to nitrocellulose membranes and subjected to Western blot analysis. Bands were stained using IRDye® secondary antibodies and visualized by the LICOR Odyssey® Fc Imaging system. Antibodies against phospho-Thr202/Tyr204-p42/p44-MAPK and phospho-Ser PKC substrate are from Cell Signaling, Frankfurt am Main, Germany. Polyclonal antisera against total p42 and total p44 were generated and characterized as previously described. (Huwiler, A.; Pfeilschifter, J. Br. J. Pharmacol. 1994, 113, 1455-1463; disclosure of which is incorporated herein by reference).

Heart rate: C57BL/6 mice are surgically implanted with DSI TA-ETAF20 electrocardiographic telemetry devices (Data Sciences International, St. Paul, Minn.). The electrocardiographic data is collected and recorded using the PhysioTel telemetry system and Dataquest A. R. T 4.0 software (DSI). The telemetry device is implanted in the mouse's abdominal cavity with biopotential leads sutured in place in the chest wall. Buprenorphine (0.05 mg/kg) is administered every 12 h after surgery for pain management and enrofloxacin (3 mg/kg) is administered 2× per day for 7 days post-surgery as an antibiotic. Mice are permitted two weeks recovery after surgery before initiation of baseline telemetry recordings. Heart rate is calculated from ECG data taken in the freely moving, conscious mice. Mice are divided into two groups of 3 mice and treated intraperitoneally with a single dose of vehicle (0.9% saline or 20% acidified DMSO in 0.9% saline), 10 mg/kg FTY720, FTY720-Phosphate, 5, or 5-P and heart rate monitored continuously for 10 h. Mice are rested for two weeks at which point the experiment is repeated with the mice assigned to the alternate group. These experiments are performed in accordance with all national or local guidelines and regulations and were approved by the UCI Institutional Animal Care and Use Committee.

Lymphocyte sequestration: Female 8-24 week old C57BL6 mice are injected intraperitoneally with vehicle (0.9% saline or 20% acidified DMSO in 0.9% saline), 10 mg/kg FTY720, FTY720-phosphate, 5, or 5-P. After 12 h, blood is collected from the retro-orbital sinus under ketamine/xylazine anesthesia. 10 µL of whole blood is added to 190 µL of ACK red blood cell lysis buffer, incubated at room temperature for 3-5 minutes at 37° C., and the white blood cells recovered by centrifugation. Nucleated cells (Hoechst33342 positive) are counted using a hemocytometer to obtain the white blood cell count. Separately, 50 µL of whole blood is added to 1 mL of ACK red blood cell lysis buffer and incubated for 3-5 minutes at room temperature. Cells are washed with FACS wash (2% FCS in PBS with 0.05% NaN3) and red blood cell lysis repeated. Tubes are decanted and resuspended in 100 µL of FACS block (10% FCS in PBS with 0.05% NaN3) with directly conjugated antibodies recognizing B220, CD4, or CD8 (all from Biolegend, San Diego) for 30 min on ice. Cells are analyzed on a BD LSR II flow cytometer; the analysis is restricted to live cells (DAPI negative). These experiments are performed in accordance with all national or local guidelines and regulations and are approved by the UCI Institutional Animal Care and Use Committee.

SW620 and SW480 xenograft studies: For SW620 xenograft studies, two and one half million luciferase-expressing SW620 colon cancer cells suspended in PBS with 2% FCS are injected subcutaneously in the flank of 7 week old male nude mice (Charles Rivers Labs, Crl:NU(NCr)-Foxn1nu). When tumors reached 100 $mm^3$ in volume, mice are assigned to groups with matched average tumor volumes and animal weights. Four groups containing 7 mice are treated intraperitoneally with either vehicle (0.9% saline), 10 mg/kg FTY720, or 20 mg/kg compound 5 or compound 15. Tumor length and width are measured with calipers at 7 and 11 days of treatment. Tumor volume is calculated using the formula volume $(mm^3)$=length [mm]×(width $[mm])^2$×0.52. The average fold change in the volume of each tumor over time is shown.

For SW480 xenograft studies, xenografts are produced by injecting 2.5 million cells subcutaneously in the flank of NSG mice. Once tumors reach 100 $mm^3$, compounds in accordance with various embodiment of the invention (compound 5/104, for example) are administered by intraperitoneal injection or oral gavage as indicated. Tumor volume is calculated using the formula above; BLI is measured using an IVIS imaging system (Xenogen). SW480 tumors are excised and fixed in 2.5% glutaraldehyde in 0.1 M phosphate buffer, pH 7.4 and stored in the dark at 4° C. until embedding.

These experiments are performed in accordance with all national or local guidelines and regulations and are approved by the UCI Institutional Animal Care and Use Committee.

Nutrient transporter expression: Surface 4F2hc expression is measured at 6 h using phycoerythrin (PE)-conjugated mouse anti-human 4F2hc antibody (BD Pharmingen, cat #556077); analysis is restricted to viable cells. PE conjugated Mouse IgG1, k (cat #555749, BD Pharmingen) is used as an isotype control. Cells are analyzed on a BD LSR II flow cytometer and with FlowJo software (Treestar).

Mass spectrometric quantification: One million PC3 or 5 million SW620 cells in one well of a 6 well plate are treated with 10 µM FTY720 or 5 for 16 h. Media (100 µl) is removed from the well and combined with 100 µl of acetonitrile. Cells are collected by scraping, pelleted, and re-suspended in 100 µl of HPLC-grade water followed by the addition of 100 µl acetonitrile. Seventy-five nanograms of the compounds not being quantified (FTY720 and FTY720-P for analysis of the phosphorylation of 5, or 5 and 5-P for the analysis of FTY720/FYT720-P) is added to serve as an internal standard to allow correction for loss of compound during sample preparation. Precipitated proteins are removed from both samples by centrifugation (10 min at 15,000 rpm in a microfuge) and the supernatant transferred to a fresh tube on ice containing 100 µl of acetonitrile+0.2% acetic acid. Insoluble material is again removed by centrifugation and the supernatant analyzed for compound content. Twenty microliters of this de-proteinated sample is analyzed by UPLC-MS/MS (Waters Micromass Quattro Premier XE) equipped with a C18 reversed phase column (Waters) using an acetonitrile (+0.2% acetic acid) gradient elution. The instrument is operated in positive ion mode. Ion transition channels for multiple reaction monitoring are 308→255 for FTY720, 388→255 for FTY720-P, 290→104 for 5, and 370→272 for 5-P with a dwell time of 200 msec. The cone voltages are 30V for FTY720 and 5, and 20V for FTY720-P and 5-P. A standard curve is generated using pure compounds to allow for quantification; standard curves were linear from 50-1000 ng/ml with an $R^2$ of 0.98 or greater. Recovery of internal standard ranged from 80-120% consistent with the established accuracy of the instrument and is similar for phosphorylated and non-phosphorylated compounds.

Cell analysis: Viability and 4F2hc expression are determined by vital dye exclusion and flow cytometry. Oxygen consumption is measured with an XF24 Extracellular Flux Analyzer (Seahorse Bioscience); values are normalized to total protein. Confocal microscopy is performed on either a Zeiss LSM780 or a Nikon Eclipse Ti; vacuolation was monitored using a Nikon TE2000-S equipped with DIC filters. Anchorage-independent growth of SW620 cells is measured in DMEM-10 containing 0.35% agarose with a 0.5% agarose bottom layer. PBMNCs are obtained from the normal blood donor program run by the CTSA-supported Institute for Clinical and Translational Science at UCI under IRB protocols 2015-1883 (Edinger) and 2001-2058 (ICTS). PBMNCs are isolated from whole blood via Ficoll-Paque density gradient sedimentation. Plates were incubated at 37° C. in a humidified atmosphere containing 5% $CO_2$ and colonies were counted after 12 days.

Biology Procedures in Further Optimization Study:

Compounds: Compound stocks (5-25 mM) were prepared in water with the exception of C2-ceramide (109), dihydro-C2-ceramide (110), 14-17, 21-24, and 31-35 which were made up in DMSO and sphingosine (106), sphinganine (107) and dimethylsphingosine (108) which were prepared in ethanol.

Cell culture studies: FL5.12 cells (murine hematopoetic cells originally obtained from Craig Thompson, Memorial Sloan Kettering Cancer Center) were maintained at 0.1-0.5 million/ml in RPMI 1640 (Mediatech) supplemented with 10% fetal calf serum (FCS, Sigma-Aldrich), 10 mM Hepes (Mediatech), 500 µg/ml recombinant IL-3 (cat #575502, Biolegend), 55 µM β-mercaptoethanol (Sigma-Aldrich), 2 mM L-glutamine (Mediatech), and antibiotics. Cells were screened for *Mycoplasma* every 3 months using the Look-Out *Mycoplasma* PCR Detection kit (cat # MP0035, Sigma).

Viability assays: $IC_{50}$ values were determined by flow cytometry at 48 h by vital dye exclusion using DAPI (4', 6 diamidino-2-phenylindole). $IC_{50}$ values were calculated using GraphPad Prism (GraphPad Software, Inc, La Jolla, Calif.).

Nutrient transporter expression: Surface CD98 (4F2hc, SLC3A2) expression was measured at 3 h using phycoerythrin (PE)-conjugated rat anti-mouse CD98 antibody (Biolegend, cat #128208); analysis was restricted to viable cells. PE conjugated Rat IgG2a, k (cat #400508, Biolegend) was used as an isotype control. For staining, 200,000 cells were pelleted, re-suspended in 100 µl FACS block (PBS with 10% FCS and 0.05% NaN3) containing 0.25 µL anti-CD98 antibody, incubated on ice for 30 min, washed twice with 1 ml FACS wash (PBS containing 2% FCS and 0.05% NaN3), and analyzed on a BD LSR II flow cytometer. Data was processed with FlowJo software (Treestar).

Vacuolation assay: Cells were evaluated at 100× using brightfield microscopy and a Nikon TE2000-S fluorescence microscope equipped with DIC filters. Vacuolation was quantified after a 3 h incubation period in 2.5 µM compound except where otherwise indicated. To calculate a vacuolation score, vacuolation severity in at least 15 individual cells/experiment was assessed qualitatively. Scores were assigned to individual cells as follows: 0=no vacuoles, 1=very small vacuoles, 2=multiple well-defined vacuoles, 3=multiple large vacuoles. To calculate the vacuolation score associated with a compound, the following formula was used: vacuolation score=[(3×% cells in category 3)+(2×% cells in category 2)+(1×% cells in category 1)]/3.

The score is divided by 3 so that a compound with 100% of its cells in category 3 would have a vacuolation score of 100. Three independent experiments were conducted and the vacuolation scores averaged to generate a mean+/− SEM. All cells were scored by one lab member after confirming that a blinded individual scored 5 compounds with similar results.

To determine how well this qualitative vacuolation score reflected the true degree of vacuolation, an ImageJ based vacuole detection macro was developed and validated. Cell contours were manually traced and a set of contours corresponding to cells in the same field of view were saved as a ZIP region of interest (ROI) file for further processing. An Otsu threshold was applied to each cell. The resulting image was inverted, a median filter with radius 2 was applied, and a watershed transform was used to separate connected components that were too close to each other. Next the ImageJ "Analyze Particles" function was used to detect all the connected components in the resulting image and to calculate their corresponding area and circularity. Connected components with area smaller than 20 pixels or circularity>0.8 were identified as vacuoles. It was verified that the other connected components were results of under-segmentation. To overcome this under-segmentation, the ImageJ "Find Maxima" function was used to detect maxima of intensity inside these connected components. If more than one maximum as found, the component was divided via watershed and each new component was subjected to the circularity and area test independently. Vacuole image processing results were compared to manually detected vacuoles and displayed 86% accuracy of detection.

To increase contrast, cells were stained with CFSE (5(6)-carboxyfluorescein N-hydroxysuccinimidyl ester). For these assays, 200,000 cells were stained in 1 ml of 1 µM CFSE for 20 min in the dark after incubation in the compound of interest for 3 h. Cells were evaluated on a Zeiss LSM780 confocal microscope. The percent of the cytosol occupied by vacuoles was determined using the ImageJ macro. The nucleus was excluded when calculating the percent vacuolation. Using this macro to evaluate cells treated with sphingosine, sphinganine, and dimethylsphingosine, it was determined that the vacuolation score≈twice the % area vacuolated validating the vacuolation score as a semi-quantitative measure of the degree of vacuolation. Quantification of all samples with this algorithm and confocal microscopy was not feasible given the large number of compounds evaluated.

Statistics. The mean of at least 3 independent experiments is shown +/− SEM (CD98 loss or vacuolation). For $IC_{50}$ studies, the $IC_{50}$ is given with the 95% confidence interval as calculated in GraphPad Prism.

General Chemistry Procedures of Further Optimization Study:

General chemistry information: All reactions involving moisture sensitive compounds were performed in flame-dried glassware under a positive pressure of dry, oxygen free, argon and in dry solvents. Anhydrous solvents were distilled under a positive pressure of argon before use and dried by standard methods. THF, ether, CH2Cl2 and toluene were dried by the SDS (Solvent Delivery System). Commercial grade reagents were used without further purification. Silica column chromatography was performed on 230-400 mesh silica gel. Thin layer chromatography (TLC) was carried out on glass-backed silica gel plates. Visualization was effected by UV light (254 nm) or by staining with potassium permanganate solution or cerium ammonium molybdate followed by heating. 1H and 13C NMR spectra were recorded on Bruker AV-400 and AV-500 MHz spectrometers at room temperature (298 K). Chemical shifts are reported in parts per million (ppm) referenced from CDCl3 ($\delta$H: 7.26 ppm and $\delta$C: 77.0 ppm) or MeOD ($\delta$H: 3.31 ppm and $\delta$C: 49.0 ppm). Coupling constants (J) are reported in Hertz (Hz). Multiplicities are given as multiplet (m), singlet (s), doublet (d), triplet (t), quartet (q), quintet (quin.) and broad (br.). Infrared spectra were recorded on a FT-IR spectrometer and are reported in reciprocal centimeters (cm-1). Optical rotations were determined on an Anton Paar MCP 300 polarimeter at 589 nm at 25° C. Specific rotations are given in units of 10-1 deg cm2 g-1. High resolution mass spectra (HRMS) were performed by the "Centre régional de spectroscopie de masse de l'Université de Montréal" with electrospray ionization (ESI) coupled to a quantitative time-of-flight (TOF) detector. Purity analysis was assessed by HPLC (blank subtracted from final trace) with the eluents $H_2O$ with 0.1% formic acid and MeOH with 0.1% formic acid at a flow rate of 0.50 mL/min (unless otherwise stated) and UV detection at 214 nm. Columns: Sunfire C8=100×4.6 mm, particle size=5µ. Hypersil Gold C8=100×2.1 mm, particle size=3µ. tert-Butyl (2R,4S)-2-(hydroxymethyl)-4-((4-octylbenzyl)oxy)pyrrolidine-1-carboxylate, tert-butyl (2S,4R)-2-(hydroxymethyl)-4-((4-octylbenzyl) oxy)pyrrolidine-1-carboxylate, (2R,4S)-2-(methoxymethyl)-4-((4-octylbenzyl)oxy) pyrrolidine hydrochloride and (2S,4S)-2-methyl-4-((4-octylbenzyl)oxy)pyrrolidine hydrochloride were prepared as described by R. Fransson et al., S. ACS Med. Chem. Lett., 2013, 4, 969-973, the disclosure of which is incorporated herein by reference).

General Method A: To the relevant alcohol (1 equiv.) in THF and DMF was added portion wise NaH (3 equiv.) at 0° C. and the resulting suspension was stirred at this temperature for 30 minutes. 1-Bromododecane (3 equiv.) and tetra-N-butylammonium iodide (TBAI) (0.1 equiv.) were simultaneously added and the resulting mixture was allowed to warm to room temperature where it was stirred for 48 hours. After the dropwise addition of water (15 mL) the solution was extracted with ethyl acetate (2×20 mL). The combined organics were dried (MgSO4), filtered and concentrated in vacuo. The residue was purified by silica column chromatography (hexanes to 10% ethyl acetate in hexanes) to give an oil.

General Method B: To the relevant allylic-ether (1 equiv.) in dry $CH_2Cl_2$ (c=0.06 M) was added alkene (10 equiv.) and Grubbs I catalyst (20 mol %) under argon. The resulting mixture was stirred at room temperature for 24 hours before the addition of further Grubbs I catalyst (15 mol %) and alkene (10 equiv.), which was stirred for a further 24 hours at room temperature. The reaction mixture was concentrated in vacuo and purified by silica column chromatography (see specific compounds for conditions) to give an oil.

General Method C: The relevant alkyne (3 equiv.) and catecholborane (1M in THF, 3 equiv.) were refluxed at 70° C. under argon for 2 hours. The reaction mixture was then allowed to cool to room temperature. To this was added the appropriate aryl bromide (1 equiv.) in 1,2-dimethoxyethane (12 mL/mmol), Pd(PPh3)4 (3 mol %) and aqueous NaHCO3 (1M, 10 mL/mmol). The resulting mixture was refluxed at 85° C. under argon for 5 hours. The reaction mixture was then allowed to cool to room temperature and was extracted three times with diethyl ether. The combined organics were dried ($Na_2SO_4$), filtered, and concentrated in vacuo. The residue was purified by silica column chromatography (hexanes to 20% ethyl acetate in hexanes, unless otherwise stated) to give an oil.

General Method D: The relevant (E)-alkene (1 equiv.) was dissolved in ethyl acetate (c=0.04M) and to this was added in one portion Pd/C (10%). The air was removed from the flask under vacuum and replaced with a balloon of hydrogen. The resulting mixture was stirred at room temperature (see specific compounds for reaction times) and then filtered through a pad of Celite to give an oil, which was used without further purification.

General Method E: To the relevant TBS-protected alcohol (1 equiv.) in dry THF was added TBAF (1M in THF, see individual compounds for equiv.) and the resulting mixture was stirred at room temperature for 17 hours. The reaction mixture was diluted with water and extracted twice with ethyl acetate. The combined organics were dried (MgSO4), filtered and concentrated in vacuo. The residue was purified by silica column chromatography (10% ethyl acetate in hexanes to 30% ethyl acetate in hexanes, unless otherwise stated) to give an oil.

General Method F: To the relevant N-Boc protected alcohol (1 equiv.) in 1,4-dioxane was added was added 4M HCl in 1,4-dioxane (see individual compounds for amounts) and the resulting mixture was stirred at room temperature for 17 hours. The reaction mixture was concentrated in vacuo and coevaporated twice more with 1,4-dioxane to ensure all HCl was removed. The resulting residue was purified either by triturating three times with diethyl ether or by silica column chromatography (see specific compounds for conditions) to give the product as a solid. For biological testing a portion of this solid was dissolved in the minimum amount of HPLC grade water, filtered (pore size=0.45 µm) and lyophilized.

General Method G: The relevant HCl salt was dissolved in $CH_2Cl_2$ and extracted three times with sat. aq. NaHCO3. The organic layer was dried (MgSO4), filtered and concentrated in vacuo to give the corresponding free base, which was used without further purification. This residue (0.9 equiv.) was dissolved in the minimum amount of $CH_2Cl_2$ and under an atmosphere of argon was added 1,3-di-Boc- 2-(trifluoromethylsulfonyl)guanidine (1 equiv.) and N,N-diisopropylethylamine (1.5 equiv.). The reaction was stirred at room temperature for 17 hours. The $CH_2Cl_2$ was evaporated and the residue was purified by silica column chromatography ($CH_2Cl_2$ to 10% MeOH in $CH_2Cl_2$) to give an oil.

General Method H: The relevant HCl salt was dissolved in $CH_2Cl_2$ and extracted three times with sat. aq. $NaHCO_3$. The organic layer was dried ($MgSO_4$), filtered and concentrated in vacuum to give the corresponding free base, which was used without further purification. This residue (1 equiv.) was dissolved in $CH_2Cl_2$ and acetic anhydride (1.5 equiv.) was added dropwise at 0° C. The reaction mixture was allowed to reach room temperature where it was stirred for a further 17 hours. The residue was purified by silica column chromatography (hexanes to 50% ethyl acetate in hexanes) to give an oil.

Procedures for In Vitro and In Vivo Characterization of SH-BC-893:

Cell culture and reagents. OP9, DLD-1, SW48, SW620, MDA-MB-231, PANC-1, HOS, MG-63, and Zr75-1 cells were obtained from the ATCC. SW480 cells were provided by Marian Waterman (UCI, Irvine Calif.), HeLa cells by Christine Sütterlin (UCI, Irvine Calif.), LS180 cells by Bruce Blumberg (UCI, Irvine Calif.) and FL5.12 cells by Craig Thompson (Memorial Sloan Kettering Cancer Center, New York, N.Y.). p53−/−; LSL-KRasG12D MEFs with and without Cre-mediated deletion of the STOP cassette were kindly provided by Dr. David Tuveson (Cold Spring Harbor Laboratory, Cold Spring Harbor N. Y.). Primary p53+/+; PTEN+/+, p53−/−; PTEN+/+, and p53−/−; PTEN−/− MEFs were generated in-house from embryos from C57BL/6 mice using standard techniques. mPCE cells generated from p53−/− PTEN−/− mouse prostate tissue were maintained in DMEM with 10% FBS, 25 µg/ml bovine pituitary extract, 5 µg/ml bovine insulin and 6 ng/ml recombinant human epidermal growth factor. FL5.12 cells were maintained in RPMI 1640 medium supplemented with 10% fetal calf serum (FCS), 10 mM HEPES, 55 µM 2-mercaptoethanol, antibiotics, 2 mM L-glutamine, and 500 µg/ml rIL-3. FL5.12 cells were adapted to grow in 25 pg/ml IL-3 by gradually reducing the IL-3 concentration over 2 wk of culture. DLD-1 and Zr75-1 cells were cultured in the same media as FL5.12 but without IL-3. HeLa, OP9, MG-63, and MEF cells were cultured in DMEM with 4.5 g/L glucose and L-glutamine supplemented with 10% FCS and antibiotics. Starvation medium was produced by making DMEM lacking amino acids and glucose from chemical components and supplementing with 10% dialyzed FCS. LS180, SW48, PANC-1, MDA-MB-231, SW480, and SW620 cells were cultured in DMEM supplemented with 10% FCS, antibiotics, and 1 mM sodium pyruvate. Cell viability was measured by vital dye exclusion using either propidium iodide or DAPI at 1 µg/ml. Analysis of cell surface 4F2hc levels with PE-conjugated anti-CD98 was restricted to viable cells as determined by DAPI exclusion. Anchorage-independent growth of SW620 cells was measured in DMEM-10 containing 0.35% low melt agarose with a 0.5% agarose bottom layer. PBMCs were obtained from the normal blood donor program run by the CTSA-supported Institute for Clinical and Translational Science at UCI under IRB protocols 2015-1883 (Edinger) and 2001-2058 (ICTS). P40Px-EGFP plasmid was provided by Seth Field (UCSD, San Diego), mCherry-Vac14WT and mCherry-Vac14L156R plasmids by Thomas Weide (University Hospital of Muenster, Germany), mCherry-TRPML1, EGFP-TRPML1, and mCherry-ML1N*2 plasmids by Haoxing Xu (University of Michigan, Ann Arbor), and PIKfyve and Vac14 shRNA by Anand Ganesan (UCI, Irvine).

Light Microscopy: Brightfield and epifluorescence microscopy were conducted using a Nikon TE2000-S fluorescence microscope; confocal microscopy was performed on a Zeiss LSM780 confocal microscope or Nikon Eclipse Ti spinning disk confocal microscope. Antibodies were obtained from: Murine 4F2hc (cat #128208) and Lamp1 (cat #53-1079-42) from eBioscience; human 4F2hc (cat #556077) from BD Biosciences; human GLUT1 (cat # NB300-666) from Novus Biologicals; LC3 (cat #4108) from Cell Signaling Technology; PIKfyve (cat #4082) from Tocris; Vac14 (cat # SAB4200074) from Sigma-Aldrich; WIPI2 (cat # LS-C154557-100) from Lifespan Biosciences. Co-localization was determined using JACoP plugin in ImageJ software. Macropinocytosis was measured after 16 h incubation in serum-free DMEM. p53−/−; LSL-K-RasG12D MEFs before (LSL) or after (KRasG12D) introduction of Cre were serum starved for 16 h and then treated with macropinocytosis inhibitor 5-(N-ethyl-N-isopropyl) amiloride (EIPA, 75 µM) for 1 h or SH-BC-893 for 6 h. Oregon Green dextran (Life Technologies, cat # D7173) (1 mg/mL) and Lysotracker Red (Life Technologies, cat # L-7525) (1:2,000 dilution) were added for 30 min and live cells were evaluated on the spinning disc confocal microscope. For DiI-LDL uptake, mPCE were incubated in media with 10% charcoal-stripped serum for 24 h then incubated with 20 µg/ml DiI-LDL (Life Technologies, cat # L3482)+/− SH-BC-893 for 6 h and Lysotracker Blue (Life Technologies, cat # L-7525), for 30 min. To detect surface LDL receptors, DiI-LDL was added at 4° C. to mPCE cells treated with SH-BC-893 for 3 h or cells were stained with LDL receptor antibody (R&D Systems, cat #AF2255). SW480 tumors were excised and fixed in 2.5% glutaraldehyde in 0.1 M phosphate buffer, pH 7.4 and stored in the dark at 4° C. until embedding. Tumor samples were processed by the Pathology Research Services Core Facility at UC Irvine.

Electron microscopy. FL5.12 cells treated with FTY720 were fixed with 2.5% glutaraldehyde/2.5% formaldehyde in 0.1 M sodium cacodylate buffer and stored at 4° C. until embedding. Cells were post-fixed with 1% osmium tetroxide, serially dehydrated, embedded in eponat12 resin, ultrathin sections cut, mounted on grids, and stained with uranyl acetate and lead citrate. Samples were analyzed on a Philips CM10 transmission electron microscope. Representative images are shown from two independent experiments.

In vivo studies. Experiments conducted in mice were performed in accordance with the Institutional Animal Care and Use Committee of University of California, Irvine following a power analysis conducted in consultation with the Biostatistics Shared Resource of Chao Family Comprehensive Cancer Center at UCI. Xenografts were produced by injecting 5 million cells subcutaneously in the flank of IQ-16 week-old male or female NSG mice. Prostate isografts were produced in the same manner but in male 6-8 wk old C57BL/6 mice. Once tumors reached 100 $mm^3$, SH-BC-893 was administered by intraperitoneal (i.p.) injection or oral gavage as indicated. Tumor volume was calculated using the formula, volume ($mm^3$)=length [mm]×(width $[mm])^2$×0.52; BLI was measured using an IVIS imaging system (Xenogen). To generate pDKO mice on the C57BL6 background, $Pten^{flox}$ mice (stock No. 0045597) and $pSS^{flox}$ mice (stock No. 008462) were obtained from the Jackson Laboratory and PB-Cre4 mice (strain #01XF5) were obtained from the NCI-Frederick Mouse Repository. Age-matched cohorts of pDKO males were generated by in vitro fertilization executed with the assistance of the Transgenic Mouse Facility at UC Irvine. Treatment was begun at 6-7 wks of age. Tumor weight was determined by isolating the complete genitourinary (GU) tract of pDKO mice and subtracting the average weight of a normal GU tract from age-matched mice (n=3) after it was determined that SH-BC-893 treatment of normal mice did not alter GU tract weight (n=3). Tumor samples were processed and imaged by the Pathology Research Services Core Facility at UC Irvine. Blood chemistry was analyzed by IDEXX BioResearch and complete blood counts were performed using a Hemavet hematology system.

NADH Fluorescence Lifetime Imaging Microscopy (FLIM). Lifetime images were acquired using a Zeiss 780 microscope coupled to a Ti:Sapphire laser system (Spectra-Physics Mai Tai). The excitation wavelength was 740 nm and a dichroic filter (690 nm) was used to separate the fluorescence signal from the laser light. A 63X 1.15 water immersion objective was used. Image acquisition settings were: image size of 256×256 pixels and scan speed of 25.21 μsec/pixel. The fluorescence was detected by a hybrid detector (HPM-100 Hamamatsu). Data was collected until 100 counts in the brightest pixel of the image were acquired. The FLIM system was calibrated during each imaging session by measuring the fluorescence decay of fluorescein with a single exponential of 4.04 nsec. Phasor transformation of FLIM images and analysis of the average lifetime in single cells were done as described previously (Digman M A, et al., *Biophys J*. 2008; 94(2):L14-L16; Pate K T, et al., *EMBO J*. 2014; 33(13): 1454-73; Stringari C, et al., Sci Rep. 2012; 2:568; the disclosures of which are incorporated herein by reference). Data was processed by the SimFCS software developed at the Laboratory of Fluorescence Dynamics at UCI. The nucleus was excluded when determining the bound NADH fraction. Means+/− SEM are shown, n≥45 cells from two independent experiments.

Coherent anti-Stokes Raman Spectroscopy (CARS). The CARS imaging system is described in detail in (Suhalim J L, et al. *Biophys J*. 2012; 102(8): 1988-1995, the disclosure of which is incorporated herein by reference). Cells were fixed with 4% formaldehyde and imaged with a 60× water objective. The laser power on the sample was at 10 mW with 10 ms pixel dwell time. The lipid droplet area was estimated from CARS images using a customized Matlab program. Four components Otsu thresholding method was used to separate the lipid droplets, cell cytoplasm, cell nucleus and the background. The lipid droplet area was defined as the number of pixels covered by lipid droplets over the number of pixels covered by cytoplasm.

PIKfyve in vitro kinase assay. FLAG-PIKfyve was expressed in HEK293T cells, purified with FLAG-beads, and eluted with FLAG peptides. PI3P and phosphatidylserine (C16) liposomes were generated by sonication in 2× lipid mixture buffer [40 mM Tris-HCl (pH 7.4), 200 mM NaCl, 1 mM EGTA] with or without FTY720. FLAG-PIKfyve and lipid mixtures were incubated with $Mg^{2+}$-ATP solution [6.5 mM HEPES (pH 7.3), 2.5 mM $MnCl_2$, 10 mM $MgCl_2$, 1 mM β-glycerophosphate, 0.1 mM ATP and [$^{32}P$]-γ-ATP] for 15 min at RT. The reaction was stopped by adding 4 M HCl, and phosphoinositides were extracted with methanol/chloroform (1:1). Phosphoinositides were spotted on silica thin-layer chromatography plates and separated with 2 M acetic acid/1-propanol (35:65). Membranes were dried, exposed to a Phospho Imager, and the counts from PI(3,5)P2 spots quantified with ImageQuant.

Measurement of PI(3,5)P2 by HPLC. HeLa cells were rinsed twice with PBS and incubated in for 48 h in inositol labeling medium (inositol-free DMEM containing 5 μg/ml transferrin, 5 μg/ml insulin, 10% dialyzed FCS, 20 mM HEPES, 2 mM L-glutamine), and 10 μCi/ml myo-[2-$^3$H] inositol. Cells were lysed with 4.5% perchloric acid, scraped, and centrifuged at 14,000×g for 10 min at 4° C. Cell pellets were rinsed with 100 mM EDTA, centrifuged again, and re-suspended in 50 μl of water. To deacylate lipids, 1 ml methanol/40% methylamine/butanol (45.7% methanol, 10.7% methylamine, 11.4% butanol) were added and then the mixture was transferred to a glass vial and incubated at 55° C. for 1 h. After cooling to room temperature, samples were vacuum dried and re-suspended in 0.5 ml water. Lipids were extracted twice with an equal volume of butanol/ethyl ether/ethyl formate (20:4:1). The aqueous phase was vacuum dried and re-suspended in 75 μl water and 50 μl of each sample was analyzed by HPLC. PI(3,5)P2 levels were expressed as a percentage of total phosphatidylinositol.

PP2A phosphatase activity. PP2A activity was measured using a PP2A immunoprecipitation phosphatase assay kit (EMD Millipore). Briefly, the catalytic subunit of PP2A was immunoprecipitated from FL5.12 cell lysates with 4 μg anti-PP2A, C subunit. After four washes, the activity of immunoprecipitated PP2A was assessed by dephosphorylation of the phosphopeptide according to the manufacturer's instructions in the presence or absence of C2-ceramide, dihydro-C2-ceramide, FTY720, SH-BC-893, or calyculinA.

Mass spectrometry quantification of SH-BC-893. As an internal standard, 75 ng FTY720 was added to 50 μl plasma or 50 μl of tumor homogenate (0.25 M sucrose, 25 mM KCl, 50 mM Tris HCl, 0.5 mM EDTA, pH 7.4; 1:9 wt:volume) combined 1:1 with acetonitrile. Proteins were precipitated and removed by centrifugation (10 min at 15,000 rpm) and the supernatant transferred to a fresh tube on ice containing 50 μl of acetonitrile+0.2% acetic acid. After a second de-proteination with acetonitrile+0.2% acetic acid, 20 μl of de-proteinated samples were analyzed by UPLC-MS/MS using a Waters Micromass Quattro Premier XE equipped with a C18 reversed phase column (Waters) with an acetonitrile+0.2% acetic acid gradient elution. The instrument was operated in positive ion mode. Ion transition channels for multiple reaction monitoring were 290→104 for SH-BC-893 with a dwell time of 200 msec. The cone voltage was 30V. Standard curves used for quantitation were linear from 50-1000 ng/ml with an $R^2$ of 0.98 or greater. Recovery of internal standard was >80%. Tumor concentrations were calculated assuming that 1 gm=1 mL.

Statistical methods and data analysis. Significance was determined using a paired t-test for a single pairwise comparison. Tukey's method was utilized and adjusted p-values are reported where multiple comparisons were made. In tumor studies where data was not normally distributed, a Mann-Whitney U test was used to compare treated mice with controls. *, P<0.05; , P<0.01; *, P<0.001; n. s., not significant (P>0.05). For lipid droplet area in CARS experiments, the mean values between the control and experiment groups were compared with a two-tailed ANOVA.

Doctrine of Equivalents

While the above description contains many specific embodiments of the invention, these should not be construed as limitations on the scope of the invention, but rather as an example of one embodiment thereof. Accordingly, the scope of the invention should be determined not by the embodiments illustrated, but by the appended claims and their equivalents.

What is claimed is:

1. A method for treating a cancer, comprising:
administering a pharmaceutical formulation to a human subject, the formulation containing one or more compounds of formula:

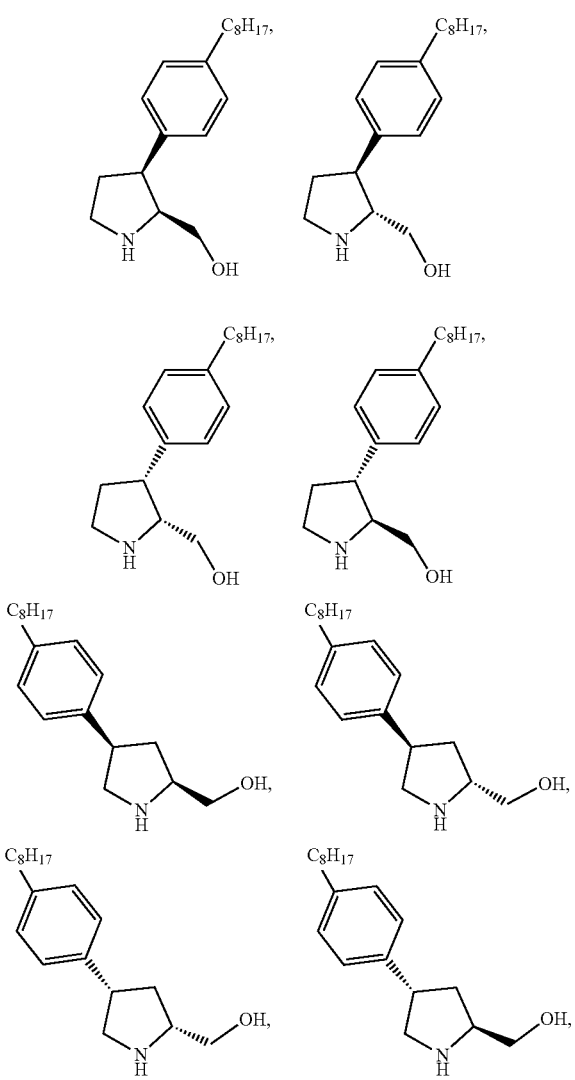

or a pharmaceutically acceptable salt thereof.

2. The method of claim 1, wherein the compound of formula is

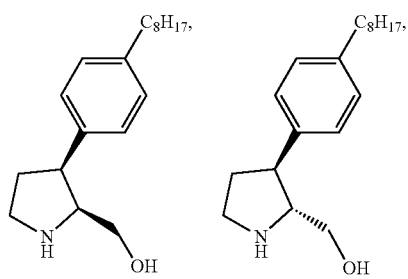

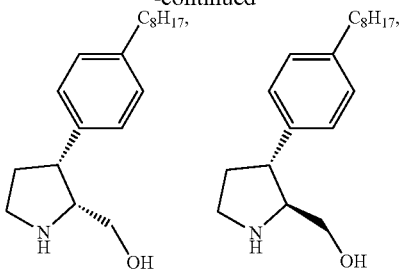

or a pharmaceutically acceptable salt thereof.

3. The method of claim 2, wherein the cancer is colon cancer.

4. The method of claim 2, wherein the cancer is prostate cancer.

5. The method of claim 2, wherein the cancer is lung cancer.

6. The method of claim 2, wherein the cancer is pancreatic cancer.

7. The method of claim 2, wherein the cancer is breast cancer.

8. The method of claim 2, wherein the cancer is leukemia.

9. The method of claim 2, wherein the pharmaceutical formulation is combined with at least one FDA-approved compound selected from one or more of the group: methotrexate, gemcitabine, tamoxifen, taxol, docetaxel, and enzalutamide.

10. The method of claim 2, wherein the pharmaceutical formulation administration is oral, transdermal, transmucosal, or parenteral.

11. The method of claim 1, wherein the compound of formula is

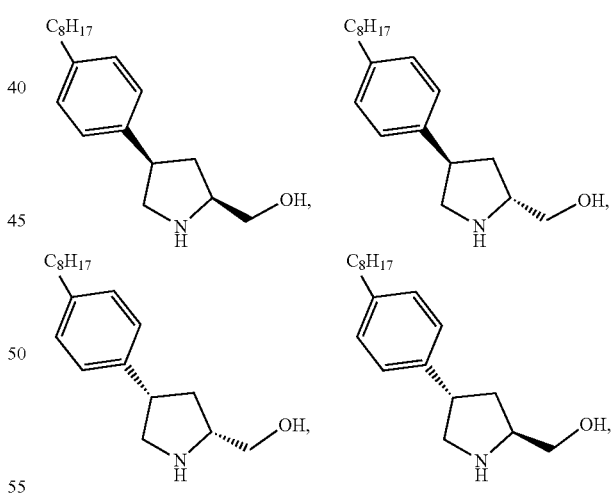

or a pharmaceutically acceptable salt thereof.

12. The method of claim 11, wherein the cancer is colon cancer.

13. The method of claim 11, wherein the cancer is prostate cancer.

14. The method of claim 11, wherein the cancer is lung cancer.

15. The method of claim 11, wherein the cancer is pancreatic cancer.

16. The method of claim 11, wherein the cancer is breast cancer.

17. The method of claim 11, wherein the cancer is leukemia.

18. The method of claim 11, wherein the pharmaceutical formulation is combined with at least one FDA-approved compound selected from one or more of the group: methotrexate, gemcitabine, tamoxifen, taxol, docetaxel, and enzalutamide.

19. The method of claim 11, wherein the pharmaceutical formulation administration is oral, transdermal, transmucosal, or parenteral.

* * * * *